US011365241B2

(12) United States Patent
Ortiz et al.

(10) Patent No.: US 11,365,241 B2
(45) Date of Patent: Jun. 21, 2022

(54) HIGH CONCENTRATION ANTI-C5 ANTIBODY FORMULATIONS

(71) Applicant: Alexion Pharmaceuticals, Inc., Boston, MA (US)

(72) Inventors: Stephan Ortiz, Guilford, CT (US); Jillian Gentile, Southington, CT (US); Leena Philominathan, Cheshire, CT (US); Eric Routhier, Killingworth, CT (US); Bruce Mason, Madison, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 87 days.

(21) Appl. No.: 16/633,930

(22) PCT Filed: Jul. 27, 2018

(86) PCT No.: PCT/US2018/044071
§ 371 (c)(1),
(2) Date: Jan. 24, 2020

(87) PCT Pub. No.: WO2019/023564
PCT Pub. Date: Jan. 31, 2019

(65) Prior Publication Data

US 2020/0369751 A1 Nov. 26, 2020

Related U.S. Application Data

(60) Provisional application No. 62/537,741, filed on Jul. 27, 2017.

(51) Int. Cl.

| | |
|---|---|
| ***A61K 39/395*** | (2006.01) |
| ***C07K 16/18*** | (2006.01) |
| ***A61K 9/00*** | (2006.01) |
| ***A61K 9/08*** | (2006.01) |
| ***A61K 47/18*** | (2017.01) |
| ***A61K 47/26*** | (2006.01) |
| *A61K 39/00* | (2006.01) |

(52) U.S. Cl.
CPC ............ *C07K 16/18* (2013.01); *A61K 9/0019* (2013.01); *A61K 9/08* (2013.01); *A61K 47/183* (2013.01); *A61K 47/26* (2013.01); *A61K 2039/505* (2013.01); *C07K 2317/526* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 3,710,795 | A | 1/1973 | Higuchi et al. |
| 4,485,045 | A | 11/1984 | Regen |
| 4,544,545 | A | 10/1985 | Ryan et al. |
| 4,816,567 | A | 3/1989 | Cabilly et al. |
| 4,863,457 | A | 9/1989 | Lee |
| 4,868,116 | A | 9/1989 | Morgan et al. |
| 4,980,286 | A | 12/1990 | Morgan et al. |
| 5,013,556 | A | 5/1991 | Woodle et al. |
| 5,308,341 | A | 5/1994 | Chanoch |
| 5,443,505 | A | 8/1995 | Wong et al. |
| 5,447,145 | A | 9/1995 | Cappello et al. |
| 5,501,856 | A | 3/1996 | Ohtori et al. |
| 5,624,821 | A | 4/1997 | Winter et al. |
| 5,648,260 | A | 7/1997 | Winter et al. |
| 5,773,019 | A | 6/1998 | Ashton et al. |
| 5,997,848 | A | 12/1999 | Patton et al. |
| 6,001,329 | A | 12/1999 | Buchsbaum et al. |
| 6,001,386 | A | 12/1999 | Ashton et al. |
| 6,005,079 | A | 12/1999 | Casterman et al. |
| 6,019,968 | A | 2/2000 | Platz et al. |
| 6,095,141 | A | 8/2000 | Armer et al. |
| 6,146,361 | A | 11/2000 | DiBiasi et al. |
| 6,170,717 | B1 | 1/2001 | Di Giovanni et al. |
| 6,192,891 | B1 | 2/2001 | Gravel et al. |
| 6,194,551 | B1 | 2/2001 | Idusogie et al. |
| 6,200,296 | B1 | 3/2001 | Dibiasi et al. |
| 6,277,099 | B1 | 8/2001 | Strowe et al. |
| 6,277,375 | B1 | 8/2001 | Ward |
| 6,300,064 | B1 | 10/2001 | Knappik et al. |

(Continued)

FOREIGN PATENT DOCUMENTS

| | | |
|---|---|---|
| EP | 0430539 A2 | 6/1991 |
| EP | 0488401 A1 | 6/1992 |

(Continued)

OTHER PUBLICATIONS

Ambati and Adamis, Prog Retin Eye Res 21(2): 145-151 (2002).
Amsterdam et al., Am J Physiol 268: H448-H457 (1995).
Appel et al., J Am Soc Nephrol 16: 1392-1404 (2005).
Armentano et al., Proc Natl Acad Sci USA 87: 6141-6145 (1990).
Baldridge et al., Methods 19: 103-107 (1999).
Barocas and Balachandran, Expert Opin Drug Delivery 5(1): 1-10 (10) (2008).
Baudino et al.l, J Immunol 181: 6664-6669 (2008).
Berge et al., J. Pharma Sci, 66: 1-19 (1977).
Berkner et al., BioTechniques 6: 616 ( 1988).
Better et al., Science 240: 1041-1043 (1988).
Bieg et al., Autoimmunity 31(1): 15-24 (1999).
Bless et al., Am J Physiol 276(1): L57-L63 (1999).

(Continued)

*Primary Examiner* — Yunsoo Kim
(74) *Attorney, Agent, or Firm* — Nelson Mullins Riley & Scarborough LLP; Jane E. Remillard, Esq.; Jill Gorny Sloper, Esq.

(57) ABSTRACT

The present disclosure relates to stable aqueous solutions comprising a high concentration of an anti-C5 antibody (e.g., ravulizumab) and methods for preparing the solutions. The disclosure also provides methods for treating or preventing complement-associated disorders, such as paroxysmal nocturnal hemoglobinuria (PNH) and atypical hemolytic uremic syndrome (aHUS), using the solutions. Also featured were therapeutic kits containing one or more of the solutions and a means for administering the solutions to a patient in need such a treatment.

17 Claims, 53 Drawing Sheets

Specification includes a Sequence Listing.

(56) References Cited

U.S. PATENT DOCUMENTS

| | | | | |
|---|---|---|---|---|
| 6,302,855 | B1 | 10/2001 | Lav et al. | |
| 6,355,245 | B1 | 3/2002 | Evans et al. | |
| 6,737,056 | B1 | 5/2004 | Presta | |
| 6,933,368 | B2 | 8/2005 | Co et al. | |
| 7,112,341 | B1 | 9/2006 | Nagarajan et al. | |
| 7,371,826 | B2 | 5/2008 | Presta | |
| 7,390,786 | B2 | 6/2008 | Warne et al. | |
| 7,556,615 | B2 | 7/2009 | Pettis et al. | |
| 7,670,600 | B2 | 3/2010 | Dall'Acqua et al. | |
| 7,704,497 | B2 | 4/2010 | Dall'Acqua et al. | |
| 8,088,376 | B2 | 1/2012 | Chamberlain et al. | |
| 8,323,962 | B2 | 12/2012 | Dall'Acqua et al. | |
| 8,367,805 | B2 | 2/2013 | Chamberlain et al. | |
| 8,802,820 | B2 | 8/2014 | Chamberlain et al. | |
| 9,079,949 | B1 | 7/2015 | Andrien, Jr. et al. | |
| 9,107,861 | B1 | 8/2015 | Andrien, Jr. et al. | |
| 9,206,251 | B2 | 12/2015 | Andrien, Jr. et al. | |
| 9,371,377 | B2 | 6/2016 | Andrien, Jr. et al. | |
| 9,556,263 | B2 | 1/2017 | Zhou et al. | |
| 9,663,574 | B2 | 5/2017 | Andrien, Jr. et al. | |
| 9,803,007 | B1 | 10/2017 | Andrien, Jr. et al. | |
| 10,227,400 | B2 | 3/2019 | Andrien, Jr. et al. | |
| 10,584,164 | B2 | 3/2020 | Andrien, Jr. et al. | |
| 2002/0026176 | A1 | 2/2002 | Varner et al. | |
| 2005/0271660 | A1 | 12/2005 | Wang | |
| 2006/0141456 | A1 | 6/2006 | Edwards et al. | |
| 2007/0172483 | A1 | 7/2007 | Schwaeble et al. | |
| 2007/0235029 | A1 | 10/2007 | Zhu et al. | |
| 2008/0202513 | A1 | 8/2008 | Birchall et al. | |
| 2008/0241223 | A1 | 10/2008 | Nivaggioli et al. | |
| 2009/0110679 | A1 | 4/2009 | Li et al. | |
| 2010/0098730 | A1 | 4/2010 | Lowman et al. | |
| 2011/0111406 | A1 | 5/2011 | Igawa et al. | |
| 2012/0230982 | A1 | 9/2012 | Zhou et al. | |
| 2013/0344088 | A1* | 12/2013 | Cosenza .............. | A61K 47/183<br>424/172.1 |
| 2014/0056888 | A1* | 2/2014 | Zhou ......................... | A61P 7/00<br>424/133.1 |
| 2016/0108115 | A1 | 4/2016 | Andrien, Jr. et al. | |
| 2016/0251433 | A1 | 9/2016 | Andrien, Jr. et al. | |
| 2017/0298123 | A1 | 10/2017 | Andrien, Jr. et al. | |
| 2018/0009885 | A1 | 1/2018 | Andrien, Jr. et al. | |
| 2020/0157200 | A1 | 5/2020 | Andrien, Jr. et al. | |

FOREIGN PATENT DOCUMENTS

| | | | |
|---|---|---|---|
| EP | 2006381 | A1 | 12/2008 |
| EP | 1610820 | B1 | 9/2010 |
| EP | 2275443 | A1 | 1/2011 |
| WO | 8902468 | A1 | 3/1989 |
| WO | 8905345 | A1 | 6/1989 |
| WO | 8907136 | A2 | 8/1989 |
| WO | 8207573 | A1 | 5/1992 |
| WO | 94/02559 | A1 | 2/1994 |
| WO | 94/04678 | A1 | 3/1994 |
| WO | 94/28027 | A1 | 12/1994 |
| WO | 9734631 | A1 | 9/1997 |
| WO | 98/23289 | A1 | 6/1998 |
| WO | 98/47531 | A2 | 10/1998 |
| WO | 0061178 | A1 | 10/2000 |
| WO | 0069887 | A2 | 11/2000 |
| WO | 0178693 | A2 | 10/2001 |
| WO | 2003/074679 | A2 | 9/2003 |
| WO | 03105757 | A2 | 12/2003 |
| WO | 2004024156 | A1 | 3/2004 |
| WO | 2004026380 | A2 | 4/2004 |
| WO | 2004029207 | A2 | 4/2004 |
| WO | 2004060407 | A1 | 7/2004 |
| WO | 2004073551 | A2 | 9/2004 |
| WO | 2005011735 | A1 | 2/2005 |
| WO | 2005040217 | A2 | 5/2005 |
| WO | 2005/077981 | A2 | 8/2005 |
| WO | 2005092925 | A2 | 10/2005 |
| WO | 06/031994 | | 3/2006 |
| WO | 2006/053301 | A2 | 5/2006 |
| WO | 2006094234 | A1 | 9/2006 |
| WO | 2006/105338 | A2 | 10/2006 |
| WO | 2006/122257 | A2 | 11/2006 |
| WO | 2007041635 | A2 | 4/2007 |
| WO | 2007/106585 | A1 | 9/2007 |
| WO | 2007114319 | A1 | 10/2007 |
| WO | 08/043822 | A2 | 4/2008 |
| WO | 2008048545 | A2 | 4/2008 |
| WO | 2008092117 | A2 | 7/2008 |
| WO | 2009/041643 | A1 | 4/2009 |
| WO | 2009058492 | A2 | 5/2009 |
| WO | 2009086320 | A1 | 7/2009 |
| WO | 2009125825 | A1 | 10/2009 |
| WO | 2010/151526 | A1 | 12/2010 |
| WO | 2011111007 | A2 | 9/2011 |
| WO | 2011122011 | A2 | 10/2011 |
| WO | 2012073992 | A1 | 6/2012 |
| WO | 2012133782 | A1 | 10/2012 |
| WO | 2013046704 | A2 | 4/2013 |
| WO | 2013047748 | A1 | 4/2013 |
| WO | 2015/134894 | A1 | 9/2015 |
| WO | 2016/160756 | A2 | 10/2016 |
| WO | 2017/218515 | A1 | 12/2017 |
| WO | 2021/091937 | A1 | 5/2021 |

OTHER PUBLICATIONS

Brodsky, R. et al., "Complement in hemolytic anemia," Blood, vol. 126(22):2459-2465 (2015).
Burmeister et al., Nature 372: 379-383 (1994).
Burton et al., Adv Immun 51:1-18 (1992).
Campistol, J., et al., "An update for atypical haemolytic uraemic syndrome: diagnosis and treatment. A consensus document," Nefrologia, vol. 33(1):27-45 (2013).
Canfield et al., J Exp Med 173: 1483-1491 (1991).
Caron et al., J Exp Med 176: 1191-1195 (1992).
Chaparro-Riggers, Biol Chem 287: 11090-11097 (2012).
Chothia et al., Nature 342: 877-883 (1989).
Chowdhury et al., Science 254: 1802-1805 (1991).
Christmann, M., et al., "Eculizumab as First-Line Therapy for Atypical Hemolytic Uremic Syndrome," Pediatrics, vol. 133, e1759: 7 pages (2014).
Co et al., Mol Immunol 30: 1361 (1993).
Cooper et al., J Exp Med 132: 775-793 (1970).
Crocker et al., J Clin Pathol 27(2): 122-124 (1974).
Dai et al., Proc Natl Acad Sci USA 89: 10892-10895 (1992).
Dall'Acqua et al., J Biol Chem 281: 23514-23524 (2006).
Dall'Acqua et al., J Immunol 117:1129-1138 (2006).
Danos and Mulligan, Proc Natl Acad Sci USA 85; 6460-6464 (1988).
Datta-Mannan et al., J Biol Chem 282(3): 1709-1717 (2007).
Daugherty, A., et al., "Formulation and delivery issues for monoclonal antibody thera-peutics," Current Trends in Monoclonal Antibody Development and Manufacture, Chapter 8:103-129 (2010).
Deans et al., Proc Natl Acad Sci USA 81: 1292 (1984).
Dong et al., Reviews in Mol Biotech 82: 303-323 (2002).
Duncan and Winter Nature 322: 738-40 (1988).
Eglitis et al., Science 230: 1395-1398 (1985).
Epstein et al., Proc Natl Acad Sci USA 82: 3688 (1985).
European Search Report, EP Application No. 161776562, dated Aug. 8, 2016, 8 pages.
Evans, et al., Mol Immunol 32(16): 1183-95 (1995).
Fakhouri, F. et al., "Terminal Complement Inhibitor Eculizumab in Adult Patients With Atypical Hemolytic Uremic Syndrome: A Single-Arm, Open-Label Trial," Am J Kidney Dis., vol. 68(1):84-93 (2016).
Fearon et al., J Exp Med 142: 856-863 (1975).
Ferry et al., Proc Natl Acad Sci USA 88: 8377-8381 (1991).
Fivash et al., Curr Opin Biotechnol 9: 97-101 (1998).
Flotte et al., Am J Respir Cell Mol Biol 7: 349-356 (1992).
Ghetie et al., Nat Biotech 15: 637-640 (1997).
Gulsen and Chauhan, Invest Opthalmol Vis Sci 45: 2342-2347 (2004).

(56) References Cited

OTHER PUBLICATIONS

Gupta et al., Vaccine 13(14): 1263-1276 (1995).
Hanauske et al., Clin Cancer Res 13(2, part 1): 523-531 (2007).
Heinen, S. et al., "Monitoring and modeling treatment of atypical hemolytic uremic syndrome," Molecular Immunology, vol. 54: 84-88 (2013).
Hetherington et al., Antimicrobial Agents and Chemotherapy 50(10): 3499-3500 (2006).
Hezareh et al., J Virol 75: 12161-12168 (2001).
Mihu et al., J Gastrointestin Liver Dis 16(4): 419-124 (2007).
Moongkarndi et al, Immunobiol 165: 323 (1983).
Moongkarndi et al., Immunobiol 162: 397 (1982).
Morell et al., J Clin Invest 49(4): 673-680 (1970).
Mueller et al., Mol Immunol 34(6): 441-452 (1997).
Muller-Eberhard, Ann Rev Biochem 57: 321-347 (1988).
Mullett et al., Methods 22: 77-91 (2000).
Mulligan and Berg Proc Natl Acad Sci USA 78: 2072 (1981).
Mullinax et al., BioTechniques 12(6): 864-869 (1992).
Muyldermans et al., Trends Biochem Sci 26: 230-235 (2001).
Newkirk et al., Clin Exp Immunol 106(2): 259-264 (1996).
Moris, M. et al., "STEC-HUS, atypical HUS and TTP are all diseases of complement activation," Nat. Rev. Nephrol., vol. 8: 622-633 (2012).
Nuttall et al., Gurr Pharm Biotech 1: 253-263 (2000).
Park et al., Anesth Analg 99(1): 42-48 (1999).
Pavisic et al., Int J Pharm 387(1-2)L 110-119 (2010).
Petkova et al., Int Immunol 18(12): 1759-69 (2006).
Poljak, Structure 2(12): 1121-1123 (1994).
Pollock et al., J Immunol Methods 231(1-2): 147-157 (1999).
Qiao et al., Proc Natl Acad Sci USA 105(27): 9337-9342 (2008).
Rabinovici et al., J Immunol 149 1744-1750 (1992).
Raju, BioProcess International 1(4): 44-53 (2003).
Ranta and Uritti, Adv Drug Delivery Rev 58(11): 1164-1181 (2006).
Rawal and Pangburn, J Immunol 166(4): 2635-2642 (2001).
Rich et al., Curr Opin Biotechnol 11: 54-61 (2000).
Riechmann et al., J Immunol Meth 231: 25-38 (1999).
Riechmann et al., Nature 332: 323-327 (1988).
Rinder et al., J Clin Invest 96: 1564-1572 (1995).
Roberts et al., Advanced Drug Delivery Reviews 54: 459-476 (2002).
Rogers et al., J Nucl Med 38: 1221-1229 (1997).
Rondon and Marasco, Annual Review of Microbiology 51: 257-284 (1997).
Roopenian et al., Methods Mol Biol 602: 93-104 (2010).
Roopenian, DC, et al., "FcRn: the neonatal Fc receptor comes of age," Nature Reviews Immunology, vol. 7(9): 115-725 (2007).
Rosenfeld et al., Cell 68: 143-155 (1992).
Rother, R. et al.,"Discovery and development of the complement inhibitor eculizumab for the treatment of paroxysmal nocturnal hemoglobinuria," Nature Biotechnology, 25 (11): 1256-1264 (1488 Supp) (2007).
Rother et al., Nature Biotechnology 25 (11): 1256-1263 (2007).
Saland, J et al., "Liver-kidney transplantation to cure atypical HUS: still an option post-eculizumab?," Pediatr Nephrol., DOI 10.1007/s00467-013-2722-2, 4 pages (2013).
Salvadori, M. et al., "Update on hemolytic uremic syndrome: Diagnostic and therapeutic recommendations," World J Nephrol., vol. 2(3): 56-76 (2013).
Samulski et al., J Virol 63: 3822-3828 (1989).
Sarkar, C.,A., et al., "Rational cytokine design for increased lifetime and enhanced potency using pH-activated histidine switching," Nature Biotechnology, vol. 20(9):908-913 (2002).
Sarver et al.. Proc Natl Acad Sci USA 79: 7147 (1982).
Sawai et al., Am J Repr Immunol 34: 26-34 (1995).
Schmid et al., Schock 8(2): 119-124 (1997).
Schoonbroodt et al., Nucleic Acids Res 33(9): e81 (2005).
Schreiber et al., Proc Natl Acad Sci USA 75: 3948-3952 (1978).
Scully, M. et al., "Systemic Involvement at Entry into the Global Atypical Hemolytic Uremic Syndrome (aHUS) Registry," Blood, vol. 128:3729 6 pages (2016).
Sharma, V.K. et al., "The formulation and delivery of monoclonal antibodies", Therapeutic Monoclonal Antibodies, Chapter 30: 675-711 (2009).
Sheerin, N.S. et al., "A national specialized service in England for atypical haemolytic uraemic syndrome-the first year's experience," QJM: An International Journal of Medicine, 27-33: 7 pages (2016).
Sheridan, D. et al., "Design and preclinical characterization of ALXN1210: A next generation anti-C5 monoclonal antibody with improved pharmacokinetics and duration of action," Immunobiology, vol. 221(Issue 10): 1158 (2016).
Sheridan, D. et al., "Design and preclinical characterization of ALXN1210: A novel anti-C5 antibody with extended duration of action," PLoS ONE 13(4): e0195909, 15 pages (2018).
Shields et al., J Biol Chem 276(9): 6591-6604 (2001).
Shields et al., J Biol Chem 277(30): 26733-26740 (2002).
Shire, S. et al., "High-concentration antibody formulations," Formulation and Process De-velopment Strategies for Manufacturing Biopharmaceuticals, Chapter 15: 349-381 (2010).
Shopes, Immunol 148: 2918-2922 (1992).
Shu et al., Proc Natl Aced Sci USA 90: 7995-7999 (1993).
Sissons et al., Proc Natl Acad Sci USA 77: 559-562 (1980).
Skerra et al., Science 240: 1038-1040 (1988).
Southern and Berg, Mol Appl Genet 1:327 (1982).
Staelens et al., Mol Immunol 43: 1243-1257 (2006).
Fabrizi, Ma et al., "Elimination mechanisms of therapeutic monoclonal antibodies ," Drug Discovery Today, vol. 11 (1-2):81-88 (2006).
Thomas et al., Mol Immunol 33(17118): 1389-1401 (1996).
Todorovska et al., J Immunol Methods 248(1): 47-66 (2001).
Tofukuji et al., J Thorac Cardiovasc Surg 166(6): 1060-1068 (1998).
Tsai, H. et al., "A Mechanistic Approach to the Diagnosis and Management of Atypical Hemolytic Uremic Syndrome," Transfusion Medicine Reviews, vol. 28:187-197 (2014).
Van Beusechem et al., Proc Natl Acad Sci USA 89: 7640-7644 (1992).
Van Gurp et al., Am J Transplantation 8(8): 1711-1718 (2008).
Van Kuik-Romeijn et al., Transgenic Res 9(2): 155-159 (2000).
Verhoeyen et al., Science 239: 1534-1536 (1988).
Wang et al., Proc Natl Acad Sci USA 93: 8563-8568 (1996).
Wang et al.,Proc Natl Acad Sci USA 92: 8955-8959 (1995).
Wang, W. et al., "Antibody Structure, Instability, and Formulation," Journal of Pharmaceu-tical Sciences, American Chemical Society and American Pharmaceutical Association, vol. 96(1):1-26 (2007).
Ward and Zvaifler, J Clin Invest 50(3): 606-16 (1971).
Waters, A. et al., "aHUS caused by complement dysregulation: new therapies on the horizon," Pediatr Nephrol., vol. 26:41-57 (2011).
Weisman et al., Science 249: 146-151 (1990).
Wetsel et al., J Biol Chem 265: 2435-2440 (1990).
Wigler et al., Cell 16: 77 (1979).
Wilson et al., Proc Natl Acad Sci USA 85: 3104-3018 (1988).
Wright et al., EMBO J 10(10): 2717-2723 (1991).
Wurzner et al., Complement Inflamm 8: 328-340 (1991).
Xu et al., Cell Immunol 200: 16-26 (2000).
Yuksel, S. et al., "First-Line, Early and Long-Term Eculizumab Therapy in Atypical Hemolytic Uremic Syndrome: A Case Series in Pediatric Patients," Pediatr Drugs, vol. 18:413-420 (2016) DOI 10.1007/s40272-016-0194-0.
Zalevsky et al., Nat Biotech 28: 157-159 (2010).
Zuber, J. et al., "new insights into postrenal transplant hemolytic uremic syndrome," Nat. Rev. Nephrol., vol. 7: 23-35 (2011).
Hillmen et al., N. Engl J Med 350(6): 552-559 (2004).
Hillmen, P. et al., "Long-term safety and efficacy of sustained eculizumab treatment in patients with paroxysmal nocturnal haemoglobinuria,"British Journal of Haematology doi:10.1111/bjh.12347, 12 pages (2013).
Hinton et al., J Biol Chem 279: 6213-6216 (2004).
Hinton et al., J Immunol 176: 346-356 (2006).
Hirt-Minkowski, P. et al., "Atypical Hemolytic Uremic Syndrome: Update on the Complement System and What Is New," Nephron Clin Pract., 114:c219-c235 (2010).
Holers and Thurman, Molecular Immunology 41: 147-152 (2004).
Holers et al., Immunological Reviews 223: 300-316 (2008).
Homeister et al., J Immunol 150:1055-1064 (1993).

(56) References Cited

OTHER PUBLICATIONS

Hou et al., Cytokine 10: 319-30 (1998).
Houdebine, Curr Opin Biotechnol 13(6): 625-629 (2002).
Huber et al., Proc Natl Acad Sci USA 88: 8039-8043 (1991).
Hudson and Kortt, J Immunol Methods 231: 177-189 (1999).
Huston et al., Methods in Enzymology 203: 46-88 (1991).
Hwang et al., Proc Natl Acad Sci USA 77: 4030 (1980).
Hwu et al., J Immunol 150: 4104-4115 (1993).
Igawa et al., "Antibody recycling by engineered pH-dependent antigen binding improves the duration of antigen neutralization," Nat. Biotechnol. 28(11):1203-1207 (2010).
International Preliminary Report on Patentability, PCT/U52018/044071, dated Jan. 28, 2020, 8 pages.
International Search Report and Written Opinion for Application No. PCT/US2015/019225, dated May 18, 2015.
International Search Report and Written Opinion, PCT/US2018/044071, dated Oct. 2, 2018, 12 pages.
Isaacs et al., J Immunol 161: 3862-3869 (1998).
Isenman et al., J Immunol 124: 326-331 (1980).
Ishii-Watabe, A. et al., "Molecular Design of Therapeutic Antibodies," Pharmaceutics 74 (1): 4-11: 17 pages (2014).
Israel et al., Immunology 89(4): 573-578 (1996).
Ito, W. et al., "The His-probe method: effects of histidine residues introduced into the complementarity-determining regions of antibodies on antigen-antibody interactions at different pH values," FEBS Letter, vol. 309(1): 85-88(1992). cited by applicant.
Johne et al., J Immunol Meth 160: 191-198 (1993).
Johnson et al., J Med Chem 42: 4640-4649 (1999).
Jones et al., Nature 321: 522-525 (1986).
Jonsson et al., Ann Biol Clin 51: 19-26 (1993).
Jonsson et al.. Biotechniques 11: 620-627 (1991).
Junghans, R. et al., "The protection receptor for IgG catabolism is the beta2-microglobulin-containing neonatal intestinal transport receptor," PNAS, USA, vol. 93(11):512-5516 (1996).
Jungi and Pepys, Immunology 43(2): 271-279 (1981).
Kaszubska et al., Protein Expression and Purification 18: 213-220 (2000).
Kay et al., Human Gene Therapy 3: 641-647 (1992).
Kim et al., Ophthalmic Res 39: 244-254 (2007).
Kinstler et al., Advanced Drug Deliveries Reviews 54: 477-485.
Klein et al., Proc. Natl Acad Sci USA 78: 524-528 (1981).
Kroshus et al., Transplantation 60: 1194-1202 (1995).
Lee, CV., et al., "High-affinity human antibodies from phage-displayed synthetic Fab libraries with a single framework scaffold," J. Molecular Biology, vol. 340 (5):1073-1093 (2004).
Lee, et al., Bioconjug Chem 10(6): 973-81 (1999).
Legendre, CM, et al., "Terminal Complement Inhibitor Eculizumab in Atypical Hemolytic-Uremic Syndrome," N Engl J Med., vol. 368:2169-2181 (2013).
Levy and Ladda, Nat New Biol 229(2): 51-52 (1971).
Licht, C., et al., "The global aHUS registry: methodology and initial patient characteristics," BMC Nephrology, vol. 16 (207) 8 pages (2015) Doi 10.1186/S12882-015-0195-1.
Lodmell et al., Vaccine 18:1059-1066 (2000).
Loirat, , C. et al., "Plasmatherapy in Atypical Hemolytic Uremic Syndrome," Seminars in Thrombosis and Hemostasis, vol. 36(6): 673-681 (2010).
Loirat, C. et al., "An international consensus approach to the management of atypical hemolytic uremic syndrome in children," Pediatr Nephrol., vol. 31:15-39 (2016).
Loirat, C. et al., "Atypical hemolytic uremic syndrome," Orphanet Journal of Rare Diseases, vol. 6:60: 30 pages (2011).
Lusky and Botchan, Nature 293: 79 (1981).
Malina, M. et al., "Peripheral Gangrene in Children With Atypical Hemolytic Uremic Syndrome," Pediatrics, vol. 131: d331-e335 (2013).
McLaughlin et al., J Virol 62: 1963-1973 (1989).
Medicus et al., J Exp Med 144: 1076-1093 (1976).
Janda A., et al., "Ig Constant Regions Effects on Variable Region Structure and Function," Frontiers in Microbiology, vol. 7 (22):10 pages. doi:10.3389/fmicb.2016.00022 (2016).
Jorgensen L., et al., "Recent trends in stabilizing peptides and proteins in pharmaceutical formulation—considerations in the choice of excipients," Expert Opinion on Drug Delivery, vol. 6(11): 1219-1230 (2009) doi:10.1517/17425240903199143.
Wang W., "Instability, stabilization and formulation of liquid protein pharmaceuticals," International Journal of Pharmaceutics, vol. 185(2): 129-188 (1999) doi:10.1016/s0378-5173(99)00152-0.

* cited by examiner

| # | Sample | Description | |
|---|---|---|---|
| 1 | Eculizumab Reference | Lot: RC50000812 | |
| 2 | 25-HIS-7, 0 mM NaCl | 25 mM Histidine pH 7, 0 mM NaCl | |
| 3 | 25-HIS-7, 50 mM NaCl | 25 mM Histidine pH 7, 50 mM NaCl | |
| 4 | 25-HIS-7, 100 mM NaCl | 25 mM Histidine pH 7, 100 mM NaCl | |
| 5 | 25-HIS-7, 150 mM NaCl | 25 mM Histidine pH 7, 150 mM NaCl | |
| 6 | 25-HIS-7, 200 mM NaCl | 25 mM Histidine pH 7, 200 mM NaCl | |

Dynamic Light Scattering, L-Arginine Titration of Buffer Exchanged ALXN1210 at 50 mg/mL

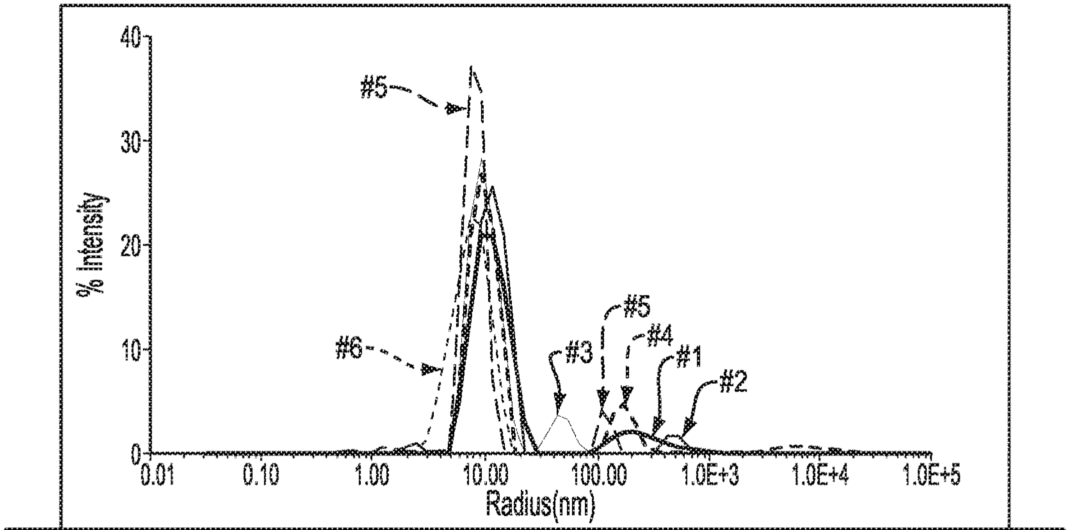

| # | Sample | Description | |
|---|---|---|---|
| 1 | 1210-SPPD-14-023, 0 mM L-Arginine | 10 mM Sodium Phosphate, 150 mM NaCl, pH 7, 50 mg/mL, 0 mM L-Arginine | |
| 2 | 1210-SPPD-14-023, 1 mM L-Arginine | 10 mM Sodium Phosphate, 150 mM NaCl, pH 7, 50 mg/mL, 1 mM L-Arginine | |
| 3 | 1210-SPPD-14-023, 2 mM L-Arginine | 10 mM Sodium Phosphate, 150 mM NaCl, pH 7, 50 mg/mL, 2 mM L-Arginine | |
| 4 | 1210-SPPD-14-023, 5 mM L-Arginine | 10 mM Sodium Phosphate, 150 mM NaCl, pH 7, 50 mg/mL, 5 mM L-Arginine | |
| 5 | 1210-SPPD-14-023, 10 mM L-Arginine | 10 mM Sodium Phosphate, 150 mM NaCl, pH 7, 50 mg/mL, 10 mM L-Arginine | |
| 6 | 1210-SPPD-14-023, 25 mM L-Arginine | 10 mM Sodium Phosphate, 150 mM NaCl, pH 7, 50 mg/mL, 25 mM L-Arginine | |

FIG. 2

Dynamic Light Scattering, Salt Titration of Phosphate Buffer Exchanged ALXN1210 at 50 mg/mL

| # | Sample | Description | |
|---|---|---|---|
| 1 | Eculizumab Reference | Lot: RC50000812 | |
| 2 | 25-PHO-7, 0 mM NaCl | 25 mM Sodium Phosphate pH 7, 0 mM NaCl | |
| 3 | 25-PHO-7, 50 mM NaCl | 25 mM Sodium Phosphate pH 7, 50 mM NaCl | |
| 4 | 25-PHO-7, 100 mM NaCl | 25 mM Sodium Phosphate pH 7, 100 mM NaCl | |
| 5 | 25-PHO-7, 150 mM NaCl | 25 mM Sodium Phosphate pH 7, 150 mM NaCl | |
| 6 | 25-PHO-7, 200 mM NaCl | 25 mM Sodium Phosphate pH 7, 200 mM NaCl | |

Differential Scanning Fluorescence Buffer Exchanged ALXN1210 at 50 mg/mL

| Buffer | Tm |
|---|---|
| Citrate-pH5 | 61.0 |
| Citrate-pH6 | 69.4 |
| Acetate-pH5 | 64.9 |
| HEPES-pH7 | 71.5 |
| Histidine-pH6 | 71.5 |
| Histidine-pH7 | 72.3 |
| Na-Phosphate-pH7 | 73.7 |
| Citrate-pH6.8 | 70.9 |
| Phosphate-citrate-pH6.9 | 72.1 |
| K-Phosphate-pH7 | 71.0 |

Short Term Stability Study Results for ALXN1210 T=0 through T=2 Weeks at 2-8°C

| 2-8 °C | | T=0 | | | | | 1 Week | | | | | 2 Weeks | | | |
|---|---|---|---|---|---|---|---|---|---|---|---|---|---|---|---|
| Sample ID | Sample Description | Appearance | Osmolality (mOsm/kg) | Concentration (mg/mL) | SEC % Monomer | iCE | Appearance | pH | Concentration (mg/mL) | SEC % Monomer | iCE | Appearance | Concentration (mg/mL) | SEC % Monomer | iCE |
| 1210-25H-8Suc-7.2 | ALXN1210, 25 mM Histidine pH 7.2, 8% Sucrose | Slightly opalescent, practically free from particles | 299 | 58.4 | 98.9 | pI range 6.02-6.53 | Slightly opalescent, practically free from particles | 6.99 | 58.0 | 98.9 | pI range 6.01-6.51 | Slightly opalescent, practically free from particles | 58.6 | 98.8 | pI range 6.02-6.53 |
| 1210-25H-5Sor-7.2 | ALXN1210, 25 mM Histidine pH 7.2, 5% Sorbitol | | 338 | 47.2 | 98.9 | pI range 6.01-6.53 | | 7.02 | 46.6 | 98.9 | pI range 6.01-6.52 | | 46.8 | 98.8 | pI range 6.02-6.53 |
| 1210-AS-25H-8Suc-7.2 | ALXN1210, 25 mM Histidine pH 7.2, 8% Sucrose | | 301 | 73.2 | 98.2 | pI range 6.02-6.53 | | 7.76 | 74.9 | 98.1 | pI range 5.91-6.52 | | 75.8 | 98.0 | pI range 6.01-6.52 |
| 1210-AS-25H-5Sor-7.2 | ALXN1210, 25 mM Histidine pH 7.2, 5% Sorbitol | | 339 | 59.3 | 98.2 | pI range 6.01-6.53 | | 7.78 | 60.8 | 98.2 | pI range 6.01-6.53 | | 61.5 | 98.0 | pI range 6.01-6.53 |
| 1210-25P-25Arg-8Suc-7 | ALXN1210, 25 mM Phosphate pH 7, 8% Sucrose | | 349 | 93.2 | 99.2 | pI range 6.02-6.53 | | 8.89 | 92.9 | 99.2 | pI range 6.03-6.54 | | 95.0 | 99.1 | pI range 6.00-6.52 |
| 1210-25P-25 Arg-5Sor-7 | ALXN1210, 25 mM Phosphate pH 7, 5% Sorbitol | | 378 | 75.2 | 99.3 | pI range 6.01-6.53 | | 9.09 | 75.3 | 99.2 | pI range 6.02-6.53 | | 75.5 | 99.2 | pI range 6.01-6.51 |

FIG. 6

Short Term Stability Study Results for ALXN1210 T=3 Weeks through T=2 Months at 2-8°C

| 2-8 °C | | 3 Weeks | | | | 1 Month | | | | 1.5 Months | | | | 2 Months | | | | | |
|---|---|---|---|---|---|---|---|---|---|---|---|---|---|---|---|---|---|---|---|
| Sample ID | Sample Description | Appearance | Concentration (mg/mL) | SEC % Monomer | ICE | Appearance | Concentration (mg/mL) | SEC % Monomer | ICE | Appearance | Concentration (mg/mL) | SEC % Monomer | ICE | Appearance | Osmolality (mOsm) | pH | Concentration (mg/mL) | SEC % Monomer | ICE |
| 1210-25H-8Suc-7.2 | ALXN1210, 25 mM Histidine pH 7.2, 8% Sucrose | Slightly opalescent, practically free from particles | 58.7 | 98.7 | pI range 6.02-6.52 | Slightly opalescent, practically free from particles | 58.9 | 98.7 | pI range 6.02-6.53 | Slightly opalescent, light particles | 58.2 | 98.6 | pI range 6.02-6.61 | Slightly opalescent, light particles | 295 | 6.74 | 58.2 | 98.4 | pI range 6.02-6.52 |
| 1210-25H-5Sor-7.2 | ALXN1210, 25 mM Histidine pH 7.2, 5% Sorbitol | | 47.3 | 98.7 | pI range 6.00-6.52 | | 51.7 | 98.7 | pI range 6.02-6.52 | Slightly opalescent, practically light particles | 46.9 | 98.6 | pI range 6.01-6.58 | Slightly opalescent, light particles | 336 | 6.58 | 46.8 | 98.3 | pI range 6.03-6.52 |
| 1210-AS-25H-8Suc-7.2 | ALXN1210, 25 mM Histidine pH 7.2, 8% Sucrose | | 76.7 | 97.9 | pI range 6.02-6.52 | | 75.4 | 97.8 | pI range 6.02-6.52 | Slightly opalescent, practically light particles | 73.7 | 97.6 | pI range 6.01-6.52 | Slightly opalescent, light particles | 311 | 7.22 | 72.5 | 97.3 | pI range 6.03-6.52 |
| 1210-AS-25H-5Sor-7.2 | ALXN1210, 25 mM Histidine pH 7.2, 5% Sorbitol | | 62.1 | 97.9 | pI range 6.01-6.52 | | 62.0 | 97.8 | pI range 6.02-6.52 | Slightly opalescent, practically free from particles | 60.7 | 97.6 | pI range 6.01-6.52 | Slightly opalescent, practically free from particles | 333 | 7.54 | 59.5 | 97.2 | pI range 6.02-6.52 |
| 1210-25P-25Arg-8Suc-7 | ALXN1210, 25 mM Phosphate pH 7, 8% Sucrose | | 94.2 | 99.1 | pI range 6.01-6.51 | | 93.3 | 99.1 | pI range 6.02-6.52 | Slightly opalescent, practically free from particles | 93.3 | 99.0 | pI range 6.01-6.52 | Slightly opalescent, practically free from particles | 348 | 8.81 | 94.2 | 98.9 | pI range 6.02-6.52 |
| 1210-25P-25Arg-5Sor-7 | ALXN1210, 25 mM Phosphate pH 7, 5% Sorbitol | | 76.1 | 99.1 | pI range 6.01-6.52 | | 75.9 | 99.1 | pI range 6.02-6.52 | Slightly opalescent, practically free from particles | 75.2 | 99.1 | pI range 6.01-6.52 | Slightly opalescent, practically free from particles | 370 | 9.01 | 76.0 | 99.0 | pI range 6.02-6.52 |

FIG. 7

Short Term Stability Study Results for ALXN1210 T=0 through T=3 Weeks at 23-27°C

| 23-27 °C | | 1 Week | | | | 2 Weeks | | | | 3 Weeks | | | |
|---|---|---|---|---|---|---|---|---|---|---|---|---|---|
| Sample ID | Sample Description | Appearance | Concentration (mg/mL) | SEC % Monomer | iCE | Appearance | Concentration (mg/mL) | SEC % Monomer | iCE | Appearance | Concentration (mg/mL) | SEC % Monomer | iCE |
| 1210-25H-8Suc-7.2 | ALXN1210, 25 mM Histidine pH 7.2, 8% Sucrose | Opalescent, light particulates | 58.5 | 98.8 | pI range 6.02-6.53 | Opalescent, very cloudy, light particulates | 59.1 | 98.8 | pI range 6.02-6.52 | Opalescent, very cloudy, light particulates | 59.3 | 99.0 | pI range 6.02-6.52 |
| 1210-25H-5Sor-7.2 | ALXN1210, 25 mM Histidine pH 7.2, 5% Sorbitol | Opalescent, light particulates | 47.0 | 98.8 | pI range 6.02-6.53 | Opalescent, light particulates | 48.1 | 98.6 | pI range 6.01-6.52 | Opalescent, light particulates | 49.4 | 98.4 | pI range 6.02-6.52 |
| 1210-25P-25Arg-8Suc-7 | ALXN1210, 25 mM Phosphate pH 7, 8% Sucrose | Slightly opalescent, practically free from particles | 95.3 | 99.1 | pI range 6.01-6.52 | Slightly opalescent, practically free from particles | 94.5 | 98.7 | pI range 5.91-6.53 | Slightly opalescent, practically free from particles | 93.8 | 98.5 | pI range 5.92-6.37 |
| 1210-25P-25Arg-5Sor-7 | ALXN1210, 25 mM Phosphate pH 7, 5% Sorbitol | Slightly opalescent, practically free from particles | 75.6 | 99.2 | pI range 5.92-6.53 | Slightly opalescent, practically free from particles | 76.2 | 98.7 | pI range 5.92-6.52 | Slightly opalescent, practically free from particles | 75.0 | 98.7 | pI range 5.92-6.38 |

FIG. 8

Short Term Stability Study Results for ALXN1210 T=1 Month through T=2 Months at 23-27°C

| 23-27 °C | | 1 Month | | | | 1.5 Months | | | | 2 Months | | | | | |
|---|---|---|---|---|---|---|---|---|---|---|---|---|---|---|---|
| Sample ID | Sample Description | Appearance | Concentration (mg/mL) | SEC % Monomer | ICE | Appearance | Concentration (mg/mL) | SEC % Monomer | ICE | Appearance | Osmolality (mOsm/kg) | pH | Concentration (mg/mL) | SEC % Monomer | ICE |
| 1210-25H-8Suc-7.2 | ALXN1210, 25 mM Histidine pH 7.2, 8% Sucrose | Opalescent, very cloudy, heavy particulates | 59.7 | 99.0 | pI range 6.01-6.52 | Opalescent, very cloudy, heavy particulates | 59.6 | 92.7 | pI range 6.12-6.62 | Opalescent, very cloudy, light particulates | 531 | 4.01 | 59.2 | 79.6 | pI range 6.13-6.68 |
| 1210-25H-5Sor-7.2 | ALXN1210, 25 mM Histidine pH 7.2, 5% Sorbitol | Opalescent, light particulates | 51.2 | 98.1 | pI range 6.04-6.53 | Opalescent, light particulates | 53.3 | 97.5 | pI range 6.01-6.52 | Opalescent, light particulates | 379 | 7.07 | 53.8 | 95.7 | pI range 6.02-6.52 |
| 1210-25P-25Arg-8Suc-7 | ALXN1210, 25 mM Phosphate pH 7, 8% Sucrose | Opalescent, light particulates | 94.7 | 98.2 | pI range 5.92-6.37 | Opalescent, light particulates | 93.3 | 98.1 | pI range 5.85-6.52 | Opalescent, light particulates | 432 | 8.21 | 94.8 | 97.9 | pI range 5.85-6.38 |
| 1210-25P-25Arg-5Sor-7 | ALXN1210, 25 mM Phosphate pH 7, 5% Sorbitol | Slightly opalescent, practically free from particles | 75.9 | 98.3 | pI range 5.85-6.38 | Slightly opalescent, practically free from particles | 75.6 | 98.1 | pI range 5.85-6.38 | Slightly opalescent, practically free from particles | 371 | 8.97 | 76.2 | 97.6 | pI range 5.79-6.37 |

FIG. 9

Short Term Stability Study Results for ALXN1210 T=1 Week through T=3 Weeks at 37°C

| 37 °C | | 1 Week | | | | 2 Weeks | | | | 3 Weeks | | | |
|---|---|---|---|---|---|---|---|---|---|---|---|---|---|
| Sample ID | Sample Description | Appearance | Concentration (mg/mL) | SEC % Monomer | iCE | Appearance | Concentration (mg/mL) | SEC % Monomer | iCE | Appearance | Concentration (mg/mL) | SEC % Monomer | iCE |
| 1210-25H-8Suc-7.2 | ALXN1210, 25 mM Histidine pH 7.2, 8% Sucrose | Opalescent, light particulates | 66.2 | 98.7 | pI range 6.01-6.52 | Opalescent, light particulates | 64.3 | 98.7 | pI range 6.01-6.52 | Opalescent, light particulates | 64.4 | 97.3 | pI range 6.02-6.51 |
| 1210-25H-5Sor-7.2 | ALXN1210, 25 mM Histidine pH 7.2, 5% Sorbitol | Opalescent, light particulates | 48.9 | 97.5 | pI range 6.02-6.52 | Opalescent, light particulates | 59.1 | 95.3 | pI range 6.02-6.64 | Opalescent, moderate particulates | 71.5 | 94.7 | pI range 6.02-6.62 |
| 1210-AS-25H-8Suc-7.2 | ALXN1210, 25 mM Histidine pH 7.2, 8% Sucrose | Opalescent, light particulates | 78.7 | 96.5 | pI range 6.02-6.53 | Opalescent, very cloudy, light particulates | 78.5 | 95.0 | pI range 5.93-6.63 | Opalescent, very cloudy, light particulates | 76.7 | 90.9 | pI range 5.94-6.61 |
| 1210-AS-25H-5Sor-7.2 | ALXN1210, 25 mM Histidine pH 7.2, 5% Sorbitol | Opalescent, light particulates | 67.6 | 97.7 | pI range 5.92-6.52 | Opalescent, light particulates | 69.4 | 97.2 | pI range 5.92-6.37 | Opalescent, light particulates | 69.6 | 97.0 | pI range 5.88-6.37 |
| 1210-25P-25Arg-8Suc-7 | ALXN1210, 25 mM Phosphate pH 7, 8% Sucrose | Slightly opalescent, practically free from particles | 93.6 | 97.1 | pI range 5.91-6.53 | Slightly opalescent, practically free from particles | 93.4 | 95.0 | pI range 5.76-6.37 | Slightly opalescent, practically free from particles | 94.4 | 92.8 | pI range 5.73-6.24 |
| 1210-25P-25 Arg-5Sor-7 | ALXN1210, 25 mM Phosphate pH 7, 5% Sorbitol | Slightly opalescent, practically free from particles | 74.7 | 97.0 | pI range 5.92-6.52 | Slightly opalescent, practically free from particles | 75.8 | 94.5 | pI range 5.77-6.38 | Slightly opalescent, practically free from particles | 76.3 | 92.7 | pI range 5.78-6.24 |

FIG. 10

Short Term Stability Study Results for ALXN1210 T=1 Month through T=2 Months at 37°C

| 37 °C | | 1 Month | | | | 1.5 Months | | | | 2 Months | | | | | |
|---|---|---|---|---|---|---|---|---|---|---|---|---|---|---|---|
| Sample ID | Sample Description | Appearance | Concentration (mg/mL) | SEC % Monomer | iCE | Appearance | Concentration (mg/mL) | SEC % Monomer | iCE | Appearance | Osmolality (mOsm/kg) | pH | Concentration (mg/mL) | SEC % Monomer | iCE |
| 1210-25H-8Suc-7.2 | ALXN1210, 25 mM Histidine pH 7.2, 8% Sucrose | Opalescent, moderate particulates | 64.9 | 94.1 | pI range 6.05-6.50 | Opalescent, moderate particulates | 64.3 | 78.8 | pI range 6.12-6.36 | Opalescent, yellow tint, moderate particulates | 558 | 3.96 | 64.5 | 46.1 | No result, Sample Degraded |
| 1210-25H-5Sor-7.2 | ALXN1210, 25 mM Histidine pH 7.2, 5% Sorbitol | Opalescent, moderate particulates | 78.9 | 93.7 | pI range 6.02-6.62 | Opalescent, moderate particulates | 82.4 | 92.3 | pI range 5.93-6.62 | Opalescent, yellow tint, moderate particulates | 393 | 7.01 | 78.1 | 91.2 | pI range 5.94-6.62 |
| 1210-AS-25H-8Suc-7.2 | ALXN1210, 25 mM Histidine pH 7.2, 8% Sucrose | Opalescent, very cloudy, light particulates | 78.8 | 82.4 | pI range 6.01-6.23 | Opalescent, very cloudy, light particulates | 75.7 | 54.8 | No result, Sample Degraded | Opalescent, yellow tint, very cloudy, light particulates | 546 | 4.08 | 77.2 | 25.1 | No result, Sample Degraded |
| 1210-AS-25H-5Sor-7.2 | ALXN1210, 25 mM Histidine pH 7.2, 5% Sorbitol | Opalescent, light particulates | 72.3 | 94.9 | pI range 5.93-6.37 | Opalescent, light particulates | 72.1 | 96.3 | pI range 5.85-6.62 | Opalescent, yellow tint, light particulates | 400 | 7.21 | 54.8 | 91.1 | |
| 1210-25P-25Arg-8Suc-7 | ALXN1210, 25 mM Phosphate pH 7, 8% Sucrose | Slightly opalescent, practically free from particles | 95.3 | 91.0 | pI range 5.79-6.25 | Slightly opalescent, practically free from particles | 94.8 | 87.6 | pI range 6.00-6.52 | Slightly opalescent, light particles | 388 | 7.79 | 93.7 | 84.9 | |
| 1210-25P-25 Arg-5Sor-7 | ALXN1210, 25 mM Phosphate pH 7, 5% Sorbitol | Slightly opalescent, practically free from particles | 76.7 | 90.8 | pI range 5.78-6.26 | Slightly opalescent, practically free from particles | 76.6 | 87.5 | pI range 6.00-6.51 | Slightly opalescent, practically free from particles | 376 | 8.90 | 76.3 | 83.1 | |

FIG. 11

Short Term Stability SEC, % Monomer for ALXN1210
T=0 through T=2 Months 23-27°C

| # | Sample | Description | Concentration | |
|---|---|---|---|---|
| 1 | 1210-PD-14-0042-8 | 25 mM Histidine pH 7.2 Stock (PD) | 65.7 mg/mL | ━━━━ |
| 2 | 1210-25H-8Suc-7.2 | 25 mM Histidine pH 7.2, 8% Sucrose, T=0 (PD) | 58.4 mg/mL | ──── |
| 3 | 1210-25H-5Sor-7.2 | 25 mM Histidine pH 7.2, 5% Sorbitol, T=0 (PD) | 47.2 mg/mL | - - - - |

Short Term Stability Dynamic Light Scattering ALXN1210
Histidine AS Samples T=0

| # | Sample | Description | Concentration | |
|---|---|---|---|---|
| 1 | Stir Cell AS | 25 mM Histidine pH 7.2 Stock (AS) | 77.1 mg/mL | |
| 2 | 1210-AS-25H-8Suc-7.2 | 25 mM Histidine pH 7.2, 8% Sucrose, T=0 (AS) | 73.2 mg/mL | |
| 3 | 1210-AS-25H-5Sor-7.2 | 25 mM Histidine pH 7.2, 5% Sorbitol, T=0 (AS) | 59.3 mg/mL | - - - - |

Short Term Stability Dynamic Light Scattering ALXN1210
Phosphate Samples T=0

| # | Sample | Description | Concentration | |
|---|---|---|---|---|
| 1 | 1210-PD-14-0042-Formulation C | 25 mM Phosphate, pH 7 (PD) | 112 mg/mL | |
| 2 | 1210-25P-25Arg-8Suc-7.2 | 25 mM Phosphate pH 7, 25 mM Arginine, 8% Sucrose, T=0 (PD) | 93.2 mg/mL | |
| 3 | 1210-25P-25Arg-5Sor-7.2 | 25 mM Phosphate pH 7, 25 mM Arginine, 5% Sorbitol, T=0 (PD) | 75.2 mg/mL | |

Short Term Stability Dynamic Light Scattering ALXN1210
Phosphate Samples T=2 Months 2-8°C

| # | Sample | Description | Concentration | |
|---|---|---|---|---|
| 1 | RM12100213 | Reference for ALXN1210 | 9.4 mg/mL | |
| 2 | 2-8_1210-25P-25Arg-8Suc-7 | 25 mM Phosphate pH 7, 25 mM Arginine, 8% Sucrose, 2-8 Deg C, T=2M (PD) | 94.2 mg/mL | |
| 3 | 2-8_1210-25P-25Arg-5Sor-7 | 25 mM Phosphate pH 7, 25 mM Arginine, 5% Sorbitol, 2-8 Deg C, T=2M (PD) | 76.0 mg/mL | - - - - |

Short Term Stability Study Results for ALXN1210
Freeze Thaw T=0 through Cycle 2 at T=1M -20°C

| -20 °C | | T=0 | | | | FT1 | | | | FT2 | | |
|---|---|---|---|---|---|---|---|---|---|---|---|---|
| Sample ID | Sample Description | Appearance | Concentration (mg/mL) | SEC % Monomer | iCE | Appearance | Concentration (mg/mL) | SEC % Monomer | iCE | Appearance | Concentration (mg/mL) | SEC % Monomer |
| 1210-25H-8Suc-7.2 | ALXN1210, 25 mM Histidine pH 7.2, 8% Sucrose | Slightly opalescent, practically free from particles | 58.4 | 98.9 | pI range 6.02-6.53 | Slightly opalescent, practically free from particles | 58.0 | 98.7 | pI range 6.02-6.60 | Slightly opalescent, practically free from particles | 58.8 | 98.8 |
| 1210-25H-5Sor-7.2 | ALXN1210, 25 mM Histidine pH 7.2, 5% Sorbitol | | 47.2 | 98.9 | pI range 6.01-6.53 | | 46.4 | 98.8 | pI range 6.00-6.52 | | 46.5 | 98.8 |
| 1210-25P-25Arg-8Suc-7 | ALXN1210, 25 mM Phosphate pH 7, 8% Sucrose | | 93.2 | 99.1 | pI range 6.02-6.53 | | 94.1 | 99.1 | pI range 6.01-6.52 | | 93.8 | 99.2 |
| 1210-25P-25Arg-5Sor-7 | ALXN1210, 25 mM Phosphate pH 7, 5% Sorbitol | | 75.2 | 99.2 | pI range 6.01-6.53 | | 75.2 | 99.2 | pI range 6.01-6.52 | | 74.5 | 99.2 |

FIG. 19

Short Term Stability Study Results for ALXN1210
Freeze Thaw Cycle 3 through Cycle 5 at T=1M -20°C

| -20 °C | | FT3 | | | | FT4 | | | FT5 | | | |
|---|---|---|---|---|---|---|---|---|---|---|---|---|
| Sample ID | Sample Description | Appearance | Concentration (mg/mL) | SEC % Monomer | iCE | Appearance | Concentration (mg/mL) | SEC % Monomer | Appearance | Concentration (mg/mL) | SEC % Monomer | iCE |
| 1210-25H-8Suc-7.2 | ALXN1210, 25 mM Histidine pH 7.2, 8% Sucrose | Slightly opalescent, practically free from particles | 57.9 | 98.8 | pI range 6.02-6.52 | Slightly opalescent, practically free from particles | 58.3 | 98.7 | Slightly opalescent, practically free from particles | 56.9 | 98.8 | pI range 6.02-6.52 |
| 1210-25H-5Sor-7.2 | ALXN1210, 25 mM Histidine pH 7.2, 5% Sorbitol | | 46.7 | 98.8 | pI range 6.03-6.61 | | 46.5 | 98.8 | | 46.2 | 98.7 | pI range 6.02-6.52 |
| 1210-25P-25Arg-8Suc-7 | ALXN1210, 25 mM Phosphate pH 7, 8% Sucrose | | 94.5 | 99.2 | pI range 6.01-6.52 | | 92.6 | 99.2 | | 91.9 | 99.2 | pI range 6.02-6.52 |
| 1210-25P-25Arg-5Sor-7 | ALXN1210, 25 mM Phosphate pH 7, 5% Sorbitol | | 75.1 | 99.2 | pI range 6.01-6.59 | | 74.5 | 99.2 | | 74.7 | 99.2 | pI range 6.02-6.52 |

FIG. 20

Prototype Stability Study Results for ALXN1210
T=0 through T=2 Months at 2-8°C (SPAS-14-007)

| 2-8 °C | | T=0 | | | | | | | | | | | 1M | | | 2M |
|---|---|---|---|---|---|---|---|---|---|---|---|---|---|---|---|---|
| Sample ID | Sample Description | Appearance | Osmolality (mOsm/kg) | pH | Concentration (mg/mL) | SEC % Monomer | Viscosity (mPas) | Density (g/cm3) | Potency | LOC Non-reduced | LOC Reduced | iCE | Appearance | Concentration (mg/mL) | SEC % Monomer | SEC % Monomer |
| 1210-75-25P-7.0-5S-25R | ALXN1210, 75 mg/mL, 25 mM Phosphate, pH 7.0, 5% Sucrose, 25 mM L-Arginine | Slightly opalescent, practically free from particles | 287 | 7.45 | 73.3 | 98.7 | 3.408 | 1.045 | 94% activity relative to reference | 98.1% IgG as main band | 100% as Heavy & Light | pI range 6.03-6.52 | Slightly opalescent, practically free from particles | 74.9 | 98.5 | 98.4 |
| 1210-75-25P-7.0-3So-25R | ALXN1210, 75 mg/mL, 25 mM Phosphate, pH 7.0, 3% Sorbitol, 25 mM L-Arginine | | 296 | 7.50 | 71.2 | 98.8 | 3.156 | 1.036 | 107% activity relative to reference | 98.0% IgG as main band | 100% as Heavy & Light | pI 6.22, pI range 6.02-6.52 | | 72.2 | 98.6 | 98.4 |
| 1210-100-25P-7.0-5S-25R_BDS | ALXN1210, 100 mg/mL, 25 mM Phosphate, pH 7.0, 5% Sucrose, 25 mM L-Arginine, BDS | | 275 | 7.44 | 96.4 | 98.4 | | | 91% activity relative to reference | 98.1% IgG as main band | 100% as Heavy & Light | pI range 6.01-6.52 | | 99.2 | 98.0 | 97.9 |
| 1210-100-25P-7.0-3So-25R_BDS | ALXN1210, 100 mg/mL, 25 mM Phosphate, pH 7.0, 3% Sorbitol, 25 mM L-Arginine, BDS | | 271 | 7.37 | 100.4 | 98.4 | 6.497 | 1.040 | 96% activity relative to reference | 98.1% IgG as main band | 100% as Heavy & Light | pI range 6.03-6.52 | | 99.4 | 98.1 | 98.3 |
| 1210-100-25P-7.0-5S-25R_DP | ALXN1210, 100 mg/mL, 25 mM Phosphate, pH 7.0, 5% Sucrose, 25 mM L-Arginine, DP | | 275 | 7.42 | 96.0 | 98.4 | | | 111% activity relative to reference | 98.0% IgG as main band | 100% as Heavy & Light | pI range 6.03-6.52 | | 96.3 | 97.9 | |
| 1210-100-25P-7.0-3So-25R_DP | ALXN1210, 100 mg/mL, 25 mM Phosphate, pH 7.0, 3% Sorbitol, 25 mM L-Arginine, DP | | 268 | 7.36 | 99.7 | 98.4 | 7.237 | 1.041 | 108% activity relative to reference | 98.1% IgG as main band | 100% as Heavy & Light | pI range 6.02-6.52 | | 101.0 | 98.1 | |

FIG. 22

Prototype Stability Study Results for ALXN1210
T=3 Months through T=6 Months at 2-8°C (SPAS-14-007)

| 2-8 °C | | 3M | | | | | | | 6M | | | | | | |
|---|---|---|---|---|---|---|---|---|---|---|---|---|---|---|---|
| Sample ID | Sample Description | Appearance | Concentration (mg/mL) | SEC % Monomer | Potency | LOC Non-reduced | LOC Reduced | iCE | Appearance | Concentration (mg/mL) | SEC % Monomer | Potency | LOC Non-reduced | LOC Reduced | iCE |
| 1210-75-25P-7.0-5S-25R | ALXN1210, 75 mg/mL, 25 mM Phosphate, pH 7.0, 5% Sucrose, 25 mM L-Arginine | Slightly opalescent, practically free from particles | 79.9 | 98.48 | | 97.5% IgG as main band | 100% as Heavy & Light | pI range 6.00-6.51 | opalescent, practically free from particles | 80.0 | 98.1 | 102 | 96.8% IgG as main band | 100% as Heavy & Light | pI range 6.0-6.5 |
| 1210-75-25P-7.0-3So-25R | ALXN1210, 75 mg/mL, 25 mM Phosphate, pH 7.0, 3% Sorbitol, 25 mM L-Arginine | Slightly opalescent, practically free from particles | 72.8 | 98.7 | 99% Activity relative to reference | 97.5% IgG as main band | 100% as Heavy & Light | pI range 6.01-6.52 | opalescent, practically free from particles | 72.9 | 98.5 | 101 | 97.5% IgG as main band | 100% as Heavy & Light | pI range 6.0-6.5 |
| 1210-100-25P-7.0-5S-25R_BDS | ALXN1210, 100 mg/mL, 25 mM Phosphate, pH 7.0, 5% Sucrose, 25 mM L-Arginine, BDS | Slightly opalescent, practically free from particles | 101.7 | 98.14 | | 97.6% IgG as main band | 100% as Heavy & Light | pI range 6.00-6.51 | opalescent, practically free from particles | 104.6 | 97.6 | 101 | 96.7% IgG as main band | 100% as Heavy & Light | pI range 6.0-6.5 |
| 1210-100-25P-7.0-3So-25R_BDS | ALXN1210, 100 mg/mL, 25 mM Phosphate, pH 7.0, 3% Sorbitol, 25 mM L-Arginine, BDS | Slightly opalescent, practically free from particles | 102.1 | 98.16 | 96% Activity relative to reference | 97.6% IgG as main band | 100% as Heavy & Light | pI range 6.02-6.51 | opalescent, practically light particles | 101.6 | 97.9 | 99 | 97.6% IgG as main band | 100% as Heavy & Light | pI range 6.0-6.5 |
| 1210-100-25P-7.0-5S-25R_DP | ALXN1210, 100 mg/mL, 25 mM Phosphate, pH 7.0, 5% Sucrose, 25 mM L-Arginine, DP | Slightly opalescent, practically free from particles | 98.9 | 97.81 | | 97.6% IgG as main band | 100% as Heavy & Light | pI range 6.02-6.51 | opalescent, practically free from particles | 104.6 | 97.8 | | 96.7% IgG as main band | 100% as Heavy & Light | pI range 6.0-6.5 |
| 1210-100-25P-7.0-3So-25R_DP | ALXN1210, 100 mg/mL, 25 mM Phosphate, pH 7.0, 3% Sorbitol, 25 mM L-Arginine, DP | Slightly opalescent, practically free from particles | 100.2 | 98.21 | 95% Activity relative to reference | 97.5% IgG as main band | 100% as Heavy & Light | pI range 6.01-6.51 | opalescent, practically free from particles | 101.6 | 97.9 | | 96.4% IgG as main band | 100% as Heavy & Light | pI range 6.0-6.5 |

FIG. 23

Prototype Stability Study Results for ALXN1210
T=9 Months through T=12 Months at 2-8°C (SPAS-14-007)

| 6M | | 9M | | | | | | 12M | | | | | | | | |
|---|---|---|---|---|---|---|---|---|---|---|---|---|---|---|---|---|
| Sample ID | Sample Description | Appearance | Concentration (mg/mL) | SEC % Monomer | LOC Non-reduced | LOC Reduced | iCE | Appearance | pH | Osmolality (mOsm/kg) | Concentration (mg/mL) | SEC % Monomer | Potency | LOC Non-reduced | LOC Reduced | iCE |
| 1210-75-25P-7.0-5S-25R | ALXN1210, 75 mg/mL, 25 mM Phosphate, pH 7.0, 5% Sucrose, 25 mM L-Arginine | opalescent, light particles | 74.0 | 98.6 | 97.3% IgG as main band | 100.0% as Heavy & Light | pI range 6.0-6.5 | very opalescent, light particles | 7.58 | 294 | 75.2 | 98.2 | 86% activity relative to reference | 98.3% IgG as main band | 100% as Heavy & Light | pI range 6.0-6.5 |
| 1210-75-25P-7.0-3So-25R | ALXN1210, 75 mg/mL, 25 mM Phosphate, pH 7.0, 3% Sorbitol, 25 mM L-Arginine | opalescent, practically free from particles | 74.7 | 98.4 | 97.3% IgG as main band | 100.0% as Heavy & Light | pI range 6.0-6.5 | opalescent, practically free from particles | 7.59 | 310 | 76.0 | 97.8 | 85% activity relative to reference | 98.3% IgG as main band | 100% as Heavy & Light | pI range 6.0-6.5 |
| 1210-100-25P-7.0-5S-25R_BDS | ALXN1210, 100 mg/mL, 25 mM Phosphate, pH 7.0, 5% Sucrose, 25 mM L-Arginine, BDS | opalescent, practically free from particles | 116.4 | 97.8 | 97.3% IgG as main band | 100.0% as Heavy & Light | pI range 6.0-6.5 | opalescent, practically free from particles | 7.47 | | 122.5 | 97.3 | 85% activity relative to reference | 98.3% IgG as main band | 100% as Heavy & Light | pI range 6.0-6.5 |
| 1210-100-25P-7.0-3So-25R_BDS | ALXN1210, 100 mg/mL, 25 mM Phosphate, pH 7.0, 3% Sorbitol, 25 mM L-Arginine, BDS | opalescent, practically light particles | 105.8 | 98.0 | 97.3% IgG as main band | 100.0% as Heavy & Light | pI range 6.0-6.5 | opalescent, practically light particles | 7.45 | 278 | 102.0 | 97.5 | 76% activity relative to reference | 98.2% IgG as main band | 100% as Heavy & Light | pI range 6.0-6.5 |
| 1210-100-25P-7.0-5S-25R_DP | ALXN1210, 100 mg/mL, 25 mM Phosphate, pH 7.0, 5% Sucrose, 25 mM L-Arginine, DP | opalescent, practically free from particles | 104.6 | 98.0 | 97.9% IgG as main band | 100.0% as Heavy & Light | pI range 6.0-6.5 | opalescent, practically free from particles | 7.51 | 296 | 100.8 | 97.4 | 78% activity relative to reference | 98.3% IgG as main band | 100% as Heavy & Light | pI range 6.0-6.5 |
| 1210-100-25P-7.0-3So-25R_DP | ALXN1210, 100 mg/mL, 25 mM Phosphate, pH 7.0, 3% Sorbitol, 25 mM L-Arginine, DP | opalescent, practically free from particles | 104.7 | 97.8 | 98.0% IgG as main band | 100.0% as Heavy & Light | pI range 6.0-6.5 | opalescent, practically free from particles | 7.46 | 274 | 103.4 | 97.5 | 92% activity relative to reference | 98.2% IgG as main band | 100% as Heavy & Light | pI range 6.0-6.5 |

FIG. 24

Prototype Stability Study Results for ALXN1210
T=1 Month through T=2 Months at 23-27°C (SPAS-14-007)

| 23-27 °C | | 1M | | | | | | | 2M | |
|---|---|---|---|---|---|---|---|---|---|---|
| Sample ID | Sample Description | Appearance | Concentration (mg/mL) | SEC % Monomer | Potency | LOC Non-reduced | LOC Reduced | iCE | pH | SEC % Monomer |
| 1210-75-25P-7.0-5S-25R | ALXN1210, 75 mg/mL, 25 mM Phosphate, pH 7.0, 5% Sucrose, 25 mM L-Arginine | Slightly opalescent, practically free from particles | 82.0 | 97.9 | 104% relative activity | 96.8% IgG as main band | 100% as Heavy & Light | pI range 6.02-6.51 | 7.41 | 96.6 |
| 1210-75-25P-7.0-3So-25R | ALXN1210, 75 mg/mL, 25 mM Phosphate, pH 7.0, 3% Sorbitol, 25 mM L-Arginine | | 74.0 | 97.3 | 92% relative activity | 96.4% IgG as main band | 100% as Heavy & Light | pI range 6.01-6.51 | 7.47 | 94.5 |
| 1210-100-25P-7.0-5S-25R_BDS | ALXN1210, 100 mg/mL, 25 mM Phosphate, pH 7.0, 5% Sucrose, 25 mM L-Arginine, BDS | | 102.2 | 97.4 | 110% relative activity | 96.7% IgG as main band | 100% as Heavy & Light | pI range 6.02-6.52 | 7.4 | 95.5 |
| 1210-100-25P-7.0-3So-25R_BDS | ALXN1210, 100 mg/mL, 25 mM Phosphate, pH 7.0, 3% Sorbitol, 25 mM L-Arginine, BDS | | 102.7 | 97.0 | 90% relative activity | 96.4% IgG as main band | 100% as Heavy & Light | pI range 6.02-6.52 | 7.41 | 94.3 |
| 1210-100-25P-7.0-5S-25R_DP | ALXN1210, 100 mg/mL, 25 mM Phosphate, pH 7.0, 5% Sucrose, 25 mM L-Arginine, DP | | 97.3 | 97.6 | 99% relative activity | 96.8% IgG as main band | 100% as Heavy & Light | pI range 6.01-6.52 | 7.34 | |
| 1210-100-25P-7.0-3So-25R_DP | ALXN1210, 100 mg/mL, 25 mM Phosphate, pH 7.0, 3% Sorbitol, 25 mM L-Arginine, DP | | 98.6 | 97.2 | 94% relative activity | 96.5% IgG as main band | 100% as Heavy & Light | pI range 6.01-6.51 | 7.17 | |

FIG. 25

Prototype Stability Study Results for ALXN1210
T=3 Month through T=6 Months at 23-27°C (SPAS-14-007)

| 23-27 °C | | 3M | | | | | | | 6M | | | | | |
|---|---|---|---|---|---|---|---|---|---|---|---|---|---|---|
| Sample ID | Sample Description | Appearance | Concentration (mg/mL) | SEC % Monomer | Potency | LOC Non-reduced | LOC Reduced | iCE | Appearance | Concentration (mg/mL) | SEC % Monomer | LOC Non-reduced | LOC Reduced | iCE |
| 1210-75-25P-7.0-5S-25R | ALXN1210, 75 mg/mL, 25 mM Phosphate, pH 7.0, 5% Sucrose, 25 mM L-Arginine | Slightly opalescent, practically free from particles | 127.9 | 96.1 | | 94.8% IgG as main band | 100% as Heavy & Light | pI range 5.92-6.51 | | | | | | |
| 1210-75-25P-7.0-3So-25R | ALXN1210, 75 mg/mL, 25 mM Phosphate, pH 7.0, 3% Sorbitol, 25 mM L-Arginine | Slightly opalescent, practically free from particles | 78.2 | 93.4 | 88% Activity relative to reference | 92.9% IgG as main band | 100% as Heavy & Light | pI range 5.86-6.51 | Opalescent, practically free from particles | 85.6 | 87.2 | 87.9% IgG as main band | 92.5% as Heavy & Light | pI range 5.8-6.4 |
| 1210-100-25P-7.0-5S-25R_BDS | ALXN1210, 100 mg/mL, 25 mM Phosphate, pH 7.0, 5% Sucrose, 25 mM L-Arginine, BDS | Slightly opalescent, practically free from particles | 122.4 | 94.5 | | 93.5% IgG as main band | 100% as Heavy & Light | pI range 5.92-6.51 | Opalescent, practically free from particles | 180.9 | 87.9 | 87.6% IgG as main band | 98.4% as Heavy & Light | pI range 5.9-6.4 |
| 1210-100-25P-7.0-3So-25R_BDS | ALXN1210, 100 mg/mL, 25 mM Phosphate, pH 7.0, 3% Sorbitol, 25 mM L-Arginine, BDS | Slightly opalescent, practically free from particles | 103.6 | 93.1 | 90% Activity relative to reference | 93.3% IgG as main band | 100% as Heavy & Light | pI range 5.93-6.51 | Opalescent, practically free from particles | 110.0 | 87 | 86.8% IgG as main band | 94.0% as Heavy & Light | pI range 5.9-6.6 |
| 1210-100-25P-7.0-5S-25R_DP | ALXN1210, 100 mg/mL, 25 mM Phosphate, pH 7.0, 5% Sucrose, 25 mM L-Arginine, DP | Slightly opalescent, light particles | 100.7 | 96.3 | | 95.2% IgG as main band | 100% as Heavy & Light | pI range 5.93-6.51 | Opalescent, light particles | 104.3 | 95.8 | 91.8% IgG as main band | 98.5% as Heavy & Light | pI range 5.9-6.6 |
| 1210-100-25P-7.0-3So-25R_DP | ALXN1210, 100 mg/mL, 25 mM Phosphate, pH 7.0, 3% Sorbitol, 25 mM L-Arginine, DP | Slightly opalescent, practically free from particles | 100.0 | 93.8 | 96% Activity relative to reference | 93.7% IgG as main band | 100% as Heavy & Light | pI range 5.93-6.51 | Opalescent, practically free from particles | 101.0 | 88.4 | 88.3% IgG as main band | 100.0% as Heavy & Light | pI range 5.9-6.5 |

FIG. 26

Prototype Stability Study Results for ALXN1210
T=9 Month through T=12 Months at 23-27°C (SPAS-14-007)

| 23-27 °C | | 9M | | | | | | | 12M | | | | | | |
|---|---|---|---|---|---|---|---|---|---|---|---|---|---|---|---|
| Sample ID | Sample Description | Appearance | Concentration (mg/mL) | SEC % Monomer | Potency | LOC Non-reduced | LOC Reduced | iCE | Appearance | Concentration (mg/mL) | SEC % Monomer | Potency | LOC Non-reduced | LOC Reduced | iCE |
| 1210-75-25P-7.0-5S-25R | ALXN1210, 75 mg/mL, 25 mM Phosphate, pH 7.0, 5% Sucrose, 25 mM L-Arginine | | | | | | | | | | | | | | |
| 1210-75-25P-7.0-3So-25R | ALXN1210, 75 mg/mL, 25 mM Phosphate, pH 7.0, 3% Sorbitol, 25 mM L-Arginine | Opalescent, slight yellowish color practically free from particles | 93.3 | 81.1 | 61% Activity relative to reference | 70.0% IgG as main band | 87.9% as Heavy & Light | pI range 5.6-6.4 | Opalescent, yellowish color practically free from particles | 93.3 | 77.3 | 40% Activity relative to reference | 67.7% IgG as main band | 84.9% as Heavy & Light | pI range 5.5-6.6 |
| 1210-100-25P-7.0-5S-25R_BDS | ALXN1210, 100 mg/mL, 25 mM Phosphate, pH 7.0, 5% Sucrose, 25 mM L-Arginine, BDS | | | | | | | | | | | | | | |
| 1210-100-25P-7.0-3So-25R_BDS | ALXN1210, 100 mg/mL, 25 mM Phosphate, pH 7.0, 3% Sorbitol, 25 mM L-Arginine, BDS | Opalescent, slight yellowish color practically free from particles | 121.1 | 81.2 | 75% Activity relative to reference | 76.7% IgG as main band | 97.4% as Heavy & Light | pI range 5.7-6.4 | Opalescent, yellowish color practically free from particles | 122.2 | 75.0 | 49% Activity relative to reference | 71.4% IgG as main band | 87.3% as Heavy & Light | pI range 5.7-6.5 |
| 1210-100-25P-7.0-5S-25R_DP | ALXN1210, 100 mg/mL, 25 mM Phosphate, pH 7.0, 5% Sucrose, 25 mM L-Arginine, DP | Opalescent, slight yellowish color light particles | 105.4 | 93.5 | 77% Activity relative to reference | 88.5% IgG as main band | 100% as Heavy & Light | pI range 5.7-6.4 | Opalescent, dark yellowish color light particles | 111.1 | 89.2 | 69% Activity relative to reference | 85.6% IgG as main band | 95.1% as Heavy & Light | pI range 5.5-6.5 |
| 1210-100-25P-7.0-3So-25R_DP | ALXN1210, 100 mg/mL, 25 mM Phosphate, pH 7.0, 3% Sorbitol, 25 mM L-Arginine, DP | Opalescent, slight yellowish color practically free from particles | 103.4 | 83.2 | 75% Activity relative to reference | 77.6% IgG as main band | 94.0% as Heavy & Light | pI range 5.7 and 6.4 | Opalescent, slight yellowish color practically free from particles | 106.9 | 77.9 | 47% Activity relative to reference | 73.5% IgG as main band | 89.1% as Heavy & Light | pI range 5.6-6.5 |

FIG. 27

Prototype Stability Study Results for ALXN1210
T=2 Weeks through T=2 Months at 37°C (SPAS-14-007)

| 37 °C | | T=2 WKS | | | | | | | 1M | | | | | | | 2M |
|---|---|---|---|---|---|---|---|---|---|---|---|---|---|---|---|---|
| Sample ID | Sample Description | Appearance | Concentration (mg/mL) | SEC % Monomer | Potency | LOC Non-reduced | LOC Reduced | iCE | Appearance | Concentration (mg/mL) | SEC % Monomer | Potency | LOC Non-reduced | LOC Reduced | iCE | SEC % Monomer |
| 1210-75-25P-7.0-5S-25R | ALXN1210, 75 mg/mL, 25 mM Phosphate, pH 7.0, 5% Sucrose, 25 mM L-Arginine | Slightly opalescent, practically free from particles | 85.2 | 93.0 | 85% Activity relative to reference | 94.0% IgG as main band | 96.5% as Heavy & Light | pI range 5.93-6.52 | Slightly opalescent, practically free from particles | 71.1 | 90.8 | 75% Activity relative to reference | 89.6% IgG as main band | 96.2% as Heavy & Light | pI range 5.92-6.51 | |
| 1210-75-25P-7.0-3So-25R | ALXN1210, 75 mg/mL, 25 mM Phosphate, pH 7.0, 3% Sorbitol, 25 mM L-Arginine | | 74.8 | 92.2 | 81% Activity relative to reference | 93.4% IgG as main band | 98.3% as Heavy & Light | pI range 5.93-6.52 | | | 72.5 | 72% Activity relative to reference | 78.2% IgG as main band | 92.0% as Heavy & Light | pI range 5.93-6.37 | 63.4 |
| 1210-100-25P-7.0-5S-25R_DP | ALXN1210, 100 mg/mL, 25 mM Phosphate, pH 7.0, 5% Sucrose, 25 mM L-Arginine, DP | | 120.1 | 93.1 | 88% Activity relative to reference | 94.0% IgG as main band | 98.8% as Heavy & Light | pI range 5.93-6.52 | | 91.1 | 81.7 | 83% Activity relative to reference | 88.6% IgG as main band | 96.5% as Heavy & Light | pI range 5.91-6.51 | 73.2 |
| 1210-100-25P-7.0-3So-25R_DP | ALXN1210, 100 mg/mL, 25 mM Phosphate, pH 7.0, 3% Sorbitol, 25 mM L-Arginine, DP | | 102.7 | 92.0 | 81% Activity relative to reference | 93.4% IgG as main band | 98.9% as Heavy & Light | pI range 5.93-6.51 | | 109.6 | 84.1 | 84% Activity relative to reference | 86.3% IgG as main band | 94.9% as Heavy & Light | pI range 5.04-6.37 | 52.0 |

FIG. 28

Prototype Stability Study Results for ALXN1210
T=1 Month through T=3 Months at -20°C (SPAS-14-007)

| -20 °C | | 1M | | | | | | | 3M | | | | | |
|---|---|---|---|---|---|---|---|---|---|---|---|---|---|---|
| Sample ID | Sample Description | Appearance | Concentration (mg/mL) | SEC % Monomer | Potency | LOC Non-reduced | LOC Reduced | iCE | Appearance | Concentration (mg/mL) | SEC % Monomer | LOC Non-reduced | LOC Reduced | iCE |
| 1210-100-25P-7.0-5S-25R_BDS | ALXN1210, 100 mg/mL, 25 mM Phosphate, pH 7.0, 5% Sucrose, 25 mM L-Arginine, BDS | Slightly opalescent, practically free from particles | 97.4 | 98.2 | 106% Activity relative to reference | 97.6% IgG as main band | 100.0% as Heavy & Light | pI range 6.02-6.52 | Slightly opalescent, light particles | 103.9 | 98.5 | 97.5% IgG as main band | 100% as Heavy & Light | pI range 6.00-6.51 |
| 1210-100-25P-7.0-3So-25R_BDS | ALXN1210, 100 mg/mL, 25 mM Phosphate, pH 7.0, 3% Sorbitol, 25 mM L-Arginine, BDS | | 99.5 | 98.2 | 118% Activity relative to reference | 97.6% IgG as main band | 100.0% as Heavy & Light | pI range 6.03-6.52 | Slightly opalescent, light particles | 101.5 | 98.6 | 97.5% IgG as main band | 100% as Heavy & Light | pI range 6.02-6.51 |

FIG. 29

Prototype Stability Study Results for ALXN1210
T=6 Months through T=12 Months at -20°C (SPAS-14-007)

| -20 °C | | 6M | | | | | | 12M | | | | | | |
|---|---|---|---|---|---|---|---|---|---|---|---|---|---|---|
| Sample ID | Sample Description | Appearance | Concentration (mg/mL) | SEC % Monomer | LOC Non-reduced | LOC Reduced | iCE | Appearance | Concentration (mg/mL) | SEC % Monomer | Potency | LOC Non-reduced | LOC Reduced | iCE |
| 1210-100-25P-7.0-5S-25R_BDS | ALXN1210, 100 mg/mL, 25 mM Phosphate, pH 7.0, 5% Sucrose, 25 mM L-Arginine, BDS | Opalescent, light particles | 111.4 | 98.2 | 97.6% IgG as main band | 100% as Heavy & Light | pI range 6.0-6.5 | Opalescent, light particles | 99.9 | 98.3 | 95% Activity relative to reference | 98.1% IgG as main band | % as Heavy & Light | pI range 6.0-6.5 |
| 1210-100-25P-7.0-3So-25R_BDS | ALXN1210, 100 mg/mL, 25 mM Phosphate, pH 7.0, 3% Sorbitol, 25 mM L-Arginine, BDS | | 101.9 | 98.3 | 97.5% IgG as main band | 100% as Heavy & Light | pI range 6.0-6.5 | Opalescent, light particles | 100.6 | 98.3 | 95% Activity relative to reference | 98.2% IgG as main band | % as Heavy & Light | pI range 6.0-6.5 |

FIG. 30

Prototype Stability Study Results for ALXN1210
T=3 Months through T=6 Months at -80°C (SPAS-14-007)

| -80 °C | | 3M | | | | | | 6M | | | | | |
|---|---|---|---|---|---|---|---|---|---|---|---|---|---|
| Sample ID | Sample Description | Appearance | Concentration (mg/mL) | SEC % Monomer | LOC Non-reduced | LOC Reduced | iCE | Appearance | Concentration (mg/mL) | SEC % Monomer | LOC Non-reduced | LOC Reduced | iCE |
| 1210-100-25P-7.0-5S-25R_BDS | ALXN1210, 100 mg/mL, 25 mM Phosphate, pH 7.0, 5% Sucrose, 25 mM L-Arginine, BDS | Slightly opalescent, light particles | 100.6 | 98.5 | 97.5% IgG as main band | 100% as Heavy & Light | pI range 6.01-6.51 | Opalescent, light particles | 99.1 | 99.1 | 97.5% IgG as main band | 100% as Heavy & Light | pI range 6.0-6.5 |
| 1210-100-25P-7.0-3So-25R_BDS | ALXN1210, 100 mg/mL, 25 mM Phosphate, pH 7.0, 3% Sorbitol, 25 mM L-Arginine, BDS | Slightly opalescent, light particles | 101.8 | 98.6 | 97.6% IgG as main band | 100% as Heavy & Light | pI range 6.02-6.51 | Opalescent, light particles | 102.9 | 98.3 | 97.5% IgG as main band | 100% as Heavy & Light | pI range 6.0-6.5 |

FIG. 31

Prototype Stability Study Results for ALXN1210
T=12 Months at -80°C (SPAS-14-007)

| -80 °C | | 12M | | | | | | |
|---|---|---|---|---|---|---|---|---|
| Sample ID | Sample Description | Appearance | Concentration (mg/mL) | SEC % Monomer | Potency | LOC Non-reduced | LOC Reduced | iCE |
| 1210-100-25P-7.0-5S-25R_BDS | ALXN1210, 100 mg/mL, 25 mM Phosphate, pH 7.0, 5% Sucrose, 25 mM L-Arginine, BDS | Opalescent, light particles | 106.4 | 98.3 | 85% Activity relative to reference | 98.1% IgG as main band | % as Heavy & Light | pI range 6.0-6.5 |
| 1210-100-25P-7.0-3So-25R_BDS | ALXN1210, 100 mg/mL, 25 mM Phosphate, pH 7.0, 3% Sorbitol, 25 mM L-Arginine, BDS | Opalescent, light particles | 103.3 | 98.3 | 83% Activity relative to reference | 98.1% IgG as main band | % as Heavy & Light | pI range 6.0-6.5 |

FIG. 32

Prototype Stability SEC, % Monomer for ALXN1210
T=0 through T=12 Months 2-8°C

Prototype Stability SEC, % Monomer for ALXN1210
T=0 through T=12 Months 37°C

Prototype Stability Dynamic Light Scattering ALXN1210
Phosphate Samples at 75 mg/mL T=0

| # | Sample | Description | Concentration | |
|---|---|---|---|---|
| 1 | RM12100213 | ALXN1210 Reference | 9.4 mg/mL | |
| 2 | 1210-75-25P-7.0-5S-25R | 1210; 75 mg/mL, 25 mM Phosphate pH 7.0, 5% Sucrose, 25 mM L-Arginine | 73.3 mg/mL | |
| 3 | 1210-75-25P-7.0-3So-25R | 1210; 75 mg/mL, 25 mM Phosphate pH 7.0, 3% Sorbitol, 25 mM L-Arginine | 71.2 mg/mL | |

Prototype Stability Dynamic Light Scattering ALXN1210
Phosphate Samples at 75 mg/mL T=1 Month 2-8°C

| # | Sample | Description | Concentration | |
|---|---|---|---|---|
| 1 | RM12100213 | ALXN1210 Reference | 9.4 mg/mL | ——— |
| 2 | 1210-75-25P-7.0-5S-25R | 1210; 75 mg/mL, 25 mM Phosphate pH 7.0, 5% Sucrose, 25 mM L-Arginine | 74.9 mg/mL | - - - - - |
| 3 | 1210-75-25P-7.0-3So-25R | 1210; 75 mg/mL, 25 mM Phosphate pH 7.0, 3% Sorbitol, 25 mM L-Arginine | 72.2 mg/mL | ━━━ |

Prototype Stability Dynamic Light Scattering ALXN1210
Phosphate Samples at 100 mg/mL T=1 Month 2-8°C

| # | Sample | Description | Concentration | |
|---|---|---|---|---|
| 1 | RM12100213 | ALXN1210 Reference | 9.4 mg/mL | |
| 2 | 1210-100-25P-7.0-5S-25R_BDS | 1210; 100 mg/mL, 25 mM Phosphate pH 7.0, 5% Sucrose, 25 mM L-Arginine, BDS Vial | 99.2 mg/mL | |
| 3 | 1210-100-25P-7.0-3So-25R_DP | 1210; 100 mg/mL, 25 mM Phosphate pH 7.0, 3% Sorbitol, 25 mM L-Arginine, DP Vial | 99.4 mg/mL | |

Prototype Stability Study Results SEC, % Monomer for ALXN1210 - Freeze Thaw Cycles 1-3 at T=1 Month -20°C (SPAS-14-007)

| -20 °C | | FT1 | | | | FT2 | | | FT3 | | | |
|---|---|---|---|---|---|---|---|---|---|---|---|---|
| Sample ID | Sample Description | Appearance | Concentration (mg/mL) | SEC % Monomer | iCE | Appearance | Concentration (mg/mL) | SEC % Monomer | Appearance | Concentration (mg/mL) | SEC % Monomer | iCE |
| 1210-100-25P-7.0-5S-25R_BDS | ALXN1210, 100 mg/mL, 25 mM Phosphate, pH 7.0, 5% Sucrose, 25 mM L-Arginine, BDS | Slightly opalescent, practically free from particles | 97.4 | 98.2 | pI range 6.00-6.51 | Slightly opalescent, practically free from particles | 97.7 | 98.1 | Slightly opalescent, practically free from particles | 98.6 | 98.2 | pI range 6.03-6.52 |
| 1210-100-25P-7.0-3So-25R_BDS | ALXN1210, 100 mg/mL, 25 mM Phosphate, pH 7.0, 3% Sorbitol, 25 mM L-Arginine, BDS | | 99.5 | 98.2 | pI range 6.02-6.51 | | 101.9 | 98.5 | | 97.6 | 98.1 | pI range 6.01-6.52 |

FIG. 41

Prototype Stability Study Results SEC, % Monomer for ALXN1210 - Freeze Thaw Cycles 4-5 at T=1 Month -20°C (SPAS-14-007)

| -20 °C | | FT4 | | | FT5 | | | |
|---|---|---|---|---|---|---|---|---|
| Sample ID | Sample Description | Appearance | Concentration (mg/mL) | SEC % Monomer | Appearance | Concentration (mg/mL) | SEC % Monomer | iCE |
| 1210-100-25P-7.0-5S-25R_BDS | ALXN1210, 100 mg/mL, 25 mM Phosphate, pH 7.0, 5% Sucrose, 25 mM L-Arginine, BDS | Slightly opalescent, practically free from particles | 96.7 | 98.0 | Slightly opalescent, practically free from particles | 100 | 98.0 | pI range 6.01-6.51 |
| 1210-100-25P-7.0-3So-25R_BDS | ALXN1210, 100 mg/mL, 25 mM Phosphate, pH 7.0, 3% Sorbitol, 25 mM L-Arginine, BDS | Slightly opalescent, practically free from particles | 98.2 | 97.9 | Slightly opalescent, practically free from particles | 101.2 | 98.0 | pI range 6.02-6.51 |

FIG. 42

Prototype Stability Study Results SEC, % Monomer for ALXN1210 - Freeze Thaw Cycles 1-3 at T=3 Months -80°C (SPAS-14-007)

| -80 °C | | FT1 | | | | FT2 | | | FT3 | | | |
|---|---|---|---|---|---|---|---|---|---|---|---|---|
| Sample ID | Sample Description | Appearance | Concentration (mg/mL) | SEC % Monomer | iCE | Appearance | Concentration (mg/mL) | SEC % Monomer | Appearance | Concentration (mg/mL) | SEC % Monomer | iCE |
| 1210-100-25P-7.0-5S-25R_BDS | ALXN1210, 100 mg/mL, 25 mM Phosphate, pH 7.0, 5% Sucrose, 25 mM L-Arginine, BDS | Slightly opalescent, practically free from particles | 100.6 | 98.5 | pI range 6.01-6.51 | Slightly opalescent, practically free from particles | 99.5 | 98.2 | Slightly opalescent, practically free from particles | 99.2 | 98.3 | pI range 6.01-6.51 |
| 1210-100-25P-7.0-3So-25R_BDS | ALXN1210, 100 mg/mL, 25 mM Phosphate, pH 7.0, 3% Sorbitol, 25 mM L-Arginine, BDS | | 101.8 | 98.6 | pI range 6.02-6.51 | | 101.2 | 98.1 | | 101.3 | 98.1 | pI range 6.00-6.51 |

FIG. 43

Prototype Stability Study Results SEC, % Monomer for ALXN1210 - Freeze Thaw Cycles 4-5 at T=3 Months -80°C (SPAS-14-007)

| -80 °C | | FT4 | | | FT5 | | | |
|---|---|---|---|---|---|---|---|---|
| Sample ID | Sample Description | Appearance | Concentration (mg/mL) | SEC % Monomer | Appearance | Concentration (mg/mL) | SEC % Monomer | iCE |
| 1210-100-25P-7.0-5S-25R_BDS | ALXN1210, 100 mg/mL, 25 mM Phosphate, pH 7.0, 5% Sucrose, 25 mM L-Arginine, BDS | Slightly opalescent, practically free from particles | 100.1 | 97.9 | Slightly opalescent, practically free from particles | 99.4 | 98.04 | pI range 6.01-6.52 |
| 1210-100-25P-7.0-3So-25R_BDS | ALXN1210, 100 mg/mL, 25 mM Phosphate, pH 7.0, 3% Sorbitol, 25 mM L-Arginine, BDS | | 101 | 98.0 | | 100.7 | 98.00 | pI range 6.01-6.51 |

FIG. 44

Abbreviations: A = active drug; IV = intravenous; P = placebo; SC = subcutaneous; SRC = Safety Review Committee
Note: The SRC will review the first 48 hours of post-dose safety data from Cohort 1a before enrollment into Cohorts 1b or 2 may begin.

Subject Disposition - All Subjects

*Percentages are based on the number of screened subjects.
** Percentages are based on the number of randomized subjects within each treatment group.
Abbreviations: IV = intravenous; N = total number of subjects; n = number of subjects; SC = subcutaneous.

Chicken Red Blood Cell Hemolysis (cRBC) Mean (± SD)
Percentage Change from Baseline Versus Nominal Time
(Pharmacodynamic Set)

HIGH CONCENTRATION ANTI-C5 ANTIBODY FORMULATIONS

CROSS-REFERENCE TO RELATED APPLICATIONS

This application is a 35 U.S.C. 371 national stage filing of International Application No. PCT/US2018/044071, filed on Jul. 27, 2018, which claims the benefit of U.S. Provisional Application Ser. No. 62/537,741, filed on Jul. 27, 2017, each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 24, 2020, is named AXJ-226US_Sequence_Listing.txt and is 33,071 bytes in size.

BACKGROUND

The complement system acts in conjunction with other immunological systems of the body to defend against intrusion of cellular and viral pathogens. There were at least 25 complement proteins, which were found as a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions. A concise summary of the biologic activities associated with complement activation is provided, for example, in The Merck Manual, $16^{th}$ Edition.

While a properly functioning complement system provides a robust defense against infecting microbes, inappropriate regulation or activation of the complement pathways has been implicated in the pathogenesis of a variety of disorders, including paroxysmal nocturnal hemoglobinuria (PNH) and atypical hemolytic uremic syndrome (aHUS) (see, e.g., Socié G, et al., French Society of Haematology. Lancet. 1996; 348(9027):573-577; Brodsky, R., Blood. 2014; 124(18):2804-2811); Hillmen, P., et al, Am. J. Hematol. 2010; 85(8):553-559; Caprioli et al. (2006) *Blood* 108: 1267-1279; and Kavanagh et al. (2006) *British Medical Bulletin* 77 *and* 78:5-22).

Patients with complement-associated disorders, such as PNH or aHUS, were at risk of substantial morbidity and mortality. Accordingly, it is an object of the present invention to provide improved compositions and methods for treating patients with complement-associated disorders.

SUMMARY

Provided herein were stable, highly-concentrated, aqueous solutions of anti-C5 antibodies, as well as methods for making and using the formulations. The disclosure provides, among other aspects, formulation conditions suitable for maintaining over considerable time the physical and functional stability of an anti-C5 antibody (e.g., ravulizumab also known as "antibody BNJ441" and "ALXN1210") in high concentration solutions. For example, the disclosure provides formulation conditions capable of maintaining an anti-C5 antibody in predominantly monomeric form for up to 2 years at 2° C. to 8° C., even when the antibody is maintained in solutions at concentrations of approximately 100 mg/mL or higher. In addition, as described herein and exemplified in the working examples, such formulations also minimize aggregation, fragmentation, or degradation of an anti-C5 antibody (e.g., ravulizumab) within the highly-concentrated solutions. For example, the disclosure provides formulation conditions capable of maintaining for two years an anti-C5 antibody in a highly-concentrated form with no detectable antibody fragmentation or degradation products (as determined using a size exclusion chromatography-high performance liquid chromatography technique (SEC-HPLC), such as HPLC-gel permeation) and no more than 2% aggregate. Also provided herein were conditions suitable for formulating solutions of an anti-C5 antibody, such as ravulizumab at greater than 200 mg/mL.

The benefits of stable, highly-concentrated aqueous solutions of an anti-C5 antibody are numerous. First, for therapeutic applications which require the antibody to be administered to a patient in a small volume, therapeutic efficacy often turns on the amount of antibody that can be administered in that small volume. In the absence of the ability to formulate an anti-C5 antibody to high concentrations, use of, for example, subcutaneous, intravitreal, and/or intraarticular delivery routes would often be precluded. Relatedly, highly-concentrated antibody formulations allow for more patient choice regarding the route of administration. For therapeutic applications that require frequent, chronic administration, and/or self-delivery, administration is made possible by high concentration formulations and can be more appealing to patients than intravenous infusion. For example, high concentration formulations of an anti-C5 antibody can allow a patient to self-administer the antibody by, e.g., subcutaneous or intravenous injection. Therefore, the ability to formulate the antibody at high concentrations can increase compliance of administration by providing an easy home administration alternative to patients with complement-associated disorders.

Furthermore, methods for producing the aqueous solutions described herein do not require a lyophilization step, nor do the featured high concentration aqueous solutions need to be reconstituted from lyophilized material. The instantly featured high concentration antibody solutions provide several advantages over reconstituted lyophilized antibody formulations. First, medical practitioners must locally reconstitute lyophilized antibody solutions aseptically, which increases the opportunity for microbial contamination of the solution prior to administration. In addition, reconstitution requires considerable care to be certain that all of the solids contained in the reconstitution vessel were properly dissolved in solution. The high concentration aqueous solutions provided herein thus provide the medical practitioner, caregiver, and/or patient with a fast, easy, safe, and efficient means for delivering a therapeutic antibody to a patient in need thereof.

Other benefits of high concentration formulations include, e.g., manufacturing cost savings from decreasing bulk storage space and/or the number of product fills. In addition, the ability to produce a product having a longer shelf-life will ultimately require fewer production runs, which ultimately reduces cost for the manufacturer and consumer of the highly-concentrated therapeutic antibody.

An exemplary anti-C5 antibody is ravulizumab (also known as antibody BNJ441 and ALXN1210) comprising the heavy and light chains having the sequences shown in SEQ ID NOs: 14 and 11, respectively, or antigen binding fragments and variants thereof. In other embodiments, the antibody comprises the heavy and light chain complementarity determining regions (CDRs) or variable regions (VRs) of ravulizumab. Accordingly, in one embodiment, the antibody comprises the CDR1, CDR2, and CDR3 domains of the heavy chain variable (VH) region of ravulizumab having the sequence shown in SEQ ID NO:12, and the CDR1, CDR2 and CDR3 domains of the light chain variable (VL) region of ravulizumab having the sequence shown in SEQ ID NO:8. In another embodiment, the antibody comprises CDR1, CDR2 and CDR3 heavy chain sequences as set forth in SEQ ID NOs:19, 18, and 3, respectively, and CDR1, CDR2 and CDR3 light chain sequences as set forth in SEQ ID NOs:4, 5, and 6, respectively.

In another embodiment, the antibody comprises VH and VL regions having the amino acid sequences set forth in SEQ ID NO:12 and SEQ ID NO:8, respectively.

In another embodiment, the antibody comprises a heavy chain constant region as set forth in SEQ ID NO:13.

In another embodiment, the antibody comprises a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering.

In another embodiment, the antibody comprises CDR1, CDR2 and CDR3 heavy chain sequences as set forth in SEQ ID NOs:19, 18, and 3, respectively, and CDR1, CDR2 and CDR3 light chain sequences as set forth in SEQ ID NOs:4, 5, and 6, respectively and a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering.

In another embodiment, the antibody competes for binding with, and/or binds to the same epitope on C5 as, the above-mentioned antibodies. In another embodiment, the antibody has at least about 90% variable region amino acid sequence identity with the above-mentioned antibodies (e.g., at least about 90%, 95% or 99% variable region identity with SEQ ID NO:12 and SEQ ID NO:8).

In another embodiment, the antibody binds to human C5 at pH 7.4 and 25° C. with an affinity dissociation constant ($K_D$) that is in the range 0.1 nM≤$K_D$≤1 nM. In another embodiment, the antibody binds to human C5 at pH 6.0 and 25° C. with a $K_D$≥10 nM. In yet another embodiment, the [($K_D$ of the antibody or antigen-binding fragment thereof for human C5 at pH 6.0 and at 25° C.)/($K_D$ of the antibody or antigen-binding fragment thereof for human C5 at pH 7.4 and at 25° C.)] of the antibody is greater than 25.

In one aspect, a stable aqueous solution is provided (e.g., a sterile solution), wherein the solution comprises an anti-C5 antibody at a concentration of about 100 mg/mL, wherein the anti-C5 antibody comprises a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6. In another embodiment, the solution comprises an anti-C5 antibody (e.g., ravulizumab) at a concentration of or about 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 mg/mL.

In another embodiment, the stable aqueous solution comprises one or more additional agents (e.g., stabilizing agents, buffering agents, surfactants, and/or preservatives). For example, in one embodiment, the stable aqueous solution comprises a stabilizer. Exemplary stabilizers include, but were not limited to polyols, sugars (e.g., sucrose or trehalose), amino acids (e.g., arginine), amines, and salting out salts. In one embodiment, the solution comprises at least one stabilizing agent at a concentration of 2-10%, inclusive. In one embodiment the solution comprises 5% sucrose. In another embodiment, the solution comprises at least one or more stabilizing agents at a concentration of 10 mM to 50 mM, inclusive. In another embodiment, the stabilizing agent is present in the solution at a concentration of at least, or equal to, 20 mM. In another embodiment, the stabilizing agent is present in the solution at a concentration of at least, or equal to, 25 mM. In another embodiment, the stabilizing agent is present in the solution at a concentration of at least, or equal to, 50 mM. In another embodiment, the solution comprises 25 mM arginine.

In another embodiment, the solution comprises at least one or more buffering agents. Non-limiting examples of typical buffers that can be included in the wash solution(s) include Tris (tris(hydroxymethyl)methylamine), bis-Tris, bis-Tris propane, histidine, triethanolamine, diethanolamine, formate, acetate, MES (2-(N-morpholino)ethanesulfonic acid), phosphate, HEPES (4-2-hydroxyethyl-1-piperazineethanesulfonic acid), citrate, MOPS (3-(N-morpholino) propanesulfonic acid), TAPS (3{[tris(hydroxymethyl) methyl]amino}propanesulfonic acid), Bicine (N,N-bis(2-hydroxyethyl)glycine), Tricine (N-tris(hydroxymethyl) methylglycine), TES (2-{[tris(hydroxymethyl)methyl] amino}ethanesulfonic acid), PIPES (piperazine-N,N'-bis(2-ethanesulfonic acid), cacodylate (dimethylarsinic acid) SSC (saline sodium citrate), and sodium phosphate. In another embodiment, the buffering agent is an amino acid. The amino acid can be, e.g., one selected from the group consisting of histidine (e.g., L-histidine), serine (e.g., L-serine), and glycine (e.g., L-glycine). In another embodiment, the solution comprises two or more buffering agents. In a particular embodiment, the buffering agent is sodium phosphate.

In another embodiment, the solution comprises at least one or more buffering agents at a concentration of 10 mM to 300 mM, inclusive. In another embodiment, the solution comprises at least one buffering agent at a concentration of 10 mM to 200 mM, inclusive. In another embodiment, the solution comprises at least one buffering agent at a concentration of 10 mM to 100 mM, inclusive. In another embodiment, the solution comprises at least one buffering agent at a concentration of 10 mM to 50 mM, inclusive. In another embodiment, the solution comprises at least one buffering agent at a concentration of 20 mM to 50 mM, inclusive. In another embodiment, buffering agent is present in the solution at a concentration of at least, or equal to, 20 mM. In another embodiment, buffering agent is present in the solution at a concentration of at least, or equal to, 25 mM. In another embodiment, buffering agent is present in the solution at a concentration of at least, or equal to, 50 mM.

In another embodiment, the solution comprises a carbohydrate excipient at a concentration of 0.1 to 5%. In one embodiment, the carbohydrate excipient is present in the solution at a concentration of at least, or equal to, 1.5%. In another embodiment, the carbohydrate excipient is present in the solution at a concentration of at least, or equal to, 3%. The carbohydrate excipient can be, e.g., one selected from the group consisting of sorbitol and mannitol. In another embodiment, the solution comprises two or more carbohydrate excipients.

In another embodiment, the solution comprises a surfactant. Surfactants suitable for use in the formulations of the present invention include, but were not limited to fatty acid esters (e.g., sorbitan monocaprylate, sorbitan monolaurate, sorbitan monopalmitate), sorbitan trioleate, glycerine fatty acid esters (e.g., glycerine monocaprylate, glycerine monomyristate, glycerine monostearate), polyglycerine fatty acid esters (e.g., decaglyceryl monostearate, decaglyceryl distearate, decaglyceryl monolinoleate), polyoxyethylene sorbitan fatty acid esters (e.g., polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate), polyoxyethylene sorbitol fatty acid esters (e.g., polyoxyethylene sorbitol tetrastearate, polyoxyethylene sorbitol tetraoleate), polyoxyethylene glycerine fatty acid esters (e.g., polyoxyethylene glyceryl monostearate), polyethylene glycol fatty acid esters (e.g., polyethylene glycol distearate), polyoxyethylene alkyl ethers (e.g., polyoxyethylene lauryl ether), polyoxyethylene polyoxypropylene alkyl ethers (e.g., polyoxyethylene polyoxypropylene glycol, polyoxyethylene polyoxypropylene propyl ether, polyoxyethylene polyoxypropylene cetyl ether), polyoxyethylene alkylphenyl ethers (e.g., polyoxyethylene nonylphenyl ether), polyoxyethylene hydrogenated castor oils (e.g., polyoxyethylene castor oil, polyoxyethylene hydrogenated castor oil), polyoxyethylene beeswax derivatives (e.g., polyoxyethylene sorbitol beeswax), polyoxyethylene lanolin derivatives (e.g., polyoxyethylene lanolin), and polyoxyethylene fatty acid amides (e.g., polyoxyethylene stearic acid amide); C12-C18 alkyl sulfates (e.g., sodium cetyl sulfate, sodium lauryl sulfate, sodium oleyl sulfate), polyoxyethylene C10-C18 alkyl ether sulfate with an average of 2 to 4 moles of ethylene oxide units added (e.g., sodium polyoxyethylene lauryl sulfate), and C10-C18 alkyl sulfosuccinate ester salts (e.g., sodium lauryl sulfosuccinate ester); and natural surfactants such as lecithin, glycerophospholipid, sphingophospholipids (e.g., sphingomyelin), and sucrose esters of C12-C18 fatty acids.

In one embodiment, the surfactant in the formulation is a non-ionic surfactant. In certain embodiments, the surfactant in the formulation is a polyoxyethylene sorbitan fatty acid ester, for example, polysorbate 20, 40, 60, 80, or a combination of one or more thereof. In one embodiment, the surfactant in the formulation is polysorbate 80 (Tween 80). In another embodiment, the surfactant in the formulation is polysorbate 60. In another embodiment, the surfactant in the formulation is polysorbate 40. In another embodiment, the surfactant in the formulation is polysorbate 20 (Tween 20). The concentration of the surfactant in the solution can be, e.g., between 0.001% to 0.02%, inclusive. For example, the surfactant may be present in the formulation in an amount from about 0.001% to about 1%, or about 0.001% to about 0.5%, or about 0.01% to about 0.2%. In one embodiment, the aqueous solutions contain a surfactant at a concentration of at least, or approximately, 0.001 (e.g., at least, or approximately, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, or 0.5 or more) %. In another embodiment, the aqueous solution contains no more than 0.2 (e.g., no more than 0.19, 0.18, 0.17, 0.16, 0.15, 0.14, 0.13, 0.12, 0.11, 0.10, 0.09, 0.08, 0.07, 0.06, 0.05, 0.04, 0.03, 0.02, 0.01, 0.009, 0.008, 0.007, 0.006, 0.005, 0.004, 0.003, 0.002, or 0.001) % of a pharmaceutically-acceptable surfactant. In a particular embodiment, the surfactant is 0.05% polysorbate 80.

In another embodiment, the solution comprises a preservative. Exemplary preservatives include, but were not limited to benzyl alcohol, m-cresol, and phenol.

In one embodiment, the stable aqueous solution comprises no more than five agents in addition to the anti-C5 antibody. In another embodiment, the stable aqueous solution comprises no more than four agents in addition to the anti-C5 antibody. In another embodiment, the stable aqueous solution comprises no more than three agents in addition to the anti-C5 antibody. In another embodiment, the stable aqueous solution comprises no more than two agents in addition to the anti-C5 antibody. In another embodiment, the stable aqueous solution comprises no more than one agent in addition to the anti-C5 antibody.

In another embodiment, the stable aqueous solution comprises an anti-C5 antibody comprising a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6 at a concentration of 100±20 (e.g., 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120) mg/mL; 50±15 (e.g., 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65) mM phosphate buffer; 5±3 (e.g., 2, 3, 4, 5, 6, 7, or 8) % sucrose; and 25±10 (e.g., 15, 16, 17, 18, 19, 20, 21, 22, 23, 24, 25, 26, 27, 28, 29, 30, 31, 32, 33, 34, or 35) mM arginine; wherein the solution has a pH of 7.4±0.5 (e.g., 6.9, 7, 7.1, 7.2, 7.3, 7.4, 7.5, 7.6, 7.7, 7.8, or 7.9).

In another embodiment, the stable aqueous solution consists of an anti-C5 antibody comprising a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6 at a concentration of 100±20 (e.g., 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120) mg/mL; 50±15 (e.g., 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65) mM phosphate buffer; 5±3 (e.g., 2, 3, 4, 5, 6, 7, or 8) % sucrose; and 25±10 (e.g., 15, 16, 17, 18, 19, 20, 21, 22, 23, 24, 25, 26, 27, 28, 29, 30, 31, 32, 33, 34, or 35) mM arginine; wherein the solution has a pH of 7.4±0.5 (e.g., 6.9, 7, 7.1, 7.2, 7.3, 7.4, 7.5, 7.6, 7.7, 7.8, or 7.9).

In another embodiment, the stable aqueous solution comprises an anti-C5 antibody comprising a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6 at a concentration of 100±20 (e.g., 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120) mg/mL; 50±15 (e.g., 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65) mM phosphate buffer; 5±3 (e.g., 2, 3, 4, 5, 6, 7, or 8) % sucrose; 25±10 (e.g., 15, 16, 17, 18, 19, 20, 21, 22, 23, 24, 25, 26, 27, 28, 29, 30, 31, 32, 33, 34, or 35) mM arginine; and 0.05±0.03 (e.g., 0.02, 0.03, 0.04, 0.05, 0.06, 0.07, and 0.08)% polysorbate 80, wherein the solution has a pH of 7.4±0.5 (e.g., 6.9, 7, 7.1, 7.2, 7.3, 7.4, 7.5, 7.6, 7.7, 7.8, or 7.9).

In another embodiment, the stable aqueous solution consists of an anti-C5 antibody comprising a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6 at a concentration of 100±20 (e.g., 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120) mg/mL; 50±15 (e.g., 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65) mM phosphate buffer; 5±3 (e.g., 2, 3, 4, 5, 6, 7, or 8) % sucrose; 25±10 (e.g., 15, 16, 17, 18, 19, 20, 21, 22, 23, 24, 25, 26, 27, 28, 29, 30, 31, 32, 33, 34, or 35) mM arginine; and 0.05±0.03 (e.g., 0.02, 0.03, 0.04, 0.05, 0.06, 0.07, and 0.08)% polysorbate 80, wherein the solution has a pH of 7.4±0.5 (e.g., 6.9, 7, 7.1, 7.2, 7.3, 7.4, 7.5, 7.6, 7.7, 7.8, or 7.9).

In another embodiment, a stable aqueous solution is provided (e.g., a sterile solution), wherein the solution comprises (a) an anti-C5 antibody (e.g., ravulizumab), (b) about 50 mM Phosphate Buffer; (c) about 5% sucrose; and (d) about 25 mM Arginine. In another embodiment, a stable aqueous solution is provided (e.g., a sterile solution), wherein the solution comprises (a) an anti-C5 antibody (e.g., ravulizumab) at a concentration of about 100 mg/mL, (b) about 50 mM Phosphate Buffer; (c) about 5% sucrose; and (d) about 25 mM Arginine. In another embodiment, the stable aqueous solution comprises a) an anti-C5 antibody (e.g., ravulizumab), (b) 50 mM Phosphate Buffer; (c) 5% sucrose; and (d) 25 mM Arginine. In another embodiment, the stable aqueous solution comprises a) an anti-C5 antibody (e.g., ravulizumab) at a concentration of 100 mg/mL, (b) 50 mM Phosphate Buffer; (c) 5% sucrose; and (d) 25 mM Arginine.

In another embodiment, the stable aqueous solution comprises (a) an anti-C5 antibody, (b) about 50 mM Phosphate Buffer, (c) about 5% sucrose, (d) about 0.05% Polysorbate 80, and (e) about 25 mM Arginine. In another embodiment, the stable aqueous solution comprises (a) an anti-C5 antibody at a concentration of about 100 mg/mL, (b) about 50 mM Phosphate Buffer, (c) about 5% sucrose, (d) about 0.05% Polysorbate 80, and (e) about 25 mM Arginine. In another embodiment, the stable aqueous solution comprises a) an anti-C5 antibody, (b) 50 mM Phosphate Buffer, (c) 5% sucrose, (d) 0.05% Polysorbate 80, and (e) 25 mM Arginine.

In another embodiment, the stable aqueous solution comprises (a) an anti-C5 antibody, (b) 50 mM Phosphate Buffer, (c) 5% sucrose, (d) 0.05% Polysorbate 80, and (e) 25 mM Arginine. In another embodiment, the stable aqueous solution comprises (a) an anti-C5 antibody at a concentration of 100 mg/mL, (b) 50 mM Phosphate Buffer, (c) 5% sucrose, (d) 0.05% Polysorbate 80, and (e) 25 mM Arginine. In another embodiment, the stable aqueous solution comprises a) an anti-C5 antibody at a concentration of 100 mg/mL, (b) 50 mM Phosphate Buffer, (c) 5% sucrose, (d) 0.05% Polysorbate 80, and (e) 25 mM Arginine.

In another embodiment, the stable aqueous solution comprises no more than four agents in addition to the anti-C5 antibody. In another embodiment, the stable aqueous solution comprises no more than three agents in addition to the anti-C5 antibody. In another embodiment, the stable aqueous solution comprises no more than two agents in addition to the anti-C5 antibody. In another embodiment, the stable aqueous solution comprises no more than one agent in addition to the anti-C5 antibody.

In another embodiment, the stable aqueous solution consists of (a) an anti-C5 antibody at a concentration of about 100 mg/mL, (b) about 50 mM Phosphate Buffer, (c) about 5% sucrose, and (d) about 25 mM Arginine. In another embodiment, the stable aqueous solution consists of (a) an anti-C5 antibody at a concentration of 100 mg/mL, (b) 50 mM Phosphate Buffer; (c) 5% sucrose, and (d) 25 mM Arginine.

In another embodiment, the stable aqueous solution consists of (a) an anti-C5 antibody at a concentration of about 100 mg/mL, (b) about 50 mM Phosphate Buffer, (c) about 5% sucrose; (d) about 0.05% Polysorbate 80, and (e) about 25 mM Arginine. In another embodiment, the stable aqueous solution consists of (a) an anti-C5 antibody at a concentration of 100 mg/mL, (b) 50 mM Phosphate Buffer, (c) 5% sucrose, (d) 0.05% Polysorbate 80, and (e) 25 mM Arginine.

In one embodiment, the stable aqueous solution comprises: (a) an anti-C5 antibody at a concentration of about 100 mg/mL, wherein the anti-C5 antibody comprises a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6, (b) about 50 mM Phosphate Buffer, (c) about 5% sucrose, and (d) about 25 mM Arginine.

In another embodiment, the stable aqueous solution comprises: (a) an anti-C5 antibody at a concentration of 100 mg/mL, wherein the anti-C5 antibody comprises a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6, (b) 50 mM Phosphate Buffer, (c) 5% sucrose; and (d) 25 mM Arginine.

In another embodiment, the stable aqueous solution comprises: (a) an anti-C5 antibody at a concentration of about 100 mg/mL, wherein the anti-C5 antibody comprises a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6, (b) about 50 mM Phosphate Buffer, (c) about 5% sucrose, (d) about 0.05% Polysorbate 80, and (e) about 25 mM Arginine.

In another embodiment, the stable aqueous solution comprises: (a) an anti-C5 antibody at a concentration of 100 mg/mL, wherein the anti-C5 antibody comprises a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6, (b) 50 mM Phosphate Buffer, (c) 5% sucrose, (d) 0.05% Polysorbate 80, and (e) about 25 mM Arginine.

In another embodiment, the stable aqueous solution consists of: (a) an anti-C5 antibody at a concentration of about 100 mg/mL, wherein the anti-C5 antibody comprises a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6, (b) about 50 mM Phosphate Buffer, (c) about 5% sucrose, (d) about 0.05% Polysorbate 80, and (e) about 25 mM Arginine.

In another embodiment, the stable aqueous solution consists of: (a) an anti-C5 antibody at a concentration of 100 mg/mL, wherein the anti-C5 antibody comprises a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6; (b) 50 mM Phosphate Buffer, (c) 5% sucrose, (d) 0.05% Polysorbate 80, and (e) 25 mM Arginine.

In one embodiment, the pH is 7.0, 7.1, 7.2, 7.3, 7.4, 7.5, 7.6, 7.7, 7.8, or 7.9. In another embodiment, the pH of the solution is between 7.0 and 7.4. In another embodiment, the pH of the solution is between 7.2 and 7.8. In another embodiment, the pH of the solution is between 7.2 and 7.6. In a particular embodiment, the pH of the solution is 7.4.

The solutions described herein can be formulated for any suitable mode of administration. In one embodiment, the solution is formulated for administration by a parenteral mode (e.g., intravenous, subcutaneous, intraperitoneal, or intramuscular injection). In a particular embodiment, the solution is formulated for subcutaneous administration. For example, in one embodiment, the stable aqueous solution comprises an anti-C5 antibody at a concentration of 100 mg/mL and is formulated for subcutaneous administration. In another particular embodiment, the solution is formulated for intravenous administration. For example, in one embodiment, the stable aqueous solution comprises an anti-C5 antibody at a concentration of 100 mg/mL and is formulated for intravenous administration.

In one embodiment of any of the solutions described herein, the anti-C5 antibody (e.g., ravulizumab) remains at least 95 (e.g., at least 96, 97, 98, or 99)% monomeric during storage at 2° C. to 8° C. for at least six months as determined by SEC-HPLC (e.g., gel permeation HPLC). In another embodiment, the anti-C5 antibody remains at least 95 (e.g., at least 96, 97, 98, or 99)% monomeric during storage at 2° C. to 8° C. for at least nine months as determined by SEC-HPLC. In another embodiment, the anti-C5 antibody remains at least 95 (e.g., at least 96, 97, 98, or 99)% monomeric during storage at 2° C. to 8° C. for at least one year as determined by SEC-HPLC. In another embodiment, the anti-C5 antibody remains at least 95 (e.g., at least 96, 97, 98, or 99)% monomeric during storage at 2° C. to 8° C. for at least 18 months as determined by SEC-HPLC. In another embodiment, the anti-C5 antibody remains at least 95 (e.g., at least 96, 97, 98, or 99)% monomeric during storage at 2° C. to 8° C. for at least two years as determined by SEC-HPLC.

In another embodiment of any of the solutions described herein, less than 5% of the anti-C5 antibody (e.g., ravulizumab) in the solution is aggregated as determined by SEC-HPLC (e.g., gel permeation HPLC). In another embodiment, less than 4% of the anti-C5 antibody in the solution is aggregated as determined by SEC-HPLC. In another embodiment, less than 3% of the anti-C5 antibody in the solution is aggregated as determined by SEC-HPLC. In another embodiment, less than 2% of the anti-C5 antibody in the solution is aggregated as determined by SEC-HPLC. In another embodiment, less than 1% of the anti-C5 antibody in the solution is aggregated as determined by SEC-HPLC.

In another embodiment of any of the solutions described herein, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its C5-binding activity during storage at 2° C. to 8° C. for at least six months, as compared to a reference anti-C5 antibody corresponding to the anti-C5 antibody prior to storage. In another embodiment, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its C5-binding activity during storage at 2° C. to 8° C. for at least nine months, as compared to a reference anti-C5 antibody corresponding to the anti-C5 antibody prior to storage. In another embodiment, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its C5-binding activity during storage at 2° C. to 8° C. for at least one year, as compared to a reference anti-C5 antibody corresponding to the anti-C5 antibody prior to storage. In another embodiment, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its C5-binding activity during storage at 2° C. to 8° C. for at least eighteen months, as compared to a reference anti-C5 antibody corresponding to the anti-C5 antibody prior to storage. In another embodiment, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its C5-binding activity during storage at 2° C. to 8° C. for at least two years, as compared to a reference anti-C5 antibody corresponding to the anti-C5 antibody prior to storage. In another embodiment, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its C5-binding activity during storage at 2° C. to 8° C. for at least three years, as compared to a reference anti-C5 antibody corresponding to the anti-C5 antibody prior to storage.

In another embodiment of any of the solutions described herein, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its ability to inhibit hemolysis during storage at 2° C. to 8° C. for at least nine months, as compared to a reference anti-C5 antibody corresponding to the anti-C5 antibody prior to storage. In another embodiment of any of the solutions described herein, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its ability to inhibit hemolysis during storage at 2° C. to 8° C. for at least six months, as compared to a reference anti-C5 antibody corresponding to the anti-C5 antibody prior to storage. In another embodiment of any of the solutions described herein, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its ability to inhibit hemolysis during storage at 2° C. to 8° C. for at least one year, as compared to a reference anti-C5 antibody corresponding to the anti-C5 antibody prior to storage. In another embodiment of any of the solutions described herein, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its ability to inhibit hemolysis during storage at 2° C. to 8° C. for at least 18 months, as compared to a reference anti-C5 antibody corresponding to the anti-C5 antibody prior to storage. In another embodiment of any of the solutions described herein, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its ability to inhibit hemolysis during storage at 2° C. to 8° C. for at least two years, as compared to a reference anti-C5 antibody corresponding to the anti-C5 antibody prior to storage. In another embodiment of any of the solutions described herein, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its ability to inhibit hemolysis during storage at 2° C. to 8° C. for at least three years, as compared to a reference anti-C5 antibody corresponding to the anti-C5 antibody prior to storage.

In another aspect, methods for producing a stable concentrated antibody solution comprising an anti-C5 antibody at a concentration of 100 mg/mL, 50 mM Phosphate Buffer, 5% sucrose; and 25 mM Arginine were provided, the method comprising:

i) providing a first aqueous solution comprising the anti-C5 antibody, the first aqueous solution having a first formulation and comprising no more than 10 mg/mL of the anti-C5 antibody;

ii) subjecting the first aqueous solution to diafiltration into a formulation comprising 50 mM Phosphate Buffer, 5% sucrose, and 25 mM Arginine, at pH 7.4 to thereby produce a second aqueous solution, wherein the second aqueous solution has a second formulation as a result of the diafiltration; and iii) concentrating the second aqueous solution to produce a stable concentrated antibody solution comprising 100 mg/mL of the anti-C5 antibody, 50 mM Phosphate Buffer, 5% sucrose; and 25 mM Arginine.

In another embodiment, a method for producing a stable concentrated antibody solution comprising an anti-C5 antibody at a concentration of 100 mg/mL, 50 mM Phosphate Buffer, 5% sucrose; 25 mM Arginine, and 0.05% Polysorbate 80, is provided, the method comprising:

i) providing a first aqueous solution comprising the anti-C5 antibody, the first aqueous solution having a first formulation and comprising no more than 10 mg/mL of the anti-C5 antibody;

ii) subjecting the first aqueous solution to diafiltration into a formulation comprising 50 mM Phosphate Buffer, 5% sucrose, 25 mM Arginine, and 0.05% Polysorbate 80, at pH 7.4 to thereby produce a second aqueous solution, wherein the second aqueous solution has a second formulation as a result of the diafiltration; and iii) concentrating the second aqueous solution to produce a stable concentrated antibody solution comprising 100 mg/mL of the anti-C5 antibody, 50 mM Phosphate Buffer, 5% sucrose, 25 mM Arginine, and 0.05% Polysorbate 80.

Also provided were methods of treating a human patient with a complement-associated condition, comprising administering to the patient a stable aqueous solution (e.g., subcutaneously or intravenously) as described herein, in an amount effective to treat the complement-associated condition. Exemplary complement-associated conditions include, but were not limited to, rheumatoid arthritis, antiphospholipid antibody syndrome, lupus nephritis, ischemia-reperfusion injury, atypical hemolytic uremic syndrome (aHUS), typical hemolytic uremic syndrome, paroxysmal nocturnal hemoglobinuria (PNH), dense deposit disease, neuromyelitis optica, multifocal motor neuropathy, multiple sclerosis, macular degeneration, HELLP syndrome, spontaneous fetal loss, thrombotic thrombocytopenic purpura, Pauci-immune vasculitis, epidermolysis bullosa, recurrent fetal loss, traumatic brain injury, myocarditis, a cerebrovascular disorder, a peripheral vascular disorder, a renovascular disorder, a mesenteric/enteric vascular disorder, vasculitis, Henoch-Schönlein purpura nephritis, systemic lupus erythematosus-associated vasculitis, vasculitis associated with rheumatoid arthritis, immune complex vasculitis, Takayasu's disease, dilated cardiomyopathy, diabetic angiopathy, Kawasaki's disease, venous gas embolus, restenosis following stent placement, rotational atherectomy, percutaneous transluminal coronary angioplasty, myasthenia gravis, cold agglutinin disease, dermatomyositis, paroxysmal cold hemoglobinuria, antiphospholipid syndrome, Graves' disease, atherosclerosis, Alzheimer's disease, systemic inflammatory response sepsis, septic shock, spinal cord injury, glomerulonephritis, transplant rejection, Hashimoto's thyroiditis, type I diabetes, psoriasis, pemphigus, autoimmune hemolytic anemia, idiopathic thrombocytopenic purpura, Goodpasture's syndrome, Degos disease, and catastrophic antiphospholipid syndrome. In a particular embodiment, the complement-associated condition is atypical hemolytic uremic syndrome (aHUS). In another embodiment, the complement-associated condition is paroxysmal nocturnal hemoglobinuria (PNH).

Further provided were kits that include a stable aqueous solution as described herein in a therapeutically effective amount adapted for use in the methods described herein. In one embodiment, the kit comprises: (i) any of the solutions described herein; and (ii) a means for delivering the solution to a patient in need thereof (e.g., a syringe). In one embodiment, the means is suitable for subcutaneous delivery of the solution to the patient. In one embodiment, the means is suitable for intravenous delivery of the solution to the patient. In another embodiment, the kits further comprises at least one additional active agent for use in treating a complement-associated disorder in a subject.

BRIEF DESCRIPTION OF THE DRAWINGS

FIG. 2 depicts the dynamic light scattering results for a L-Arginine titration of buffer exchanged ravulizumab (ALXN1210) at 50 mg/mL.

FIG. 6 shows the stability data for ravulizumab (ALXN1210) (T=0 through T=2; Weeks at 2-8° C.).

FIG. 7 shows the stability data for ravulizumab (ALXN1210) (T=3 Weeks through T=2; Months at 2-8° C.).

FIG. 8 shows the stability data for ravulizumab (ALXN1210) (T=0 through T=3; Weeks at 23-27° C.).

FIG. 9 shows the stability data ravulizumab (ALXN1210) (T=1 Month through T=2; Months at 23-27° C.).

FIG. 10 shows the stability data for ravulizumab (ALXN1210) (T=1 Week through T=3 Weeks at 37° C.).

FIG. 11 shows the stability data for ravulizumab (ALXN1210) (T=1 Month through T=2 Months at 37° C.).

FIG. 19 shows the stability data for ravulizumab (ALXN1210) Freeze Thaw (T=0 through Cycle 2 at T=1M −20° C.).

FIG. 20 shows the stability data for ravulizumab (ALXN1210) Freeze Thaw Cycle 3 through Cycle 5 at T=1M −20° C.

FIG. 22 shows the prototype stability data for ravulizumab (ALXN1210) (T=0 through T=2 Months at 2-8° C.).

FIG. 23 shows the prototype stability data for ravulizumab (ALXN1210) (T=3 Months through T=6 Months at 2-8° C.).

FIG. 24 shows the prototype stability data for ravulizumab (ALXN1210) (T=9 Months through T=12 Months at 2-8° C.).

FIG. 25 shows the prototype stability data for ravulizumab (ALXN1210) (T=1 Month through T=2 Months at 23-27° C.).

FIG. 26 shows the prototype stability data for ravulizumab (ALXN1210) (T=3 Month through T=6 Months at 23-27° C.

FIG. 27 shows the prototype stability data for ravulizumab (ALXN1210) (T=9 Month through T=12 Months at 23-27° C.).

FIG. 28 shows the prototype stability data for ravulizumab (ALXN1210) (T=2 Weeks through T=2 Months at 37° C.

FIG. 29 shows the prototype stability data for ravulizumab (ALXN1210) (T=1 Month through T=3 Months at −20° C.).

FIG. 30 shows the prototype stability data for ravulizumab (ALXN1210) (T=6 Months through T=12 Months at −20° C.

FIG. 31 shows the prototype stability study results for ravulizumab (ALXN1210) (T=3 Months through T=6 Months at −80° C.).

FIG. 32 shows the prototype stability study results for ravulizumab (ALXN1210) (T=12 Months at −80° C.).

FIG. 41 shows the prototype stability size exclusion chromatography (SEC) data, % Monomer for ravulizumab (ALXN1210)—Freeze Thaw Cycles 1-3 at T=1 Month −20° C.

FIG. 42 shows the prototype stability size exclusion chromatography (SEC) data, % Monomer for ravulizumab (ALXN1210)—Freeze Thaw Cycles 4-5 at T=1 Month −20° C.

FIG. 43 shows the prototype stability size exclusion chromatography (SEC) data, % Monomer for ravulizumab (ALXN1210)—Freeze Thaw Cycles 1-3 at T=3 Months −80° C.

FIG. 44 shows the prototype stability size exclusion chromatography (SEC) data, % Monomer for ravulizumab (ALXN1210)—Freeze Thaw Cycles 4-5 at T=3 Months −80° C.

DETAILED DESCRIPTION

Figure 1:
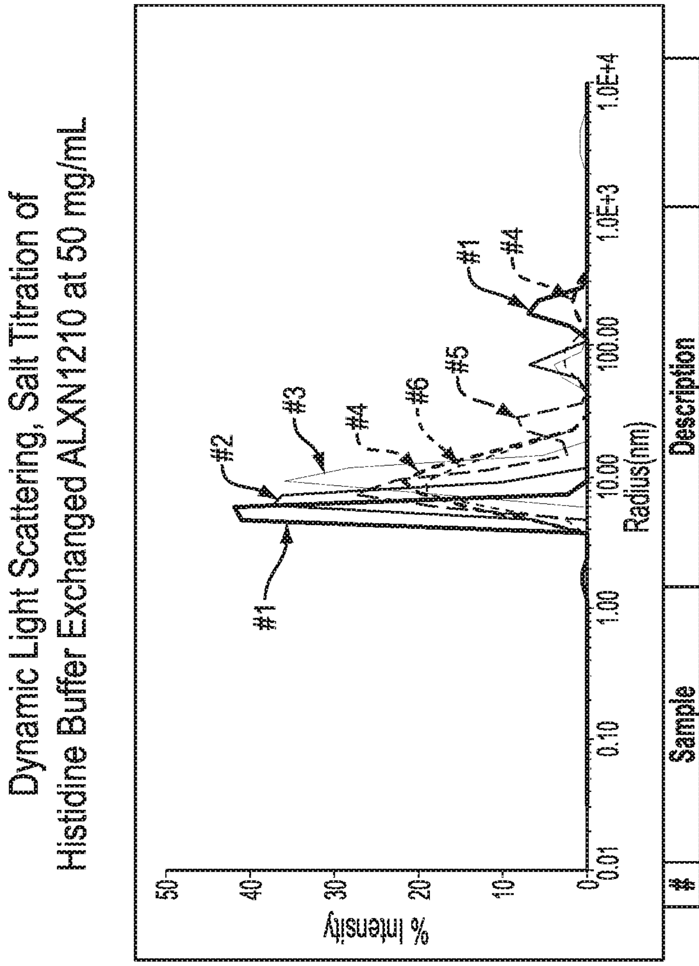
FIG. 1 depicts the dynamic light scattering results for a salt titration of histidine buffer exchanged ravulizumab (ALXN1210) at 50 mg/mL.

The disclosure features stable, aqueous solutions containing a high concentration of anti-C5 antibody (e.g., ravulizumab). The solutions can be used in a variety of therapeutic applications, such as methods for treating or preventing complement-associated disorders. While in no way intended to be limiting, exemplary solutions, formulations, therapeutic kits, and methods for making and using any of the foregoing are elaborated on below and are exemplified in the working Examples.

I. Definitions

Unless defined otherwise, all technical and scientific terms used herein have the same meaning as commonly understood by the skilled artisan. Although any methods and compositions similar or equivalent to those described herein can be used in practice or testing of the present invention, the preferred methods and compositions are described herein.

The singular form "a," "an," and "the" include plural reference unless the context clearly dictates otherwise.

The term "about", particularly in reference to a given quantity or number, is meant to encompass deviations within plus or minus ten percent (±10%), (e.g., ±5%).

The term "pharmaceutical formulation" refers to preparations which are in such form as to permit the biological activity of the active ingredients to be unequivocally effective, and which contain no additional components which are significantly toxic to the subjects to which the formulation would be administered.

As used herein, an "aqueous" pharmaceutical composition is a composition suitable for pharmaceutical use, wherein the aqueous carrier is water. A composition suitable for pharmaceutical use may be sterile, homogeneous and/or isotonic. Aqueous pharmaceutical compositions may be prepared directly in an aqueous form and/or may be reconstituted from a lyophilisate.

An "isotonic" formulation is one which has essentially the same osmotic pressure as human blood. Isotonic formulations will generally have an osmotic pressure from about 275 to 350 mOsm/kg. The term "hypotonic" describes a formulation with an osmotic pressure below that of human blood. Correspondingly, the term "hypertonic" is used to describe a formulation with an osmotic pressure above that of human blood. Isotonicity can be measured, for example, using a vapor pressure or ice-freezing type osmometer. A "tonicity agent" is a compound which renders the formulation isotonic.

As used herein, the "osmolality" of a solution is the number of osmoles of solute per kilogram of solvent. Osmolality is a measure of the number of particles present in solution and is independent of the size or weight of the particles. It can be measured only by use of a property of the solution that is dependent only on the particle concentration. These properties are vapour pressure depression, freezing point depression, boiling point elevation, and osmotic pressure, and are collectively referred to as colligative properties.

A "sterile" formulation is asceptic or free or essentially free from all living microorganisms and their spores.

A "stable" formulation, as used herein, is one in which the antibody therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability of the anti-C5 antibody formulations can be measured at selected temperatures after selected time periods. For example, an increase in aggregate formation following storage is an indicator for instability of an aqueous anti-C5 antibody formulation. In addition to aggregate formation, retention of original clarity, color and odor throughout shelf life are indicators utilized to monitor stability of the aqueous anti-C5 antibody solutions described herein.

An antibody "retains its physical stability" in a pharmaceutical formulation if it shows substantially no signs of aggregation, precipitation and/or denaturation upon visual examination of color and/or clarity, or as measured by UV light scattering or by size exclusion chromatography.

The term "aggregation" refers to the assembly of native, folded proteins to from aggregates containing non-native structures. Aggregation can occur even under physiological, non-denaturing conditions, and is often irreversible, resulting in non-native aggregates that are inactive, and sometimes immunogenic and toxic.

The phrase "low to undetectable levels of aggregation" as used herein refers to samples containing no more than about 5%, no more than about 4%, no more than about 3%, no more than about 2%, no more than about 1% and no more than about 0.5% aggregation by weight of protein as measured by gel permeation high-performance liquid chromatography (GP-IPLC), high performance size exclusion chromatography (HPSEC) or static light scattering (SLS) techniques.

An antibody "retains its chemical stability" in a pharmaceutical formulation, if the chemical stability at a given time is such that the antibody is considered to still retain its biological activity as defined below. Chemical stability can be assessed by detecting and quantifying chemically altered forms of the antibody. Chemical alteration may involve size modification (e.g., clipping), deamidation, racemization, hydrolysis, oxidation, beta elimination and disulfide exchange which can be evaluated using known techniques, for example, size exclusion chromatography, SDS-PAGE, matrix-assisted laser desorption ionization/time-of-flight mass spectrometry (MALDI/TOF MS), and/or ion-exchange chromatography.

An antibody "retains its biological activity" in a pharmaceutical formulation, if the antibody in a pharmaceutical formulation is biologically active for its intended purpose. For example, biological activity is retained if the biological activity of the antibody in the pharmaceutical formulation is within about 30%, about 20%, or about 10% (within the errors of the assay) of the biological activity exhibited at the time the pharmaceutical formulation was prepared (e.g., as determined in an antigen binding assay). Herein, "biological activity" of a monoclonal antibody refers to the ability of the antibody to bind to antigen. It can further include antibody binding to antigen and resulting in a measurable biological response which can be measured in vitro or in vivo.

"Shelf-life" of a pharmaceutical product, e.g., an aqueous solution comprising an anti-C5 antibody is the length of time the product is stored before decomposition occurs. For example, shelf-life may be defined as the time for decomposition of 0.1%, 0.5%, 1%, 5%, or 10% of the product.

As used herein, the term "antibody" describes polypeptides comprising at least one antibody derived antigen binding site (e.g., VH/VL region or Fv, or CDR). Antibodies include known forms of antibodies. For example, the antibody can be a human antibody, a humanized antibody, a bispecific antibody, or a chimeric antibody. The antibody also can be a Fab, Fab'2, ScFv, SMIP, Affibody®, nanobody, or a domain antibody. The antibody also can be of any of the following isotypes: IgG1, IgG2, IgG3, IgG4, IgM, IgA1, IgA2, IgAsec, IgD, and IgE. The antibody may be a naturally occurring antibody or may be an antibody that has been altered by a protein engineering technique (e.g., by mutation, deletion, substitution, conjugation to a non-antibody moiety). For example, an antibody may include one or more variant amino acids (compared to a naturally occurring antibody) which changes a property (e.g., a functional property) of the antibody. For example, numerous such alterations are known in the art which affect, e.g., half-life, effector function, and/or immune responses to the antibody in a patient. The term antibody also includes artificial or engineered polypeptide constructs which comprise at least one antibody-derived antigen binding site.

As used herein, the terms "specific binding," "selective binding," "selectively binds," and "specifically binds," refer to antibody binding to an epitope on a predetermined antigen but not to other antigens. Typically, the antibody (i) binds with an equilibrium dissociation constant ($K_D$) of approximately less than $10^{-7}$ M, such as approximately less than $10^{-8}$M, $10^{-9}$ M or $10^{-10}$ M or even lower when determined by, e.g., surface plasmon resonance (SPR) technology in a BIACORE® 2000 surface plasmon resonance instrument using the predetermined antigen, e.g., C5, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Accordingly, unless otherwise indicated, an antibody that "specifically binds to human C5" refers to an antibody that binds to soluble or cell bound human C5 with a $K_D$ of $10^{-7}$ M or less, such as approximately less than $10^{-8}$ M, $10^{-9}$ M or $10^{-10}$ M or even lower.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

As used herein, the terms "subject" or "patient" are used interchangeably herein and refer to a mammal such as a human, mouse, rat, hamster, guinea pig, rabbit, cat, dog, monkey, cow, horse, pig and the like. In one embodiment, the patient is a human patient (e.g., a human patient having a complement-associated condition).

The terms "treat," "treating," and "treatment," as used herein, refer to therapeutic measures described herein. The methods of "treatment" employ administration to a subject the combination disclosed herein in order to cure, delay, reduce the severity of, or ameliorate one or more symptoms of the disease or disorder or recurring disease or disorder, or in order to prolong the survival of a subject beyond that expected in the absence of such treatment.

As used herein, "effective treatment" refers to treatment producing a beneficial effect, e.g., amelioration of at least one symptom of a disease or disorder. A beneficial effect can take the form of an improvement over baseline, i.e., an improvement over a measurement or observation made prior to initiation of therapy according to the method. Effective treatment may refer to alleviation of at least one symptom of a disease or condition.

The term "effective amount" refers to an amount of an agent that provides the desired biological, therapeutic, and/or prophylactic result. That result can be reduction, amelioration, palliation, lessening, delaying, and/or alleviation of one or more of the signs, symptoms, or causes of a disease or condition, or any other desired alteration of a biological system. In one example, an "effective amount" is the amount of a stable aqueous solution to alleviate at least one symptom of a disease or condition An effective amount can be administered in one or more administrations.

As used herein, the terms "induction" and "induction phase" are used interchangeably and refer to the first phase of treatment.

As used herein, the terms "maintenance" and "maintenance phase" are used interchangeably and refer to the second phase of treatment. In certain embodiments, treatment is continued as long as clinical benefit is observed or until unmanageable toxicity or disease progression occurs.

II. Anti-C5 Antibodies

The anti-C5 antibodies described herein bind to complement component C5 (e.g., human C5) and inhibit the cleavage of C5 into fragments C5a and C5b. As described above, such antibodies also have, for example, improved pharmacokinetic properties relative to other anti-C5 antibodies (e.g., eculizumab) used for therapeutic purposes.

Anti-C5 antibodies (or VH/VL domains derived therefrom) suitable for use in the invention can be generated using methods well known in the art. Alternatively, art recognized anti-C5 antibodies can be used. Antibodies that compete with any of these art-recognized antibodies for binding to C5 also can be used.

An exemplary anti-C5 antibody is ravulizumab comprising heavy and light chains having the sequences shown in SEQ ID NOs:14 and 11, respectively, or antigen binding fragments and variants thereof. Ravulizumab (also known as BNJ441 and ALXN1210) is described in PCT/US2015/019225 and U.S. Pat. No. 9,079,949, the teachings or which are hereby incorporated by reference. The terms ravulizumab, BNJ441, and ALXN1210 may be used interchangeably throughout this document. Ravulizumab selectively binds to human complement protein C5, inhibiting its cleavage to C5a and C5b during complement activation. This inhibition prevents the release of the proinflammatory mediator C5a and the formation of the cytolytic pore-forming membrane attack complex (MAC) C5b-9 while preserving the proximal or early components of complement activation (e.g., C3 and C3b) essential for the opsonization of microorganisms and clearance of immune complexes.

In other embodiments, the antibody comprises the heavy and light chain CDRs or variable regions of ravulizumab. Accordingly, in one embodiment, the antibody comprises the CDR1, CDR2, and CDR3 domains of the VH region of ravulizumab having the sequence set forth in SEQ ID NO:12, and the CDR1, CDR2 and CDR3 domains of the VL region of ravulizumab having the sequence set forth in SEQ ID NO:8. In another embodiment, the antibody comprises heavy chain CDR1, CDR2 and CDR3 domains having the sequences set forth in SEQ ID NOs:19, 18, and 3, respectively, and light chain CDR1, CDR2 and CDR3 domains having the sequences set forth in SEQ ID NOs:4, 5, and 6, respectively. In another embodiment, the antibody comprises VH and VL regions having the amino acid sequences set forth in SEQ ID NO:12 and SEQ ID NO:8, respectively.

Another exemplary anti-C5 antibody is antibody BNJ421 comprising heavy and light chains having the sequences shown in SEQ ID NOs:20 and 11, respectively, or antigen binding fragments and variants thereof. BNJ421 (also known as ALXN1211) is described in PCT/US2015/019225 and U.S. Pat. No. 9,079,949, the teachings or which are hereby incorporated by reference.

In other embodiments, the antibody comprises the heavy and light chain CDRs or variable regions of BNJ421. Accordingly, in one embodiment, the antibody comprises the CDR1, CDR2, and CDR3 domains of the VH region of BNJ421 having the sequence set forth in SEQ ID NO:12, and the CDR1, CDR2 and CDR3 domains of the VL region of BNJ421 having the sequence set forth in SEQ ID NO:8. In another embodiment, the antibody comprises heavy chain CDR1, CDR2 and CDR3 domains having the sequences set forth in SEQ ID NOs:19, 18, and 3, respectively, and light chain CDR1, CDR2 and CDR3 domains having the sequences set forth in SEQ ID NOs:4, 5, and 6, respectively. In another embodiment, the antibody comprises VH and VL regions having the amino acid sequences set forth in SEQ ID NO:12 and SEQ ID NO:8, respectively.

The exact boundaries of CDRs have been defined differently according to different methods. In some embodiments, the positions of the CDRs or framework regions within a light or heavy chain variable domain can be as defined by Kabat et al. [(1991) "Sequences of Proteins of Immunological Interest." NIH Publication No. 91-3242, U.S. Department of Health and Human Services, Bethesda, Md.]. In such cases, the CDRs can be referred to as "Kabat CDRs" (e.g., "Kabat LCDR2" or "Kabat HCDR1"). In some embodiments, the positions of the CDRs of a light or heavy chain variable region can be as defined by Chothia et al. (1989) *Nature* 342:877-883. Accordingly, these regions can be referred to as "Chothia CDRs" (e.g., "Chothia LCDR2" or "Chothia HCDR3"). In some embodiments, the positions of the CDRs of the light and heavy chain variable regions can be as defined by a Kabat-Chothia combined definition. In such embodiments, these regions can be referred to as "combined Kabat-Chothia CDRs". Thomas et al. [(1996) *Mol Immunol* 33(17/18):1389-1401] exemplifies the identification of CDR boundaries according to Kabat and Chothia definitions.

In some embodiments, an anti-C5 antibody described herein comprises a heavy chain CDR1 comprising, or consisting of, the following amino acid sequence: GHIFSNYWIQ (SEQ ID NO:19). In some embodiments, an anti-C5 antibody described herein comprises a heavy chain CDR2 comprising, or consisting of, the following amino acid sequence: EILPGSGHTEYTENFKD (SEQ ID NO:18). In some embodiments, an anti-C5 antibody described herein comprises a heavy chain variable region comprising the following amino acid sequence:

(SEQ ID NO: 12)
QVQLVQSGAEVKKPGASVKVSCKASGHIFSNYWIQWVRQAPGQGLEWMGE
ILPGSGHTEYTENFKDRVTMTRDTSTSTVYMELSSLRSEDTAVYYCARYF
FGSSPNWYFDVWGQGTLVTVSS.

In some embodiments, an anti-C5 antibody described herein comprises a light chain variable region comprising the following amino acid sequence:

(SEQ ID NO: 8)
DIQMTQSPSSLSASVGDRVTITCGASENIYGALNWYQQKPGKAPKLLIYG
ATNLADGVPSRFSGSGSGTDFTLTISSLQPEDFATYYCQNVLNTPLTFGQ
GTKVEIK.

An anti-C5 antibody described herein can, in some embodiments, comprise a variant human Fc constant region that binds to human neonatal Fc receptor (FcRn) with greater affinity than that of the native human Fc constant region from which the variant human Fc constant region was derived. For example, the Fc constant region can comprise one or more (e.g., two, three, four, five, six, seven, or eight or more) amino acid substitutions relative to the native human Fc constant region from which the variant human Fc constant region was derived. The substitutions can increase the binding affinity of an IgG antibody containing the variant Fc constant region to FcRn at pH 6.0, while maintaining the pH dependence of the interaction. Methods for testing whether one or more substitutions in the Fc constant region of an antibody increase the affinity of the Fc constant region for FcRn at pH 6.0 (while maintaining pH dependence of the interaction) are known in the art and exemplified in the working examples. See, e.g., PCT/US2015/019225 and U.S. Pat. No. 9,079,949 the disclosures of each of which are incorporated herein by reference in their entirety.

Substitutions that enhance the binding affinity of an antibody Fc constant region for FcRn are known in the art and include, e.g., (1) the M252Y/S254T/T256E triple substitution described by Dall'Acqua et al. (2006) *J Biol Chem* 281: 23514-23524; (2) the M428L or T250Q/M428L substitutions described in Hinton et al. (2004) *J Biol Chem* 279:6213-6216 and Hinton et al. (2006) *J Immunol* 176: 346-356; and (3) the N434A or T307/E380A/N434A substitutions described in Petkova et al. (2006) *Int Immunol* 18(12):1759-69. The additional substitution pairings: P257I/Q311I, P257I/N434H, and D376V/N434H are described in, e.g., Datta-Mannan et al. (2007) *J Biol Chem* 282(3):1709-1717, the disclosure of which is incorporated herein by reference in its entirety.

In some embodiments, the variant constant region has a substitution at EU amino acid residue 255 for valine. In some embodiments, the variant constant region has a substitution at EU amino acid residue 309 for asparagine. In some embodiments, the variant constant region has a substitution at EU amino acid residue 312 for isoleucine. In some embodiments, the variant constant region has a substitution at EU amino acid residue 386.

In some embodiments, the variant Fc constant region comprises no more than 30 (e.g., no more than 29, 28, 27, 26, 25, 24, 23, 22, 21, 20, 19, 18, 17, 16, 15, 14, 13, 12, 11, 10, nine, eight, seven, six, five, four, three, or two) amino acid substitutions, insertions, or deletions relative to the native constant region from which it was derived. In some embodiments, the variant Fc constant region comprises one or more amino acid substitutions selected from the group consisting of: M252Y, S254T, T256E, N434S, M428L, V259I, T250I, and V308F. In some embodiments, the variant human Fc constant region comprises a methionine at position 428 and an asparagine at position 434, each in EU numbering. In some embodiments, the variant Fc constant region comprises a 428L/434S double substitution as described in, e.g., U.S. Pat. No. 8,088,376.

In some embodiments the precise location of these mutations may be shifted from the native human Fc constant region position due to antibody engineering. For example, the 428L/434S double substitution when used in a IgG2/4 chimeric Fc may correspond to 429L and 435S as in the M429L and N435S variants found in ravulizumab (BNJ441) and described in U.S. Pat. No. 9,079,949 the disclosure of which is incorporated herein by reference in its entirety.

In some embodiments, the variant constant region comprises a substitution at amino acid position 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434, or 436 (EU numbering) relative to the native human Fc constant region. In some embodiments, the substitution is selected from the group consisting of: methionine for glycine at position 237; alanine for proline at position 238; lysine for serine at position 239; isoleucine for lysine at position 248; alanine, phenylalanine, isoleucine, methionine, glutamine, serine, valine, tryptophan, or tyrosine for threonine at position 250; phenylalanine, tryptophan, or tyrosine for methionine at position 252; threonine for serine at position 254; glutamic acid for arginine at position 255; aspartic acid, glutamic acid, or glutamine for threonine at position 256; alanine, glycine, isoleucine, leucine, methionine, asparagine, serine, threonine, or valine for proline at position 257; histidine for glutamic acid at position 258; alanine for aspartic acid at position 265; phenylalanine for aspartic acid at position 270; alanine, or glutamic acid for asparagine at position 286; histidine for threonine at position 289; alanine for asparagine at position 297; glycine for serine at position 298; alanine for valine at position 303; alanine for valine at position 305; alanine, aspartic acid, phenylalanine, glycine, histidine, isoleucine, lysine, leucine, methionine, asparagine, proline, glutamine, arginine, serine, valine, tryptophan, or tyrosine for threonine at position 307; alanine, phenylalanine, isoleucine, leucine, methionine, proline, glutamine, or threonine for valine at position 308; alanine, aspartic acid, glutamic acid, proline, or arginine for leucine or valine at position 309; alanine, histidine, or isoleucine for glutamine at position 311; alanine or histidine for aspartic acid at position 312; lysine or arginine for leucine at position 314; alanine or histidine for asparagine at position 315; alanine for lysine at position 317; glycine for asparagine at position 325; valine for isoleucine at position 332; leucine for lysine at position 334; histidine for lysine at position 360; alanine for aspartic acid at position 376; alanine for glutamic acid at position 380; alanine for glutamic acid at position 382; alanine for asparagine or serine at position 384; aspartic acid or histidine for glycine at position 385; proline for glutamine at position 386; glutamic acid for proline at position 387; alanine or serine for asparagine at position 389; alanine for serine at position 424; alanine, aspartic acid, phenylalanine, glycine, histidine, isoleucine, lysine, leucine, asparagine, proline, glutamine, serine, threonine, valine, tryptophan, or tyrosine for methionine at position 428; lysine for histidine at position 433; alanine, phenylalanine, histidine, serine, tryptophan, or tyrosine for asparagine at position 434; and histidine for tyrosine or phenylalanine at position 436, all in EU numbering.

Suitable anti-C5 antibodies for use in the methods described herein, in some embodiments, comprise a heavy chain polypeptide comprising the amino acid sequence depicted in SEQ ID NO:14 and/or a light chain polypeptide comprising the amino acid sequence depicted in SEQ ID NO:11. Alternatively, the anti-C5 antibodies for use in the methods described herein, in some embodiments, comprise a heavy chain polypeptide comprising the amino acid sequence depicted in SEQ ID NO:20 and/or a light chain polypeptide comprising the amino acid sequence depicted in SEQ ID NO:11.

In one embodiment, the antibody binds to C5 at pH 7.4 and 25° C. (and, otherwise, under physiologic conditions) with an affinity dissociation constant ($K_D$) that is at least 0.1 (e.g., at least 0.15, 0.175, 0.2, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, or 0.975) nM. In some embodiments, the $K_D$ of the anti-C5 antibody, or antigen binding fragment thereof, is no greater than 1 (e.g., no greater than 0.9, 0.8, 0.7, 0.6, 0.5, 0.4, 0.3, or 0.2) nM.

In other embodiments, the [($K_D$ of the antibody for C5 at pH 6.0 at C)/($K_D$ of the antibody for C5 at pH 7.4 at 25° C.)] is greater than 21 (e.g., greater than 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 350, 400, 450, 500, 600, 700, 800, 900, 1000, 1500, 2000, 2500, 3000, 3500, 4000, 4500, 5000, 5500, 6000, 6500, 7000, 7500, or 8000).

Methods for determining whether an antibody binds to a protein antigen and/or the affinity for an antibody to a protein antigen are known in the art. For example, the binding of an antibody to a protein antigen can be detected and/or quantified using a variety of techniques such as, but not limited to, Western blot, dot blot, surface plasmon resonance (SPR) method (e.g., BIAcore system; Pharmacia Biosensor AB, Uppsala, Sweden and Piscataway, N.J.), or enzyme-linked immunosorbent assay (ELISA). See, e.g., Benny K. C. Lo (2004) "Antibody Engineering: Methods and Protocols," Humana Press (ISBN: 1588290921); Johne et al. (1993) *J Immunol Meth* 160:191-198; Jonsson et al. (1993) *Ann Biol Clin* 5:19-26; and Jonsson et al. (1991) *Biotechniques* 11:620-627. In addition, methods for measuring the affinity (e.g., dissociation and association constants) are set forth in the working examples.

As used herein, the term "$k_a$" refers to the rate constant for association of an antibody to an antigen. The term "$k_d$" refers to the rate constant for dissociation of an antibody from the antibody/antigen complex. And the term "$K_D$" refers to the equilibrium dissociation constant of an antibody-antigen interaction. The equilibrium dissociation constant is deduced from the ratio of the kinetic rate constants, $K_D=k_a/k_d$. Such determinations preferably are measured at 25° C. or 37° C. (see the working examples). For example, the kinetics of antibody binding to human C5 can be determined at pH 8.0, 7.4, 7.0, 6.5 and 6.0 via surface plasmon resonance (SPR) on a BIAcore 3000 instrument using an anti-Fc capture method to immobilize the antibody.

In one embodiment, the anti-C5 antibody, or antigen binding fragment thereof, blocks the generation or activity of the C5a and/or C5b active fragments of a C5 protein (e.g., a human C5 protein). Through this blocking effect, the antibodies inhibit, e.g., the pro-inflammatory effects of C5a and the generation of the C5b-9 membrane attack complex (MAC) at the surface of a cell.

Methods for determining whether a particular antibody described herein inhibits C5 cleavage are known in the art. Inhibition of human complement component C5 can reduce the cell-lysing ability of complement in a subject's body fluids. Such reductions of the cell-lysing ability of complement present in the body fluid(s) can be measured by methods well known in the art such as, for example, by a conventional hemolytic assay such as the hemolysis assay described by Kabat and Mayer (eds.), "Experimental Immunochemistry, $2^{nd}$ Edition," 135-240, Springfield, Ill., C C Thomas (1961), pages 135-139, or a conventional variation of that assay such as the chicken erythrocyte hemolysis method as described in, e.g., Hillmen et al. (2004) *N Engl J Med* 350(6):552. Methods for determining whether a candidate compound inhibits the cleavage of human C5 into forms C5a and C5b are known in the art and described in Evans et al. (1995) *Mol Immunol* 32(16):1183-95. For example, the concentration and/or physiologic activity of C5a and C5b in a body fluid can be measured by methods well known in the art. For C5b, hemolytic assays or assays for soluble C5b-9 as discussed herein can be used. Other assays known in the art can also be used. Using assays of these or other suitable types, candidate agents capable of inhibiting human complement component C5 can be screened.

Immunological techniques such as, but not limited to, ELISA can be used to measure the protein concentration of C5 and/or its split products to determine the ability of an anti-C5 antibody, or antigen binding fragment thereof, to inhibit conversion of C5 into biologically active products. In some embodiments, C5a generation is measured. In some embodiments, C5b-9 neoepitope-specific antibodies are used to detect the formation of terminal complement.

Hemolytic assays can be used to determine the inhibitory activity of an anti-C5 antibody, or antigen binding fragment thereof, on complement activation. In order to determine the effect of an anti-C5 antibody, or antigen binding fragment thereof, on classical complement pathway-mediated hemolysis in a serum test solution in vitro, for example, sheep erythrocytes coated with hemolysin or chicken erythrocytes sensitized with anti-chicken erythrocyte antibody are used as target cells. The percentage of lysis is normalized by considering 100% lysis equal to the lysis occurring in the absence of the inhibitor. In some embodiments, the classical complement pathway is activated by a human IgM antibody, for example, as utilized in the Wieslab® Classical Pathway Complement Kit (Wieslab® COMPL CP310, Euro-Diagnostica, Sweden). Briefly, the test serum is incubated with an anti-C5 antibody, or antigen binding fragment thereof, in the presence of a human IgM antibody. The amount of C5b-9 that is generated is measured by contacting the mixture with an enzyme conjugated anti-C5b-9 antibody and a fluorogenic substrate and measuring the absorbance at the appropriate wavelength. As a control, the test serum is incubated in the absence of the anti-C5 antibody, or antigen binding fragment thereof. In some embodiments, the test serum is a C5-deficient serum reconstituted with a C5 polypeptide.

To determine the effect of an anti-C5 antibody, or antigen binding fragment thereof, on alternative pathway-mediated hemolysis, unsensitized rabbit or guinea pig erythrocytes can be used as the target cells. In some embodiments, the serum test solution is a C5-deficient serum reconstituted with a C5 polypeptide. The percentage of lysis is normalized by considering 100% lysis equal to the lysis occurring in the absence of the inhibitor. In some embodiments, the alternative complement pathway is activated by lipopolysaccharide molecules, for example, as utilized in the Wieslab® Alternative Pathway Complement Kit (Wieslab® COMPL AP330, Euro-Diagnostica, Sweden). Briefly, the test serum is incubated with an anti-C5 antibody, or antigen binding fragment thereof, in the presence of lipopolysaccharide. The amount of C5b-9 that is generated is measured by contacting the mixture with an enzyme conjugated anti-C5b-9 antibody and a fluorogenic substrate and measuring the fluorescence at the appropriate wavelength. As a control, the test serum is incubated in the absence of the anti-C5 antibody, or antigen binding fragment thereof.

In some embodiments, C5 activity, or inhibition thereof, is quantified using a CH50eq assay. The CH50eq assay is a method for measuring the total classical complement activity in serum. This test is a lytic assay, which uses antibody-sensitized erythrocytes as the activator of the classical complement pathway and various dilutions of the test serum to determine the amount required to give 50% lysis (CH50). The percent hemolysis can be determined, for example, using a spectrophotometer. The CH50eq assay provides an indirect measure of terminal complement complex (TCC) formation, since the TCC themselves are directly responsible for the hemolysis that is measured.

The assay is well known and commonly practiced by those of skill in the art. Briefly, to activate the classical complement pathway, undiluted serum samples (e.g., reconstituted human serum samples) are added to microassay wells containing the antibody-sensitized erythrocytes to thereby generate TCC. Next, the activated sera are diluted in microassay wells, which are coated with a capture reagent (e.g., an antibody that binds to one or more components of the TCC). The TCC present in the activated samples bind to the monoclonal antibodies coating the surface of the microassay wells. The wells are washed and to each well is added a detection reagent that is detectably labeled and recognizes the bound TCC. The detectable label can be, e.g., a fluorescent label or an enzymatic label. The assay results are expressed in CH50 unit equivalents per milliliter (CH50 U Eq/mL).

Inhibition, e.g., as it pertains to terminal complement activity, includes at least a 5 (e.g., at least a 6, 7, 8, 9, 10, 15, 20, 25, 30, 35, 40, 45, 50, 55, or 60) % decrease in the activity of terminal complement in, e.g., a hemolytic assay or CH50eq assay as compared to the effect of a control antibody (or antigen-binding fragment thereof) under similar conditions and at an equimolar concentration. Substantial inhibition, as used herein, refers to inhibition of a given activity (e.g., terminal complement activity) of at least 40 (e.g., at least 45, 50, 55, 60, 65, 70, 75, 80, 85, 90, or 95 or greater) %. In some embodiments, an anti-C5 antibody described herein contains one or more amino acid substitutions relative to the CDRs of eculizumab (i.e., SEQ ID NOs:1-6), yet retains at least 30 (e.g., at least 31, 32, 33, 34, 35, 36, 37, 38, 39, 40, 41, 42, 43, 44, 45, 46, 47, 48, 49, 50, 55, 60, 65, 70, 75, 80, 85, 90, or 95) % of the complement inhibitory activity of eculizumab in a hemolytic assay or CH50eq assay.

An anti-C5 antibody described herein has a serum half-life in humans that is at least 20 (e.g., at least 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55) days. In another embodiment, the anti-C5 antibody described herein has a serum half-life in humans that is at least 40 days. In another embodiment, the anti-C5 antibody described herein has a serum half-life in humans that is approximately 43 days. In another embodiment, the anti-C5 antibody described herein has a serum half-life in humans that is between 39-48 days. Methods for measuring the serum half-life of an antibody are known in the art. In some embodiments, an anti-C5 antibody, or antigen binding fragment thereof, described herein has a serum half-life that is at least 20 (e.g., at least 30, 35, 40, 45, 50, 55, 60, 65, 70, 75, 80, 85, 90, 95, 100, 125, 150, 175, 200, 250, 300, 400, 500) % greater than the serum half-life of eculizumab, e.g., as measured in one of the mouse model systems described in the working examples (e.g., the C5-deficient/NOD/scid mouse or hFcRn transgenic mouse model system).

In one embodiment, the antibody competes for binding with, and/or binds to the same epitope on C5 as, the antibodies described herein. The term "binds to the same epitope" with reference to two or more antibodies means that the antibodies bind to the same segment of amino acid residues, as determined by a given method. Techniques for determining whether antibodies bind to the "same epitope on C5" with the antibodies described herein include, for example, epitope mapping methods, such as, x-ray analyses of crystals of antigen:antibody complexes which provides atomic resolution of the epitope and hydrogen/deuterium exchange mass spectrometry (HDX-MS). Other methods monitor the binding of the antibody to peptide antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competing antibodies bind to the same epitope, an overlapping epitope or to adjacent epitopes (e.g., as evidenced by steric hindrance).

Anti-C5 antibodies, or antigen-binding fragments thereof described herein, used in the methods described herein can be generated using a variety of art-recognized techniques. Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, Eur. J. Immunol. 6: 511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., Science 246: 1275-1281 (1989).

III. Highly-Concentrated Anti-C5 Antibody Solutions

Provided herein are stable aqueous solutions comprising an anti-C5 antibody (e.g., ravulizumab). The aqueous solutions described herein can be sterile, pharmaceutical-grade compositions, e.g., for administration to a subject for the treatment or prevention of a complement-associated disorder, such as PNH or aHUS. The solutions described herein can be formulated according to standard methods. Pharmaceutical formulation is a well-established art, and is further described in, e.g., Gennaro (2000) "Remington: The Science and Practice of Pharmacy," $20^{th}$ Edition, Lippincott, Williams & Wilkins (ISBN: 0683306472); Ansel et al. (1999) "Pharmaceutical Dosage Forms and Drug Delivery Systems," $7^{th}$ Edition, Lippincott Williams & Wilkins Publishers (ISBN: 0683305727); and Kibbe (2000) "Handbook of Pharmaceutical Excipients American Pharmaceutical Association," $3^{rd}$ Edition (ISBN: 091733096X). Suitable formulation methods for the high concentration antibody solutions described herein are exemplified in the working examples.

The aqueous solutions described herein comprise a high concentration of an antibody that binds to human complement component C5, such as ravulizumab. Such solutions are sometimes referred to herein as "high concentration antibody solutions." As used herein, a "high concentration" of an anti-C5 antibody (e.g., ravulizumab) in an aqueous solution is a concentration of the antibody that is at least, equal to, or greater than, 40 (e.g., at least, equal to, or greater than, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300) mg/mL. In one embodiment, the anti-C5 antibody is present in the solution at a concentration of more than 100 (e.g., more than 105, 110, 115, 120, 125, 130, 135, 140, 145, 150, 155, 160, 165, 170, 175, 180, 185, 190, or 195) mg/mL. In another embodiment, the anti-C5 antibody is present in the solution at a concentration of more than 200 (e.g., more than 200, 205, 210, 215, 220, 225, 230, 235, 240, 245, 250, 255, 260, 265, 270, 275, 280, 285, 290, or 295) mg/mL. In another embodiment, the anti-C5 antibody is present in the solution at a concentration of more than 300 mg/mL. In another embodiment, the antibody is present in the solution at a concentration of, e.g., 40 mg/mL to 200 mg/mL, 50 mg/mL to 200 mg/mL, 60 mg/mL to 200 mg/mL, 70 mg/mL to 200 mg/mL, 80 mg/mL to 200 mg/mL, 90 mg/mL to 200 mg/mL, 100 mg/mL to 200 mg/mL, 110 mg/mL to 200 mg/mL, 120 mg/mL to 200 mg/mL, 130 mg/mL to 200 mg/mL, 140 mg/mL to 200 mg/mL, 150 mg/mL to 200 mg/mL, 40 mg/mL to 100 mg/mL, 50 mg/mL to 100 mg/mL, 60 mg/mL to 100 mg/mL, 70 mg/mL to 100 mg/mL, 80 mg/mL to 100 mg/mL, 90 mg/mL to 100 mg/mL, 40 mg/mL to 150 mg/mL, 50 mg/mL to 150 mg/mL, 60 mg/mL to 150 mg/mL, 70 mg/mL to 150 mg/mL, 80 mg/mL to 150 mg/mL, 90 mg/mL to 150 mg/mL, 100 mg/mL to 150 mg/mL, 110 mg/mL to 150 mg/mL, 120 mg/mL to 150 mg/mL, 40 mg/mL to 50 mg/mL, 40 mg/mL to 250 mg/mL, 50 mg/mL to 250 mg/mL, 60 mg/mL to 250 mg/mL, 70 mg/mL to 250 mg/mL, 80 mg/mL to 250 mg/mL, 90 mg/mL to 250 mg/mL, 100 mg/mL to 250 mg/mL, 110 mg/mL to 250 mg/mL, 120 mg/mL to 250 mg/mL, 130 mg/mL to 250 mg/mL, 140 mg/mL to 250 mg/mL, 150 mg/mL to 250 mg/mL, 160 mg/mL to 250 mg/mL, 170 mg/mL to 250 mg/mL, 180 mg/mL to 250 mg/mL, 190 mg/mL to 250 mg/mL, 200 mg/mL to 250 mg/mL, greater than 200 mg/mL (e.g., at least 201 mg/mL) to 250 mg/mL, or greater than 200 mg/mL (e.g., 201 mg/mL or greater) to 300 mg/mL.

As described herein and exemplified in the working examples, the featured aqueous solutions provide the anti-C5 antibody formulated therein with marked physical and chemical stability, as well as functional stability. For example, the formulations described herein are capable of maintaining the structural integrity of an anti-C5 antibody (e.g., ravulizumab) present at high concentrations in a solution. In one embodiment, the solution is suitable for storage at 2-8° C. (e.g., 4° C.). In another embodiment, the solution is formulated for storage at a temperature below 0° C. (e.g., −20° C. or −80° C.). In another embodiment, the solution is formulated for storage for up to three years (e.g., one month, two months, three months, four months, five months, six months, seven months, eight months, nine months, 10 months, 11 months, 1 year, 1½ years, 2 years, 2½ years, or 3 years) at 2-8° C. (e.g., 4° C.). In another embodiment, the solution is suitable for storage for at least 1, 2, or 3 years at 2-8° C. (e.g., 4° C.).

As exemplified in the working examples described herein, the solutions described herein are suitable for maintaining an anti-C5 antibody at approximately 100 mg/mL in predominantly monomeric form for up to two years at approximately 2° C. to 8° C. As used herein, an anti-C5 antibody formulated at a high concentration in a featured aqueous solution is "predominantly monomeric," or in "predominantly monomeric form," if the antibody present in the solution is at least 95 (e.g., at least 95.1, 95.2, 95.3, 95.4, 95.5, 95.6, 95.7, 95.8, 95.9, 96, 96.1, 96.2, 96.3, 96.4, 96.5, 96.6, 96.7, 96.8, 96.9, 97, 97.1, 97.2, 97.3, 97.4, 97.5, 97.6, 97.7, 97.8, 97.9, 98, 98.1, 98.2, 98.3, 98.4, 98.5, 98.6, 98.7, 98.8, 98.9, 99, 99.1, 99.2, 99.3, 99.4, 99.5, 99.6, 99.7, 99.8, or 99.9 or greater) % monomeric, e.g., as determined using size exclusion chromatography high performance liquid chromatography (SEC-HPLC, such as gel permeation HPLC). In one embodiment, the anti-C5 antibody in the solutions described here can remain predominantly monomeric after storage for at least one month (e.g., at least two months, three months, four months, five months, six months, seven months, eight months, nine months, 10 months, 11 months, 12 months, 13 months, 14 months, 15 months, 16 months, 17 months, 18 months, 19 months, 20 months, 21 months, 22 months, 23 months, 24 months, or more) at approximately 2° C. to 8° C. (e.g., storage at, e.g., 1, 2, 3, 4, 5, 6, 7, 8, 9, or 10° C.).

In one embodiment of any of the solutions described herein, the anti-C5 antibody (e.g., ravulizumab) remains at least 95 (e.g., at least 96, 97, 98, or 99)% monomeric during storage at 2° C. to 8° C. for at least six months as determined by SEC-HPLC (e.g., gel permeation HPLC). In another embodiment, the anti-C5 antibody remains at least 95 (e.g., at least 96, 97, 98, or 99)% monomeric during storage at 2° C. to 8° C. for at least nine months as determined by SEC-HPLC. In another embodiment, the anti-C5 antibody remains at least 95 (e.g., at least 96, 97, 98, or 99)% monomeric during storage at 2° C. to 8° C. for at least one year as determined by SEC-HPLC. In another embodiment, the anti-C5 antibody remains at least 95 (e.g., at least 96, 97, 98, or 99)% monomeric during storage at 2° C. to 8° C. for at least 18 months as determined by SEC-HPLC. In another embodiment, the anti-C5 antibody remains at least 95 (e.g., at least 96, 97, 98, or 99)% monomeric during storage at 2° C. to 8° C. for at least two years as determined by SEC-HPLC.

In another embodiment, less than 5 (e.g., less than 4.9. 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1) % of the antibody in the solution is oligomeric, aggregated, and/or fragmented. As used herein, antibody fragmentation refers to improperly assembled constituents or degradation products of a whole antibody having a lower molecular weight than the whole antibody. Such fragmentation forms include, but are not limited to, a free monomeric heavy chain polypeptide, a dimeric heavy chain polypeptide (e.g., disulfide-linked heavy chain polypeptide), a dimeric heavy chain polypeptide bound to one light chain polypeptide, a monomeric heavy chain polypeptide bound to one light chain polypeptide, or further degradation product(s) or fragment(s) of a light chain or heavy chain polypeptide. In some embodiments, less than 2 (e.g., less than 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1) % of the antibody is aggregated after storage for at least one month (e.g., at least two months, three months, four months, five months, six months, seven months, eight months, nine months, 10 months, 11 months, 12 months, 13 months, 14 months, 15 months, 16 months, 17 months, 18 months, 19 months, 20 months, 21 months, 22 months, 23 months, 24 months, or more) at 2° C. to 8° C. In some embodiments, less than 1 (e.g., less than 0.9, 0.8, 0.7, 0.6, 0.5, 0.4, 0.3, 0.2, or 0.1) % of the antibody is fragmented after storage for at least one month (e.g., at least two months, three months, four months, five months, six months, seven months, eight months, nine months, 10 months, 11 months, 12 months, 13 months, 14 months, 15 months, 16 months, 17 months, 18 months, 19 months, 20 months, 21 months, 22 months, 23 months, 24 months, or more) at 2° C. to 8° C. Methods for determining the amount of monomeric antibody, as well as the amount of oligomeric, aggregated, or fragmented forms of the anti-C5 antibody present in solution are described herein and exemplified in the working examples. For example, a skilled artisan can determine the percentage of whole, fragmented, unfolded intermediates, and/or aggregated antibody species present in a given solution using, e.g., size exclusion chromatography high-performance liquid chromatography (SEC-HPLC, such as gel permeation HPLC), static light scattering (SLS), Fourier transform infrared spectroscopy (FTIR), circular dichroism (CD), urea-induced protein unfolding techniques, intrinsic tryptophan fluorescence, non-reducing sodium dodecyl sulfate polyacrylamide gel electrophoresis (SDS-PAGE), and differential scanning calorimetry (DSC).

In one embodiment of any of the solutions described herein, less than 5% of the anti-C5 antibody (e.g., ravulizumab) in the solution is aggregated as determined by SEC-HPLC (e.g., gel permeation HPLC). In another embodiment, less than 4% of the anti-C5 antibody in the solution is aggregated as determined by SEC-HPLC. In another embodiment, less than 3% of the anti-C5 antibody in the solution is aggregated as determined by SEC-HPLC. In another embodiment, less than 2% of the anti-C5 antibody in the solution is aggregated as determined by SEC-HPLC. In another embodiment, less than 1% of the anti-C5 antibody in the solution is aggregated as determined by SEC-HPLC.

As described herein and exemplified in the working examples, the anti-C5 antibody containing solutions featured herein can retain at least 90 (e.g., 91, 92, 93, 94, 95, 96, 97, 98, 99, or even 100) % of their biological/functional activity (e.g., ability to bind to human C5) after storage for at least one month (e.g., at least two months, three months, four months, five months, six months, seven months, eight months, nine months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, 36 months or more) at 2° C. to 8° C.

In another embodiment, anti-C5 antibody (e.g., ravulizumab) present in a solution described herein can retain, at least 90 (e.g., 91, 92, 93, 94, 95, 96, 97, 98, 99, or even 100) % of its activity to inhibit hemolysis after storage for at least one month (e.g., at least two months, three months, four months, five months, six months, seven months, eight months, nine months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, 36 months or more at 2° C. to 8° C. Suitable hemolytic assay methods for determining whether an antibody in a featured solution retains its activity are described herein and known in the art, e.g., in vitro hemolytic assays using avian or porcine erythrocytes. Suitable methods for evaluating the ability of an antibody preparation to bind to human complement component C5 are known in the art and described herein.

In another embodiment of any of the solutions described herein, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its C5-binding activity during storage at 2° C. to 8° C. for at least six months, as compared to a reference anti-C5 antibody corresponding to the anti-C5 antibody prior to storage. In another embodiment, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its C5-binding activity during storage at 2° C. to 8° C. for at least nine months, as compared to a reference anti-C5 antibody corresponding to the anti-C5 antibody prior to storage. In another embodiment, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its C5-binding activity during storage at 2° C. to 8° C. for at least one year, as compared to a reference anti-C5 antibody corresponding to the anti-C5 antibody prior to storage. In another embodiment, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its C5-binding activity during storage at 2° C. to 8° C. for at least eighteen months, as compared to a reference anti-C5 antibody corresponding to the anti-C5 antibody prior to storage. In another embodiment, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its C5-binding activity during storage at 2° C. to 8° C. for at least two years, as compared to a reference anti-C5 antibody corresponding to the anti-C5 antibody prior to storage.

In another embodiment, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its C5-binding activity during storage at 2° C. to 8° C. for at least three years, as compared to a reference anti-C5 antibody corresponding to the anti-C5 antibody prior to storage.

In another embodiment of any of the solutions described herein, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its ability to inhibit hemolysis during storage at 2° C. to 8° C. for at least nine months, as compared to a reference anti-C5 antibody corresponding to the anti-C5 antibody prior to storage. In another embodiment of any of the solutions described herein, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its ability to inhibit hemolysis during storage at 2° C. to 8° C. for at least six months, as compared to a reference anti-C5 antibody corresponding to the anti-C5 antibody prior to storage. In another embodiment of any of the solutions described herein, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its ability to inhibit hemolysis during storage at 2° C. to 8° C. for at least one year, as compared to a reference anti-C5 antibody corresponding to the anti-C5 antibody prior to storage. In another embodiment of any of the solutions described herein, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its ability to inhibit hemolysis during storage at 2° C. to 8° C. for at least 18 months, as compared to a reference anti-C5 antibody corresponding to the anti-C5 antibody prior to storage. In another embodiment of any of the solutions described herein, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its ability to inhibit hemolysis during storage at 2° C. to 8° C. for at least two years, as compared to a reference anti-C5 antibody corresponding to the anti-C5 antibody prior to storage. In another embodiment of any of the solutions described herein, the anti-C5 antibody (e.g., ravulizumab) retains at least 80 (e.g., at least 81, 82, 83, 84, 85, 86, 87, 88, 89, 90, 91, 92, 93, 94, 95, 96, 97, 98, or 99)% of its ability to inhibit hemolysis during storage at 2° C. to 8° C. for at least three years, as compared to a reference anti-C5 antibody corresponding to the anti-C5 antibody prior to storage.

The aqueous solutions described herein can contain one or more common agents (e.g., one or more excipients and/or additives, such as buffering agents, sugars or saccharides, salts, surfactants, solubilizers, diluents, binders, stabilizers, salts, lipophilic solvents, amino acids, chelators, and/or preservatives).

In one embodiment, the aqueous solution contains one or more buffering agents. As used herein, the term "buffering agent" refers to one or more components that when added to an aqueous solution is able to protect the solution against variations in pH when adding acid or alkali, or upon dilution with a solvent. In one embodiment, the solution comprises at least one or more buffering agents. Non-limiting examples of typical buffers that can be included in the wash solution(s) include Tris (tris(hydroxymethyl)methylamine), bis-Tris, bis-Tris propane, histidine, triethanolamine, diethanolamine, formate, acetate, MES (2-(N-morpholino)ethanesulfonic acid), phosphate, HEPES (4-2-hydroxyethyl-1-piperazineethanesulfonic acid), citrate, MOPS (3-(N-morpholino) propanesulfonic acid), TAPS (3{[tris(hydroxymethyl) methyl]amino}propanesulfonic acid), Bicine (N,N-bis(2-hydroxyethyl)glycine), Tricine (N-tris(hydroxymethyl) methylglycine), TES (2-{[tris(hydroxymethyl)methyl] amino}ethanesulfonic acid), PIPES (piperazine-N,N'-bis(2-ethanesulfonic acid), cacodylate (dimethylarsinic acid) SSC (saline sodium citrate), and sodium phosphate.

In another embodiment, the buffering agent is an amino acid. The amino acid can be, e.g., one selected from the group consisting of histidine (e.g., L-histidine), serine (e.g., L-serine), and glycine (e.g., L-glycine). In another embodiment, the solution comprises two or more buffering agents. In a particular embodiment, the buffering agent is sodium phosphate. In one embodiment, the featured solutions do not include a free amino acid as a buffering agent. In another embodiment, the featured solutions include but one free amino acid (e.g., histidine) as a buffering agent. In another embodiment, the featured solutions can include two or more (e.g., two, three, four, five, six, or seven or more) different amino acids as buffering agents, e.g., serine and histidine.

The concentration of the buffer is sufficient to maintain the desired pH and may also be varied, for example, to maintain the isotonicity of the formulation. Typical concentrations of conventional buffering agents employed in parenteral formulations can be found in: Pharmaceutical Dosage Form: Parenteral Medications, Volume 1, 2nd Edition, Chapter 5, p. 194, De Luca and Boylan, "Formulation of Small Volume Parenterals", Table 5: Commonly used additives in Parenteral Product. In one embodiment, the concentration of the one or more buffering agents in the formulation is about 10 mM to 300 mM, inclusive. In another embodiment, the solution comprises at least one buffering agent at a concentration of 10 mM to 200 mM, inclusive. In another embodiment, the aqueous solution described herein contains a buffering agent at a concentration of at least 10 (e.g., at least 15, 20, 25, 30, 35, 40, 50, 60, 70, 80, 90, 100, 110, 120, 130, 140, 150, 160, 170, 180, 190, 200, 210, 220, 230, 240, 250, 260, 270, 280, 290, or 300 or more) mM. In another embodiment, the aqueous solution includes a buffering agent at a concentration of between about 10 mM to 50 mM, 15 mM to 50 mM, 20 mM to 50 mM, 25 mM to 50 mM, 30 mM to 50 mM, 40 mM to 50 mM, 10 mM to 100 mM, 15 mM to 100 mM, 20 mM to 100 mM, 25 mM to 100 mM, 30 mM to 100 mM, 40 mM to 100 mM, 10 mM to 150 mM, 15 mM to 150 mM, 20 mM to 150 mM, 25 mM to 150 mM, 30 mM to 150 mM, 40 mM to 150 mM, 50 mM to 100 mM, 60 mM to 100 mM, 70 mM to 100 mM, 80 mM to 100 mM, 50 mM to 150 mM, 60 mM to 150 mM, 70 mM to 150 mM, 80 mM to 150 mM, 90 mM to 150 mM, 100 mM to 150 mM, 10 mM to 200 mM, 15 mM to 200 mM, 20 mM to 200 mM, 25 mM to 200 mM, 30 mM to 200 mM, 40 mM to 200 mM, 50 mM to 200 mM, 60 mM to 200 mM, 70 mM to 200 mM, 80 mM to 200 mM, 90 mM to 200 mM, 100 mM to 200 mM, 150 mM to 200 mM, 10 mM to 250 mM, 15 mM to 250 mM, 20 mM to 250 mM, 25 mM to 250 mM, 30 mM to 250 mM, 40 mM to 250 mM, 50 mM to 250 mM, 60 mM to 250 mM, 70 mM to 250 mM, 80 mM to 250 mM, 90 mM to 250 mM, 100 mM to 250 mM, 150 mM to 250 mM, or 200 mM to 250 mM. In another embodiment, the concentration of the buffer in the formulation is about 20 mM, 25 mM, 30 mM, 35 mM, 40 mM, 45 mM, 50 mM, 55 mM, 60 mM, 65 mM, 70 mM, 75 mM, 80 mM, 90 mM, 95 mM or about 100 mM. In another embodiment, the buffering agent is present in the solution at a concentration of at least, or equal to, 20 mM. In another embodiment, buffering agent is present in the solution at a concentration of at least, or equal to, 25 mM. In another embodiment, buffering agent is present in the solution at a concentration of at least, or equal to, 50 mM. In embodiments where a featured solution contains two or more (e.g., at least two, three, four, five, six, seven, eight, nine, or 10 or more) different buffering agents, each of the two or more buffering agents can independently be present at, e.g., one of the above described concentrations.

In one embodiment, the aqueous solution has, or can be adjusted to have, a neutral pH. As used herein, "neutral pH" is a pH that is between, and inclusive of, 7 and 8. Accordingly, as used herein neutral pH is inclusive of particular pH values such as 7, 7.1, 7.2, 7.3, 7.4, 7.5, 7.6, 7.7, 7.8, 7.9, and 8.0. In some embodiments, neutral pH is at least pH 7 (e.g., at least pH 7.1, 7.2, 7.3, 7.4, 7.5, 7.6, 7.7, 7.7 or 7.9), but less than pH 8 (e.g., less than pH 7.9, 7.8, 7.7, 7.6, 7.5, 7.4, 7.3, 7.2, or 7.1). That is, in some embodiments neutral pH can be, e.g., at least pH 7, but less than pH 7.5. In some embodiments, neutral pH can be between pH 7 and pH 7.5. In some embodiments, neutral pH can be between pH 7 and pH 7.2. In another embodiment, the pH of the solution is between 7.0 and 7.4. In another embodiment, the pH of the solution is between 7.2 and 7.8. In another embodiment, the pH of the solution is between 7.2 and 7.6. In some embodiments, neutral pH can be, e.g., pH 7. One of skill in the art will also appreciate that human blood (such as human blood from a healthy patient) has a neutral pH as defined herein, e.g., the pH of human blood is approximately pH 7.35 to pH 7.45. See, e.g., Boron and Boulpaep (2003) "Medical physiology: a cellular and molecular approach," W.B. Saunders, New York (ISBN:0721632564). In some embodiments, the pH of a highly-concentrated antibody solution described herein is between approximately 6.4 and 7.5, inclusive (e.g., approximately 6.2, 6.3, 6.4, 6.5, 6.6, 6.7, 6.8. 6.9, 7, 7.1, 7.2, 7.3, 7.4, 7.5, 7.6, or 7.7). In one embodiment, the pH of the solution is between 7.2 and 7.6. In a particular embodiment, the pH of the solution is 7.4.

In one embodiment, the solution contains one or more surfactants, such as an anionic, cationic, or nonionic surfactant. As used herein, the term "surfactant" refers to a surface active molecule containing both a hydrophobic portion (e.g., alkyl chain) and a hydrophilic portion (e.g., carboxyl and carboxylate groups). Surfactants suitable for use in the formulations of the present invention include, but are not limited to fatty acid esters (e.g., sorbitan monocaprylate, sorbitan monolaurate, sorbitan monopalmitate), sorbitan trioleate, glycerine fatty acid esters (e.g., glycerine monocaprylate, glycerine monomyristate, glycerine monostearate), polyglycerine fatty acid esters (e.g., decaglyceryl monostearate, decaglyceryl distearate, decaglyceryl monolinoleate), polyoxyethylene sorbitan fatty acid esters (e.g., polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate), polyoxyethylene sorbitol fatty acid esters (e.g., polyoxyethylene sorbitol tetrastearate, polyoxyethylene sorbitol tetraoleate), polyoxyethylene glycerine fatty acid esters (e.g., polyoxyethylene glyceryl monostearate), polyethylene glycol fatty acid esters (e.g., polyethylene glycol distearate), polyoxyethylene alkyl ethers (e.g., polyoxyethylene lauryl ether), polyoxyethylene polyoxypropylene alkyl ethers (e.g., polyoxyethylene polyoxypropylene glycol, polyoxyethylene polyoxypropylene propyl ether, polyoxyethylene polyoxypropylene cetyl ether), polyoxyethylene alkylphenyl ethers (e.g., polyoxyethylene nonylphenyl ether), polyoxyethylene hydrogenated castor oils (e.g., polyoxyethylene castor oil, polyoxyethylene hydrogenated castor oil), polyoxyethylene beeswax derivatives (e.g., polyoxyethylene sorbitol beeswax), polyoxyethylene lanolin derivatives (e.g., polyoxyethylene lanolin), and polyoxyethylene fatty acid amides (e.g., polyoxyethylene stearic acid amide); C12-C18 alkyl sulfates (e.g., sodium cetyl sulfate, sodium lauryl sulfate, sodium oleyl sulfate), polyoxyethylene C10-C18 alkyl ether sulfate with an average of 2 to 4 moles of ethylene oxide units added (e.g., sodium polyoxyethylene lauryl sulfate), and C10-C18 alkyl sulfosuccinate ester salts (e.g., sodium lauryl sulfosuccinate ester); and natural surfactants such as lecithin, glycerophospholipid, sphingophospholipids (e.g., sphingomyelin), and sucrose esters of C12-C18 fatty acids.

In one embodiment, the surfactant in the formulation is a non-ionic surfactant. In certain embodiments, the surfactant in the formulation is a polyoxyethylene sorbitan fatty acid ester, for example, polysorbate 20, 40, 60, 80, or a combination of one or more thereof. In one embodiment, the surfactant in the formulation is polysorbate 80 (Tween 80). In another embodiment, the surfactant in the formulation is polysorbate 60. In another embodiment, the surfactant in the formulation is polysorbate 40. In another embodiment, the surfactant in the formulation is polysorbate 20 (Tween 20).

The amount of surfactant added to the formulation is sufficient to reduce aggregation of the formulated antibody and/or minimize the formation of particulates in the formulation. For example, the surfactant may be present in the formulation in an amount from about 0.001% to about 1%, or about 0.001% to about 0.5%, or about 0.01% to about 0.2%. In one embodiment, the aqueous solutions contain a surfactant at a concentration of at least, or approximately, 0.001 (e.g., at least, or approximately, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, or 0.5 or more) %. In another embodiment, the aqueous solution contains no more than 0.2 (e.g., no more than 0.19, 0.18, 0.17, 0.16, 0.15, 0.14, 0.13, 0.12, 0.11, 0.10, 0.09, 0.08, 0.07, 0.06, 0.05, 0.04, 0.03, 0.02, 0.01, 0.009, 0.008, 0.007, 0.006, 0.005, 0.004, 0.003, 0.002, or 0.001) % of a pharmaceutically-acceptable surfactant.

In another embodiment, the formulations comprise polysorbate at a concentration from about 0.001% to about 0.5%, from about 0.005% to about 0.2%, from about 0.01% to about 0.1%, or from about 0.02% to about 0.06%, or about 0.03% to about 0.05% (w/v). In certain embodiments, the formulation comprises a polysorbate at a concentration of 0.01%, or 0.02%, or 0.03%, or 0.04%, or 0.05%, or 0.06%, or 0.07%, or 0.08%, or 0.09%, or 0.1%, or 0.15%, or 0.2% (w/v). In certain embodiments, the surfactant is present in the formulation in an amount of 0.02% or about 0.04% (w/v). In one embodiment, the surfactant is present in the formulation in an amount of 0.05% (w/v).

In one embodiment, the formulation comprises at least about 0.01%, at least about 0.02%, at least about 0.05%, at least about 0.1%, at least about 0.2%, at least about 0.3%, at least about 0.4%, or at least about 0.5% Polysorbate 80. In certain embodiment, the formulation comprises between about 0.01% and about 0.5%, between about 0.01% and about 0.3%, between about 0.001% and about 0.2%, between about 0.02% and about 0.5%, between about 0.02% and about 0.3%, between about 0.02% and about 0.2%, between about 0.05% and about 0.5%, between about 0.05% and about 0.3%, between about 0.05% and about 0.2%, between about 0.075% and about 0.5%, between about 0.075% and about 0.3%, or between about 0.075% and about 0.2% Polysorbate 80. In a further embodiment, the formulation comprises about 0.01%, about 0.02%, about 0.05%, about 0.1%, about 0.2%, about 0.3%, about 0.4%, or about 0.5% Polysorbate 80. In one embodiment, the formulation comprises about 0.05% polysorbate 80. In one embodiment, the formulation comprises about comprises about 0.04% polysorbate 80. In one embodiment, the formulation comprises about 0.03% polysorbate 80. In one embodiment, the formulation comprises about 0.02% polysorbate 80. In one embodiment, the formulation comprises about 0.01% polysorbate 80.

In one embodiment, the aqueous solution contains one or more salts, e.g., sodium chloride, potassium chloride, or magnesium chloride. In some embodiments, an aqueous solution described herein contains a salt at a concentration of at least 10 (e.g., at least 15, 20, 25, 30, 35, 40, 50, 60, 70, 80, 90, 100, 110, 120, 130, 140, 150, 160, 170, 180, 190, 200, 210, 220, 230, 240, 250, 260, 270, 280, 290, or 300 or more) mM. In some embodiments, an aqueous solution described herein can include a salt at a concentration of less than, or approximately, 200 (e.g., less than, or approximately, 190, 180, 170, 160, 150, 140, 130, 120, 110, 100, 90, 80, 70, 60, 50, 40, 30, 25, 20, 15, or 10) mM. In some embodiments, an aqueous solution described herein can include a salt at a concentration of between about 10 mM to 50 mM, 15 mM to 50 mM, 20 mM to 50 mM, 25 mM to 50 mM, 30 mM to 50 mM, 40 mM to 50 mM, 10 mM to 100 mM, 15 mM to 100 mM, 20 mM to 100 mM, 25 mM to 100 mM, 30 mM to 100 mM, 40 mM to 100 mM, 10 mM to 150 mM, 15 mM to 150 mM, 20 mM to 150 mM, 25 mM to 150 mM, 30 mM to 150 mM, 40 mM to 150 mM, 50 mM to 100 mM, 60 mM to 100 mM, 70 mM to 100 mM, 80 mM to 100 mM, 50 mM to 150 mM, 60 mM to 150 mM, 70 mM to 150 mM, 80 mM to 150 mM, 90 mM to 150 mM, 100 mM to 150 mM, 10 mM to 200 mM, 15 mM to 200 mM, 20 mM to 200 mM, 25 mM to 200 mM, 30 mM to 200 mM, 40 mM to 200 mM, 50 mM to 200 mM, 60 mM to 200 mM, 70 mM to 200 mM, 80 mM to 200 mM, 90 mM to 200 mM, 100 mM to 200 mM, 150 mM to 200 mM, 10 mM to 250 mM, 15 mM to 250 mM, 20 mM to 250 mM, 25 mM to 250 mM, 30 mM to 250 mM, 40 mM to 250 mM, 50 mM to 250 mM, 60 mM to 250 mM, 70 mM to 250 mM, 80 mM to 250 mM, 90 mM to 250 mM, 100 mM to 250 mM, 150 mM to 250 mM, or 200 mM to 250 mM. In embodiments where a featured solution contains two or more (e.g., at least two, three, four, five, six, seven, eight, nine, or 10 or more) different salts, each of the two or more salts can independently be present at, e.g., one of the above described concentrations.

In one embodiment, the aqueous solution contains one or more carbohydrate excipients. Suitable carbohydrate excipients are described in, e.g., Katakam and Banga (1995) *J Pharm Pharmacol* 47(2):103-107; Andya et al. (2003) *AAPS PharmSci* 5(2: Article 10; and Shire (2009) "Current Trends in Monoclonal Antibody Development and Manufacturing," Volume 11, Springer, 354 pages. Carbohydrate excipients suitable for use in the solutions described herein include, without limitation, monosaccharides such as fructose, maltose, galactose, glucose, D-mannose, and sorbose; disaccharides such as lactose, sucrose, trehalose, and cellobiose; polysaccharides such as maltodextrins, dextrans, and starches; and sugar alcohols such as mannitol, xylitol, maltitol, lactitol, and sorbitol. In one embodiment, a carbohydrate excipient is present in a solution featured herein at a concentration of at least, or approximately, 0.5 (e.g., at least, or approximately, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.25, 3.5, 3.75, 4, 4.25, 4.5, 4.75, 5, 5.5, 6, 6.5, 7, 7.5, 8, 8.5, 9, 9.5, 10, or more) %. In embodiments where a featured solution contains two or more (e.g., at least two, three, four, five, six, seven, eight, nine, or 10 or more) different carbohydrate excipients, each excipient can, independently, be present at any of the above-described concentrations.

In another embodiment, the stable aqueous solution comprises one or more stabilizing agents. Exemplary stabilizers include, but are not limited to polyols, sugars (e.g., sucrose or trehalose), amino acids (e.g., arginine), amines, and salting out salts. In one embodiment, the solution comprises at least one stabilizing agent at a concentration of 2-10%, inclusive. In one embodiment the solution comprises 5% sucrose. In another embodiment, the solution comprises at least one or more stabilizing agents at a concentration of 10 mM to 50 mM, inclusive. In another embodiment, the stabilizing agent is present in the solution at a concentration of at least, or equal to, 20 mM. In another embodiment, the stabilizing agent is present in the solution at a concentration of at least, or equal to, 25 mM. In another embodiment, the stabilizing agent is present in the solution at a concentration of at least, or equal to, 50 mM. In another embodiment, the solution comprises 25 mM arginine.

In one embodiment, the solutions described herein contain one or more preservatives. As used herein, the term "preservative" refers to an agent that reduces bacterial action and may be optionally added to the formulations herein. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3pentanol, and m-cresol.

In one embodiment, the stable aqueous solution comprises no more than five agents in addition to the anti-C5 antibody. In another embodiment, the stable aqueous solution comprises no more than four agents in addition to the anti-C5 antibody. In another embodiment, the stable aqueous solution comprises no more than three agents in addition to the anti-C5 antibody. In another embodiment, the stable aqueous solution comprises no more than two agents in addition to the anti-C5 antibody. In another embodiment, the stable aqueous solution comprises no more than one agent in addition to the anti-C5 antibody.

In one embodiment, the stable aqueous solution comprises an anti-C5 antibody comprising a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6 at a concentration of 100±20 (e.g., 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120) mg/mL; 50±15 (e.g., 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65) mM phosphate buffer; 5±3 (e.g., 2, 3, 4, 5, 6, 7, or 8) % sucrose; and 25±10 (e.g., 15, 16, 17, 18, 19, 20, 21, 22, 23, 24, 25, 26, 27, 28, 29, 30, 31, 32, 33, 34, or 35) mM arginine; wherein the solution has a pH of 7.4±0.5 (e.g., 6.9, 7, 7.1, 7.2, 7.3, 7.4, 7.5, 7.6, 7.7, 7.8, or 7.9).

In another embodiment, the stable aqueous solution consists of an anti-C5 antibody comprising a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6 at a concentration of 100±20 (e.g., 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120) mg/mL; 50±15 (e.g., 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65) mM phosphate buffer; 5±3 (e.g., 2, 3, 4, 5, 6, 7, or 8) % sucrose; and 25±10 (e.g., 15, 16, 17, 18, 19, 20, 21, 22, 23, 24, 25, 26, 27, 28, 29, 30, 31, 32, 33, 34, or 35) mM arginine; wherein the solution has a pH of 7.4±0.5 (e.g., 6.9, 7, 7.1, 7.2, 7.3, 7.4, 7.5, 7.6, 7.7, 7.8, or 7.9).

In another embodiment, the stable aqueous solution comprises an anti-C5 antibody comprising a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6 at a concentration of 100±20 (e.g., 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120) mg/mL; 50±15 (e.g., 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65) mM phosphate buffer; 5±3 (e.g., 2, 3, 4, 5, 6, 7, or 8) % sucrose; 25±10 (e.g., 15, 16, 17, 18, 19, 20, 21, 22, 23, 24, 25, 26, 27, 28, 29, 30, 31, 32, 33, 34, or 35) mM arginine; and 0.05±0.03 (e.g., 0.02, 0.03, 0.04, 0.05, 0.06, 0.07, and 0.08)% polysorbate 80, wherein the solution has a pH of 7.4±0.5 (e.g., 6.9, 7, 7.1, 7.2, 7.3, 7.4, 7.5, 7.6, 7.7, 7.8, or 7.9).

In another embodiment, the stable aqueous solution consists of an anti-C5 antibody comprising a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6 at a concentration of 100±20 (e.g., 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120) mg/mL; 50±15 (e.g., 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65) mM phosphate buffer; 5±3 (e.g., 2, 3, 4, 5, 6, 7, or 8) % sucrose; 25±10 (e.g., 15, 16, 17, 18, 19, 20, 21, 22, 23, 24, 25, 26, 27, 28, 29, 30, 31, 32, 33, 34, or 35) mM arginine; and 0.05±0.03 (e.g., 0.02, 0.03, 0.04, 0.05, 0.06, 0.07, and 0.08)% polysorbate 80, wherein the solution has a pH of 7.4±0.5 (e.g., 6.9, 7, 7.1, 7.2, 7.3, 7.4, 7.5, 7.6, 7.7, 7.8, or 7.9).

In another embodiment, a stable aqueous solution is provided (e.g., a sterile solution), wherein the solution comprises (a) an anti-C5 antibody (e.g., ravulizumab) at a concentration of about 100 mg/mL, (b) about 50 mM Phosphate Buffer; (c) about 5% sucrose; and (d) about 25 mM Arginine. In another embodiment, the stable aqueous solution comprises a) an anti-C5 antibody (e.g., ravulizumab) at a concentration of 100 mg/mL, (b) 50 mM Phosphate Buffer; (c) 5% sucrose; and (d) 25 mM Arginine.

In another embodiment, the stable aqueous solution comprises (a) an anti-C5 antibody at a concentration of about 100 mg/mL, (b) about 50 mM Phosphate Buffer, (c) about 5% sucrose, (d) about 0.05% Polysorbate 80, and (e) about 25 mM Arginine. In another embodiment, the stable aqueous solution comprises a) an anti-C5 antibody at a concentration of 100 mg/mL, (b) 50 mM Phosphate Buffer, (c) 5% sucrose, (d) 0.05% Polysorbate 80, and (e) 25 mM Arginine.

In another embodiment, the stable aqueous solution comprises no more than three additional agents. In another embodiment, the stable aqueous solution comprises no more than two additional agents. In another embodiment, the stable aqueous solution comprises no more than one additional agent.

In another embodiment, the stable aqueous solution consists of (a) an anti-C5 antibody at a concentration of about 100 mg/mL, (b) about 50 mM Phosphate Buffer, (c) about 5% sucrose, and (d) about 25 mM Arginine. In another embodiment, the stable aqueous solution consists of (a) an anti-C5 antibody at a concentration of 100 mg/mL, (b) 50 mM Phosphate Buffer; (c) 5% sucrose, and (d) 25 mM Arginine.

In another embodiment, the stable aqueous solution consists of (a) an anti-C5 antibody at a concentration of about 100 mg/mL, (b) about 50 mM Phosphate Buffer, (c) about 5% sucrose; (d) about 0.05% Polysorbate 80, and (e) about 25 mM Arginine. In another embodiment, the stable aqueous solution consists of (a) an anti-C5 antibody at a concentration of 100 mg/mL, (b) 50 mM Phosphate Buffer, (c) 5% sucrose, (d) 0.05% Polysorbate 80, and (e) 25 mM Arginine.

In one embodiment, the stable aqueous solution comprises: (a) an anti-C5 antibody at a concentration of about 100 mg/mL, wherein the anti-C5 antibody comprises a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6, (b) about 50 mM Phosphate Buffer, (c) about 5% sucrose, and (d) about 25 mM Arginine.

In another embodiment, the stable aqueous solution comprises: (a) an anti-C5 antibody at a concentration of 100 mg/mL, wherein the anti-C5 antibody comprises a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6, (b) 50 mM Phosphate Buffer, (c) 5% sucrose; and (d) 25 mM Arginine.

In another embodiment, the stable aqueous solution comprises: (a) an anti-C5 antibody at a concentration of about 100 mg/mL, wherein the anti-C5 antibody comprises a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6, (b) about 50 mM Phosphate Buffer, (c) about 5% sucrose, (d) about 0.05% Polysorbate 80, and (e) about 25 mM Arginine.

In another embodiment, the stable aqueous solution comprises: (a) an anti-C5 antibody at a concentration of 100 mg/mL, wherein the anti-C5 antibody comprises a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6, (b) 50 mM Phosphate Buffer, (c) 5% sucrose, (d) 0.05% Polysorbate 80, and (e) about 25 mM Arginine.

In another embodiment, the stable aqueous solution consists of: (a) an anti-C5 antibody at a concentration of about 100 mg/mL, wherein the anti-C5 antibody comprises a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6, (b) about 50 mM Phosphate Buffer, (c) about 5% sucrose, (d) about 0.05% Polysorbate 80, and (e) about 25 mM Arginine.

In another embodiment, the stable aqueous solution consists of: (a) an anti-C5 antibody at a concentration of 100 mg/mL, wherein the anti-C5 antibody comprises a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6; (b) 50 mM Phosphate Buffer, (c) 5% sucrose, (d) 0.05% Polysorbate 80, and (e) 25 mM Arginine.

IV. Methods for Preparing the Highly-Concentrated Antibody Solutions

Also provided herein are methods for preparing a highly-concentrated anti-C5 antibody solution. In one embodiment, methods for producing a stable concentrated antibody solution comprising an anti-C5 antibody at a concentration of 100 mg/mL, 50 mM Phosphate Buffer, 5% sucrose; and 25 mM Arginine are provided, the method comprising:

i) providing a first aqueous solution comprising the anti-C5 antibody, the first aqueous solution having a first formulation and comprising no more than 10 mg/mL of the anti-C5 antibody;

ii) subjecting the first aqueous solution to diafiltration into a formulation comprising 50 mM Phosphate Buffer, 5% sucrose, and 25 mM Arginine at pH 7.4 to thereby produce a second aqueous solution, wherein the second aqueous solution has a second formulation as a result of the diafiltration; and iii) concentrating the second aqueous solution to produce a stable concentrated antibody solution comprising 100 mg/mL of the anti-C5 antibody, 50 mM Phosphate Buffer, 5% sucrose; and 25 mM Arginine.

In another embodiment, a method for producing a stable concentrated antibody solution comprising an anti-C5 antibody at a concentration of 100 mg/mL, 50 mM Phosphate Buffer, 5% sucrose; 25 mM Arginine, and 0.05% Polysorbate 80, is provided, the method comprising:

i) providing a first aqueous solution comprising the anti-C5 antibody, the first aqueous solution having a first formulation and comprising no more than 10 mg/mL of the anti-C5 antibody;

ii) subjecting the first aqueous solution to diafiltration into a formulation comprising 50 mM Phosphate Buffer, 5% sucrose, 25 mM Arginine, and 0.05% Polysorbate 80, at pH 7.4 to thereby produce a second aqueous solution, wherein the second aqueous solution has a second formulation as a result of the diafiltration; and iii) concentrating the second aqueous solution to produce a stable concentrated antibody solution comprising 100 mg/mL of the anti-C5 antibody, 50 mM Phosphate Buffer, 5% sucrose, 25 mM Arginine, and 0.05% Polysorbate 80.

V. Routes of Administration

The solutions described herein can be administered to a patient using a variety of methods that depend, in part, on the route of administration. The route can be a parenteral mode, e.g., intravenous injection or infusion (IV), subcutaneous injection (SC), intraperitoneal (IP) injection, intraocular injection, intraarticular injection, or intramuscular injection (IM). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion.

In a particular embodiment, the solution is administered via subcutaneous injection. Subcutaneous administration can be accomplished by means of a device. The device means may be a syringe, a prefilled syringe, an auto-injector either disposable or reusable, a pen injector, a patch injector, a wearable injector, an ambulatory syringe infusion pump with subcutaneous infusion sets or other device.

In one embodiment, a solution described herein is delivered to a subject by way of local administration. As used herein, "local administration" or "local delivery," refers to delivery that does not rely upon transport of the composition or active agent (e.g., an anti-C5 antibody) to its intended target tissue or site via the vascular system. Following local administration in the vicinity of a target tissue or site, the solution, or one or more components thereof, may diffuse to the intended target tissue or site.

For example, the solution may be delivered by injection or via implantation of a device containing the solution. The implant can be of a porous, non-porous, or gelatinous material, including membranes, such as sialastic membranes, or fibers. The implant can be configured for sustained or periodic release of the solution to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. A solution described herein can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

In one embodiment, a solution described herein can be locally administered to a joint (e.g., an articulated joint). For example, in embodiments where the disorder is arthritis, a therapeutically appropriate solution can be administered directly to a joint (e.g., into a joint space) or in the vicinity of a joint. Examples of intraarticular joints to which a composition described herein can be locally administered include, e.g., the hip, knee, elbow, wrist, sternoclavicular, temperomandibular, carpal, tarsal, ankle, and any other joint subject to arthritic conditions. A composition described herein can also be administered to bursa such as, e.g., acromial, bicipitoradial, cubitoradial, deltoid, infrapatellar, ischial, and any other bursa known in the art of medicine.

In another embodiment, a solution described herein can be locally administered to the eye. As used herein, the term "eye" refers to any and all anatomical tissues and structures associated with an eye. In one embodiment, a solution described herein is administered to the posterior chamber of the eye. In another embodiment, a solution described herein is administered intravitreally. In another embodiment, a solution described herein is administered trans-sclerally.

In some embodiments, e.g., in embodiments for treatment or prevention of a disorder such as COPD or asthma, a solution described herein can be administered to a subject by way of the lung. Pulmonary drug delivery may be achieved by inhalation, and administration by inhalation herein may be oral and/or nasal. In one embodiment, a solution as described herein can be administered to the lungs of a subject by way of a nebulizer. Nebulizers use compressed air to deliver a compound as a liquefied aerosol or mist. A nebulizer can be, e.g., a jet nebulizer (e.g., air or liquid-jet nebulizers) or an ultrasonic nebulizer. Additional devices and intrapulmonary administration methods are set forth in, e.g., U.S. Patent Application Publication Nos. 20050271660 and 20090110679, the disclosures of each of which are incorporated herein by reference in their entirety.

In another embodiments, the solutions described herein are present in unit dosage form, which can be particularly suitable for self-administration. A formulated product of the present disclosure can be included within a container, typically, for example, a vial, cartridge, prefilled syringe or disposable pen. A doser, such as the doser device described in U.S. Pat. No. 6,302,855 may also be used. An injection system can include delivery pen as described in U.S. Pat. No. 5,308,341. Pen devices, most commonly used for self-delivery of insulin to patients with diabetes, are well known in the art. Such devices can comprise at least one injection needle (e.g., a 31 gauge needle of about 5 to 8 mm in length), are typically pre-filled with one or more therapeutic unit doses of a solution, and are useful for rapidly delivering the solution to a subject with as little pain as possible.

VI. Methods of Treatment

The solutions described can be used to treat a variety of diseases and conditions in a human patient. In one embodiment, the solutions can be used to treat a complement-associated disorder, including, but not limited to: rheumatoid arthritis (RA); antiphospholipid antibody syndrome; lupus nephritis; ischemia-reperfusion injury; atypical hemolytic uremic syndrome (aHUS); typical or infectious hemolytic uremic syndrome (tHUS); dense deposit disease (DDD); paroxysmal nocturnal hemoglobinuria (PNH); neuromyelitis optica (NMO); multifocal motor neuropathy (MMN); multiple sclerosis (MS); macular degeneration (e.g., age-related macular degeneration (AMD)); hemolysis, elevated liver enzymes, and low platelets (HELLP) syndrome; thrombotic thrombocytopenic purpura (TTP); spontaneous fetal loss; Pauci-immune vasculitis; epidermolysis bullosa; recurrent fetal loss; and traumatic brain injury (see, e.g., Holers (2008) *Immunological Reviews* 223:300-316 and Holers and Thurman (2004) *Molecular Immunology* 41:147-152.)

In another embodiment, the complement-associated disorder is a complement-associated vascular disorder such as, but not limited to, a diabetes-associated vascular disorder (e.g., of the eye), central retinal vein occlusion, a cardiovascular disorder, myocarditis, a cerebrovascular disorder, a peripheral (e.g., musculoskeletal) vascular disorder, a renovascular disorder, a mesenteric/enteric vascular disorder, revascularization to transplants and/or replants, vasculitis, Henoch-Schönlein purpura nephritis, systemic lupus erythematosus-associated vasculitis, vasculitis associated with rheumatoid arthritis, immune complex vasculitis, Takayasu's disease, dilated cardiomyopathy, diabetic angiopathy, Kawasaki's disease (arteritis), venous gas embolus (VGE), and restenosis following stent placement, rotational atherectomy, and percutaneous transluminal coronary angioplasty (PTCA) (see, e.g., U.S. patent application publication no. 20070172483.)

Additional complement-associated disorders include, without limitation, myasthenia gravis, cold agglutinin disease, dermatomyositis, Graves' disease, atherosclerosis, Alzheimer's disease, Guillain-Barré Syndrome, Degos' disease, graft rejection (e.g., transplant rejection), sepsis, burn (e.g., severe burn), systemic inflammatory response sepsis, septic shock, spinal cord injury, glomerulonephritis, Hashimoto's thyroiditis, type I diabetes, psoriasis, pemphigus, autoimmune hemolytic anemia (AIHA), idiopathic thrombocytopenic purpura (ITP), Goodpasture syndrome, antiphospholipid syndrome (APS), catastrophic APS (CAPS), amyotrophic lateral sclerosis (ALS), Alzheimer's disease, and chronic inflammatory demyelinating neuropathy.

In another embodiment, the solutions described herein can be used to treat thrombotic microangiopathy (TMA), e.g., TMA associated with a complement-associated disorder such as any of the complement-associated disorders described herein.

Complement-associated disorders also include complement-associated pulmonary disorders such as, but not limited to, asthma, bronchitis, a chronic obstructive pulmonary disease (COPD), an interstitial lung disease, α-1 anti-trypsin deficiency, emphysema, bronchiectasis, bronchiolitis obliterans, alveolitis, sarcoidosis, pulmonary fibrosis, and collagen vascular disorders.

In another embodiment, the a solution described herein is administered to a subject to treat, prevent, or ameliorate at least one symptom of a complement-associated inflammatory response (e.g., the complement-associated inflammatory response aspect of a complement-associated disorder) in a subject. For example, a composition can be used to treat, prevent, and/or ameliorate one or more symptoms associated with a complement-associated inflammatory response such as graft rejection/graft-versus-host disease (GVHD), reperfusion injuries (e.g., following cardiopulmonary bypass or a tissue transplant), and tissue damage following other forms of traumatic injury such as a burn (e.g., a severe burn), blunt trauma, spinal injury, or frostbite. See, e.g., Park et al. (1999) *Anesth Analg* 99(1):42-48; Tofukuji et al. (1998) *J Thorac Cardiovasc Surg* 116(6):1060-1068; Schmid et al. (1997) Shock 8(2):119-124; and Bless et al. (1999) *Am J Physiol* 276(1):L57-L63.

In another embodiment, the complement-mediated disorder is a complement-mediated vascular disorder such as, but not limited to, a cardiovascular disorder, myocarditis, a cerebrovascular disorder, a peripheral (e.g., musculoskeletal) vascular disorder, a renovascular disorder, a mesenteric/enteric vascular disorder, revascularization to transplants and/or replants, vasculitis, Henoch-Schönlein purpura nephritis, systemic lupus erythematosus-associated vasculitis, vasculitis associated with rheumatoid arthritis, immune complex vasculitis, organ or tissue transplantation, Takayasu's disease, capillary leak syndrome, dilated cardiomyopathy, diabetic angiopathy, thoracic-abdominal aortic aneurysm, Kawasaki's disease (arteritis), venous gas embolus (VGE), and restenosis following stent placement, rotational atherectomy, and percutaneous transluminal coronary angioplasty (PTCA) (see, e.g., U.S. patent application publication no. 20070172483.)

VII. Combination Treatments

In one embodiment, the solutions described herein are administered to a patient as a monotherapy. In another embodiment, they are administered in conjunction with one or more additional agents and/or other therapies (e.g., which are suitable for treating complement-associated disorders). For example, the combination therapy can include administering to the human patient one or more additional agents (e.g., anti-coagulants, anti-hypertensives, or anti-inflammatory drugs (e.g., steroids)) that provide a therapeutic benefit to a patient. In one embodiment, the solutions described herein are administered in combination with an anti-inflammatory agent (e.g., NSAIDs, corticosteroids, methotrexate, hydroxychloroquine, anti-TNF agents such as etanercept and infliximab, a B cell depleting agent such as rituximab, an interleukin-1 antagonist, or a T cell costimulatory blocking agent such as abatacept).

Additional agents for treating a complement-associated disorder in a subject will vary depending on the particular disorder being treated, but can include, without limitation, one or more antihypertensives (e.g., an angiotensin-converting enzyme inhibitor, labetalol, hydralazine, nifedipine, calcium channel antagonists, nitroglycerin, or sodium nitroprussiate), anticoagulants, corticosteroids (e.g., prednisone), immunosuppressive agents (e.g., vincristine or cyclosporine A), anticoagulants (e.g., warfarin (Coumadin), aspirin, heparin, phenindione, fondaparinux, idraparinux), thrombin inhibitors (e.g., argatroban, lepirudin, bivalirudin, or dabigatran), fibrinolytic agents (e.g., ancrod, α-aminocaproic acid, antiplasmin-$a_1$, prostacyclin, and defibrotide), anti-hypertensive agents (e.g., labetalol, hydralazine, nifedipine, calcium channel antagonists, nitroglycerin, or sodium nitroprussiate), lipid-lowering agents (e.g., an inhibitor of hydroxymethylglutaryl CoA reductase), anti-seizure agents (e.g., magnesium sulfate), anti-thrombotic agents (e.g., heparin, antithrombin, prostacyclin, or low dose aspirin), sympathomimetics (e.g., albuterol), antibiotics, deoxyribonucleases (e.g., Pulmozyme®), anticholinergic drugs, anti-IgE inhibitors (e.g., anti-IgE antibodies), corticosteroids, or non-steroidal anti-inflammatory drugs (NSAID). Many different NSAIDS are available, some over the counter including ibuprofen (Advil®, Motrin®, Nuprin®) and naproxen (Alleve®) and many others are available by prescription including meloxicam (Mobic®), etodolac (Lodine®), nabumetone (Relafen®), sulindac (Clinoril®), tolementin (Tolectin®), choline magnesium salicylate (Trilasate®), diclofenac (Cataflam®, Voltaren®, Arthrotec®), Diflusinal (Dolobid®), indomethicin (Indocin®), ketoprofen (Orudis®, Oruvail®), oxaprozin (Daypro®), and piroxicam (Feldene®) (see, e.g., Mihu et al. (2007) *J Gastrointestin Liver Dis* 16(4):419-424). In another embodiment, a solution described herein can be formulated for administration to a patient along with intravenous gamma globulin therapy (IVIG), plasmapheresis, plasma replacement, or plasma exchange.

In one embodiment, the solution and one or more additional agents and/or therapies are administered at the same time. In another embodiment, the solution is administered prior to administration of one or more additional agents and/or therapies. In another embodiment, the solution is administered after administration of one or more additional agents and/or therapies. When an antibody solution described herein is used in combination with a second active agent, the agents (e.g., the anti-C5 antibody and second agent) can be formulated separately or together. For example, the solution and agent can be mixed, e.g., just prior to administration, and administered together or separately, e.g., at the same or different times.

VIII. Kits and Unit Dosage Forms

Also provided herein are kits which include a stable aqueous solution containing an anti-C5 antibody, or antigen binding fragment thereof, such as ravulizumab or BNJ421, in a therapeutically effective amount, suitable for administration to a human patient (e.g., a patient having a complement-associated disorder). The kits optionally also can include instructions, e.g., comprising administration schedules, to allow a practitioner (e.g., a physician, nurse, or patient) to administer the composition contained therein to administer the solution to a patient.

The kits can also contain a suitable means for delivery of one or more solutions to a patient in need thereof, e.g., a patient afflicted with, suspected of having, or at risk for developing, a complement-associated disorder. In one embodiment, the means is suitable for invasive (e.g., intravascular (e.g., intravenous), subcutaneous, intraarticular, intraocular, intravitreal, or intramuscular) delivery of the solution to a patient. In another embodiment, the means is suitable for subcutaneous delivery of the solution to the patient. In another embodiment, the means is suitable for intravenous delivery of the solution to the patient. For example, the means can be a syringe or an osmotic pump. In another embodiment, the solution can be formulated as an eye drop, the means being an eye dropper.

Optionally, the kits include multiple packages of a single-dose solution, each containing an effective amount of the solution for a single administration. Instruments or devices necessary for administering the solution also may be included in the kits. For instance, a kit may provide one or more pre-filled syringes containing the solution.

The following examples are merely illustrative and should not be construed as limiting the scope of this disclosure in any way as many variations and equivalents will become apparent to those skilled in the art upon reading the present disclosure.

The contents of all references, Genbank entries, patents and published patent applications cited throughout this application are expressly incorporated herein by reference.

EXAMPLES

Example 1: Development of Ravulizumab (AXLN1210) High Concentration Formulation for Subcutaneous Administration This example summarizes the development of a ALXN1210 high concentration formulation for subcutaneous administration (e.g., 50 mM Phosphate Buffer, 5% Sucrose, 25 mM Arginine, pH 7.4 at 100 mg/mL). Preliminary experiments were performed in early formulation development to obtain pre-formulation screening data and to evaluate the reduction in the opalescent appearance at higher concentrations for ALXN1210. The initial formulation of ALXN1210 (10 mM Phosphate, 150 mM Sodium Chloride, pH 7.0, 0.02% Tween 80, at 10 mg/mL) was colorless and slightly opalescent. As the concentration in ALXN1210 increased, the opalescent appearance also increased. With the results from the pre-formulation screening, a stability study was executed to obtain lead stability data. Following the initial stability study, a prototype stability study was executed to obtain an optimal formulation for bulk drug substance and drug product. The preliminary and stability studies are discussed in detail below.

1. Methods

A. Appearance

Appearance was determined by visual observation using normal laboratory light, against both a white and a black background.

B. C5 Binding

The C5 Binding ELISA is a potency assay for ALXN1210. This test procedure is a direct-binding immunoassay with colorimetric detection, used to test the ability of ALXN1210 to bind to its target, human C5 complement protein. A Polysorp microtiter plate was coated with human C5 protein and blocked with bovine serum albumin (BSA). A standard curve was prepared from ALXN1210 reference material. Reference material and test samples were prepared at three dilutions targeted to fall within the working range of the assay. Following incubation with the standards and samples, the plate was then washed and incubated with mouse anti-human IgG4 conjugated to horseradish peroxidase (HRP). The plate was washed again and then developed using substrate, 2,2'-azino-bis(3-ethylbenzothiazoline-6-sulphonic acid), (ABTS). The amount of reacted substrate was read spectrophotometrically on a plate reader at 405 nm. The absorbance reading was proportional to the concentration of ALXN1210 bound to C5 on the plate. A four parameter curve fit was applied to the standard curve and reference material and test sample results were interpolated from the curve. Sample test results were compared with the reference material results and relative activity (%) was reported.

C. Density

Density measurements using the DMA 4500 density meter were determined via the U-tube principle. A hollow, U-shaped glass tube was filled with sample, then electronically excited at the lowest possible amplitude. Density was determined via the following relationship:

$$\rho=A(\tau^2)-B$$

ρ=density

τ=the period of oscillation

A and B are instrumental constants, determined via instrument calibration with two substances of known density.

D. Differential Scanning Fluorescence

Differential Scanning Fluorescence measures the thermal stability change by performing a thermal denaturation curve in the presence of a fluorescent dye, such as Sypro Orange. When the protein unfolds the exposed hydrophobic surfaces bind to the dye increasing the fluorescence and generating a stability curve with a characteristic midpoint value at the temperature of hydrophobic exposure $T_h$.

E. Dynamic Light Scattering

Dynamic light scattering measures the size and interactions of proteins, nanoparticles and other macromolecules in situ in micro well plates by using a lighting system that allows the wells in a micro plate to be imaged using a 3 megapixel onboard camera. Fluctuations of the light scattering due to Brownian motion gives a diffusion coefficient which were related to the hydrodynamic radius of particles present in the solution.

F. HPLC Gel Permeation

Gel permeation (size exclusion) HPLC was used to distinguish monomeric IgG from the larger, multimer antibody species that may result from aggregation of monomers. Test samples were injected onto a TSK gel G3000 SWXL column equilibrated with phosphate buffered saline, pH 7.0, followed by isocratic elution. Protein peaks were monitored at 214 nm and the percent purity of the monomeric IgG was expressed as a percentage of the total integrated peak area. Detection of the larger mass multimers was by observation of peaks eluting prior to the monomer peak.

G. Imaged Capillary Electrophoresis (iCE)

This method uses the Protein Simple iCE280 or iCE3 system which performs free solution IEF in a capillary column and detects focused protein zones using a whole column UV detector. Samples were prepared by premixing ALXN1210, carrier ampholytes and pI markers. The sample was loaded into a capillary cartridge and the electrolytic tanks at each end of the capillary are filled with acid and base. Voltage was applied and the analytes were focused at their pI. A CCD camera took a UV light absorption image of the entire capillary column every 30 seconds, allowing real time monitoring of the focusing step. The resulting separation pattern was captured and analyzed. pI of proteins present in the sample was interpolated from the position of pI markers spiked into the sample.

H. Lab on Chip (LoC)

This method tests the homogeneity and purity of the product. Non-reduced samples were denatured by treatment with lithium dodecyl sulfate (LDS). Reduced samples were denatured by treatment with lithium dodecyl sulfate (LDS) and the disulfide bonds were disrupted with dithiothreitol (DTT). Polypeptide chains were mixed with fluorescent dye, which binds to LDS and separated according to molecular size by micro-capillary electrophoresis. Protein was detected and quantified by laser induced fluorescence.

I. Osmolality

Sample osmolality was determined using a freezing point depression osmometer. The osmometer was calibrated prior to use with commercially available, certified osmolality standards at 50 mOsm/kg and 850 mOsm/kg, which bracket the sample range. A reference 290 mOsm/kg solution was used to confirm successful calibration prior to testing samples. Samples were tested in triplicate and the mean of sample determinations was reported.

J. pH pH measurement was performed using a protein resistant saturated silver free KCl combination electrode and associated meter and temperature monitor. The meter was calibrated prior to use using commercially available solutions in the appropriate pH range (i.e., pH 4.0-pH 7.0).

K. Protein Concentration Using SoloVPE

Absorbance at 280 nm was used to determine the protein concentration using variable pathlength technology in the test samples using a theoretically determined extinction coefficient of 1.479. Triplicate absorbance readings per the method were performed per sample.

L. Viscosity

Viscosity measurements using the AMVn viscometer were determined via the rolling ball principle. A hollow tube was filled with sample and solid ball of known density, and then inclined at a known angle. The time it takes the ball to move from one side of the tube to the other was determined and used to calculate viscosity via the following relationship:

$$\eta=K*(\rho b-\rho s)*tr$$

η=dynamic viscosity (mPa*s)

K=proportionality constant

ρb=density of the ball (g/mL)

ρs=density of the sample (g/mL)

tr=rolling time of the ball

To calculate viscosity, sample density determined using the DMA 4500 M density meter was used as ρs.

M. Determination of Sub-Visible Particles by Micro Flow Imaging (MGI)

The objective is to assess all sub-visible particles in a formulation by micro flow imaging (MFI). The sample was removed from 2-8° C. storage and tested directly in MFI using the BOT1 autosampler. Inversion of the sample was done six times before loading the sample into BOT1 to ensure complete mixing of particles. Samples were loaded into three consecutive wells, and each well had one measurement for a total of 3 replicates. Three mixing cycles were built within BOT1 to further ensure uniform mixing 2. Formulation Development FIGS. 1-5 and Tables 1-5 show the experimental results for early formulation development of ALXN1210 at high concentration.

In the first experiment, the effect of adding an amino acid to ALXN1210 in sodium phosphate buffer on opalescence was observed. The cause of the opalescence was determined to be a lack of charge to charge repulsion between antibody molecules in solution at high concentration. A series of experiments were conducted as described below to optimize the particular amino acid and the concentration necessary to produce a stable clear solution. Based on these experiments, it was determined that the addition of positively charged amino acid (L-Arginine) reduced the opalescence in a 50 mg/mL ALXN1210 sample in sodium phosphate buffer. The same conclusion was reached by visual inspection of the vials (data not shown).

In addition, the following experiments were conducted by using ALXN1210 IV formulation at 10 mg/ml and concentrating the antibody and conducting buffer exchange to assess various initial buffer systems for use in finding a high concentration ALXN1210 formulation. As shown in Table 1 below, all pooled samples had a final buffer exchange of 1:1000 to obtain the desired pH. The pooled samples had a concentration range from 35.3 to 54.0 mg/mL. The % recovery following buffer exchange ranged from 70.6% to 108%. The appearance results show 25 mM Histidine pH 7 and 25 mM Phosphate pH 7 buffer exchanged vials were clear and colorless, comparable to Eculizumab, and solutions in all other buffer exchanged vials were opalescent. Imaged capillary electrophoresis (iCE) results showed a pI range from 5.98 to 6.54, main pI range of 6.19 to 6.24 and area % range of 63.1% to 65.9%. Size exclusion chromatography (SEC) results showed a % monomer (purity) from 98.48% to 98.98%.

TABLE 1

Buffer Exchange ALXN1210 from 10 mg/mL to 50 mg/mL (Pooled Sets 1-3)

| Buffer | pH of Buffer Post Exchange | Measured Concentration (mg/mL) | Buffer Exchange % Recovery | Appearance | iCE | SEC (% Monomer) |
|---|---|---|---|---|---|---|
| 25 mM Citrate Buffer pH 5 | 5.05 | 54.0 | 108.0 | Opalescent | pI range 6.01-6.53 | 98.48 |
| 25 mM Citrate Buffer pH 6 | 6.09 | 41.7 | 83.4 | Opalescent | pI range 6.01-6.53 | 98.70 |
| 25 mM Acetate Buffer pH 5 | 4.98 | 42.1 | 84.2 | Opalescent | pI range 6.01-6.53 | 98.98 |
| 25 mM Acetate Buffer pH 6 | 5.86 | 35.3 | 70.6 | Opalescent | pI range 6.01-6.53 | 98.79 |
| 25 mM HEPES Buffer pH 7 | 6.93 | 49.7 | 99.4 | Opalescent | pI range 6.03-6.54 | 98.59 |
| 25 mM Histidine pH 6 | 5.90 | 37.4 | 74.8 | Opalescent | pI range 6.02-6.53 | 98.93 |
| 25 mM Histidine pH 7 | 6.94 | 47.2 | 94.4 | *Clear, colorless | pI range 5.98-6.48 | 98.82 |
| 25 mM Phosphate pH 7 | 7.10 | 48.6 | 97.2 | *Clear, colorless | pI range 6.01-6.53 | 98.50 |
| 25 mM Citrate Buffer pH 6.8 | 6.83 | 49.6 | 99.2 | Opalescent | | |
| 25 mM Phosphate-Citrate pH 6.9 | 6.89 | 46.5 | 93.1 | Opalescent | | |
| 25 mM Potassium Phosphate Buffer pH 7 | 7.05 | 49.0 | 97.9 | Opalescent | | |
| 25 mM Sodium Phosphate Buffer pH 7.5 | 7.55 | 44.5 | 89.1 | Opalescent | | |

*Comparable to Eculizumab

As shown in FIG. 1, the results from the salt titration for Histidine buffer exchanged samples at pH 7 using DLS show that as the salt concentration increased, the self-association also increased in ALXN1210.

As shown in FIG. 2, the results from the L-Arginine titration using the dynamic light scattering (DLS) show that 25 mM L-Arginine is the minimum amount required to reduce the opalescence in ALXN1210 at 50 mg/mL.

Figure 3:
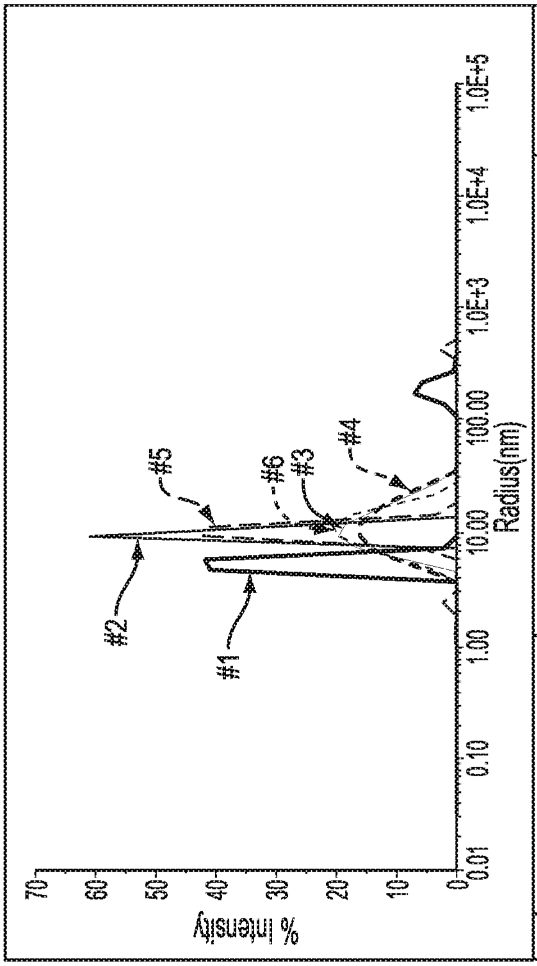
FIG. 3 depicts the dynamic light scattering results for a salt titration of phosphate buffer exchanged ravulizumab (ALXN1210) at 50 mg/mL.

As shown in FIG. 3, the results from the salt titration for Phosphate buffer exchanged samples at pH 7 using DLS show that the no salt and 150 mM salt addition had the least self-association also in ALXN1210. Compare peaks labelled 2 and 5.

Figure 4:
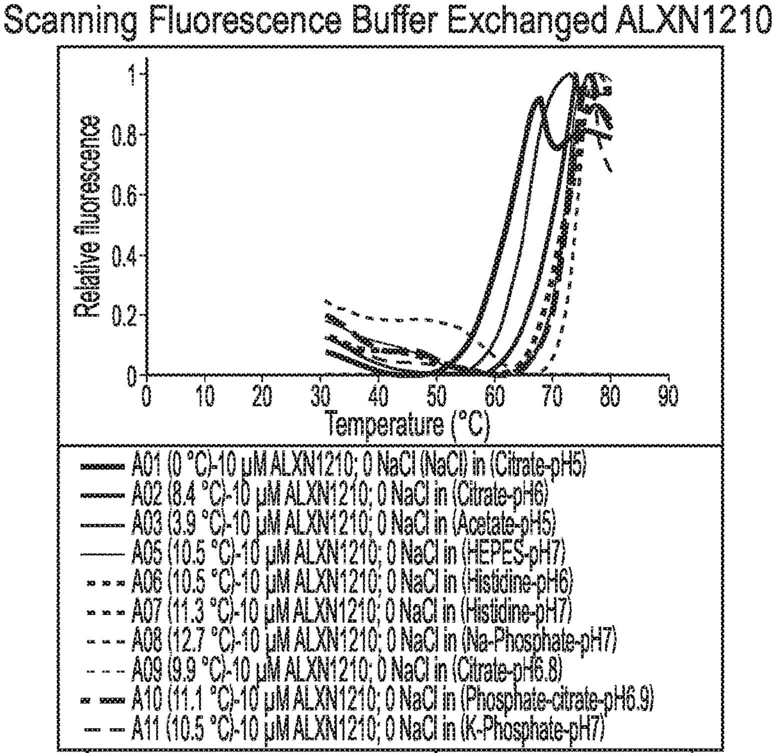
FIG. 4 depicts the differential scanning fluorescence results of buffer exchanged ravulizumab (ALXN1210) at 50 mg/mL.

As shown in FIG. 4, the results from the buffer exchanged samples using DSF show that the hydrophobic pockets are not exposed in ALXN1210. Citrate and Acetate buffers at pH 5 and 6 have low thermal stability with the lowest melting temperature (Tm), and Histidine and Phosphate buffers at pH 7 are the most stable with the highest Tm.

As shown in the appearance results set forth in Table 2, ALXN1210 at about 100 mg/mL is clear and colorless with the addition of 25 mM L-Arginine in 25 mM phosphate buffer at pH 7.

TABLE 2

Appearance of ALXN1210 100 mg/mL Samples

| Sample ID | Buffer | Measured Concentration (mg/mL) | Appearance |
|---|---|---|---|
| | 10 mM Sodium Phosphate, pH 7 | 100.0 | Opalescent |
| SPPD-14-0042-8 | 25 mM Histidine, pH 7.2 | 66.0 | Opalescent |
| SPPD-14-0042-9 | 10 mM Phosphate, 25 mM L-Arginine, pH 7 | 114.5 | Opalescent |
| SPPD-14-0042-Formulation C | 25 mM Phosphate, pH 7 | 112.0 | Opalescent |
| SPPD-14-0042-Formulation C with L-Arginine spike | 25 mM Phosphate, 25 mM L-Arginine (spike in), pH 7 | 112.0 | Clear, colorless |

Figure 5:
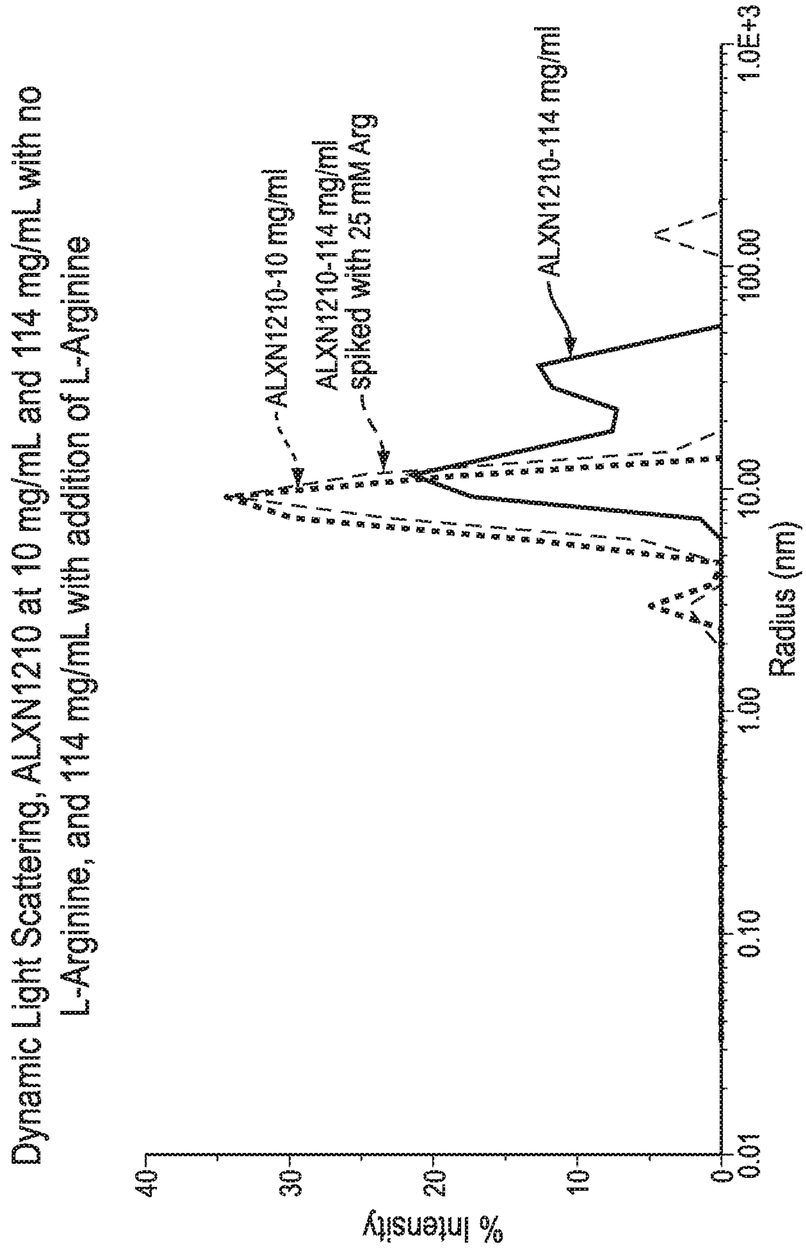
FIG. 5 depicts the dynamic light scattering results for ravulizumab (ALXN1210) at 10 mg/mL and 114 mg/mL with no L-Arginine, and 114 mg/mL with addition of L-Arginine.
Figure 12:
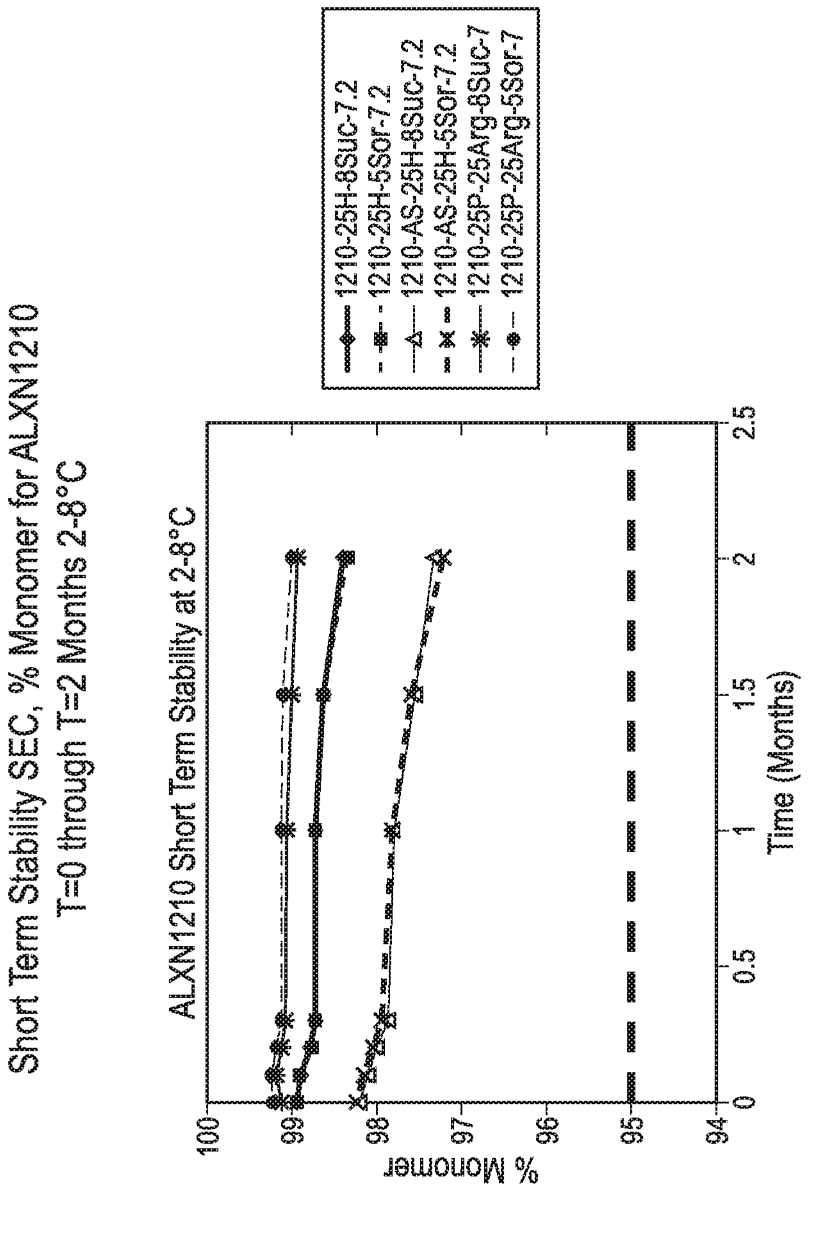
FIG. 12 shows the stability size exclusion chromatography (SEC) data, % Monomer for ravulizumab (ALXN1210) (T=0 through T=2 Months 2-8° C.).
Figure 13:
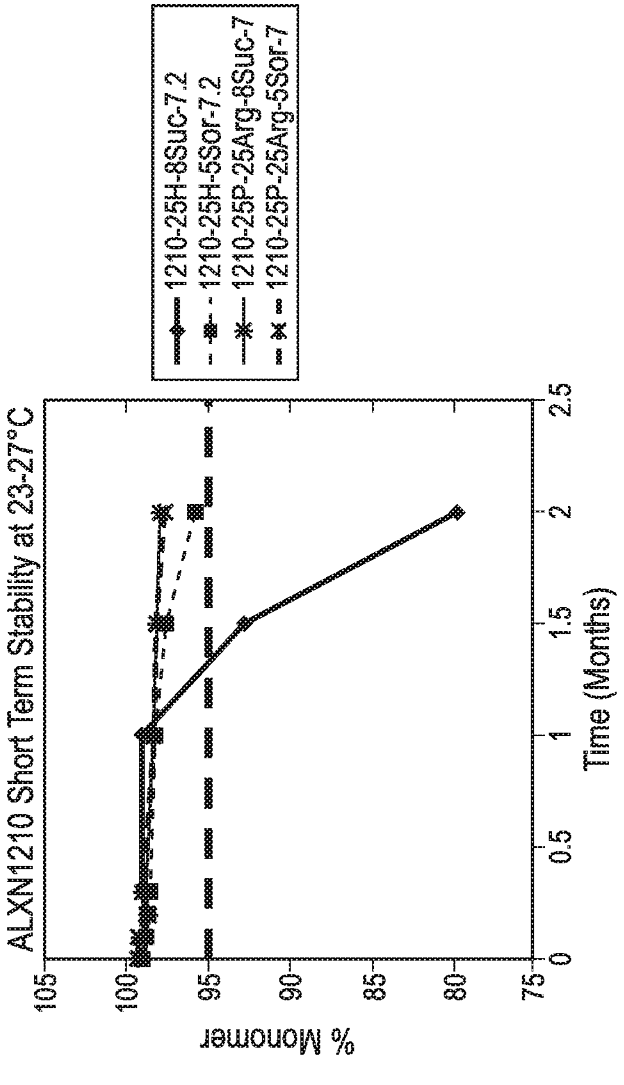
FIG. 13 shows the stability size exclusion chromatography (SEC) data, % Monomer for ravulizumab (ALXN1210) (T=0 through T=2 Months 23-27° C.).
Figure 14:
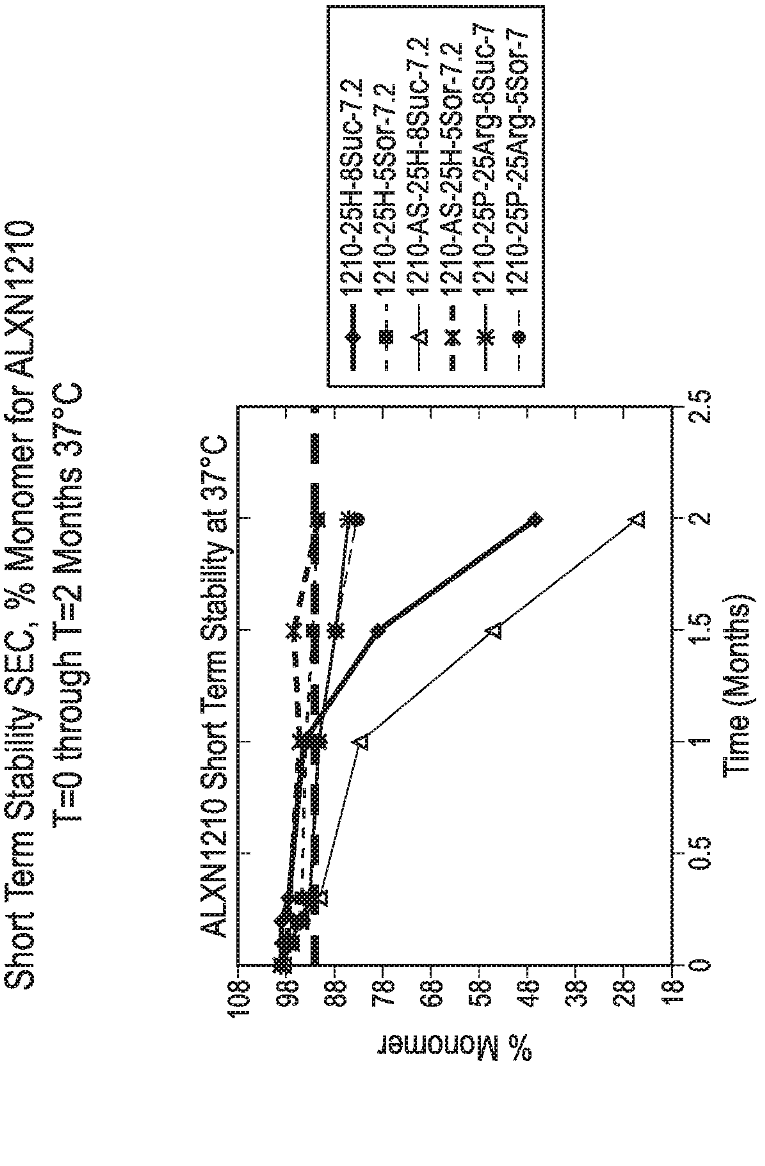
FIG. 14 shows the stability size exclusion chromatography (SEC) data, % Monomer for ravulizumab (ALXN1210) (T=0 through T=2 Months 37° C.).
Figure 15:
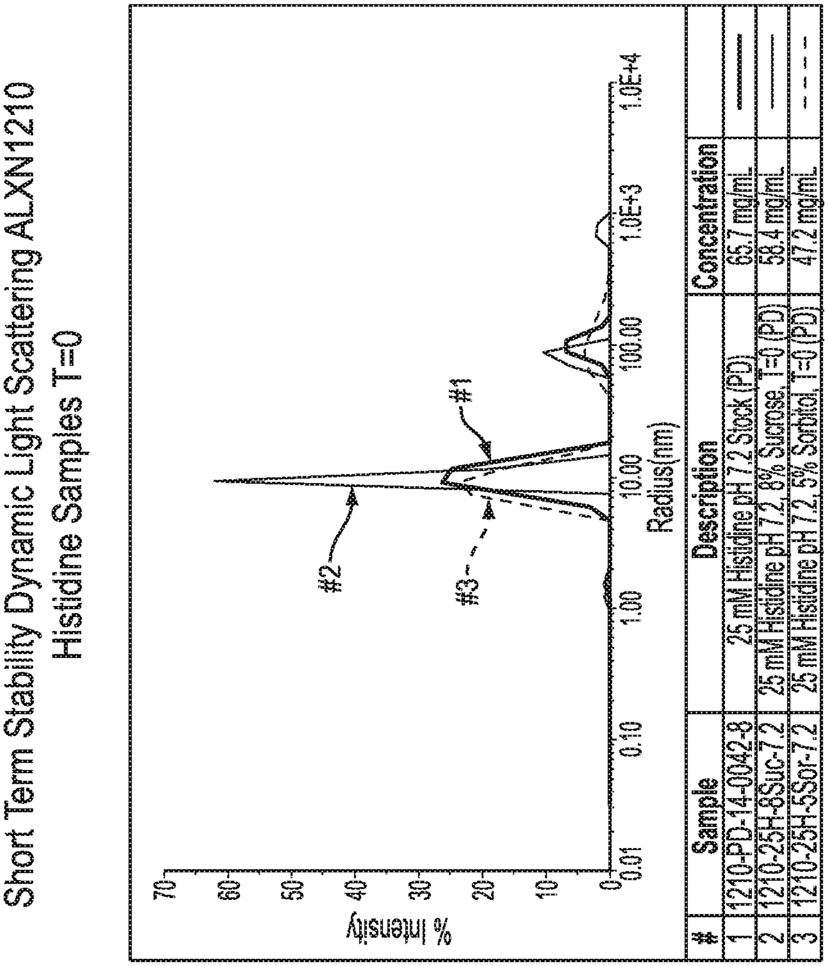
FIG. 15 shows the stability dynamic light scattering data for ravulizumab (ALXN1210) and histidine samples (T=0).
Figure 16:
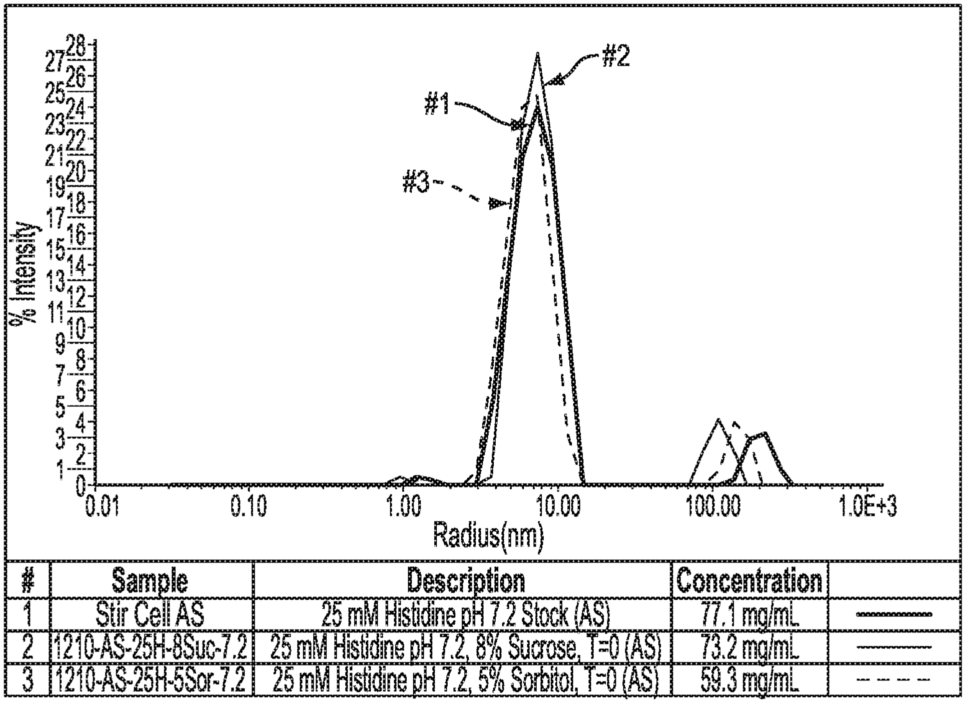
FIG. 16 shows the stability dynamic light scattering data for the ravulizumab (ALXN1210) histidine AS Samples (T=0).
Figure 17:
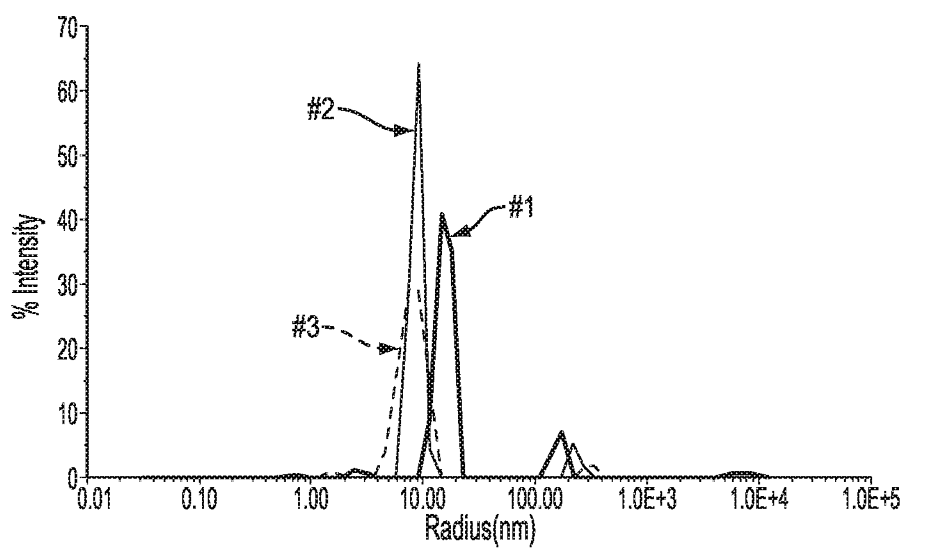
FIG. 17 shows the stability dynamic light scattering data for the ravulizumab (ALXN1210) Phosphate Samples (T=0).
Figure 18:
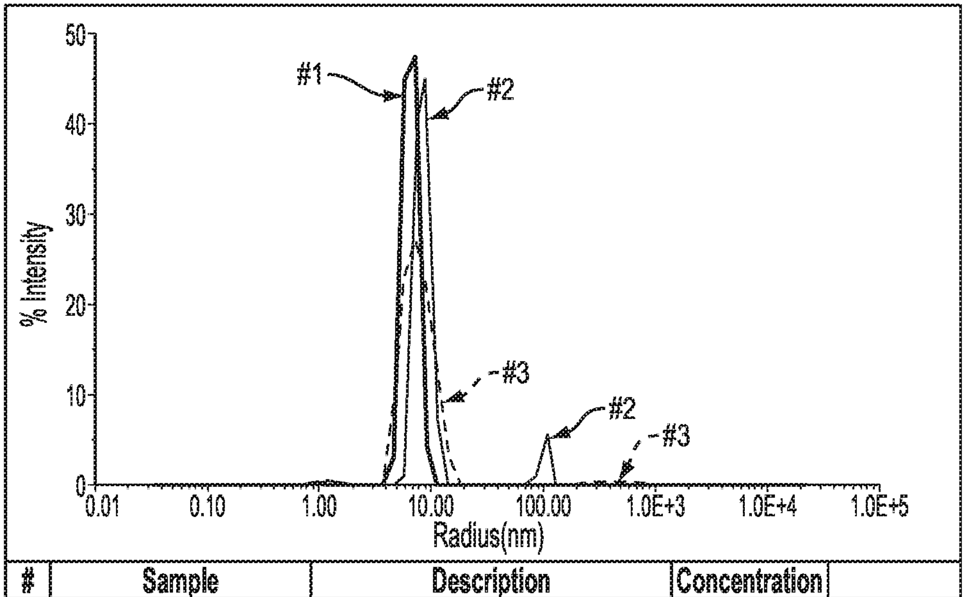
FIG. 18 shows the stability dynamic light scattering data for the ravulizumab (ALXN1210) Phosphate Samples (T=2 Months 2-8° C.).
Figure 21:
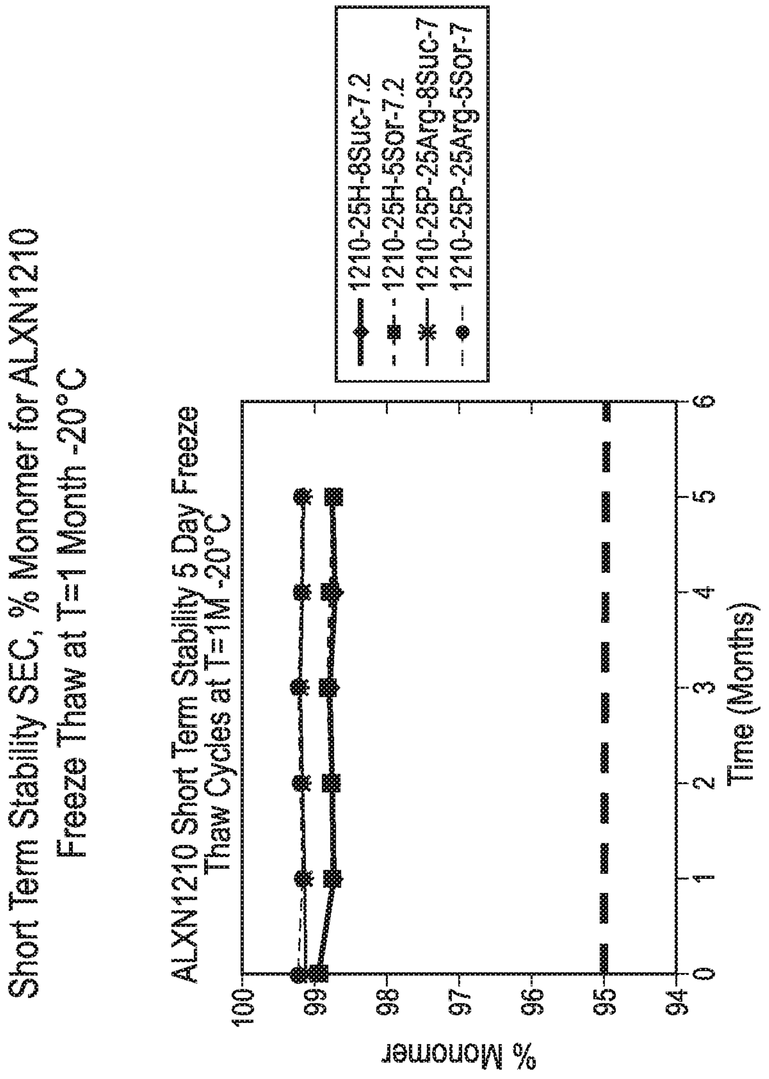
FIG. 21 shows the stability size exclusion chromatography (SEC) data, % Monomer for ravulizumab (ALXN1210) (Freeze Thaw at T=1 Month −20° C.).
Figure 33:
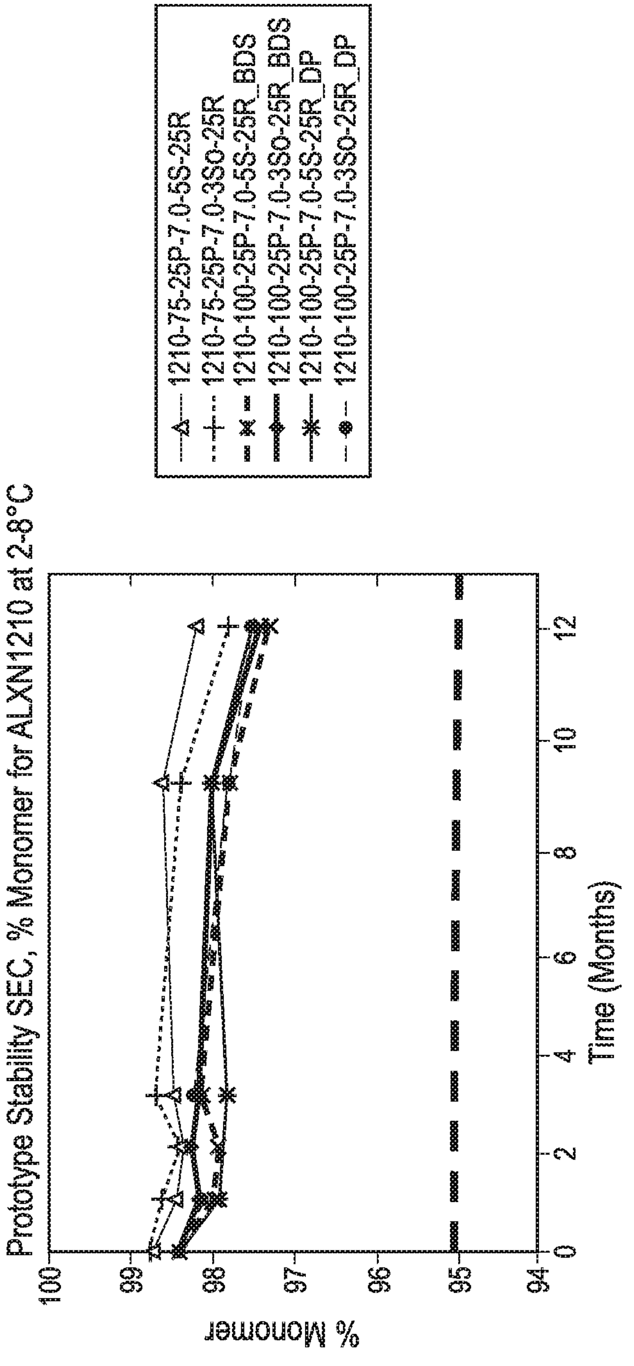
FIG. 33 shows the prototype stability size exclusion chromatography (SEC) data, % Monomer for ravulizumab (ALXN1210) (T=0 through T=12 Months 2-8° C.).
Figure 34:
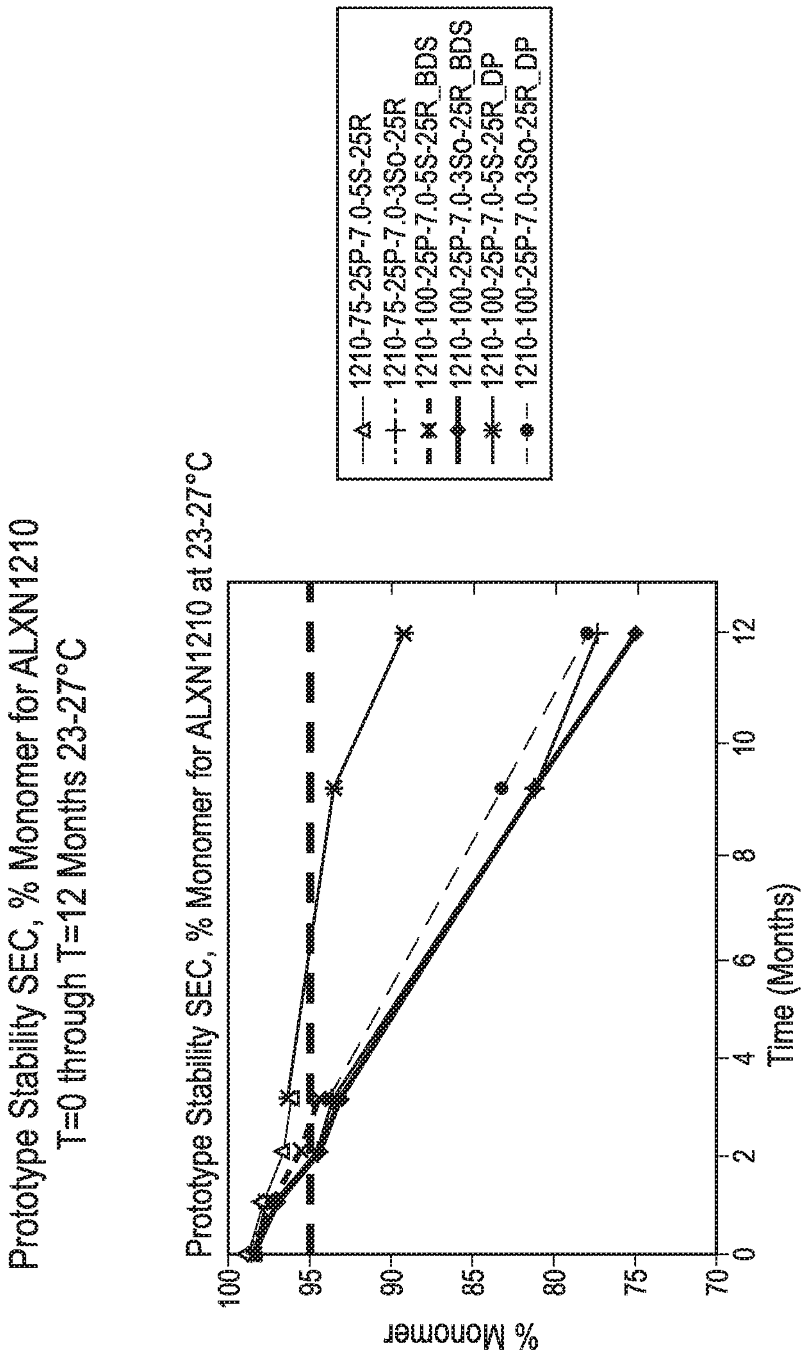
FIG. 34 shows the prototype stability size exclusion chromatography (SEC) data, % Monomer for ravulizumab (ALXN1210) (T=0 through T=12 Months 23-27° C.).
Figure 35:
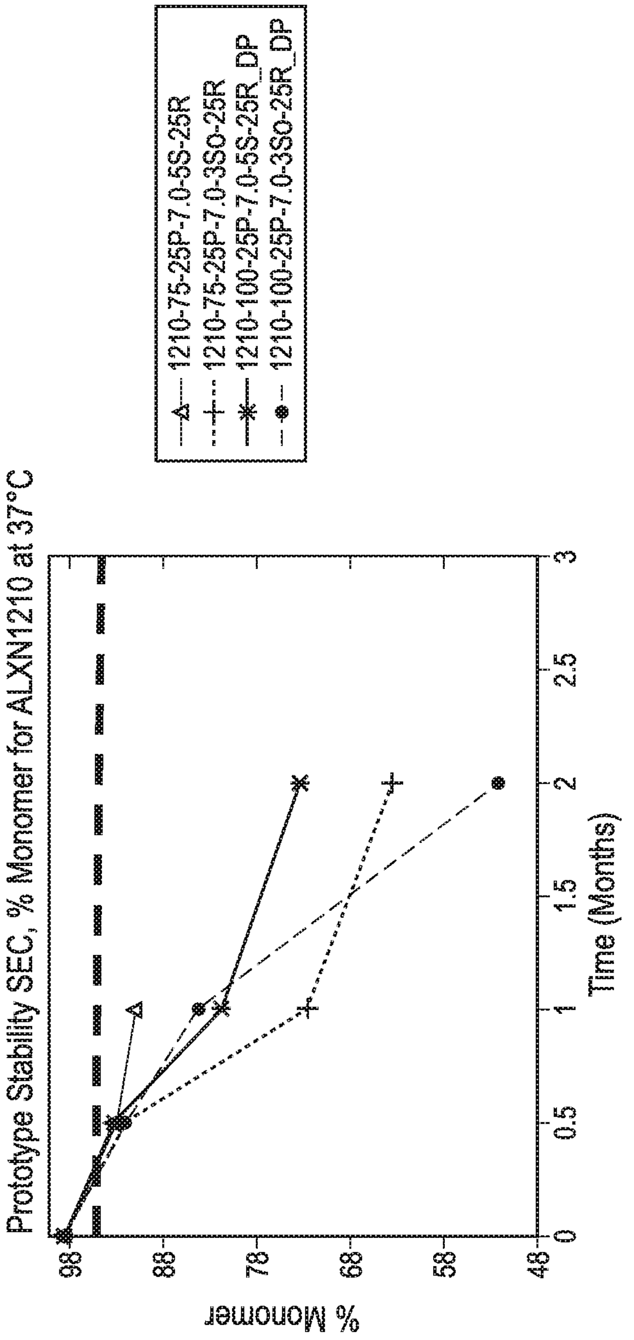
FIG. 35 shows the prototype stability size exclusion chromatography (SEC) data, % Monomer for ravulizumab (ALXN1210) (T=0 through T=12 Months 37° C.).
Figure 36:
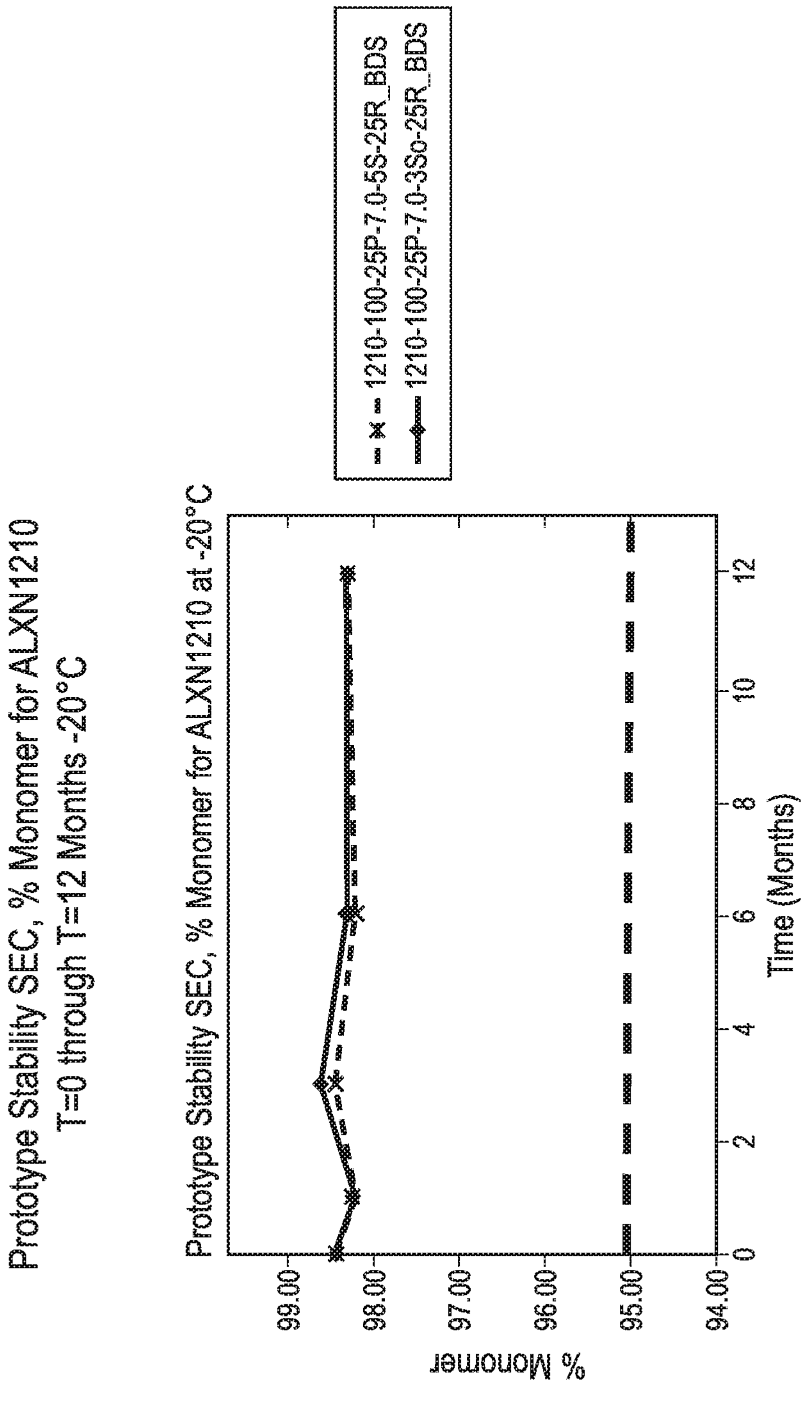
FIG. 36 shows the prototype stability size exclusion chromatography (SEC) data, % Monomer for ravulizumab (ALXN1210) (T=0 through T=12 Months −20° C.).
Figure 37:
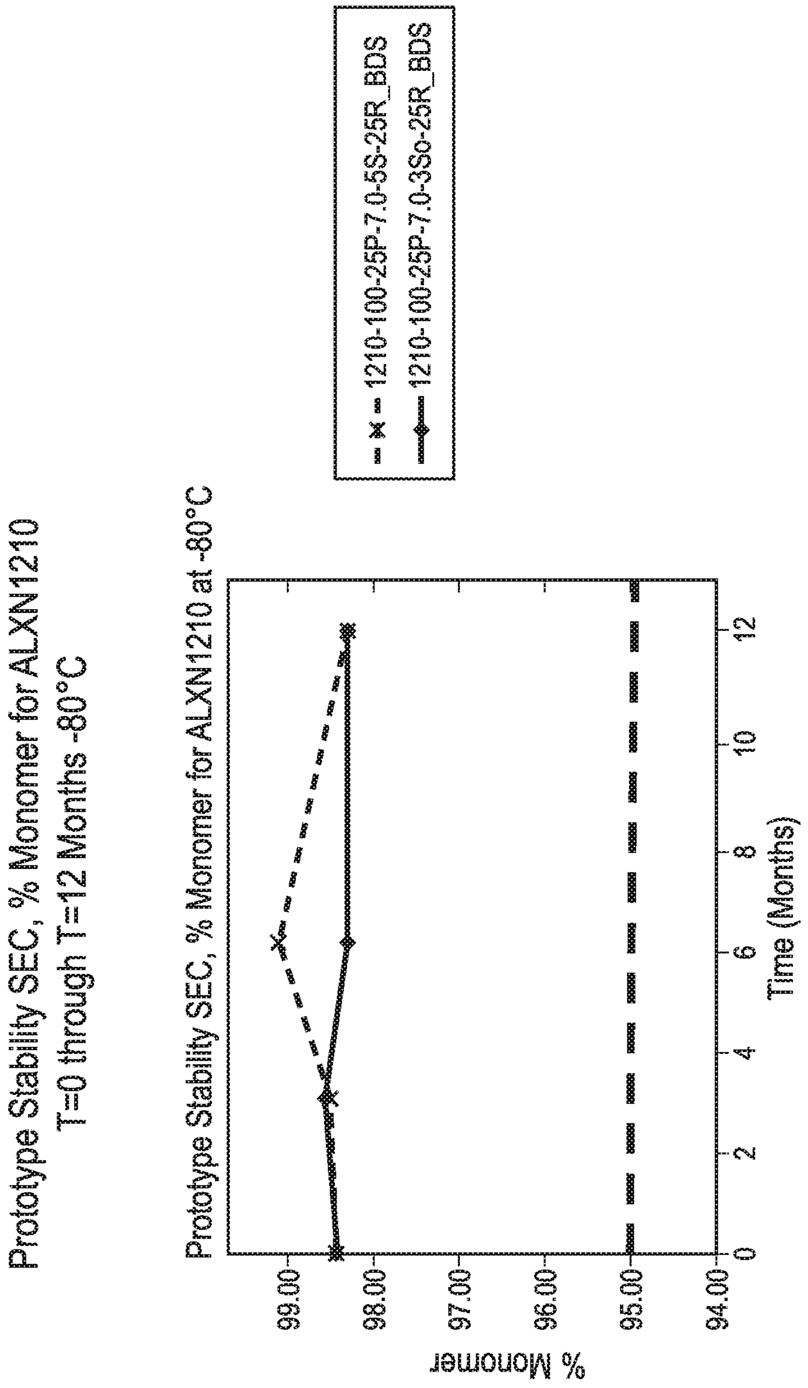
FIG. 37 shows the prototype stability size exclusion chromatography (SEC) data, % Monomer for ravulizumab (ALXN1210) (T=0 through T=12 Months −80° C.).
Figure 38:
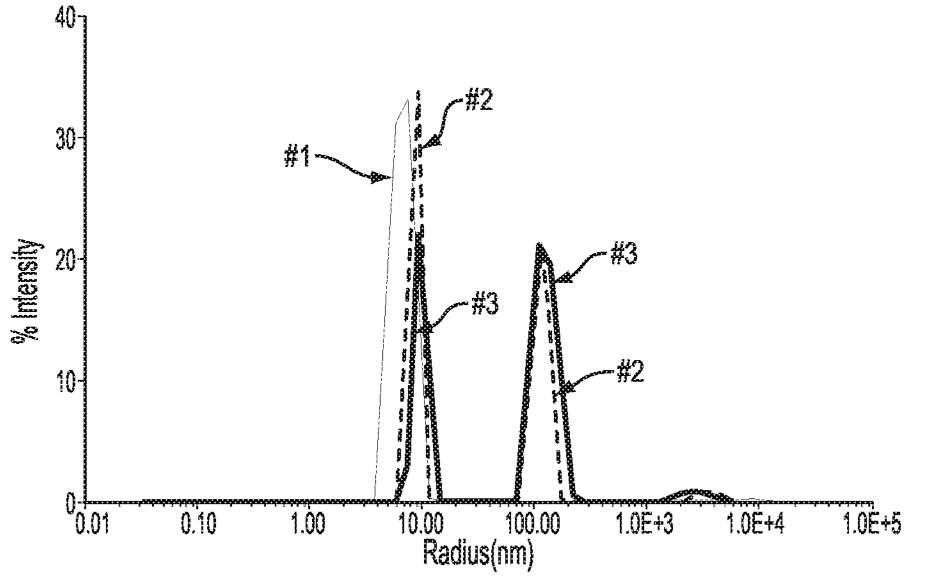
FIG. 38 shows the prototype stability dynamic light scattering data for ravulizumab ALXN1210 Phosphate Samples at 75 mg/mL (T=0).
Figure 39:
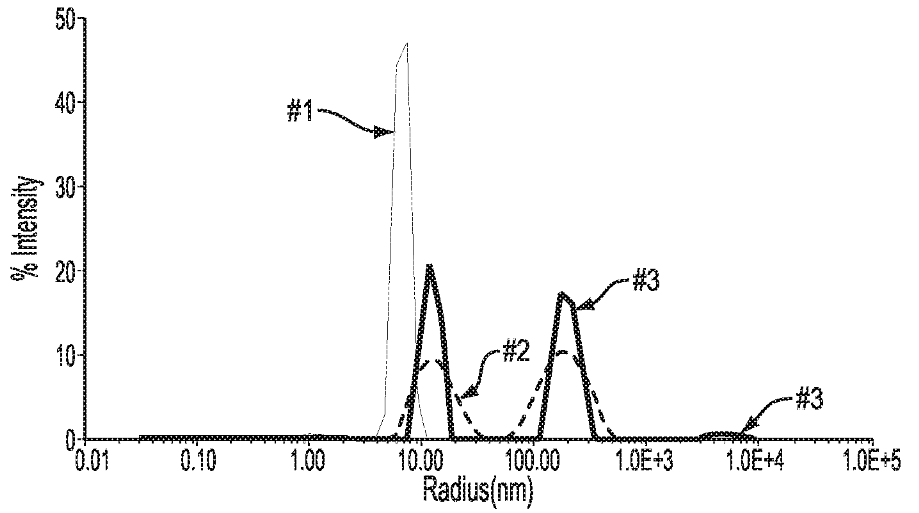
FIG. 39 shows the prototype stability dynamic light scattering data for ravulizumab (ALXN1210) Phosphate Samples at 75 mg/mL (T=1 Month 2-8° C.).
Figure 40:
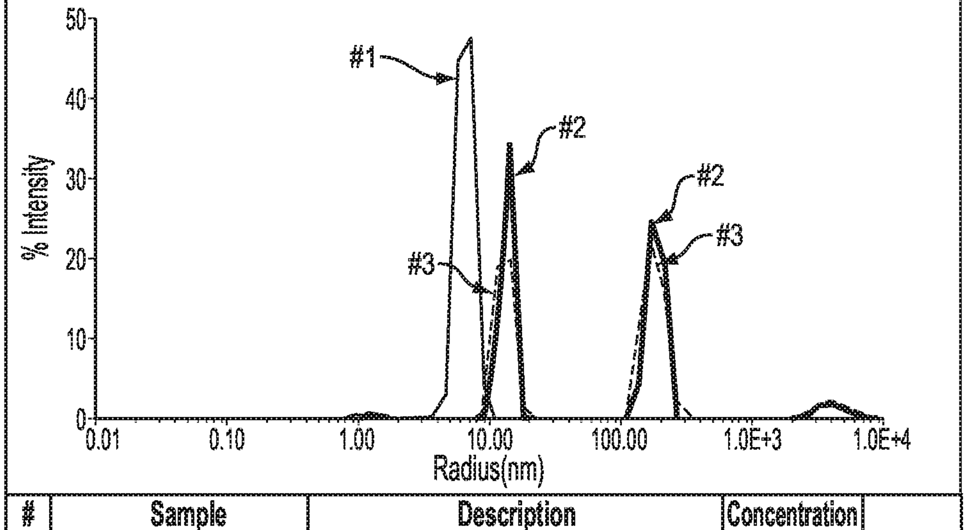
FIG. 40 shows the prototype stability dynamic light scattering data for ravulizumab (ALXN1210) Phosphate Samples at 100 mg/mL (T=1 Month 2-8° C.).
Figure 45:
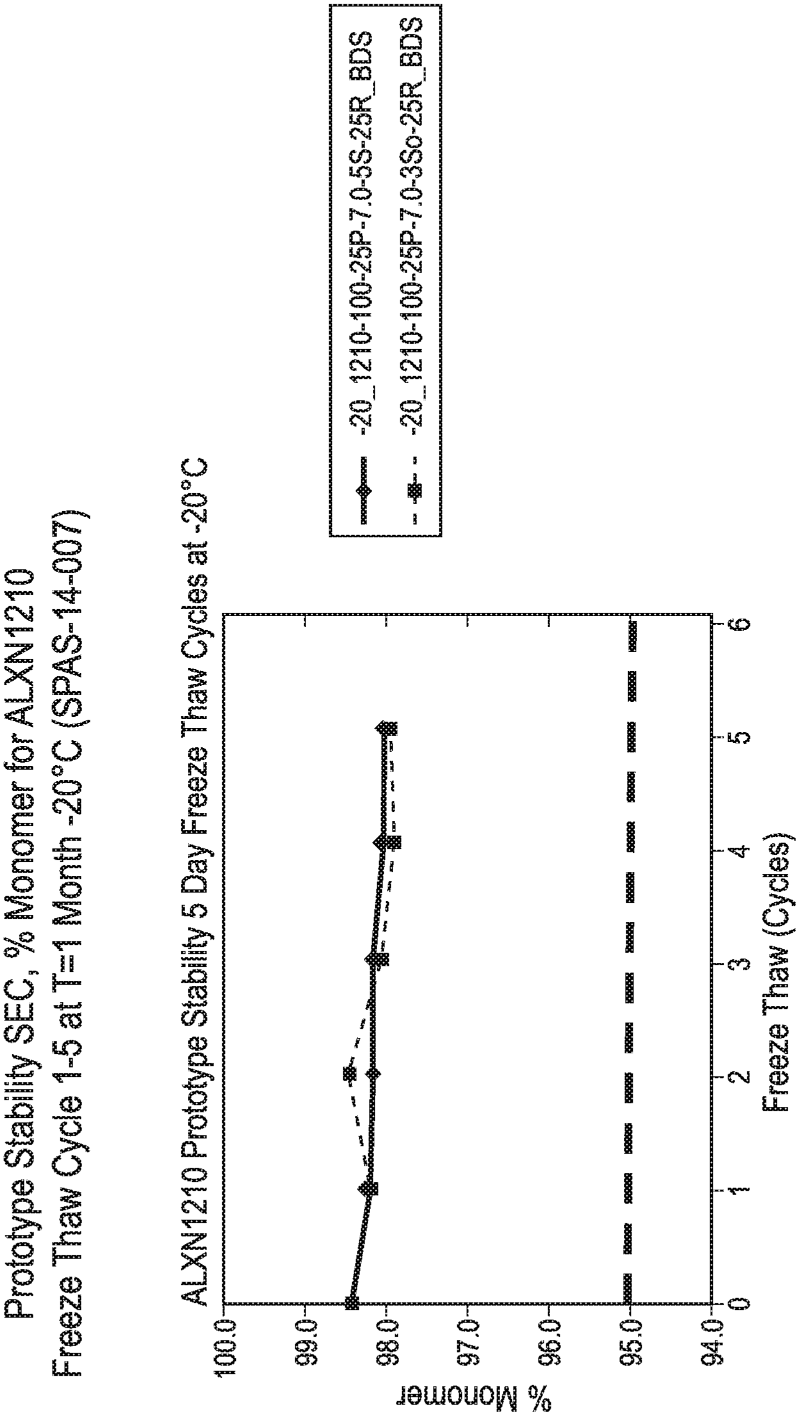
FIG. 45 shows the prototype stability size exclusion chromatography (SEC) data, % Monomer for ravulizumab (ALXN1210) Freeze Thaw Cycle 1-5 at T=1 Month −20° C.
Figure 46:
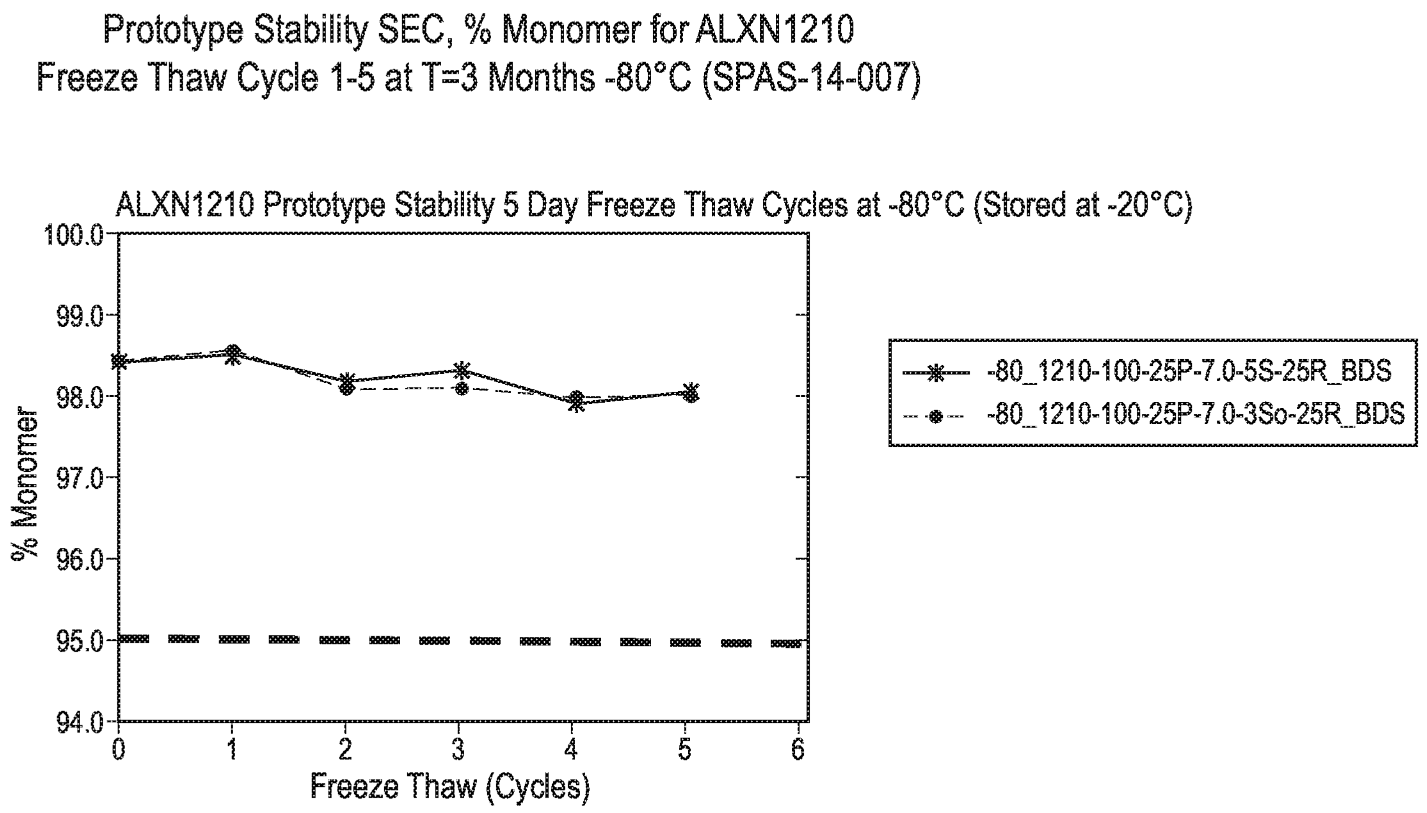
FIG. 46 shows the prototype stability size exclusion chromatography (SEC) data, % Monomer for ravulizumab (ALXN1210) Freeze Thaw Cycle 1-5 at T=3 Months −80° C.

As shown in FIG. 5, the results for ALXN1210 at 10 mg/mL, and 114 mg/mL with and without L-Arginine spike using the DLS showed that the addition of the 25 mM L-Arginine to an at least 100 mg/mL sample is most closely comparable to the 10 mg/mL reference. The at least 100 mg/mL sample without the L-Arginine addition resulted in higher order species, which indicates self-association.

The results for osmolality set forth in Table 3 show that ALXN1210 in 25 mM Histidine pH7.2 with 8% sucrose or 4.5% sorbitol are within the desired Osmolality range of 275-320. Osmolality of ALXN121 in 25 mM Phosphate, 25 mM L-Arginine, pH7 supplemented with 7% sucrose or 4% sorbitol also fell within the desired Osmolality range.

TABLE 3

Osmolality for ALXN1210 at Various Formulations

| Sample Description | Butter Used | Concentration (mg/mL) | % Excipient | Osmolality (mOsm/kg) |
|---|---|---|---|---|
| SPPD-14-0042-8 | 25 mM Histidine pH 7.2 | 66.0 | | 55 |
| SPPD-14-0042-8 | 25 mM Histidine pH 7.2 | 66.0 | 8% Sucrose | 299 |
| SPPD-14-0042-8 | 25 mM Histidine pH 7.2 | 66.0 | 4.5% Sorbitol | 295 |
| SPPD-14-0042-Formulalion C with L-Arginine spike | 25 mM Phosphate, 25 mM L-Arginine, pH 7 | 112.0 | | 69 |
| SPPD-14-0042-Formulation C with L-Arginine spike | 25 mM Phosphate, 25 mM L-Arginine, pH 7 | 112.0 | 7% Sucrose | 302 |
| SPPD-14-0042-Formulation C with L-Arginine spike | 25 mM Phosphate, 25 mM L-Arginine, pH 7 | 112.0 | 4% Sorbitol | 317 |

The viscosity results set forth in Table 4 show that as the concentration of ALXN1210 increases, the viscosity also increases for solutions of ALXN1210 in histidine and phosphate buffers. The density results set forth in Table 4 show no significant change in density for histidine and phosphate buffers as the concentration changes.

TABLE 4

Viscosity and Density for ALXN1210 Samples at Various Concentrations

| Sample Description/Sample Matrix | ALXN1210 Conc. (mg/mL) | Dynamic Viscosity (mPa · S) | Density (g/cm3) |
|---|---|---|---|
| 25 mM Histidine, pH 7.2 Buffer | 0 | 1.014 | 0.999 |
| ALXN1210, Histidine, pH 7.2 | 66.0 | 3.368 | 1.018 |
| 10 mM Sodium Phosphate pH 7 Buffer | 0 | 1.014 | 0.999 |
| 10 mM Sodium Phosphate | 100 | 8.788 | 1.027 |
| 25 mM Phosphate, 25 mM Arginine pH 7 Buffer | 0 | 1.030 | 1.002 |
| ALXN1210, Phosphate, 25 mM Arginine pH 7 | 114.5 | 10.387 | 1.034 |
| ALXN1210, Phosphate, 25 mM Arginine pH 7 | 100.3 | 6.605 | 1.002 |
| ALXN1210, Phosphate, 25 mM Arginine pH 7 | 95.1 | 5.714 | 1.002 |
| ALXN1210, Phosphate, 25 mM Arginine pH 7 | 90.0 | 4.906 | 1.002 |
| ALXN1210, Phosphate, 25 mM Arginine pH 7 | 75.7 | 3.476 | 1.002 |
| ALXN1210, 25 mM Phosphate, 25 mM L-Arginine, pH 7, 7% Sucrose Buffer | 0 | 1.250 | 1.028 |
| ALXN1210, 25 mM Phosphate, 25 mM L-Arginine, pH 7, 7% Sucrose (SPPD-14-0042-Formulation C with L-Arginine spike) | 93.6 | 4.109 | 1.056 |
| ALXN1210, 25 mM Phosphate, 25 mM L-Arginine, pH 7, 4% Sorbitol Buffer | | 1.153 | 1.016 |
| ALXN1210, 25 mM Phosphate, 25 mM L-Arginine, pH 7, 4% Sorbitol (SPPD-14-0042-Formulation C with L-Arginine spike) | 80.0 | 2.877 | 1.038 |

As shown in Table 5, the addition L-Arginine base significantly increased the pH of the sample. L-Arginine QS with sodium phosphate monobasic spiked into a sample raised the pH by 1 pH unit. L-Arginine HCl spiked into a sample dropped the pH about 0.25 pH units. However the appearance decreased in opalescence from L-Arginine HCl spike to L-Arginine QS sodium phosphate monobasic spike to L-Arginine base spike.

TABLE 5

L-Arginine Buffers for 25 mM L-Arginine Spike pH and Appearance Effects for ALXN1210

| Sample Description | pH | Appearance |
|---|---|---|
| 0.5M L-Arginine base Solution | 11.47 | |
| 1210-PD-14-0042-Formulation C | 7.04 | |
| SPPD-14-0042-Formulation C with 25 mM L-Arginine spike | 8.85 | |
| 0.5M Sodium Phosphate Monobasic Solution | 4.23 | |
| 0.5M Sodium Phosphate Dibasic Solution | 8.94 | |
| 0.5M L-Arginine base, QS with 0.5M Sodium Phosphate Monobasic Solution | 8.31 | |
| SPPD-14-0042-Formulation C with 25 mM L-Arginine spike QS Sodium Phosphate Monobasic Solution | 7.38 | |
| 0.5M L-Arginine HCl | 5.48 | |
| 25 mM Sodium Phosphate, 7% Sucrose, pH 7, 25 mM L-Arginine HCl spike | 6.79 | |
| 25 mM Sodium Phosphate, 4% Soribitol, pH 7, 25 mM L-Arginine HCl spike | 6.81 | |
| 1210-75-25P-7.0-5S Bulk (SPAS-14-007), 25 mM L-Arginine HCl spike | 7.07 | Very opalescent |
| 1210-75-25P-7.0-3So Bulk (SPAS-14-007), 25 mM L-Arginine QS Sodium Phosphate Monobasic | 7.55 | Moderately opalescent |
| 1210-75-25P-7.0-3So Bulk (SPAS-14-007), 25 mM L-Arginine Base | 9.17 | Slightly opalescent |

3. Term Stability

FIGS. 6-21 show the results for the initial stability study. These results show that the histidine formulations are the least stable and the phosphate formulations are most stable after 2 months at 2-8° C., 23-27° C., and 37° C. Also, as evidenced by size exclusion chromatography, in the phosphate formulations sorbitol and sucrose were comparable after 2 months at 2-8° C. and 23-27° C. However, sorbitol was slightly more stable at 37° C. compared to sucrose after 2 months. The dynamic light scattering results showed no significant change in phosphate samples with 25 mM L-Arginine after 2 months at 2-8° C. with the addition or sucrose or sorbitol. The dynamic light scattering results for the histidine samples at T=2 Months could not be overlaid due to high polydispersity between acquisitions, indicating a less stable formulation over the phosphate formulations. The 5 day freeze thaw cycle results did not show any significant change between T=0 and the 5 freeze thaw cycles.

4. Prototype Formulation

FIGS. 22-46 show the results for the stability prototype study. These results show that all phosphate formulations at 75 mg/mL and 100 mg/mL (bulk drug substance (BDS) and drug product (DP)) are stable over the course of the stability study at 2-8° C., −20° C. and −80° C. All 100 mg/mL bulk drug substance formulations after 5 freeze thaw cycles at −20° C. and −80° C. were stable and showed no significant change.

5. Interim Conclusions Prior to Short Term Degradation Tests

Based on the results of these studies, the optimal formulation for ALXN1210 high concentration material was determined. The preliminary experiments suggested addition of L-Arginine to reduce the opalescent appearance of ALXN1210 at 100 mg/mL. The initial stability study resulted in the lead formulation selection of phosphate buffer with L-Arginine at >50 mg/mL. The results from the prototype stability study determined the initial optimal formulation for ALXN1210 to be 50 mM Phosphate Buffer, 5% Sucrose, 25 mM Arginine, pH 7.4 at 100 mg/mL.

6. Development of Final Optimal Formulation

The suitability of the initial optimal formulation (100 mg/mL ALXN1210 in a formulation buffer (50 mM Sodium Phosphate, 25 mM Arginine, and 5% Sucrose, at pH 7.4) was subjected to short term degradation studies to assess whether polysorbate 80 (PS80) or other surfactant was necessary to prevent degradation. The two brands of PS 80 were 0.05% (w/v) NOF America Corporation POLYSORBATE 80 (HX2)™ which is reported to be comprised of >99% pure oleic acid and AVANTOR™ 4117, J. T. Baker® polysorbate 80 is a widely used surfactant that consists of a blend of fatty acids including oleic acid and palmitic acid. Both products are often referred to as TWEEN 80® and is a nonionic surfactant derived from polyethoxylated sorbitan and oleic acid with the hydrophilic groups derived from polymers of ethylene oxide.

The test methods used for the evaluation for the potential use J. T. baker avantor 4117PS80 in the 100 mg/mL ALXN1210 formulation are listed in Table 6 below. Refer to the individual test method for further detail and method description.

TABLE 6

Test Methods for Potential Use of J.T. Baker Avantor 4117 PS80

| Test | Assay Type | Objective and Rationale |
|---|---|---|
| Appearance | General Characteristic | A change in appearance may indicate product degradation. |
| Protein Concentration | Protein Concentration | Altered protein concentration results could indicate changes in product solubility or stability. |
| Turbidity (UV-vis) | General Characteristic | Increases in turbidity could indicate changes in product solubility or stability. |
| SE UPLC | Purity | To ensure that the sample remains intact, and meets the purity requirements. |
| Small volume HIAC | General Characteristic | To quantify changes in the number of subvisible particles in solution. An increase in subvisible particles may indicate physical changes in the profile of the product which may impact safety. |
| CE-SDS | Purity | An alteration in the CE-SDS pattern may indicate product degradation, such as cleavage of the polypeptide chain(s) or aggregation of the product. |
| iCE | Identity | A failing result may indicate protein degradation with the formation of uncharacteristic isoforms. |
| Dynamic Light Scattering (DLS) | Stability | To estimate the extent of aggregation/degradation. |
| Polysorbate 80 content | General Characteristic | To quantify the concentration of polysorbate 80 in the formulation. A decrease in polysorbate 80 concentration may result in antibody aggregation. |

TABLE 6-continued

| Test Methods for Potential Use of J.T. Baker Avantor 4117 PS80 | | |
|---|---|---|
| Test | Assay Type | Objective and Rationale |
| Polysorbate 80 degradation | General Characteristic | To quantify the amount of polysorbate 80 degradation in the formulation. An increase in polysorbate 80 degradation could lead to antibody aggregation. |

Vials containing 100 mg/mL ALXN1210 with either J. T. Baker avantor 4117 PS80 or HX2 NOF PS80 were visually inspected. All samples showed no visible particles or distinct color changes across all samples exposed to degradation storage at 45° C. and additional agitation for 5 days in 2-8° C. The results are shown in Table 7.

TABLE 7

| Visual inspection of 100 mg/mL ALXN1210 in 5 cc vials containing either J.T. Baker avantor 4117 PS80 or HX2 NOF PS80 | | | | |
|---|---|---|---|---|
| Sample ID | Clarity | Color | Interim Particles | Final Particles |
| ALXN1210 100 mg/mL + Avantor T = 0 | Clear | Slightly yellowish color | Practically free from particles | Practically free from particles |
| ALXN1210 100 mg/mL + NOF T = 0 | Clear | Slightly yellowish color | Practically free from particles | Practically free from particles |
| ALXN1210 100 mg/mL + Avantor T = 7 days at 45° C. | Clear | Slightly yellowish color | Practically free from particles | Practically free from particles |
| ALXN1210 100 mg/mL + NOF T = 7 days at 45° C. | Clear | Slightly yellowish color | Practically free from particles | Practically free from particles |
| ALXN1210 100 mg/mL Avantor T = 7 days at 45° C. + 5 day shake at 2-8° C. | Clear | Slightly yellowish color | Practically free from particles | Practically free from particles |
| ALXN1210 100 mg/mL NOF T = 7 days at 45° C. + 5 day shake at 2-8° C. | Clear | Slightly yellowish color | Practically free from particles | Practically free from particles |
| ALXN1210 100 mg/mL Avantor T = 4 days at 45° C. | Clear | Slightly yellowish color | Practically free from particles | Practically free from particles |
| ALXN1210 100 mg/mL NOF T = 14 days at 45° C. | Clear | Slightly yellowish color | Practically free from particles | Practically free from particles |
| ALXN1210 100 mg/mL Avantor T = 14 days at 45° C. + 5 day shake at 2-8° C. | Clear | Slightly yellowish color | Practically free from particles | Practically free from particles |
| ALXN1210 100 mg/mL NOF T = 14 day at 45° C. + 5 day shake@ 5° C. | Clear | Slightly yellowish color | Practically free from particles | Practically free from particles |

Concentration of ALXN1210 mg/mL shows as light decrease caused by the degradation condition. Refer to Table 8 for all concentration measurements.

ALXN1210 100 mg/mL formulations containing either 0.05% Avantor PS80 or HX2 NOF PS80 had no significant change in concentration when exposed to the same degradation condition as shown in FIG. 2.

TABLE 8

| Concentration Measurements | | | |
|---|---|---|---|
| Sample ID | Conc. (mg/mL) | Sample ID | Concen. (mg/mL) |
| ALXN1210 100 mg/mL + Avantor T = 0 | 98.6 | ALXN1210 100 mg/mL + NOF T = 0 | 100.5 |
| ALXN1210 100 mg/mL + Avantor T = 7 days at 45° C. | 88.9 | ALXN1210 100 mg/mL + NOF T = 7 days at 45° C. | 91.3 |
| ALXN1210 100 mg/mL Avantor T = 7 days at 45° C. + 5 day shake at 2-8° C. | 97.1 | ALXN1210 100 mg/mL NOF T = 7 days at 45° C. + 5 day shake at 2-8° C. | 98.2 |
| ALXN1210 100 mg/mL Avantor T = 4 days at 45° C. | 98.4 | ALXN1210 100 mg/mL NOF T = 14 days at 45° C. | 96.5 |
| ALXN1210 100 mg/mL Avantor T = 14 days at 45° C. + 5 day shake at 2-8° C. | 98.5 | ALXN1210 100 mg/mL NOF T = 14 day at 45° C. + 5 day shake @ 5° C. | 96.9 |

As shown above in Table 8, ALXN1210 100 mg/mL formulations containing either 0.05% Avantor P80 or HX2 NOF P80 had no significant change in concentration when exposed to the same degradation condition. Concentration remained comparable between ALXN1210 100 mg/mL formulations containing either 0.05% Avantor 80 or HX2 NOF PS80.

Turbidity was measured by monitoring absorbance at 650 nm. Measurements are shown in Table 9.

ALXN1210 100 mg/mL formulations containing either 10.0% Avantor PS80 or 0.05% HX2 NOF PS8 has no significant turbidity changes. Turbidity remains stable throughout all the time points and degradation conditions in this study

TABLE 9

| Turbidity Measured by Monitoring Abs 650 nm | | | |
|---|---|---|---|
| Sample ID | Abs (650 nm) | Sample ID | Abs (650 nm) |
| ALXN1210 100 mg/mL + Avantor T = 0 | 5.02E−03 | ALXN1210 100 mg/mL + NOF T = 0 | −9.28E−04 |
| ALXN1210 100 mg/mL + Avantor T = 7 days at 45° C. | 9.10E−04 | ALXN1210 100 mg/mL + NOF T = 7 days at 45° C. | 7.31 E−03 |
| ALXN1210 100 mg/mL Avantor T = 7 days at 45° C. + 5 day shake at 2-8° C. | −6.80E−04 | ALXN1210 100 mg/mL NOF T = 7 days at 45° C. + 5 day shake at 2-8° C. | 4.02E−04 |
| ALXN1210 100 mg/mL Avantor T = 4 days at 45° C. | −1.21E−03 | ALXN1210 100 mg/mL NOF T = 14 days at 45° C. | 1.12E−03 |
| ALXN1210 100 mg/mL Avantor T = 14 days at 45° C. + 5 day shake at 2-8° C. | 6.82E−04 | ALXN1210 100 mg/mL NOF T = 14 day at 45° C. + 5 day shake @ 5° C. | 2.12E−03 |

A decrease in percent monomer was observed for samples incubated at 45° C. for 7 days or 14 days plus additional shaking (200 RPM) at 2-8° C. as expected due to degradation conditions. However, the percent monomer showed no substantial difference between both ALXN1210 100 mg/mL formulations containing either 0.05% Avantor PS80 or 0.05% HX2 NOF PS80 when exposed to the same time point and condition.

The percent monomer data is shown in Table 10. FIG. 4 shows the % monomer decrease as expected after degrading conditions and no significant difference between both ALXN1210 100 mg/mL formulations containing either 0.05% Avantor PS80 or 0.05% HX2 NOF PS80 when exposed to the same time point and condition.

TABLE 10

Percent Monomer Samples Incubated at 45° C. for 7 days or 14 days Plus Additional Shaking (200 RPM) at 2-8° C.

| Sample ID | % Monomer | Sample ID | % Monomer |
|---|---|---|---|
| ALXN1210 100 mg/mL + Avantor T = 0 | 98.2 | ALXN1210 100 mg/mL + NOF T = 0 | 98.2 |
| ALXN1210 100 mg/mL + Avantor T = 7 days at 45° C. | 93.0 | ALXN1210 100 mg/mL + NOF T = 7 days at 45° C. | 93.0 |
| ALXN1210 100 mg/mL Avantor T = 7 days at 45° C. + 5 day shake at 2-8° C. | 92.8 | ALXN1210 100 mg/mL NOF T = 7 days at 45° C. + 5 day shake at 2-8° C. | 92.9 |
| ALXN1210 100 mg/mL Avantor T = 4 days at 45° C. | 88.1 | ALXN1210 100 mg/mL NOF T = 14 days at 45° C. | 88.0 |
| ALXN1210 100 mg/mL Avantor T = 14 days at 45° C. + 5 day shake at 2-8° C. | 85.3 | ALXN1210 100 mg/mL NOF T = 14 day at 45° C. + 5 day shake@ 5° C. | 87.7 |

A shift towards acidic species was detected by isoelectric focusing after incubation of ALXN1210 with either 0.05% J. T. Baker Avantor Polysorbate 80 or 0.05% HX2 NOF Polysorbate 80 at 45° C. for 7 days and 14 days as shown in Table 11. Additional shaking to samples did not have a significant impact on further shifting of main peak to acidic species.

TABLE 11

Isoelectric Focusing by CE-SDS

| Sample ID | Main PI | Main Area % | Acidic Area % | Basic Area % |
|---|---|---|---|---|
| Avantor-T0 | 6.2 | 64.2 | 23.4 | 12.4 |
| NOF-T0 | 6.2 | 65.0 | 21.4 | 13.6 |
| Avantor-7 d | 6.2 | 38.9 | 52.2 | 8.9 |
| NOF-7 D + 5 D | 6.2 | 41.7 | 50.4 | 8.0 |

TABLE 11-continued

Isoelectric Focusing by CE-SDS

| Sample ID | Main PI | Main Area % | Acidic Area % | Basic Area % |
|---|---|---|---|---|
| Avantor-7 d + 5 d/s | 6.2 | 41.6 | 49.2 | 9.2 |
| NOF-7 d + 5 d/s | 6.2 | 42.3 | 48.7 | 9.1 |
| T = 14 D_Avantor_45 C. | 6.2 | 21.4 | 74.8 | 3.8 |
| T = 14 D_NOF_45 C. | 6.2 | 18.1 | 79.0 | 2.9 |
| T = 14 D_Avantor_45 C + 5 d/s | 6.2 | 19.3 | 75.8 | 4.9 |
| T = 14 D_NOF_45 C + 5 d/s | 6.2 | 19.3 | 77.8 | 2.9 |

A shaking stress test was performed on the initial optimal formulation a 100 mg/mL ALXN1210 formulation buffer containing 50 mM Sodium Phosphate, 25 mM Arginine, and 5% sucrose, at pH 7.4 in the presence and absence of two brands of PS80 included at 0.05% concentration. The formation of sub-visible particles was used to assess degradation. The samples were shaken at 200 rpm at a temperature of between 2-8° C. The time points for measuring whether there was sub-visible particle formation was 0, 1, 3, and 5 days. The results as shown in Table 12 indicate that the addition of 0.05% of PS8 to the formulation greatly reduces the formation of sub-visible particles when the high concentration formulation is subjected to short term stress, such as 200 rpm shaking.

TABLE 12

Subvisible Particle Development Reduced by Addition of PS80 and Filtration

| Sample ID | Run Number | Total Particle Conc (#/mL) | Total Particle Count (#) | Particle Count 1-10.5 μm | Particle Count 11.5-25.5 μm | Particle Count >25.5 μm | Volume Analzyed |
|---|---|---|---|---|---|---|---|
| Not filtered, No PS80 | 1 | 869,694 | 454,725 | 419,989 | 33,722 | 1,014 | 0.5229 mL |
| POST filtered, No PS80 | 1 | 221,485 | 115,805 | 96,661 | 18,111 | 1,033 | 0.5229 mL |
| Not filtered - NOF PS80 | 1 | 605,402 | 316,239 | 312,238 | 3,414 | 587 | 0.5224 mL |
| POST filtered, NOF PS80 | 1 | 199 | 104 | 101 | 2 | 1 | 0.5321 mL |
| POST filtered, 4500 PS80 | 1 | 185 | 97 | 95 | 1 | 1 | 0.5231 mL |

7. Conclusion

In conclusion, the optimal subQ formulation for ALXN1210 at 100 mg/ml is buffer containing 50 mM Sodium Phosphate, 25 mM Arginine, and 5% sucrose, and 0.05% PS80 at pH 7.4

Example 2: Phase 1 Study to Evaluate Single Dose of ALXN1210 Administered Subcutaneously Compared to Intravenously in Healthy Subjects A Phase 1 study was conducted to evaluate the safety, tolerability, efficacy pharmacokinetics (PK)/pharmacodynamics (PD), and immunogenicity of antibody BNJ441 (also known as ALXN1210) administered subcutaneously (SC) compared to intravenously (IV) in healthy subject.

1. Objectives

The primary objectives of this study were to (1) evaluate the safety and tolerability of a single dose of ALXN1210 administered subcutaneously compared to ALXN1210 administered intravenously in healthy subjects, as assessed by physical examination findings, vital sign measurements, immunogenicity, laboratory analysis, and assessments of Adverse Events (AEs) and (2) determine the absolute bioavailability of ALXN1210 administered subcutaneously.

A secondary objective was to evaluate the PD effects of ALXN1210 administered subcutaneously compared to ALXN1210 administered intravenously, as assessed by the level of free C5 and chicken red blood cell (cRBC) hemolysis.

2. Study Design

Figure 47:
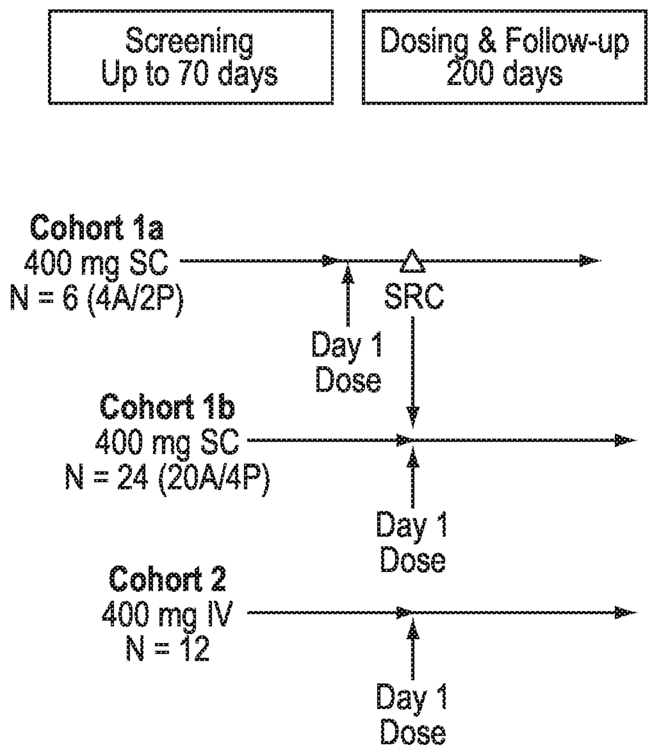
FIG. 47 depicts the overall design is of a Phase 1 study designed to evaluate the safety, tolerability, PK, PD, and immunogenicity of a single 400 mg dose of ravulizumab (ALXN1210) administered subcutaneously compared to a single 400-mg dose of ravulizumab (ALXN1210) administered intravenously or placebo administered subcutaneously in 42 healthy subjects.

The overall study design was conducted as shown depicted in FIG. 47. This was a Phase 1 study designed to evaluate the safety, tolerability, PK, PD, and immunogenicity of a single 400 mg dose of ALXN1210 administered subcutaneously compared to a single 400-mg dose of ALXN1210 administered intravenously or placebo administered subcutaneously in 42 healthy subjects. All subjects were screened for eligibility. Subjects who failed to meet eligibility criteria were not rescreened for participation in the study, unless the condition that led to eligibility failure was transient, self-limited, and easily treatable, and was expected to be resolved at the time of dosing.

Six subjects were initially randomly assigned in a 2:1 ratio to Cohort 1a, in a blinded fashion, to receive either a single 400-mg dose of ALXN1210 subcutaneously or single dose of placebo subcutaneously. The first 48 hours of post-dose clinical safety data was evaluated for subjects in Cohort 1a before enrollment into Cohorts 1b or 2 begins. Thirty-six subjects were then randomly assigned, in a 2:1 ratio, to either Cohort 1b (N=24) or Cohort 2 (N=12). Within Cohort 1b, the 24 subjects further were randomly assigned, in a 5:1 ratio and blinded fashion, to receive either a single 400-mg dose of ALXN1210 subcutaneously (20 subjects) or a single dose of placebo subcutaneously (4 subjects), respectively. The 12 subjects in Cohort 2 received a single 400 mg dose of ALXN1210 intravenously in an open-label fashion.

All enrolled subjects were included in analyses, as appropriate. Subjects in Cohorts 1a and 1b were combined for analyses. Subjects participated in the study for up to 39 weeks, including a screening period of up to 70 days, followed by a 200-day follow-up period for safety, PK, PD, and immunogenicity assessments after study drug administration.

Forty-two subjects were evaluated for the primary and secondary objectives in this study: 6 (4 received ALXN1210 subcutaneously, 2 received placebo subcutaneously) subjects in Cohort 1a; 24 (20 received ALXN1210 subcutaneously, 4 received placebo subcutaneously) subjects in Cohort 1b, and 12 (ALXN1210 IV) subjects in Cohort 2.

3. Dose Rationale

A single dose of 400 mg, equivalent to 4 mL, was administered subcutaneously via 4×1 mL injections in the abdominal area. Administration of a single 400-mg dose of ALXN1210 SC was expected to have an acceptable safety profile. Single doses of 400 mg of ALXN1210 SC and placebo SC, administered as described in this protocol, were anticipated to provide data from which multiple dose simulations could be generated in order to project the dosing regimens necessary to achieve therapeutic serum concentrations (>50 g/mL) in patients.

Parallel randomization of 36 subjects into Cohort 1b and Cohort 2 occurred based on review of the first 48 hours of post-dose clinical safety data from the 6 subjects in Cohort 1a. Enrollment into Cohort 1b and Cohort 2 proceeded as described in Table 13.

The group toxicity rules were as follows. Toxicity refers to clinically significant drug-related adverse reaction(s). "Cohort progression" refers to progression to a consecutive dose/dosing regimen in line with the dose progression rules and minimum data requirements. "Suspension" refers to no further IMP was administered at the dose level/dosing regimen concerned and that further cohort progression was suspended.

TABLE 13

Toxicity Rules

| CTCAE Grade | Severity/ Seriousness | Number of Subjects Affected | Action | Effect on cohort progression |
|---|---|---|---|---|
| I | Mild | N/A | Dose regimen continued. | Study continued as per clinical study protocol. |
| II | Moderate | ≤2 subjects in different SOC | | |
| | | 2 subjects in same SOC OR 3 subjects in different SOC | Dose regimen continued. | Cohorts 1b and 2 commenced, if they have not already. |
| | | ≥3 subjects in same SOC OR ≥4 subjects in different SOC | All dose regimens suspended UNLESS toxicity was either local tolerability event or injection/infusion site reaction, in which case only affected cohort was suspended. | Study continuation (if both cohorts stopped) required substantial amendment. Continuation of affected cohort (for local tolerability or injection/infusion site reactions) required substantial amendment. |
| III | Severe | 1 subject | Dose regimen continues. | Cohorts 1b and 2 commenced, if they have not already. |
| | | ≥2 subjects | All dose regimens suspended UNLESS the toxicity was either a local tolerability event or and injection/infusion site reaction, in which case only the affected cohort was suspended. | Study continuation (if both cohorts stopped) required substantial amendment. Continuation of the affected cohort (for local tolerability or injection/infusion site reactions) required substantial amendment. |
| IV | Life-threatening | ≥1 subject | Study suspended. | Study continuation required substantial amendment. |
| V | Fatal | | | |
| SAE | Serious | ≥1 subject | Study suspended. | Study continuation required substantial amendment. |

Abbreviations: CTCAE = Common Terminology Criteria for Adverse Events;
SAE = serious adverse event;
SOC = system organ class.

4. Schedule of Assessments

The timing of study procedures used is provided in Tables 14-15.

TABLE 14

Schedule of Assessments: Screening through Visit 1

| | Screening | | Visit 1 | | | | | | | | | | |
|---|---|---|---|---|---|---|---|---|---|---|---|---|---|
| | Study Day | | | | | | | | | | | | |
| | Screening | | Day 1 Assessments[1] | | | | | | | | | | |
| | Day −70 to Day −2 | Day −1 Admit Day −1 | Pre-dose | 0 h (SOI) | EOI[2] | 15 min post EOI | 30 min post EOI | 2 h post SOI | 4 h post SOI | 8 h post SOI | Day 2 24 h | Day 3 48 h | Day 5 96 h |
| Status (OP or CRU) | OP | Admit | CRU | CRU | CRU | CRU | CRU | CRU | CRU | CRU | CRU | CRU | CRU[3] |
| Informed consent[4] | X | | | | | | | | | | | | |
| MCV4 immunization (Day −56)[5] | X | | | | | | | | | | | | |
| Meningococcal | X | | | | | | | | | | | | |
| Status (OP or CRU) | OP | Admit | CRU | CRU | CRU | CRU | CRU | CRU | CRU | CRU | CRU | CRU | CRU[3] |
| serogroup B immunization (Day −56 and Day −28)[5] | | | | | | | | | | | | | |
| Serum bactericidal antibody (meningococcal serogroups A, C, W135, and Y) | X | | | | | | | | | | | | |
| Medical history & demographics | X | | | | | | | | | | | | |
| Physical examination | X | X | | | | | | | | | | | X |
| Height, weight, and BMI | X | | | | | | | | | | | | |
| QuantiFERON ®-TB test | X | | | | | | | | | | | | |
| Chemistry | X | X | | | | | | | | | X | | X |
| Hematology | X | X | | | | | | | | | X | | X |
| Coagulation | X | X | | | | | | | | | X | | X |
| Hepatitis B and C screen | X | | | | | | | | | | | | |
| HIV, types I and II screen | X | | | | | | | | | | | | |
| Complement activity[6] | X | | | | | | | | | | | | |
| CH50[7] | | X | | | | | | | | | | | |
| Serum pregnancy test[8] | X | X | | | | | | | | | | | |
| Alcohol breath test | X | X | | | | | | | | | | | |
| Urinalysis and urine chemistry | X | X | | | | | | | | | X | | X |
| Urine drug screen | X | X | | | | | | | | | | | |
| Vital sign measurements | X | X | X[9] | | X | | X[9] | X[9] | X[9] | X[9] | X | X | X |
| ECG | X | | X[10] | | | X | | | | | X | X | X |
| Cardiac telemetry[11] | | | X | X | (X) | (X) | (X) | (X) | | | | | |
| Randomization | | | | X | | | | | | | | | |
| Study drug administration | | | | X | | | | | | | | | |
| PK samples | | | X | | X | | X | X | X | X | X | X | X |
| PD panel (serum C5, cRBC | | X | X | | X | | X | X | X | X | X | X | X |
| Status (OP or CRU) | OP | Admit | CRU | CRU | CRU | CRU | CRU | CRU | CRU | CRU | CRU | CRU | CRU[3] |
| hemolysis) | | | | | | | | | | | | | |

TABLE 14-continued

Schedule of Assessments: Screening through Visit 1

| | Screening | | Visit 1 Study Day Day 1 Assessments[1] | | | | | | | | | | |
|---|---|---|---|---|---|---|---|---|---|---|---|---|---|
| | Day −70 to Day −2 | Day −1 Admit Day −1 | Pre-dose | 0 h (SOI) | EOI [2] | 15 min post EOI | 30 min post EOI | 2 h post SOI | 4 h post SOI | 8 h post SOI | Day 2 24 h | Day 3 48 h | Day 5 96 h |
| Infusion site evaluation[12] | | | X | | | | X | X | X | X | X | X | |
| Immunogenicity (ADA) | | | X | | | | | | | | | | |
| Review potential safety risks of ALXN1210[13] | X | X | | | | | | | | | | | X |
| Concomitant medications | | | | ←Monitor continuously (after ICF was signed at screening)→ | | | | | | | | | |
| Adverse events[14] | | | | ←Monitor continuously (after ICF was signed at screening)→ | | | | | | | | | |
| Antibiotic prophylactic treatment[15] | | | | | | ←Antibiotic prophylaxis→ | | | | | | | |

[1]Permissible windows for study assessments are described in the study operations manual.

[2] End of infusion (EOI) was approximately 15 minutes after start of infusion (SOI).

[3]Subject was discharged from clinical research unit after completing all Day 5 assessments. Subjects are provided a "Study Participant ID card" with information for Healthcare Provider and participant on symptoms of meningitis infection.

[4]Signed and dated informed consent forms were obtained before any study-specific screening procedures are performed.

[5]For subjects who did not have adequate documentation of prior MCV4 immunization or serogroup B vaccination, MCV4 immunization was performed at least 56 days prior to first dose on Day 1, and vaccination for serogroup B meningococcal infections was administered at least 56 days prior to Day 1 dosing with a booster administered at least 28 days prior to dosing on Day 1.

[6]Complement activity, confirmed by a suitable assay such as complement alternative pathway (CAP) ELISA/C5 (hemolysis) inhibition, was performed at screening to confirm subjects do not have a complement deficiency.

[7]The sample drawn on Day −1 was stored for future analysis should the post-dose sample indicate that complement has not normalized.

[8]Serum pregnancy test for all female subjects to confirm a female subject was not pregnant.

[9]On Day 1, vital sign measurements were assessed pre-dose (within 15 minutes prior to SOI) and at end of infusion, 30 minutes after end of infusion, 2 hours after start of infusion, 4 hours after start of infusion, and 8 hours after start of infusion.

[10]On Day 1, triplicate 12-lead ECGs were performed pre-dose and approximately 15 minutes post-end of infusion.

[11]Continuous cardiac registration predose through duration of IV infusion (Cohort 2) and until 3 hours post SC injection (Cohorts 1a and 1b).

[12]Infusion or injection site evaluations were done within 15 minutes of the start of infusion/injection and ±15 minutes of the other scheduled times on Day 1. Indurations or reactions <1 cm were not listed as an adverse event unless it persisted for more than 24 hr. Pain at site of infusion or injection was assessed using a Visual Analog Scale (0-10). Pain was not assessed pre-dose.

[13]The investigator or designee met with the subject at each visit to discuss the potential safety risks of ALXN1210, and to address any safety concerns on the part of the subject.

[14]Collection of adverse events (AEs) and serious adverse events (SAEs) began at informed consent form signing.

[15]Subjects were administered prophylactic antibiotic treatment, oral penicillin V 500 mg twice daily (equivalent to $1 \times 10^6$ units), beginning on the evening of Day −1, until complement activity normalized, as determined by CH50 assay.

Abbreviations: ADA = antidrug antibody; BMI = body mass index; cRBC = chicken red blood cell; CRU = clinical research unit; ECG = electrocardiogram; EOI = end-of-infusion/injection; HIV = human immunodeficiency virus; ICF = informed consent form; MCV4 = tetravalent meningococcal conjugate vaccine; OP = outpatient; SOI = start-of-infusion/injection; TB = tuberculosis

TABLE 15

Schedule of Assessments: Visit 2 through Visit 14

| | Visit 2 | Visit 3 | Visit 4 | Visit 5 | Visit 6 | Visit 7 | Visit 8 | Visit 9 | Visit 10 | Visit 11 | Visit 12 | Visit 13 | Visit 14 |
|---|---|---|---|---|---|---|---|---|---|---|---|---|---|
| | Procedures | | | | | | | | | | | | |
| | Day 8 | Day 15 | Day 22 | Day 29 | Day 36 | Day 43 | Day 50 | Day 57 | Day 71 | Day 90 | Day 120 | Day 150 | Day 200 |
| Status (OP or CRU) | OP | OP | OP | OP | OP | OP | OP | OP | OP | OP | OP | OP | OP |
| Physical | | X | | | | X | | | | X | X | X | X |
| Vital Sign | X | X | X | X | X | X | X | X | X | X | X | X | X |
| ECG | | | | | | | | | | | | X | X |
| Chemistry | X | X | | X | | X | | X | | X | X | X | X |
| Hematology | X | X | | X | | X | | X | | X | X | X | X |
| Coagulation | X | X | | X | | X | | X | | X | X | X | X |
| Urinalysis and Urine | | X | | | | X | | | | X | X | X | X |
| Serum Pregnancy | | | | | | | | | | | | X | X |
| CH50 Testing | | | | | | X | | X[1] | | | | | |
| Pharmacokinetic | X | X | X | X | X | X | X | X | X | X | X | X | X |
| Pharmacodynamics | X | X | X | X | X | X | X | X | X | X | X | X | X |
| Panel (serum C5, | | | | | | | | | | | | | |

TABLE 15-continued

| Schedule of Assessments: Visit 2 through Visit 14 | | | | | | | | | | | | | |
|---|---|---|---|---|---|---|---|---|---|---|---|---|---|
| | Visit 2 | Visit 3 | Visit 4 | Visit 5 | Visit 6 | Visit 7 | Visit 8 | Visit 9 | Visit 10 | Visit 11 | Visit 12 | Visit 13 | Visit 14 |
| Procedures | Day 8 | Day 15 | Day 22 | Day 29 | Day 36 | Day 43 | Day 50 | Day 57 | Day 71 | Day 90 | Day 120 | Day 150 | Day 200 |
| Immunogenicity | | X | | X | | | | X | | X | X | X | X |
| Review Potential | <--- Discuss potential safety risks of ALXN1210--> | | | | | | | | | | | | |
| Safety Risks of | | | | | | | | | | | | | |
| Concomitant | <--- Monitor continuously (after ICF was signed at screening)--> | | | | | | | | | | | | |
| Adverse Events[3] | <--- Monitor continuously (after ICF was signed at screening)--> | | | | | | | | | | | | |
| Antibiotic | <--- Antibiotic prophylaxis--> | | | | | | | | | | | | |

[1]Additional samples were taken after Day 57.

[2] The investigator or designee met with the subject at each visit to discuss the potential safety risks of ALXN1210, and to address any safety concerns on the part of the subject.

[3]Collection of adverse events began at informed consent form signing.

[4] Subjects were administered prophylactic antibiotic treatment, oral penicillin V 500 mg twice daily (equivalent to $1 \times 10^6$ units) until complement activity normalized, as determined by CH50 assay.

Abbreviations: ADA = antidrug antibody; cRBC = chicken red blood cell; CRU = clinical research unit; ECG = electrocardiogram; ICF = informed consent form; OP = outpatient 5. Selection and Withdrawal of Subjects Subjects must have met all of the following criteria to be eligible for the study:

1. Healthy subjects, aged 25 through 55 years, inclusive, at the time of dosing.
2. Body mass index (BMI) from 18 through 29.9 kg/m$^2$, inclusive, and weight between 50 and 100 kg, inclusive.
3. QT interval corrected using the Fridericia's formula (QTcF)≤450 msec for males and ≤470 msec for females at screening and prior to dosing on Day 1.
4. Willing and able to give written informed consent and comply with the study visit schedule.
5. Documented vaccination with MCV4 at least 56 days and not more than 3 years prior to dosing. Documentation must have included a positive antibody titer to confirm an immune response before study drug administration.
6. Vaccination with serogroup B meningococcal vaccine at least 56 days prior to dosing on Day 1, with a booster administered at least 28 days prior to dosing on Day 1, with at least 28 days between the first and second injections.
7. Female subjects of childbearing potential, if heterosexually active, must have used highly effective or acceptable contraception as defined below, starting at screening and continuing until at least 6 months after study drug administration. Antibiotic prophylaxis was required during this study, which can compromise the efficacy of hormonal contraception. Therefore, it was recommended that subjects using hormonal contraception also use barrier contraception (e.g., condom or diaphragm with spermicide) for the duration of antibiotic prophylaxis. Male subjects, if heterosexually active and with a female spouse or partner of childbearing potential or a pregnant or breastfeeding spouse or partner, must agree to use barrier contraception (male condom) during the treatment period and for at least 6 months after study drug administration. Barrier contraception was required even with documented medical assessment of surgical success of a vasectomy. Female spouses or partners of male subjects who are of childbearing potential must have used highly effective contraception as defined above, or acceptable contraception as defined below, starting at screening and continuing until at least 6 months after study drug administration. Male subjects must not have donated sperm during the screening and treatment periods and for at least 6 months after study drug administration.

Subjects meeting any of the following exclusion criteria were not eligible to participate in the study:

1. Subjects who were in intimate and prolonged contact with (defined as living under the same roof or providing personal care to) people younger than 2 years of age or older than 65 years of age, or who were either immunocompromised or had one of the following underlying medical conditions: anatomic or functional asplenia (including sickle cell disease); congenital complement, properdin, factor D, or primary antibody deficiencies; acquired complement deficiencies (eg, those receiving eculizumab); or human immunodeficiency virus (HIV).
2. Subjects who were one of the following: professionals who were exposed to environments of greater risk for meningococcal disease; research, industrial, and clinical laboratory personnel who were routinely exposed to *N meningitides*; military personnel during recruit training (military personnel may be at increased risk of meningococcal infection when accommodated in close quarters); daycare center workers; those living on a college or university campus; and those who planned to travel during the course of the study to or have travelled to endemic areas for meningococcal meningitis (e.g., India, Sub-Saharan Africa, pilgrimage to Saudi Arabia for Hajj) within 6 months prior to dosing
3. History of any *Neisseria* infection.
4. History of unexplained, recurrent infection, or infection requiring treatment with systemic antibiotics within 90 days prior to dosing.
5. HIV infection (evidenced by HIV-1 or HIV-2 antibody titer).
6. Acute or chronic hepatitis B virus (HBV) infection. Hepatitis B surface antigen (HBsAg) testing was required for all subjects prior to enrollment. Subjects with positive HBsAg will not be enrolled. For subjects with negative HBsAg, the following testing algorithm was required: If hepatitis B core antibody (HBcAb) was negative, the subject was eligible to enroll. If HBcAb was positive, the hepatitis B surface antibody (HBsAb) was tested. If both HBcAb and HBsAb were positive, the subject was eligible to enroll. If HBcAb was positive and HBsAb was negative, the subject was not enrolled.

7. Acute or chronic hepatitis C virus (HCV) infection (evidenced by antibody titer).
8. Active systemic viral or fungal infection within 14 days prior to dosing.
9. Positive or indeterminate QuantiFERON®-TB test indicating possible tuberculosis (TB) infection.
10. History of latent or active TB or exposure to endemic areas within 8 weeks prior to the screening visit.
11. Female subjects who were breastfeeding or were heterosexually active and unwilling to practice contraception and are not postmenopausal. Postmenopausal was defined as amenorrhea ≥12 consecutive months without another cause and a documented serum follicle-stimulating hormone level ≥40 mIU/mL and estradiol concentration ≤110 pmol/L within the 6 months prior to study drug administration.
12. Positive serum pregnancy test at screening or on Day −1.
13. Serum creatinine greater than the upper limit of normal (ULN) of the reference range of the testing laboratory at screening or on Day −1.
14. Alanine aminotransferase (ALT) or aspartate aminotransferase (AST) >ULN of the reference range of the testing laboratory at screening or >1.5×ULN of the reference range of the testing laboratory on Day −1.
15. Any of the following hematology results: hemoglobin <130 g/L for males and <115 g/L for females, hematocrit <0.37 L/L for males and <0.33 L/L for females, white blood cell (WBC) count $<3.0\times10^3/\mu L$, absolute neutrophil count $<2.0\times10^3/\mu L$, and platelet count <150 or $>400\times10^3/\mu L$ at screening or on Day −1. Complete blood count (CBC) clinical laboratory results that are considered clinically relevant and unacceptable by the investigator at Day −1.
16. History of complement deficiency or complement activity below the normal reference range as evaluated by CAP ELISA at screening.
17. History of malignancy with the exception of a non-melanoma skin cancer or carcinoma in situ of the cervix that has been treated with no evidence of recurrence.
18. Participation in a clinical study within 30 days before initiation of dosing on Day 1 or use of any experimental small-molecule therapy within 30 days prior to dosing on Day 1.
19. Participation in more than one clinical study of an mAb, or participation in a clinical study of an mAb within the 12 months prior to screening, during which the subject was exposed to the active study drug. Subjects who have participated in only one study of a mAb could have been considered for enrollment if they completed that study more than 12 months prior to screening.
20. Prior exposure to ALXN1210.
21. Major surgery or hospitalization within 90 days prior to dosing.
22. History of allergy to excipients of ALXN1210 (e.g., polysorbate 80).
23. Documented history of allergy to penicillin or cephalosporin.
24. History of significant allergic reaction (e.g., anaphylaxis or angioedema) to any product (food, pharmaceutical, etc.).
25. Currently smoked >10 cigarettes daily (former smokers may be permitted to enroll at the investigator's discretion).
26. History of illicit drug abuse, history of significant alcohol abuse within 1 year prior to the screening visit, or regular use of alcohol within 6 months prior to the screening visit (more than 14 units of alcohol per week [1 unit=150 mL of wine, 360 mL of beer, or 45 mL of 40% alcohol]).
27. Positive urine drug toxicology screen at screening or on Day −1.
28. Alcohol consumption within 48 hours prior to study drug administration or positive alcohol breath test on Day −1.
29. Donation of plasma within 7 days prior to dosing. Donation or loss (excluding volume drawn at screening) of more than 50 mL of blood within 30 days prior to dosing or more than 499 mL of blood within 56 days prior to dosing.
30. History of continuous topical, inhaled, or systemic steroid use >28 days or history of any inhaled or topical immunosuppressive therapy within 90 days prior to study drug administration.
31. Use of prescription medications (excluding oral contraceptives) within 14 days prior to study drug administration, except with prior approval of the sponsor.
32. Regular use of nonprescription, over-the-counter medications, including herbal remedies and supplements, within 14 days prior to study drug administration. Multivitamins, acetaminophen ≤2 g per day, and topical skin products without significant systemic absorption are allowed.
33. Clinical diagnosis of any autoimmune or rheumatologic disease (e.g., systemic lupus erythematosus, rheumatoid arthritis).
34. Immunization with a live-attenuated vaccine 28 days prior to dosing or planned vaccination during the course of the study (except for the vaccination planned by the study protocol). Immunization with inactivated or recombinant influenza vaccine was permitted.
35. Presence of fever (confirmed body temperature >37.6° C.) (e.g., a fever associated with a symptomatic viral or bacterial infection) within 14 days prior to dosing.
36. Subjects with any medical history, conditions, or risks that, in the opinion of the investigator, could have interfered with the subject's full participation in the study or compliance with the protocol, or could have posed any additional risk for the subject or confounded the assessment of the subject or outcome of the study.

6. Infection

To mitigate the risk of infection associated with terminal complement inhibition, subjects in this study were administered the following:

1. A MCV4 vaccination at least 56 days prior to dosing of ALXN1210 on Day 1 (if not vaccinated with MCV4 within the last 3 years, or if subjects were previously vaccinated, but there was not adequate documentation to verify prior vaccination).
2. Two injections of the serogroup B meningococcal vaccine. The first injection must have been administered at least 56 days prior to dosing on Day 1, with a booster administered at least 28 days prior to dosing on Day 1, with at least 28 days between the first and second injections.

3. Prophylactic antibiotic treatment, oral penicillin V 500 mg twice daily (equivalent to $1\times10^6$ units) until complement activity normalized (as determined by CH50 assay).

The first dose of antibiotic are administered orally on Day −1 in the evening, prior to the Day 1 (dose administration) of study drug. For the outpatient portion of the study, subjects were instructed to take the antibiotic approximately at the same times (twice daily) on each scheduled day. A suitable system (such as text messaging) was used for daily monitoring of subjects' compliance with the antibiotic prophylaxis regimen.

The following observations support the administration of antibiotic prophylaxis in this single-dose study:

1. Penicillin was the drug of choice in eradication of *N meningitidis* in carriers.
2. Complement-deficient patients who received monthly injections with benzathine penicillin G as prophylaxis for recurrent meningococcal disease during a 2- to 4-year period experienced significantly fewer episodes of *Neisseria* infection than deficient individuals not receiving prophylaxis (Figueroa J E, et al., *Clin. Microbiol. Rev.* 1991 July; 4(3):359-95).
3. High levels of resistance to penicillin caused by plasmid-encoded β-lactamases were rarely encountered in meningococcal strains (Yazdankhah S P, et al., *J. Med. Microbiol.* 2004 September; 53(Pt 9):821-32).
4. Antibiotic prophylaxis with orally administered penicillin V 500 mg twice daily has been provided in the treatment of PNH and aHUS patients with eculizumab by some physicians (Kelly R J, et al., *Blood* 2011 Jun. 23; 117(25):6786-92 and Leeds Teaching Hospitals NHS Trust, Kings College Hospital NHS Foundation Trust. National Specialised Commissioning Team (NSCT) Service Specification Paroxysmal Nocturnal Haemoglobinuria (PNH). 2013).
5. Uncertainty around the effectiveness of vaccines in immunocompromised patients has prompted several countries, such as France, to recommend continuous antibiotic prophylaxis for the duration of eculizumab treatment in PNH and aHUS patients (Zuber J, Fakhouri F, Roumenina L T, Loirat C, Fremeaux-Bacchi V. Use of eculizumab for atypical haemolytic uraemic syndrome and C3 glomerulopathies. Nat. Rev. Nephrol. 2012 November; 8(11):643-57).

7. Prior and Concomitant Medications and Procedures

Prior medications (any drug or substance taken by the subject within 14 days prior to the time the subject signs the ICF until study drug administration) and concomitant medications (any drug or substance taken by the subject after study drug administration until completion of the last study visit) were recorded on the subject's electronic case report form (eCRF). Prior procedures (any therapeutic intervention [e.g., surgery/biopsy, physical therapy] performed within 14 days prior to the time the subject signs the informed consent until study drug administration) and concomitant procedures (any therapeutic intervention [e.g., surgery/biopsy, physical therapy] performed after study drug administration until completion of the last study visit) were recorded on the subject's eCRF.

A concomitant therapy was any drug or substance administered from the time the subject was screened for the study until completion of the last study visit. For the duration of the study, subjects were instructed not to start taking any new medications, including nonprescription drugs and herbal preparations, unless they have received permission from the investigator. The occasional use of over-the-counter antipyretics or analgesics (e.g., acetaminophen) was allowed during the study.

A concomitant procedure was any therapeutic intervention (e.g., surgery/biopsy, physical therapy) or nonstudy diagnostic assessment (e.g., blood gas measurement, bacterial cultures) performed from the time the subject signs the informed consent until the last study visit. Concomitant procedures were not allowed unless medically indicated.

8. Randomization and Blinding

Eligible subjects who met the inclusion and exclusion criteria were assigned unique numbers for enrollment and randomization.

This was a partially blinded study such that:

Cohort 1a. Dosing (a single 400-mg dose of ALXN1210 SC or placebo SC) was double-blind. Subjects in Cohort 1a were randomly assigned in a 2:1 ratio (4 ALXN1210 SC, 2 placebo SC; N=6).

Cohort 1b. Dosing (a single 400-mg dose of ALXN1210 SC or placebo SC) was double-blind. Subjects in Cohort 1b were randomly assigned in an 5:1 ratio (20 ALXN1210 SC, 4 placebo SC; N=24).

Cohort 2. Dosing (a single 400-mg dose of ALXN1210 IV) was open-label (N=12).

During Cohort 2 dosing, both subjects and onsite medical/nursing staff knew the drug/dose being administered.

During Cohorts 1a and 1b dosing, subjects and onsite medical/nursing staff at the study center were blinded to study drug assignment. The pharmacy staff preparing the SC injections was not blinded, nor were the study drug administrator(s), while all other study center staff involved in the safety evaluations remain blinded to study drug assignment. Sponsor staff were unblinded as needed (e.g., to monitor that the SC injections were being prepared appropriately, to determine reportability of SAEs), and refrained from sharing any information on study drug assignment with the study center staff.

9. Description of Study Drug

The investigational product is described in Table 16.

TABLE 16

Investigational Product

| | Investigational Product | | |
|---|---|---|---|
| Product Name | ALXN1210 IV | ALXN1210 SC | Placebo SC |
| Dosage Form | Sterile solution for infusion | Sterile solution for injection | Sterile solution for injection |
| Unit Dose | 150 mg/vial[1] | 100 mg/vial[2] | NA |
| Route of Administration | Intravenous | Subcutaneous injection | Subcutaneous injection |
| Physical Description | Sterile, preservative-free solution | Sterile, preservative-free solution | 0.9% sodium chloride for injection, Ph Eur or BP, sterile, preservative-free solution |
| Manufacturer | Alexion Pharmaceuticals, Inc. | Alexion Pharmaceuticals, Inc. | Saline solution marketed in UK |

[1]Each vial of ALXN1210 IV drug product included a nominal overfill to ensure that 15 mL (150 mg of ALXN1210) could be withdrawn for administration.
[2]Each vial of ALXN1210 SC drug product included a nominal overfill to ensure that 1 mL (100 mg of ALXN1210) could be withdrawn for administration.
Abbreviations: BP = British Pharmacopoeia;
IV = intravenous;
NA = not applicable;
Ph Eur = European Pharmacopoeia;
SC = subcutaneous 10. ALXN1210 and Placebo Each vial of ALXN1210 SC contained 100 mg of ALXN1210 (100 mg/mL) in 50 mM sodium phosphate, 25 mM arginine, 5% sucrose, and 0.05% polysorbate 80. ALXN1210 SC is formulated at pH 7.4 and was provided as a fully-formulated, sterile, preservative-free, 100 mg/mL aqueous solution of ALXN1210 supplied in 2-mL single-use vials. Each vial of ALXN1210 SC included a nominal overfill to ensure that 1 mL (100 mg of ALXN1210) could have been withdrawn for administration.

Each dose of placebo SC contained 0.9% sodium chloride injection, Ph Eur or BP, to the same volume as specified for Cohorts 1a and 1b.

Each vial of ALXN1210 IV contains 150 mg of ALXN1210 in 10 mM sodium phosphate, 150 mM sodium chloride, 0.02% polysorbate 80, and water for injection. ALXN1210 IV was formulated at pH 7.0 and was provided as a fully-formulated, sterile, preservative-free, 10-mg/mL aqueous solution of ALXN1210, supplied in 20-mL single-use vials. ALXN1210 IV was diluted in 0.9% sodium chloride injection, Ph Eur or BP, and administered by IV infusion at a maximum rate of 333 mL/hr, excluding interruption for safety or technical reasons.

ALXN1210 vials were stored in refrigerated conditions at 2° C. to 8° C. (36° F. to 46° F.) and protected from light. ALXN1210 vials were not frozen or shaken.

ALXN1210 SC and placebo SC were prepared in a blinded fashion in a syringe for SC administration. There was no dilution of ALXN1210 SC or placebo SC. ALXN1210 SC and placebo SC was placed directly into the syringe.

ALXN1210 IV was designed for infusion by diluting into commercially available saline (0.9% sodium chloride injection; Ph Eur or BP) for IV infusion at a maximum rate of 333 mL/hr, excluding interruption for safety or technical reasons.

ALXN1210 IV was diluted with 0.9% sodium chloride injection, Ph Eur or BP, before administration (dosing solution). The in-use shelf life of the dosing solution was 4 hours at room temperature 15° C. to 25° C. (59° F. to 77F). The expiration date and time of the dosing solution was calculated from breach of the first vial. The dose was administered within the expiration date and time. Each 1-mL syringe of ALXN1210 SC or placebo SC that was drawn up (4 syringes per subject) was administered within 1 hour once drawn up from vial to syringe.

11. Administration

All doses of ALXN1210 SC or placebo SC were administered by four 100-mg SC injections of 1 mL each (Table 17) in the abdominal area. All four 1-mL injections were administered over a 15-minute period, and there should have been at least 15 minutes between the end of injection in one subject and the start of injection in the next subject.

TABLE 17

Dosing Reference Chart for ALXN1210 SC and Placebo SC Preparation

| Cohort | Study drug and dose | Number of 1-mL syringes prepared | Total volume administered |
|---|---|---|---|
| 1a | 1 close of 400 mg ALXN1210 SC or placebo SC | 4 | 4 mL |
| 1b | 1 dose of 400 mg ALXN1210 SC or placebo SC | 4 | 4 mL |

All doses of ALXN1210 IV were administered by IV infusion, using IV sets with in-line filters, at a maximum rate of 333 mL/hr, excluding interruption for safety or technical reason. There should have been at least 15 minutes between the end of infusion in one subject and the start of infusion in the next subject.

TABLE 18

Dosing Reference Chart for ALXN1210 IV Preparation

| Cohort | Study drug and dose | ALXN1210 volume per dose (mL) | Diluent volume per dose (mL) | Infusion volume (mL) | Maximum infusion rate (mL/h) | Minimum infusion duration [1] minutes (hour) |
|---|---|---|---|---|---|---|
| 2 | 1 dose of 400 mg ALXN1210 IV | 40 | 40 | 80 | 333 | 15 (0.25) |

[1] Infusion duration was approximate.

12. Management of Potential Adverse Events During Study Drug Administration

Some subjects treated with IV infusions of monoclonal antibodies have experienced concurrent infusion-related reactions with signs or symptoms that can be classified as acute allergic reactions/hypersensitivity reactions or cytokine release syndrome.

Subjects were closely monitored during and after study drug administration for any symptoms of anaphylaxis and other hypersensitivity reactions, including circulatory and/or respiratory changes or arrest, or urticaria, arthralgias, myalgias, or other signs of related reactions. Adequate treatment was immediately available. Infusion-associated adverse events could have occurred, and depending on their type and severity, discontinuation of infusion could have been required. Subjects were informed of early symptoms and signs of hypersensitivity reactions including hives, swollen face, eyelids, lips, or tongue, or trouble with breathing. An acute infusion-reaction algorithm was used to manage infusion-related reactions. In this study, regular assessments to monitor infusion reactions and infusion site reactions were done. To ensure that reactions could have been dealt with promptly, there was at least 15 minutes between the end of infusion/injection in one subject and the start of infusion/injection in the next subject. No more than 6 subjects were dosed per day. Any reactions were treated and taken into account in the dose continuation/escalation and toxicity rules. If anaphylactic reactions occurred, the current "UK Treatment Guideline for Anaphylactic Reactions" of the UK Resuscitation Council were followed.

13. Pharmacokinetic (PK) and Pharmacodynamic (PD) Assessments

After study drug administration, serum samples for the determination of serum ALXN1210 concentrations and for analyses of total and free C5 concentrations, cRBC hemolysis, and potentially other measures of C5 activation were collected at the following time points, with the actual serum sampling dates and times being recorded and used in the PK and PD calculations:

Serum concentrations of ALXN1210 were assayed from the following sampling time points: pre-dose (within 15 minutes prior to start-of-infusion/injection [SOI]); Day 1 at end of infusion/injection (EOI), 30 minutes post EOI, and the following time points following SOL: 2 h, 4 h, and 8 h; Day 2 (24 h); Day 3 (48 h); Day 5 (96 h); Day 8 (168 h); Day 15 (336 h); Day 22 (504 h); Day 29 (672 h); Day 36 (840 h); Day 43 (1008 h); Day 50 (1176 h); Day 57 (1344 h); Day 71 (1680 h); Day 90 (2136 h); Day 120 (2856 h); Day 150 (3576 h); and Day 200 (4776 h).

All subjects who provided an adequate number of serum PK samples to characterize a concentration-time profile were included in the PK analysis population. All subjects who provided PD samples were included in the PD analysis population.

14. Immunogenicity Assessments

Serum samples were collected at the following time points: pre-dose (within 15 minutes prior to SOI), and on Days 15 (336 h), 29 (672 h), 57 (1344 h), 90 (2136 h), 120 (2856 h), 150 (3576 h), and 200 (4776 h) and analyzed for ADA to ALXN1210. Further characterization of antibody response was conducted as appropriate based on PK/PD and safety data of ALXN1210.

All subjects who provide a pre-dose and a post-dose sample for ADA were included in the immunogenicity analysis population.

The immunogenicity assay evaluates antidrug antibody (ADA) to ALXN1210. Detailed instructions on the procedure for collecting, processing, storing, and shipping serum samples for immunogenicity analysis were provided in the laboratory manual.

15. Assessment of Safety

Safety assessments included TB testing, physical examination findings, vital sign measurements, immunogenicity (ADA) testing, laboratory evaluations, ECGs, infusion site and injection site evaluations (e.g., bleeding, bruising, erythema, swelling, induration, and pain), and monitoring of adverse events. Adverse events were graded according to the National Cancer Institute Common Terminology Criteria for Adverse Events v4.03 (CTCAE v4.03), published 14 Jun. 2010. Laboratory evaluations included hematology, chemistry, and coagulation panels; CBC with differential; urinalysis; and serum pregnancy test for female subjects.

Clinical and laboratory assessments were performed to assess safety of ALXN1210. The timing of the assessments is described in the Schedule of Assessments. Abnormal results were followed until resolution or stabilization.

A review of demographic parameters, including age, gender, race, and ethnicity was performed as described in the Schedule of Assessments. A complete medical history was taken.

Vital sign measurements were taken after the subject has been resting in the supine or semirecumbent position for at least 5 minutes and will include temperature (° C.; oral), respiratory rate, supine blood pressure, and pulse. The timing of vital sign measurements is described in the Schedule of Assessments. Out-of-range blood pressure or pulse measurements were repeated at the investigator's discretion. Any confirmed, clinically significant vital sign measurements were recorded as adverse events.

Weight, height, and BMI were recorded as described in the Schedule of Assessments. Each examination included the following assessments: general appearance; skin; head, ears, eyes, nose, and throat; neck; lymph nodes; chest; heart; abdominal cavity; limbs; central nervous system; and musculoskeletal system.

A triplicate 12-lead ECG was obtained after the subject had been resting for at least 5 minutes. The timing of ECGs is described in the Schedule of Assessments. In addition, continuous cardiac registration was performed at each dose administration from pre-dose to end of IV infusion in Cohort 2 and from pre-dose to 3 hours post end of SC injection in Cohorts 1a and 1b. Heart rate, PR, QRS, RR, and QT were measured and corrected QTcF intervals were calculated.

Blood samples for analysis of hematology, clinical chemistry, coagulation, and virus serology, and urine samples for urinalysis, urine chemistry, and drug and alcohol screens were collected as described in the Schedule of Assessments.

Blood samples were analyzed for the following hematology parameters: platelet, red blood cell (RBC) count, and WBC counts; automated differential (neutrophils, lymphocytes, monocytes, eosinophils, basophils); hemoglobin; hematocrit; and RBC indices (mean corpuscular volume, mean corpuscular hemoglobin, and mean corpuscular hemoglobin concentration). The timing of hematology assessments is described in the Schedule of Assessments.

Blood samples were analyzed for the following clinical chemistry parameters: blood urea nitrogen; creatinine; glucose; sodium; phosphorus; potassium; chloride; total carbon dioxide; total calcium; magnesium; AST; ALT; gamma-glutamyltransferase; alkaline phosphatase; lactate dehydrogenase; total, direct, and indirect bilirubin; uric acid; albumin; and total protein. Considering that indirect bilirubin was calculated from total and direct bilirubin values, indirect bilirubin results were not available if direct bilirubin was below the limit of quantification.

Serum follicle-stimulating hormone level and estradiol concentrations were measured at screening for postmenopausal female subjects to confirm their postmenopausal status. The timing of chemistry assessments is described in the Schedule of Assessments.

Blood samples were analyzed for prothrombin time, international normalized ratio, and partial thromboplastin time. The timing of coagulation assessments is described in the Schedule of Assessments.

Urinalysis includes specific gravity, pH, glucose, protein, blood, and ketones. A microscopic examination of urine samples was performed only on abnormal findings. Urine samples were also sent to the pathology laboratory to measure protein and creatinine in order to calculate the urine protein:creatinine ratio. The timing of urinalysis and urine chemistry assessments are described in the Schedule of Assessments.

Blood samples collected at screening were analyzed for HIV-1, HIV-2, HBsAg, and HCV antibody titers. Hepatitis B surface antigen testing was required for all subjects prior to enrollment. Subjects with positive HBsAg were not enrolled. For subjects with negative HBsAg, the following testing algorithm was required:

1. If HBcAb was negative, the subject was eligible to enroll.
2. If HBcAb was positive, the hepatitis B surface antibody (HBsAb) was tested.
   a. If both HBcAb and HBsAb were positive, the subject was eligible to enroll.
   b. If HBcAb was positive and HBsAb was negative, the subject was not enrolled.

A urine sample for drug screen was analyzed for the following compounds: amphetamines, barbiturates, benzodiazepines, cocaine, methadone, opiates, phencyclidine, methamphetamine, 3,4-methylenedioxy-methamphetamine, and tetrahydrocannabinol (cannabinoids). An alcohol breath test was performed. If positive prior to dosing, dosing did not proceed. Timing of urine drug and alcohol breath tests is described in the Schedule of Assessments.

Pregnancy testing (beta human chorionic gonadotropin) was performed in all female subjects. The timing of pregnancy testing is described in the Schedule of Assessments.

Serum samples for a QuantiFERON-TB test were collected as described in the Schedule of Assessments.

A suitable assay for determining complement activity, such as CAP ELISA/C5 (hemolysis) inhibition, was performed at screening to confirm subjects do not have a complement deficiency. Subjects found to be complement deficient were excluded from participating in the study.

Serum samples were collected at baseline and during follow-up for measurement of CH50 activity using an in vitro LIA to confirm normalization of complement activity. If a normal CH50 result was obtained from a subject's first CH50 sample collected during follow-up, antibiotic prophylaxis could have been stopped and the second scheduled CH50 sample was not required. If the first and second CH50 samples were not normal, the baseline sample could have been analyzed, and further CH50 samples were taken until complement activity has been restored.

A serum bactericidal antibody (SBA) titer against meningococcal serogroups A, C, W135, and Y was performed at screening. Titer measurements were used to exclude subjects without an immune response from being dosed.

Subcutaneous injection or IV infusion site evaluations was performed. Pain at the site of SC injection or IV infusion was assessed using a Visual Analog Scale (0-10). Pain was not assessed pre-dose. Indurations or reactions 1 cm in size were not listed as an adverse event unless they persisted for more than 24 hours.

Serum samples were analyzed for antidrug antibody (ADA). The timing of ADA serum sample collection was described in the Schedule of Assessments.

16. Adverse Event Management

The investigator was responsible for detecting, assessing, documenting, and reporting all adverse events (AEs). All AEs were recorded from the signing of informed consent form until study completion. There was no time limit for SAEs that were considered causally related. All observed or volunteered AEs, regardless of causal relationship, were reported and recorded in the data capture system. Adverse events reported by the subject and/or parent or legal guardian, and/or identified in response to an open-ended question from study personnel, or revealed by observation, physical examination, or other study procedures were collected and recorded.

An AE was defined as any unfavorable and unintended sign (e.g., including an abnormal laboratory finding), symptom, or disease temporally associated with the use of a medicinal product or procedure, whether or not considered related to the medicinal product or procedure, that occurs during the course of the clinical study.

Exacerbations of a chronic or intermittent pre-existing condition, including either an increase in frequency and/or intensity of the condition, were all considered AEs. Abnormal test findings were considered AEs. If an abnormal laboratory value was identified, investigators were strongly encouraged to report a diagnosis, or a sign or symptom, rather than an isolated abnormal test value. An abnormal test finding was documented as an AE if any of the following conditions were met: was associated with a sign or symptom; required additional diagnostic testing (repeat tests were not considered additional testing); required a medical or surgical intervention; lead to a change in study dosing outside of the protocol-defined dosing or lead to discontinuation from the study; required significant additional treatment; did not meet any of the conditions above.

This definition also includes the signs or symptoms resulting from the following: drug overdose, drug withdrawal, drug misuse, drug interactions, extravasation, exposure during pregnancy, exposure via breastfeeding, medication error and occupational exposure An AE does not necessarily include the following:

- Medical or surgical procedures (e.g., surgery, endoscopies, tooth extraction, transfusion); the condition that leads to the procedure was the AE (e.g., laparoscopic cholecystectomy was the procedure or treatment for an SAE of necrotic gallbladder)
- Pre-existing diseases or conditions, present at or detected prior to the screening evaluation, that do not worsen
- Situations where an untoward medical occurrence has not occurred (e.g., hospitalization for elective surgery, if planned prior to the start of the study; social and/or convenience admissions)

Any AE that fulfills any 1 of the criteria listed below was to be recorded as an SAE.

An SAE was described as any untoward medical occurrence that, at any dose:

1. Results in death
2. Is life threatening[a]
3. Requires hospitalization or prolongation of hospitalization[b]. Hospitalization does not necessarily include the following:
   - Rehabilitation/hospice/nursing facility
   - Emergency department visit of less than 24 hours
   - Elective or preplanned admission/surgery/day surgery
   - Protocol-specified admission
   - Admission for a pre-existing condition not associated with either a new AE or with worsening of a pre-existing AE
4. Results in persistent or significant disability/incapacity
5. Is a congenital anomaly/birth defect
6. Is an important medical event[c]

[a] The term "life threatening" in the definition of "serious" refers to an event in which the subject was at risk of death at the time of the event; it does not refer to an event that hypothetically might have caused death if it were more severe.

[b] Hospitalization requires inpatient admission or prolongation of an existing hospitalization. The AEs that were associated with hospitalization or prolongation of hospitalization were considered SAEs.

[c] Important medical event: Medical and scientific judgment should be exercised in deciding whether expedited reporting was appropriate in other situations, such as important medical events that may not be immediately life threatening, or result in death or hospitalization, but may jeopardize the subject or may require intervention to prevent 1 of the other outcomes listed in the definition above. These should also usually be considered serious. Examples of such events were intensive treatment in an emergency department or at home for allergic bronchospasm; blood dyscrasias or convulsions that do not result in hospitalization; or development of drug dependency or drug abuse.

Severity and seriousness were to be be differentiated. Severity describes the intensity of an AE, while the term seriousness refers to an AE that has met the criteria for an SAE, as described above.

All AEs were graded according to the following criteria from CTCAE v4.03, published 14 Jun. 2010.

Grade 1: Mild (awareness of sign or symptom, but easily tolerated)

Grade 2: Moderate (discomfort sufficient to cause interference with normal activities)

Grade 3: Severe (incapacitating, with inability to perform normal activities)

Grade 4: Life threatening

Grade 5: Fatal

Changes in the severity of an AE were documented to allow an assessment of the AE duration at each level of intensity to be evaluated. Adverse events characterized as intermittent required documentation of onset and duration of each episode, if the severity of the intermittent event changed.

An investigator causality assessment was provided for all AEs (both nonserious and serious). This assessment was recorded in the data capture system and on any additional forms, as appropriate. The definitions for the causality assessments were as follows:

Not related (unrelated): This relationship suggests that there was no association between the investigational product and the reported event.

Unlikely related: This relationship suggests that the clinical picture was highly consistent with a cause other than the investigational product, but attribution cannot be made with absolute certainty, and a relationship between the investigational product and AE cannot be excluded with complete confidence.

Possibly related: This relationship suggests that treatment with the investigational product may have caused or contributed to the AE; i.e., the event follows a reasonable temporal sequence from the time of study drug administration, and/or follows a known response pattern to the investigational product, but could also have been produced by other factors.

Probably related: This relationship suggests that a reasonable temporal sequence of the event with the investigational product administration exists, as well as the likely association of the event with the investigational product. This will be based upon the known pharmacological action of the investigational product, known or previously reported adverse reactions to the investigational product or class of drugs, or judgment based on the investigator's clinical experience.

Definitely related: Temporal relationship to the investigational product. Other conditions (concurrent illness, concurrent medication reaction, or progression/expression of disease state) do not appear to explain the event; the event corresponds with the known pharmaceutical profile; improvement on discontinuation; reappearance on rechallenge.

If a subject experiences an SAE with an outcome of death, the following procedures were performed: The SAE resulting in death has an outcome documented as death/fatal, with an end date being the date of death. If the subject had additional AE/SAEs that were ongoing at the time of death, these events were documented as ongoing with no end date. Only 1 event has an outcome of death/fatal, unless an autopsy report or investigator states otherwise.

17. Statistics

A formal statistical analysis plan (SAP) was developed and finalized before database lock.

The safety population consists of all subjects who received at least 1 dose of study drug. Subjects in this population were used for the safety analysis.

The PK population consists of all subjects who had sufficient serum concentration data to enable the calculation of PK parameters. The PK population was used for PK summaries.

The PD population consists of all subjects who had sufficient total and free C5 concentration data and cRBC hemolysis data. The PD population was used for PD summaries.

The immunogenicity analysis population consists of all subjects who had a pre-dose and post-dose ADA sample collected.

A total evaluable sample size of 36 subjects, 24 ALXN1210 SC subjects from Cohort 1 and 12 ALXN1210 IV subjects from Cohort 2, provided >80% power to infer that the lower bound of a 90% confidence interval for the ratio of the bioavailability of ALXN1210 SC to IV was >0.4 assuming an absolute bioavailability of 0.6 and a coefficient of variation of 0.35. Additionally, 6 subjects received placebo SC, 2 in Cohort 1a and 4 in Cohort 1b. Randomization to Cohort 1a was conducted in a 2:1 ratio, and Cohort 1b in a 5:1 ratio, to receive either ALXN1210 SC or placebo SC. This brought the total planned number of subjects to N=42.

In general, descriptive statistics for continuous variables include number of nonmissing values, arithmetic mean, standard deviation, median, minimum, and maximum. Descriptive statistics for PK parameters included number of observations, arithmetic mean, standard deviation, arithmetic coefficient of variation (% CV), median, minimum, maximum, geometric mean and geometric % CV. Categorical variables were summarized using percentages and frequency counts, by cohort and time point.

All subjects were included in the summary of subject disposition, which summarizes the frequency and percentage of subjects screened and treated who completed or discontinued from the study, along with reason for discontinuation, by cohort. Demographics and baseline characteristics were summarized for all subjects by each cohort and overall.

Safety analyses were performed on the safety population, and reported by each cohort. Safety analyses included an analysis of all AEs, ECGs, clinical laboratory data, physical examinations, and vital sign measurements, and were presented using descriptive statistics. No inferential statistical analyses were planned on the safety parameters of this study. The incidence of treatment-emergent AEs and SAEs were summarized, by system organ class and preferred term for each cohort and overall, by relationship to study drug. Treatment-emergent AEs were also summarized by cohort and overall by severity. Serious AEs and AEs resulting in withdrawal from the study were listed. Subjects having multiple AEs within a category (e.g., overall, system organ class, preferred term) were counted once in that category. For severity tables, a subject's most severe event within a category was counted.

Changes from baseline in vital sign measurements and laboratory assessments (e.g., chemistry, CBC with differential, and urinalysis) were summarized by each cohort. Laboratory parameter values were graded according to the CTCAE. Shift tables by cohort were produced for these laboratory parameters. These tables summarize the number of subjects with each baseline grade relative to the reference ranges and changes to the worst highest grade assessed post-dose during the study.

The ECG parameters were measured at the specified time points, including heart rate, PR, RR, QRS, QT, and corrected QTcF intervals. The average of the triplicate ECG readings at the time points collected was calculated, and changes from pretreatment baseline values were assessed by each cohort.

An outlier analysis was performed that summarizes the frequency and percentage of subjects who meet any of the following outlier criteria at each visit by cohort:

QT, QTcF interval >450 msec

QT, QTcF interval >480 msec

QT, QTcF interval >500 msec

QT, QTcF interval increases from baseline >30 msec

QT, QTcF interval increases from baseline >60 msec

All concomitant medications were coded using the WHO Drug Dictionary, and the frequency and percentage of concomitant medications was summarized.

The individual serum concentration data for ALXN1210-treated subjects, with actual sampling dates and times, was used to derive the PK parameters by noncompartmental analyses methods using Phoenix WinNonlin 6.3 or higher.

The following PK parameters were derived: maximum observed serum concentration ($C_{max}$), time to maximum observed serum concentration ($T_{max}$), area under the serum concentration versus time curve from time zero to the last quantifiable concentration ($AUC_t$) area under the curve from time zero to infinity ($AUC_\infty$), terminal elimination rate constant ($\lambda_z$), terminal elimination half-life ($T_{1/2}$), total clearance (CL or CL/F), and volume of distribution ($V_d$ or $V_d$/F).

The geometric means ratio (ALXN1210 SC/ALXN1210 IV) and its 90% CI was computed for $C_{max}$, $AUC_t$, and $AUC_\infty$, and were tabulated. The CI was computed using the between-subject variance. Assessments of concentration over time were presented.

The PD effects of ALXN1210 SC and IV were evaluated by assessing changes in serum total and free C5 concentrations, cRBC hemolysis, and other measures of C5 activation over time. Analyses were performed on samples collected as described in the Schedule of Assessments.

Immunogenicity, as measured by ADA, was summarized in tabular form by cohort and by-subject listings.

Example 3: Results of Phase 1 Study to Evaluate Single Dose of ALXN1210 Administered Subcutaneously Compared to Intravenously in Healthy Subjects The following is a summary of data from a single dose phase 1 study that was conducted substantially as described above in Example 2. Specifically, the study was designed to evaluate the safety, tolerability, pharmacokinetics (PK), pharmacodynamics (PD), and immunogenicity of a single 400-mg dose of ALXN1210 administered subcutaneously compared to a single 400-mg dose of ALXN1210 administered intravenously or placebo administered subcutaneously in 42 healthy subjects.

1. Disposition of Subjects

Figure 48:
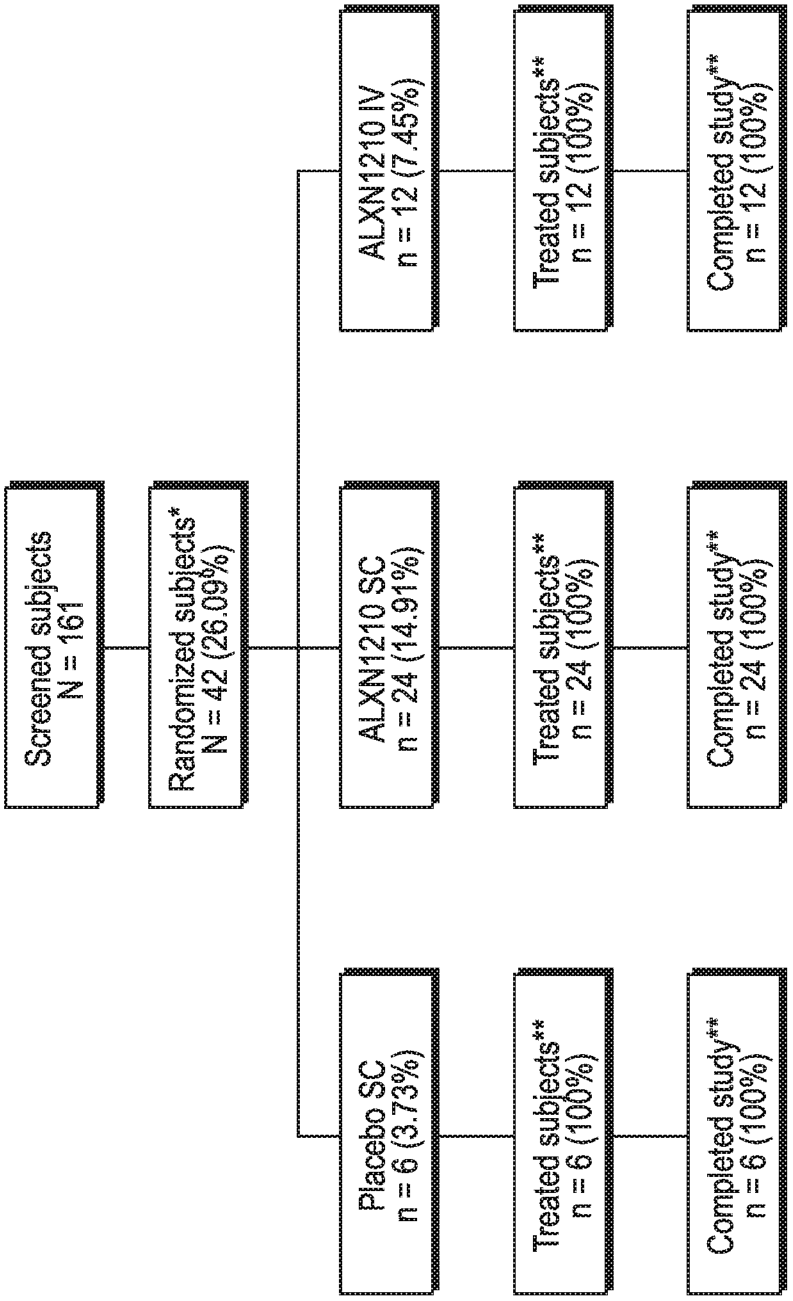
FIG. 48 provides an overview of the disposition of all subjects.

Of the 161 screened subjects, 42 (26.09%) subjects were randomly assigned to receive the study drug: placebo SC (n=6), ALXN1210 SC (n=24), and ALXN1210 IV (n=12) (FIG. 48). None of the randomized subjects prematurely discontinued the study.

2. Protocol Deviations

At least one protocol deviation was reported for 36 subjects (placebo SC: n=6; ALXN1210 SC: n=20; and ALXN1210 IV: n=10). The categories of protocol deviation included time window deviation, subject compliance, assessment not performed, exclusion criteria, and dose administration.

In two subjects in the ALXN1210 IV group, protocol deviations were assessed as major. In one subject, Day 29 ADA, PK, PD, and laboratory assessments were not performed as the subject did not attend the follow-up visit. In the other subject, Day 71 PK and PD samples were not collected as the subject did not attend the follow-up visit. While these deviations were assessed as major due to the nature of the study design (PK-related primary endpoint), these were not considered to have had an effect on the interpretation of the results. None of the other protocol deviations was considered to have affected the interpretation of results or the safety of the subjects. The serum pregnancy test results were negative in all the subjects during the study.

3. Pharmacokinetics, Pharmacodynamics, and Immunogenicity Evaluation

All 42 randomized subjects received the study drug and were included in the Safety Set (Table 19). All of these subjects were also included in the PD Set and the Immunogenicity Analysis Set based on the definitions. The 36 subjects in the Safety Set who received either ALXN1210 SC or ALXN1210 IV had sufficient serum concentration data to enable the calculation of PK parameters and were included in the PK Set (Table 19).

TABLE 19

Analysis Populations (All Randomized Subjects)

| | Placebo SC (N = 6) n (%) | ALXN1210 SC (N = 24) n (%) | ALXN1210 IV (N = 12) n (%) |
|---|---|---|---|
| Safety Set | 6 (100.0) | 24 (100.0) | 12 (100.0) |
| Pharmacokinetics Set | 0 | 24 (100.0) | 12 (100.0) |
| Pharmacodynamics Set | 6 (100.0) | 24 (100.0) | 12 (100.0) |
| Immunogenicity analysis Set | 6 (100.0) | 24 (100.0) | 12 (100.0) |

Note:
Percentage (%) is equal to n/N × 100.
Abbreviations: IV = intravenous;
N = total number of subjects;
n = number of subjects;
SC = subcutaneous.

4. Demographic and Other Baseline Characteristics

Across the treatment groups, the majority of subjects were male (66.7%) and White (69.0%) with a mean (±SD) age of 35.0 (±7.65) years. The mean (±SD) BMI for the overall population was 24.035 (±3.1582). In general, the demographics were well balanced across the treatment groups (Table 20).

TABLE 20

| Demographic Data - Descriptive Statistics by Treatment (Safety Set) | | | | | |
|---|---|---|---|---|---|
| Demographic Parameter | | Placebo SC (N = 6) | ALXN1210 SC (N = 24) | ALXN1210 IV (N = 12) | Overall (N = 42) |
| Sex, n (%) | Male | 4 (66.7) | 16 (66.7) | 8 (66.7) | 28 (66.7) |
| | Female | 2 (33.3) | 8 (33.3) | 4 (33.3) | 14 (33.3) |
| Age (years) | N | 6 | 24 | 12 | 42 |
| | Mean (±SD) | 34.2 (±6.46) | 36.2 (±7.73) | 33.2 (±8.20) | 35.0 (±7.65) |
| Weight (kg) | N | 6 | 24 | 12 | 42 |
| | Mean (±SD) | 71.30 (±6.727) | 72.69 (±12.892) | 72.45 (±11.882) | 72.42 (±11.698) |
| BMI (kg/$m^2$) | N | 6 | 24 | 12 | 42 |
| | Mean (±SD) | 23.220 (±2.4948) | 23.846 (±3.3895) | 24.820 (±3.0353) | 24.035 (±3.1582) |
| Ethnicity, n (%) | Hispanic or Latino | 0 | 1 (4.2) | 1 (8.3) | 2 (4.8) |
| | Not Hispanic or Latino | 6 (100.0) | 23 (95.8) | 11 (91.7) | 40 (95.2) |
| Race, n (%) | Asian | 1 (16.7) | 2 (8.3) | 2 (16.7) | 5 (11.9) |
| | Black or African American | 1 (16.7) | 5 (20.8) | 0 | 6 (14.3) |
| | White | 2 (33.3) | 17 (70.8) | 10 (83.3) | 29 (69.0) |
| | Other | 2 (33.3) | 0 | 0 | 2 (4.8) |

Note:
Percentage (%) is equal to n/N × 100.
Abbreviations: BMI = body mass index;
IV = intravenous;
max = maximum;
min = minimum;
N = total number of subjects;
n = number of subjects;
SC = subcutaneous;
SD = standard deviation.

The use of prior medications was reported by 5 (20.8%) subjects in the ALXN1210 SC group. There were no reports of use of prior medications in the placebo SC and the ALXN1210 IV groups. The use of concomitant medications was reported by 3 (50.0%), 13 (54.2%), and 8 (66.7%) subjects in the placebo SC, ALXN1210 SC, and ALXN1210 IV groups, respectively. The most commonly used concomitant medications were anilides, such as acetaminophen/paracetamol (15 subjects) for treatment of AEs, followed by progestogens and estrogens, fixed combinations (7 subjects) for contraception. None of the reported concomitant medications are expected to have influenced the results of the study.

No subjects had any nonpharmacologic therapies and procedures. All doses of ALXN1210 SC or placebo SC were administered by four 100 mg SC injections of 1 mL each in the abdominal area. All doses of ALXN1210 IV were administered by IV infusion, using IV sets with in-line filters. All subjects received their assigned doses.

5. Pharmacokinetics, Pharmacodynamics, and Immunogenicity Results and Tabulations of Individual Subject Data The PK analyses were performed on the PK Set which consisted of all subjects from the Safety Set who received either ALXN1210 SC or ALXN1210 IV and who had sufficient serum concentration data to enable the calculation of PK parameters.

Figure 49:
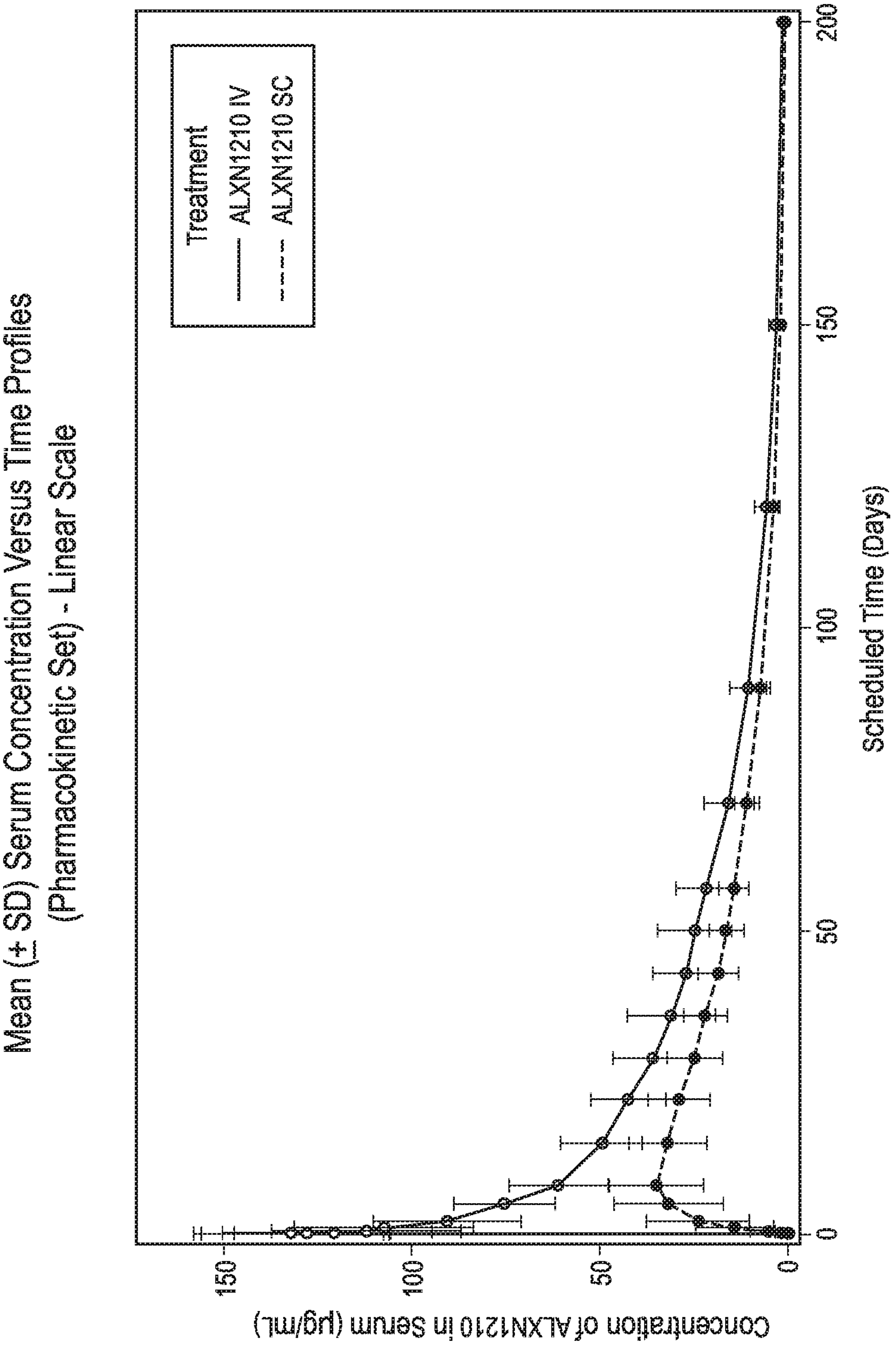
FIG. 49 is a graph depicting individual ALXN1210 serum concentrations versus nominal time using a linear scale
Figure 50:
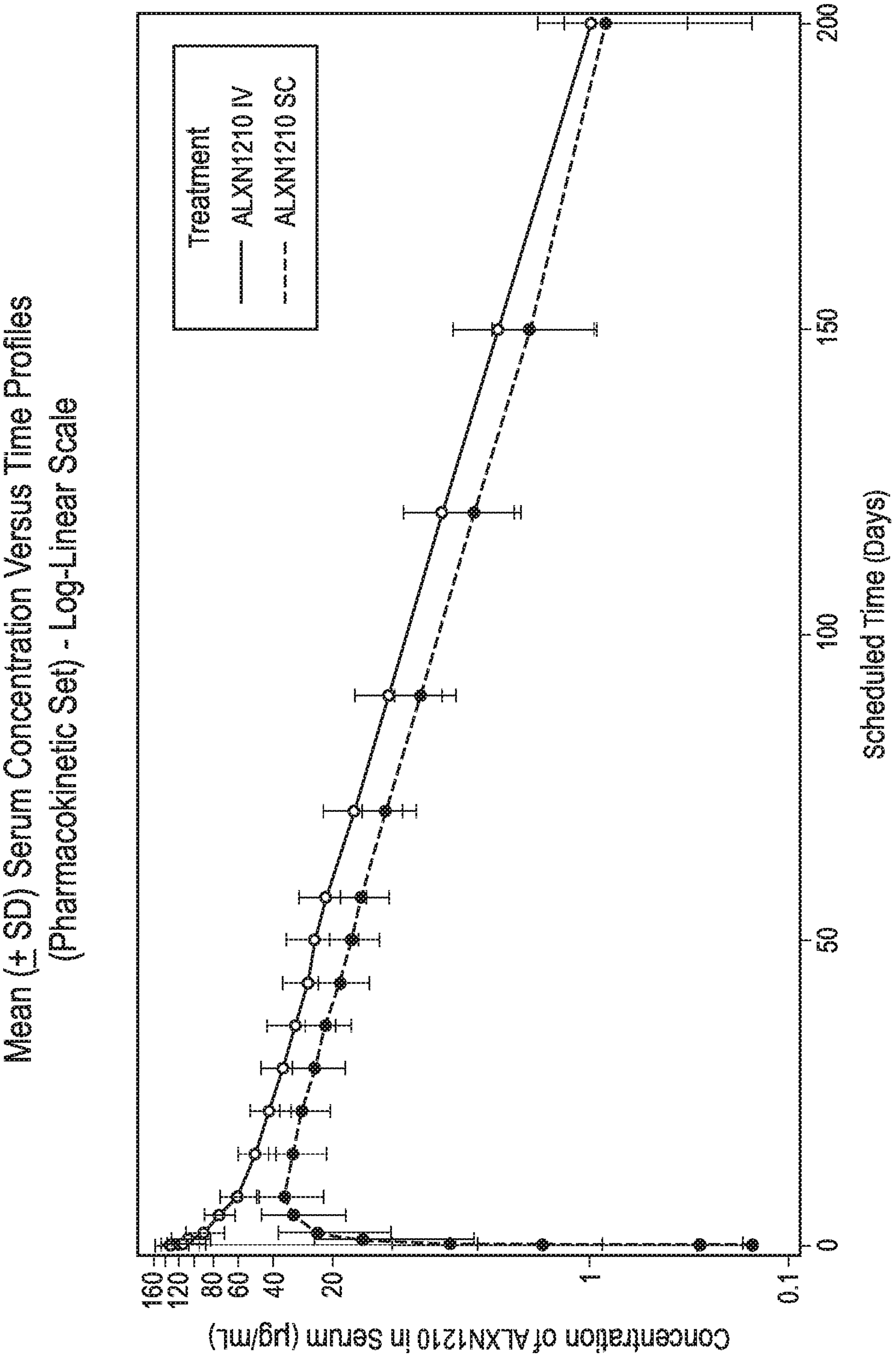
FIG. 50 is a graph depicting individual ALXN1210 serum concentrations versus nominal time using a log-linear scale

FIGS. 49-50 illustrate the mean (±SD) serum concentration-time profiles for healthy subjects following SC and IV administration of ALXN1210 (linear and log-linear scales). The plots of the individual ALXN1210 serum concentrations versus nominal time are presented using a linear scale (FIG. 49) and log-linear scale (FIG. 50), respectively.

Pharmacokinetic parameters of ALXN1210 following SC and IV administration are summarized in Table 21. A total of 24 subjects received ALXN1210 SC administration; the median (range) $t_{max}$ was 169.8 (96.0 to 508.1) hours following SC injection. The geometric mean (CV %) $t_{1/2}$ was similar at 31.3 (13.6) days and 29.9 (15.4) days for ALXN1210 SC and IV administration, respectively. The elimination of ALXN1210 was similar between IV and SC routes (FIG. 49).

TABLE 21

| Summary of ALXN1210 Pharmacokinetic Parameters (Pharmacokinetic Set) | | | | | | | | | |
|---|---|---|---|---|---|---|---|---|---|
| Treatment | Statistic | $C_{max}$ [µg/mL] | $t_{max}$ [h] | $AUC_t$ [h*µg/mL] | $AUC_\infty$ [h*µg/mL] | $\lambda_z$ [/h] | $t_{1/2}$ [h] | CL or CL/F [L/h] | $V_d$ or $V_d$/F [L] |
| ALXN1210 SC | Geometric mean | 35.1 | 169.8[a] | 46734.5 | 47653.4 | 0.001 | 751.6 | 0.009 | 9.1 |
| (n = 24) | Geometric CV (%) | 32.9 | NA | 28.4 | 28.5 | 0.00 | 13.6 | 27.7 | 24.7 |
| | Range (min, max) | 19.5, 65.2 | 96.0, 508.1 | 26294.3, 99354.7 | 26834.0, 103195.2 | 0.001, 0.001 | 614.4, 1012.2 | 0.004, 0.015 | 5.7, 14.3 |
| | Geometric mean | 134.6 | 0.8[a] | 77892.8 | 78902.9 | 0.001 | 718.4 | 0.005 | 5.3 |

TABLE 21-continued

Summary of ALXN1210 Pharmacokinetic Parameters (Pharmacokinetic Set)

| Treatment | Statistic | $C_{max}$ [μg/mL] | $t_{max}$ [h] | $AUC_t$ [h*μg/mL] | $AUC_\infty$ [h*μg/mL] | $\lambda_z$ [/h] | $t_{1/2}$ [h] | CL or CL/F [L/h] | $V_d$ or $V_d$/F [L] |
|---|---|---|---|---|---|---|---|---|---|
| ALXN1210 IV | Geometric CV (%) | 19.0 | NA | 24.9 | 25.4 | 0.00 | 15.4 | 22.6 | 24.8 |
| (n = 12) | Range (min, max) | 99.6, 170.0 | 0.27, 2.0 | 57748.3, 151090.9 | 58146.6, 155019.7 | 0.001, 0.001 | 601.5, 990.1 | 0.003, 0.007 | 3.1, 7.1 |

[a]Median presented for $t_{max}$.

Note:

For ALXN1210 SC treatment, the columns CL and $V_d$ represent CL/F and $V_d$/F, respectively.

Abbreviations: $AUC_t$ = area under the serum concentration versus time curve from time 0 to the last quantifiable concentration; $AUC_\infty$ = area under the serum concentration versus time curve from time 0 extrapolated to infinity; CL or CL/F = total body clearance of drug from the serum; $C_{max}$ = maximum observed serum concentration; CV = coefficient of variation; h = hour; IV = intravenous; L = liter; max = maximum; min = minimum; n = number of subjects; NA = not applicable; SC = subcutaneous; $t_{1/2}$ = terminal elimination half-life; $t_{max}$ = time to maximum observed serum concentration; $V_d$ or $V_d$/F = volume of distribution; $\lambda_z$ = terminal elimination rate constant.

Table 22 summarizes the absolute bioavailability of ALXN1210 SC. The PK parameters for ALXN1210 SC ($C_{max}$, $AUC_t$, and $AUC_\infty$) were compared to the reference (ALXN1210 IV) by means of statistical analysis using a mixed model after logarithmic transformation of the data. The GMR of $C_{max}$ for ALXN1210 (SC/IV) was 26.1% (95% CI: 21.3, 32.0). The absolute bioavailability of ALXN1210 SC, determined based on the GMR of $AUC_\infty$ estimates (SC/IV), was 60.4% (95% CI: 49.7, 73.3).

TABLE 22

Statistical Analysis of Absolute Bioavailability of ALXN1210 Subcutaneous (Pharmacokinetic Set)

| Pharmacokinetic Parameter | ALXN1210 SC (n = 24) | ALXN1210 IV (n = 12) | GMR (%) | 90% CI | 95% CI |
|---|---|---|---|---|---|
| $C_{max}$ [μg/mL] | 35.1 | 134.6 | 26.1 | 22.0-30.9 | 21.3-32.0 |
| $AUC_t$ [h*μg/mL] | 46734.5 | 77892.8 | 60.0 | 51.1-70.4 | 49.5-72.8 |
| $AUC_\infty$ [h*μg/mL] | 47653.4 | 78902.9 | 60.4 | 51.4-71.0 | 49.7-73.3 |

Note:

Ratio is defined as geometric mean of the ALXN1210 SC group divided by geometric mean of the ALXN1210 IV group x 100. Linear mixed model with fixed and random effects for subject was used.

Abbreviations: $AUC_t$ = area under the serum concentration versus time curve from time 0 to the last quantifiable concentration;

$AUC_\infty$ = area under the serum concentration versus time curve from time 0 extrapolated to infinity;

CI = confidence interval;

$C_{max}$ = maximum observed serum concentration;

GMR = geometric mean ratio;

h = hour;

IV = intravenous;

n = number of subjects;

SC = subcutaneous.

The PD analyses were performed on the PD Set which consisted of all subjects from the Safety Set who had sufficient free and total C5 concentration data and cRBC hemolysis data.

Figure 51:
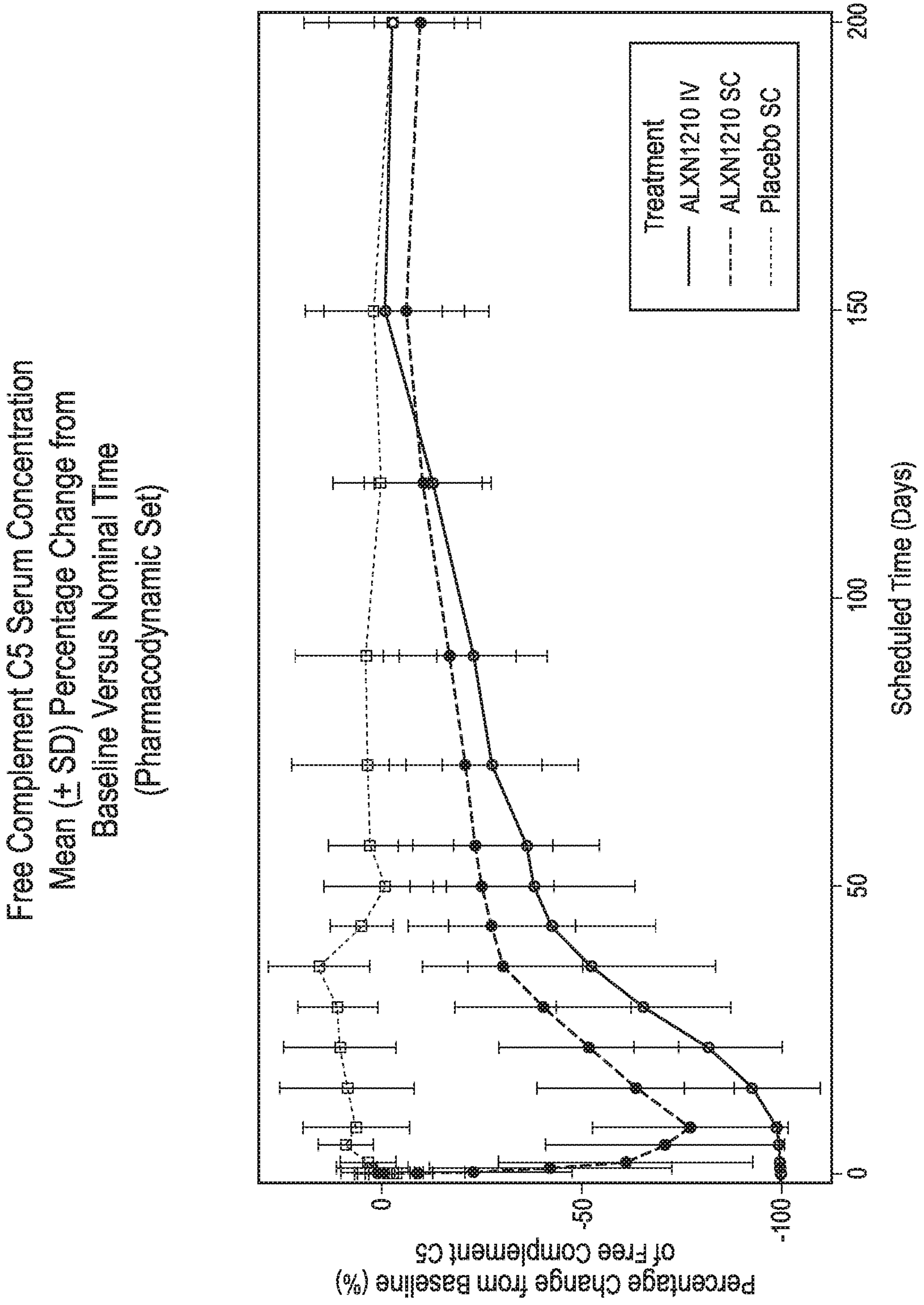
FIG. 51 is a graph depicting the mean (±SD) percent change in free C5 serum concentration from baseline over time for subjects administered placebo SC, ALXN1210 SC, and ALXN1210 IV.

FIG. 51 depicts the mean (±SD) percent change in free C5 serum concentration from baseline over time for subjects administered placebo SC, ALXN1210 SC, and ALXN1210 IV. Mean free C5 remained relatively constant following SC administration of placebo. Administration of a single dose of ALXN1210 IV 400 mg resulted in an immediate and nearly complete inhibition of free C5 (≥99%) through Day 8 following IV administration. Administration of a single dose of ALXN1210 SC 400 mg also resulted in a reduction in free C5, but not to the same extent or with as rapid an onset as seen following IV administration. Following ALXN1210 SC administration, the maximum mean inhibition in free C5 (77%) occurred 1 week after dosing.

Figure 52:
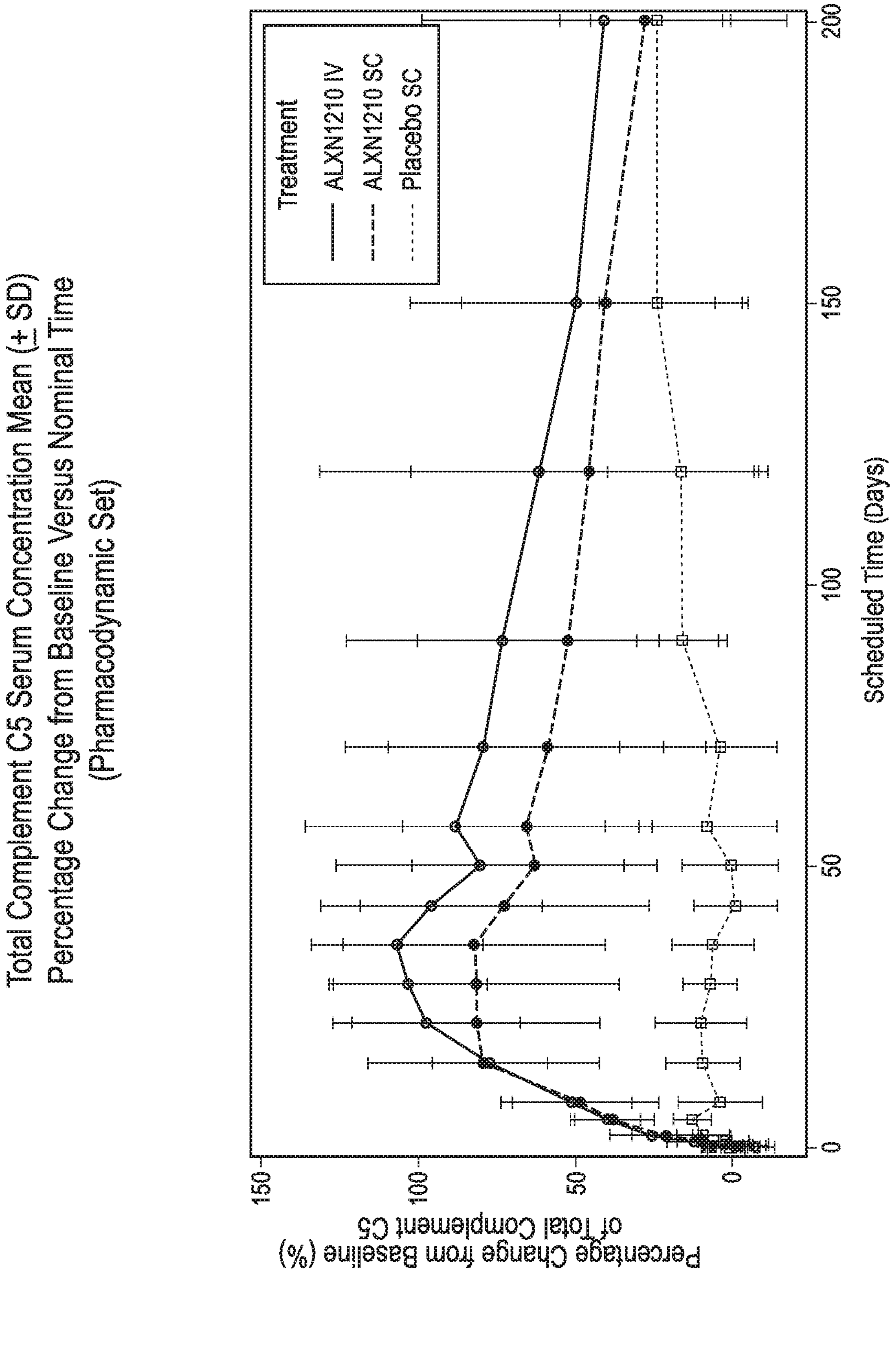
FIG. 52 is a graph depicting the mean (±SD) percent change in total C5 serum concentrations from baseline over time for subjects administered placebo SC, ALXN1210 SC, and ALXN1210 IV.

The duration and extent of reduced mean free C5 concentration were exposure dependent. FIG. 52 depicts the mean (±SD) percent change in total C5 serum concentrations from baseline over time for subjects administered placebo SC, ALXN1210 SC, and ALXN1210 IV. Mean total C5 concentrations remained relatively constant following SC administration of placebo. However, administration of a single dose of ALXN1210 400 mg led to a maximum mean increase of 82% and 107% relative to baseline in total C5 following SC and IV dosing, respectively.

Figure 53:
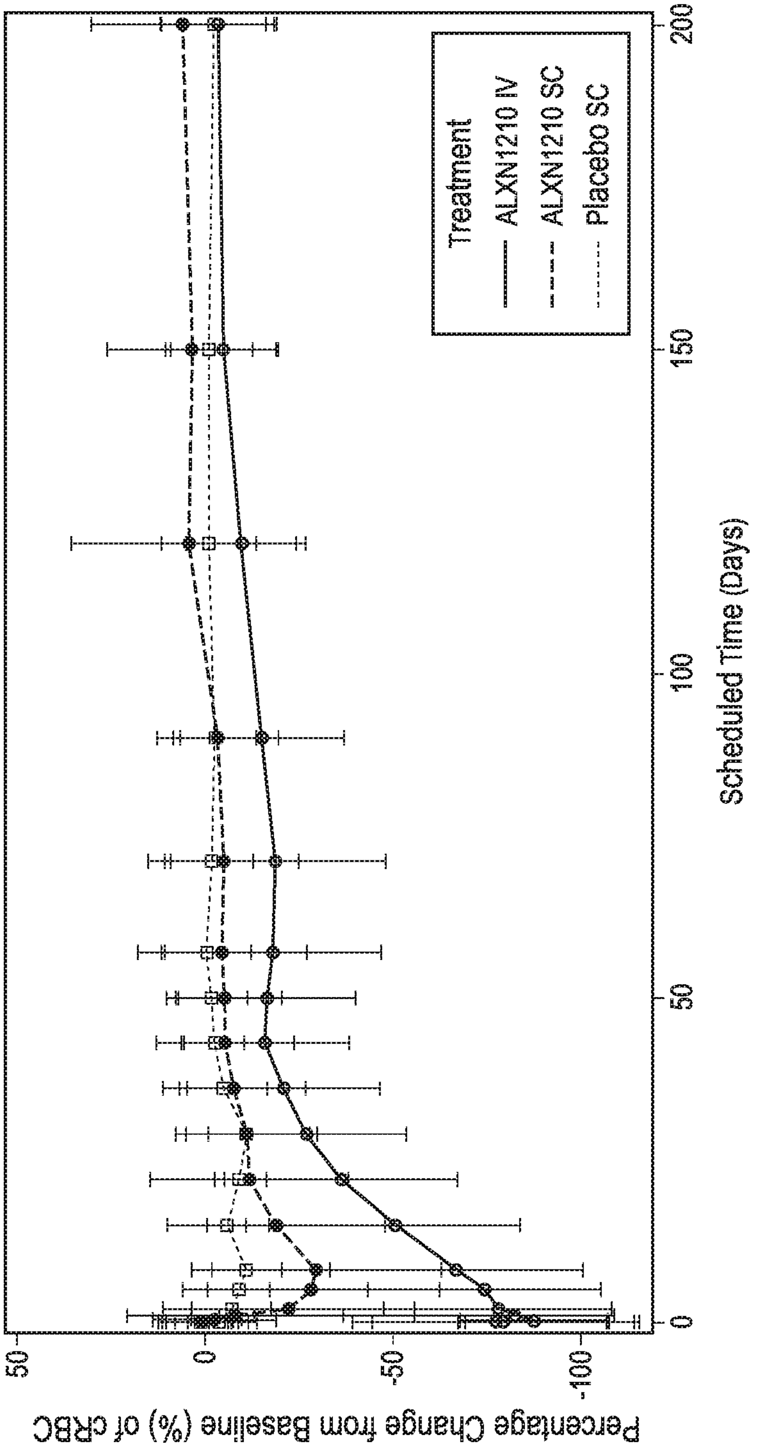
FIG. 53 is a graph depicting the mean (±SD) percent change in chicken red blood cell (cRBC) hemolysis from baseline over time for subjects administered placebo SC, ALXN1210 SC, and ALXN1210 IV.

FIG. 53 depicts the mean (±SD) percent change in chicken red blood cell (cRBC) hemolysis from baseline over time for subjects administered placebo SC, ALXN1210 SC, and ALXN1210 IV. Mean cRBC hemolysis remained relatively constant following SC administration of placebo. Administration of a single dose of ALXN1210 IV 400 mg resulted in an immediate inhibition in mean cRBC hemolysis with maximum mean reduction at 88%. Administration of a single dose ALXN1210 SC 400 mg also resulted in an inhibition of cRBC hemolysis, but not to the same extent or with as rapid an onset compared with IV administration. Maximum mean inhibition of cRBC hemolysis of 29% occurred at approximately 1 week post ALXN1210 SC dosing. The duration and extent of cRBC inhibition were exposure dependent.

Immunogenicity analysis was performed on the Immunogenicity Analysis Set which consisted of all subjects from the Safety Set who had a predose and postdose ADA sample collected. Antidrug antibody testing was performed predose and postdose on Days 15, 29, 57, 90, 120, 150, and 200.

One subject (Subject 0344-185) in the ALXN1210 SC treatment group had a confirmed ADA positive sample at baseline (predose) and all postdose samples. All postdose antibody titers in this subject were below the predose titer value. Antidrug antibody positive response in this subject was not considered clinically significant or related to ALXN1210. Therefore, this subject is not included in the immunogenicity summaries provided below.

A total of 4 subjects (ALXN1210 SC group: 3/23 [13%] subjects and ALXN1210 IV group: 1/12 [8.3%] subject) developed treatment-emergent ADA. In the ALXN1210 SC group: A first subject was ADA positive on Days 57, 90, 120, 150, and 200. All ADA positive values were positive for eculizumab cross-reactivity. A second subject was ADA positive on Days 29, 57, 90, 120, 150, and 200. All ADA positive values were positive for eculizumab cross-reactivity except on Day 90 which was negative. A third subject was ADA positive on Days 90, 120, 150, and 200. All ADA positive values were positive for eculizumab cross-reactivity.

In the ALXN1210 IV group: one subject was ADA positive on Days 15, 29, 90, 120, 150, and 200. All ADA positive values were negative for eculizumab cross-reactivity.

The earliest positive ADA responses postdose were seen on Day 29 and Day 15, for SC and IV dosing, respectively. The ADA titers for the ADA positive samples were low and ranged from <1.0 to 27. In most ADA positive samples following SC administration, the ADAs were cross-reactive to eculizumab. Following IV administration, the ADAs were not cross-reactive to eculizumab. All the ADA positive subjects remained positive until the end of the follow-up period. A formal assessment of impact of ADA on PK and PD could not be made due to the small numbers of ADA positive subjects. Examination of the limited individual PK and PD results in these subjects suggests that there is no apparent impact of immunogenicity on the PK or PD of ALXN1210.

6. Pharmacokinetic, Pharmacodynamic, and Immunogenicity Conclusions

The median (range) $t_{max}$ was 169.8 (96.0 to 508.1 hours) following SC injection. The geometric mean terminal elimination half-life was similar at 31.3 days and 29.9 days following ALXN1210 SC and IV administration, respectively.

The GMR of $C_{max}$ estimates (SC/IV) was 26.1% (95% CI: 21.3, 32.0). The absolute bioavailability of ALXN1210 SC, based on the GMR of $AUC_{\infty}$ estimates (SC/IV), was 60.4% (95% CI: 49.7, 73.3).

The extent and duration of PD response, as assessed by free and total C5 serum concentration and cRBC hemolysis, were exposure dependent. Administration of single dose of ALXN1210 IV 400 mg resulted in an immediate and nearly complete inhibition of free C5 (≥99%) through Day 8 following study drug administration. Administration of single dose of ALXN1210 SC 400 mg, administered as four 100 mg SC injections, also resulted in a reduction in free C5, but not to the same extent or with as rapid an onset as IV administration. Maximum mean inhibition in free C5 was 77% which occurred approximately 1 week after SC administration. Administration of 400 mg ALXN1210 led to a maximum mean increase of 82% and 107% relative to baseline in total C5 following SC and IV dosing, respectively. Administration of single dose of ALXN1210 IV 400 mg resulted in an immediate inhibition in mean cRBC hemolysis with maximum mean reduction at 87%. Administration of single dose of ALXN1210 SC 400 mg also resulted in an inhibition of cRBC hemolysis, but not to the same extent or with as rapid an onset compared with IV administration. Maximum mean inhibition of cRBC hemolysis of 29% occurred at approximately Day 8 following SC administration.

Treatment-emergent ADAs were reported for 3/23 (13%) subjects and 1/12 (8.3%) subject in the ALXN1210 SC and ALXN1210 IV groups, respectively, with low ADA titer values ranging from <1.0 to 27. The earliest postdose ADA response was seen on Day 29 and Day 15, for the SC and IV dosing, respectively. Following SC administration, the ADAs were cross-reactive to eculizumab in most of the ADA positive samples. Following IV administration, the ADAs were not cross-reactive to eculizumab. All ADA positive subjects remained positive until the end of the follow-up period. There was no apparent impact of immunogenicity on the PK or PD of ALXN1210.

One additional subject in the ALXN1210 SC treatment group had a confirmed ADA positive sample at baseline (predose) and all postdose samples. All postdose antibody titers in this subject were below the predose titer value. Antidrug antibody positive response in this subject was not related to ALXN1210.

7. Extent of Exposure

All subjects who received the single dose of study drug were included in the Safety Set (N=42): placebo SC (n=6); ALXN1210 SC (n=24); and ALXN1210 IV (n=12). The total infusion volume (80 mL) of study drug was administered in each subject assigned to receive ALXN1210 IV. In one subject, the infusion was interrupted for a minute, as insufficient time was programmed into the pump for full infusion. The total volume of study drug (4 mL) was administered in each subject who received either ALXN1210 SC or placebo SC.

8. Adverse Events

Across the three treatment groups, 35/42 (83.3%) subjects experienced 75 TEAEs (all Grade 1). The proportion of subjects with at least 1 TEAE was 91.7%, 83.3%, and 79.2%, respectively in the ALXN1210 IV group, placebo SC group, and ALXN1210 SC group. There were no deaths or SAEs reported during the study. None of the subjects discontinued the study drug or withdrew from the study due to TEAEs (Table 23). All TEAEs resolved during the course of the study. The majority of the TEAEs did not require any medication, and no subjects at any time required nonpharmacologic interventions.

TABLE 22

Treatment-Emergent Adverse Events (TEAEs) - Overall Summary (Safety Set)

| | Placebo SC (N = 6) | | ALXN1210 SC (N = 24) | | ALXN1210 IV (N = 12) | | Overall (N = 42) | |
|---|---|---|---|---|---|---|---|---|
| | E | n (%) | E | n (%) | E | n (%) | E | n (%) |
| Subjects with at least 1 TEAE | 15 | 5 (83.3) | 38 | 19 (79.2) | 22 | 11 (91.7) | 75 | 35 (83.3) |
| Related TEAE | 0 | 0 | 2 | 2 (8.3) | 1 | 1 (8.3) | 3 | 3 (7.1) |
| Unrelated TEAE | 15 | 5 (83.3) | 36 | 18 (75.0) | 21 | 11 (91.7) | 72 | 34 (81.0) |
| Grade 1 | 15 | 5 (83.3) | 38 | 19 (79.2) | 22 | 11 (91.7) | 75 | 35 (83.3) |
| Grade 2 | 0 | 0 | 0 | 0 | 0 | 0 | 0 | 0 |
| Grade 3 | 0 | 0 | 0 | 0 | 0 | 0 | 0 | 0 |

TABLE 22-continued

Treatment-Emergent Adverse Events (TEAEs) - Overall Summary (Safety Set)

| | Placebo SC (N = 6) | | ALXN1210 SC (N = 24) | | ALXN1210 IV (N = 12) | | Overall (N = 42) | |
|---|---|---|---|---|---|---|---|---|
| | E | n (%) | E | n (%) | E | n (%) | E | n (%) |
| Grade 4 | 0 | 0 | 0 | 0 | 0 | 0 | 0 | 0 |
| Grade 5 | 0 | 0 | 0 | 0 | 0 | 0 | 0 | 0 |
| Subjects with at least 1 SAE | 0 | 0 | 0 | 0 | 0 | 0 | 0 | 0 |
| Subjects with TEAE leading to discontinuation | 0 | 0 | 0 | 0 | 0 | 0 | 0 | 0 |
| Subjects with TEAE during study drug administration[a] | 0 | 0 | 0 | 0 | 0 | 0 | 0 | 0 |
| Deaths | 0 | 0 | 0 | 0 | 0 | 0 | 0 | 0 |

Note:
Percentage (%) is equal to n/N × 100.
Grade 1 = mild; Grade 2 = moderate; Grade 3 = severe; Grade 4 = life-threatening or disabling; Grade 5 = death related to TEAE.
Related TEAE = possibly related, probably related or definitely related TEAE; Unrelated TEAE = not related or unlikely related TEAE.
[a]For ALXN1210 IV, a TEAE was considered to have occurred during study drug administration if the TEAE occurred during infusion; for Placebo SC and ALXN1210 SC an adverse event was considered to have occurred during study drug administration if the adverse event occurred between first and last injection.
Abbreviations: E = number of events; IV = intravenous; N = total number of subjects at risk; n = number of subjects having an AE; SC = subcutaneous; SAE = serious adverse event; TEAE = treatment-emergent adverse event.

In total, 75 TEAEs were reported for 35 subjects. Across the treatment groups, the most frequently reported TEAEs were nasopharyngitis (23/42 subjects, 54.8%) and headache (7/42 subjects, 16.7%). All TEAEs are summarized by system organ class (SOC) and Preferred Term by treatment in Table 23.

TABLE 23

Treatment-Emergent Adverse Events - Frequency Table by System Organ Class and Preferred Term (Safety Set)

| Primary System Organ Class | Placebo SC (N = 6) | | ALXN1210 SC (N = 24) | | ALXN1210 IV (N = 12) | | Overall (N = 42) | |
|---|---|---|---|---|---|---|---|---|
| Preferred Term | E | n (%) | E | n (%) | E | n (%) | E | n (%) |
| Subjects with TEAEs | 15 | 5 (83.3) | 38 | 19 (79.2) | 22 | 11 (91.7) | 75 | 35 (83.3) |
| Infections and infestations | 10 | 5 (83.3) | 18 | 14 (58.3) | 9 | 8 (66.7) | 37 | 27 (64.3) |
| Nasopharyngitis | 7 | 5 (83.3) | 13 | 11 (45.8) | 8 | 7 (58.3) | 28 | 23 (54.8) |
| Lower respiratory tract infection | 1 | 1 (16.7) | 1 | 1 (4.2) | 0 | 0 | 2 | 2 (4.8) |
| Balanitis Candida | 0 | 0 | 1 | 1 (4.2) | 0 | 0 | 1 | 1 (2.4) |
| Cellulitis | 0 | 0 | 0 | 0 | 1 | 1 (8.3) | 1 | 1 (2.4) |
| Gastroenteritis | 1 | 1 (16.7) | 0 | 0 | 0 | 0 | 1 | 1 (2.4) |
| Tinea pedis | 0 | 0 | 1 | 1 (4.2) | 0 | 0 | 1 | 1 (2.4) |
| Upper respiratory tract infection | 0 | 0 | 1 | 1 (4.2) | 0 | 0 | 1 | 1 (2.4) |
| Viral upper respiratory tract infection | 0 | 0 | 1 | 1 (4.2) | 0 | 0 | 1 | 1 (2.4) |
| Vulvovaginal candidiasis | 1 | 1 (16.7) | 0 | 0 | 0 | 0 | 1 | 1 (2.4) |
| Nervous system disorders | 3 | 3 (50.0) | 5 | 3 (12.5) | 4 | 4 (33.3) | 12 | 10 (23.8) |
| Headache | 3 | 3 (50.0) | 2 | 1 (4.2) | 3 | 3 (25.0) | 8 | 7 (16.7) |
| Migraine | 0 | 0 | 2 | 2 (8.3) | 1 | 1 (8.3) | 3 | 3 (7.1) |
| Migraine with aura | 0 | 0 | 1 | 1 (4.2) | 0 | 0 | 1 | 1 (2.4) |
| Gastrointestinal disorders | 2 | 1 (16.7) | 4 | 3 (12.5) | 3 | 3 (25.0) | 9 | 7 (16.7) |
| Diarrhoea | 1 | 1 (16.7) | 2 | 1 (4.2) | 1 | 1 (8.3) | 4 | 3 (7.1) |
| Nausea | 1 | 1 (16.7) | 0 | 0 | 1 | 1 (8.3) | 2 | 2 (4.8) |
| Dyspepsia | 0 | 0 | 1 | 1 (4.2) | 0 | 0 | 1 | 1 (2.4) |
| Toothache | 0 | 0 | 0 | 0 | 1 | 1 (8.3) | 1 | 1 (2.4) |
| Vomiting | 0 | 0 | 1 | 1 (4.2) | 0 | 0 | 1 | 1 (2.4) |
| Musculoskeletal and connective tissue disorders | 0 | 0 | 3 | 3 (12.5) | 3 | 3 (25.0) | 6 | 6 (14.3) |

TABLE 23-continued

Treatment-Emergent Adverse Events - Frequency Table by System Organ Class and Preferred Term (Safety Set)

| Primary System Organ Class | Placebo SC (N = 6) | | ALXN1210 SC (N = 24) | | ALXN1210 IV (N = 12) | | Overall (N = 42) | |
|---|---|---|---|---|---|---|---|---|
| Preferred Term | E | n (%) | E | n (%) | E | n (%) | E | n (%) |
| Musculoskeletal pain | 0 | 0 | 1 | 1 (4.2) | 1 | 1 (8.3) | 2 | 2 (4.8) |
| Myalgia | 0 | 0 | 1 | 1 (4.2) | 1 | 1 (8.3) | 2 | 2 (4.8) |
| Back pain | 0 | 0 | 1 | 1 (4.2) | 0 | 0 | 1 | 1 (2.4) |
| Pain in extremity | 0 | 0 | 0 | 0 | 1 | 1 (8.3) | 1 | 1 (2.4) |
| Respiratory, thoracic, and mediastinal disorders | 0 | 0 | 3 | 3 (12.5) | 3 | 3 (25.0) | 6 | 6 (14.3) |
| Cough | 0 | 0 | 0 | 0 | 2 | 2 (16.7) | 2 | 2 (4.8) |
| Nasal congestion | 0 | 0 | 1 | 1 (4.2) | 1 | 1 (8.3) | 2 | 2 (4.8) |
| Allergic sinusitis | 0 | 0 | 1 | 1 (4.2) | 0 | 0 | 1 | 1 (2.4) |
| Oropharyngeal pain | 0 | 0 | 1 | 1 (4.2) | 0 | 0 | 1 | 1 (2.4) |
| Injury, poisoning, and procedural complications | 0 | 0 | 2 | 2 (8.3) | 0 | 0 | 2 | 2 (4.8) |
| Arthropod bite | 0 | 0 | 1 | 1 (4.2) | 0 | 0 | 1 | 1 (2.4) |
| Joint dislocation | 0 | 0 | 1 | 1 (4.2) | 0 | 0 | 1 | 1 (2.4) |
| General disorders and administration site conditions | 0 | 0 | 1 | 1 (4.2) | 0 | 0 | 1 | 1 (2.4) |
| Vessel puncture site bruise | 0 | 0 | 1 | 1 (4.2) | 0 | 0 | 1 | 1 (2.4) |
| Immune system disorders | 0 | 0 | 1 | 1 (4.2) | 0 | 0 | 1 | 1 (2.4) |
| Seasonal allergy | 0 | 0 | 1 | 1 (4.2) | 0 | 0 | 1 | 1 (2.4) |
| Skin and subcutaneous tissues disorders | 0 | 0 | 1 | 1 (4.2) | 0 | 0 | 1 | 1 (2.4) |
| Rash popular | 0 | 0 | 1 | 1 (4.2) | 0 | 0 | 1 | 1 (2.4) |

Note:

Percentage (%) is equal to n/N x 100.

Each subject is only counted once for a given SOC and Preferred Term, regardless of the actual number of occurred adverse events.

Classification of SOC and Preferred Term is according to MedDRA v20.0.

Abbreviations: E = number of events; IV = intravenous; MedDRA = Medical Dictionary for Regulatory Activities; N = total number of subjects at risk; n = number of subjects having an adverse event; SC = subcutaneous; SOC = System Organ Class; TEAE = treatment-emergent adverse event.

The majority of the TEAEs (72/75 TEAEs, 96%) were considered to be unrelated to ALXN1210 treatment. Across the treatment groups, 3/42 (7.1%) subjects reported 3 TEAEs which were assessed by the Investigator as related ("possibly related") to ALXN1210 treatment and Grade 1 (mild): (1) upper respiratory tract infection in one subject from the ALXN1210 SC group (2), migraine in one subject in the ALXN1210 SC, and (3) headache in one subject in the ALXN1210 IV group. All 75 TEAEs were classified as Grade 1 (mild). No subjects died, experienced SAEs, or discontinued study drug or study due to a TEAE.

In general, the mean values for hematology, coagulation, blood chemistry, urinalysis, and urine chemistry were within the reference ranges and there were no apparent trends in mean change from baseline.

The majority of subjects entered the study with normal values (i.e., within the respective reference ranges) for hematology, urinalysis, coagulation, blood chemistry, and urine chemistry parameters. No apparent trends in shifts were observed across the treatment groups. Shift from normal at baseline to abnormal values (Grade 1 [mild] or Grade 2 [moderate]) during the study were observed for some of the laboratory parameters, which were however not considered clinically significant. Most of the shifts were transient and resolved during the study.

Shift to Grade 3 abnormal values was reported in 3 subjects in the ALXN1210 SC group during the study. None of the shifts to Grade 3 abnormal values were reported as AEs.

First, a decrease in the neutrophil count was reported in one subject. The neutrophil count in this subject at baseline was 3.77×10^9/L. The assessed neutrophil count on Day 43 was 0.95×10^9/L (normal range: 2.0 to 7.5×10^9/L). The neutrophil count was in the normal range on Day 57.

An increase in potassium levels (normal range: 3.5 to 5.1 mmol/L) was reported in two subjects. In 1 subject with a baseline potassium level of 4.5 mmol/L, the assessed potassium level on Day 150 was 6.1 mmol/L. A repeat potassium level was in the normal range on the same day (unscheduled visit). In another subject with a baseline potassium level of 4.6 mmol/L, the assessed potassium level on Day 90 was 6.4 mmol/L. This subject presented with abnormal potassium values at Screening (ranging from 5.2 to 6.2 mmol/L during different screening visits) and through most of the study visits. Increases in potassium levels were transient; the recorded values were within the normal range on Day 150 and Day 200.

There were neither any observable changes from baseline in vital sign measurements nor any clinically significant abnormalities in vital signs consistently observed for individual subjects.

No subjects had physical examination findings that were of clinical significance other than those findings reported as AEs. There were no notable mean changes from baseline in ECG or telemetry monitoring results.

Changes in QT intervals were corrected using Fridericia's formula (QTcF). In one subject in the placebo SC group, mean QT interval >500 msec was observed at Screening (510.0 msec) and on Day 2 (508.7 msec), Day 150 (516.6 msec), and Day 200 (612.9 msec). The mean QTcF interval in the same subject was 449.7 msec, 443.7 msec, 451.9 msec, and 501.3 msec at Screening and on Days 2, 150, and 200, respectively. The increase in the QT and QTcF interval was not considered clinically significant in this female subject on placebo. These changes were also not reported as an AE. No notable changes from baseline in the mean QT and QTcF interval were observed during the study.

Infusion or injection site evaluations were done within 15 minutes of the SOI and ±15 minutes at 30 minutes, 2 h, 4 h, 8 h and on Day 2 (48 h), Day 3 (72 h, total of 6 assessments). Indurations or reactions <1 cm were not considered as an AE unless it persisted for more than 24 hours. Erythema was observed 30 minutes post EOI in 5/24 subjects in the ALXN1210 SC group, and in 1 subject, 2/4 injection sites had minimal (3 mm) erythema 2 hours after injection and none at last timepoints. Minimal induration or swelling (10 mm) was reported 30 minutes post EOI in 1/24 subject in the ALXN1210 SC group that was not observed at last assessments. However, none of these met the protocol-defined criteria to be considered as an AE. Pain at the site of infusion or injection was rated by subjects using VAS (0 to 100 mm). For the majority of the infusions and injections, pain at the infusion site was rated as 0 mm at all assessments. Two subjects in the SC group reported transient pain of 3-5 mm on Day 1, and three subjects in the IV group reported minimal (1-5 mm) pain after infusion.

9. Safety Conclusions

All subjects who received the single dose of study drug (placebo SC, ALXN1210 SC, or ALXN1210 IV) were included in the Safety Set (N=42). Across the 3 treatment groups, 35/42 subjects (83.3%) experienced 75 TEAEs. Only 3/75 TEAEs (4%) were considered related to ALXN1210, while 72/75 (96%) were considered unrelated to ALXN1210 treatment. All TEAEs were mild (Grade 1) and resolved during the course of the study. The majority of the TEAEs did not require any medication, and no subjects at any time required nonpharmacologic interventions. The most frequently reported TEAEs were nasopharyngitis (23/42 subjects, 54.8%) and headache (7/42 subjects, 16.7%).

There were no deaths or SAEs during the study. None of the reported TEAEs led to study drug discontinuation or withdrawal of subject from the study. In general, there were no clinically significant changes in laboratory parameters, vital signs, physical examinations, ECG, or telemetry during the study or follow-up. There was no clinical evidence of hypersensitivity during or after any single dose of SC injection or IV infusion. No clinical signs or symptoms associated with allergic reaction or hypersensitivity were noted in subjects with ADA positive results.

10. Discussion and Overall Conclusions

The purpose of this Phase 1 study was to evaluate the safety, tolerability, PK, PD, and immunogenicity of a single dose of ALXN1210 SC 400 mg compared to a single dose of ALXN1210 IV 400 mg or placebo SC injection in healthy subjects. A total of 42 subjects were randomized and received the study drug: placebo SC (n=6); ALXN1210 SC (n=24); and ALXN1210 IV (n=12).

Administration of ALXN1210 at a dose of 400 mg was well tolerated via a SC route of administration in healthy subjects. The absolute bioavailability of ALXN1210 SC, based on the GMR of $AUC_{\infty}$ estimates (SC/IV), was 60.4% (95% CI: 49.7, 73.3). The geometric mean $t_{1/2}$ estimates were 31.3 days and 29.9 days following ALXN1210 SC and IV administration, respectively. The extent and duration of PD response, as assessed by free and total C5 serum concentration and cRBC hemolysis, were exposure dependent.

Antidrug antibodies were reported for 3/23 (13%) subjects and 1/12 (8.3%) subject in the ALXN1210 SC and ALXN1210 IV groups, respectively, with ADA positive titer values ranging from <1.0 to 27. The earliest response postdose was seen on Day 29 and Day 15, for SC and IV dosing, respectively. In most ADA positive samples following SC administration, the ADAs were cross-reactive to eculizumab. In the subjects showing positive ADA response, there were no clinical signs or symptoms consistent with allergic reaction or hypersensitivity (including anaphylaxis). In addition, no apparent impact on the PK or PD of ALXN1210 could be identified.

There were no unexpected safety concerns in any of the treatment groups during the study. No deaths or SAEs occurred during the study and no subjects experienced any TEAE leading to study drug discontinuation or withdrawal from study.

SEQUENCE SUMMARY amino acid sequence of heavy chain CDR1 of eculizumab (as defined under combined Kabat-Chothia definition)

SEQ ID NO: 1

GYIFSNYWIQ amino acid sequence of heavy chain CDR2 of eculizumab (as defined under Kabat definition)

SEQ ID NO: 2

EILPGSGSTEYTENFKD amino acid sequence of the heavy chain CDR3 of eculizumab (as defined under combined Kabat definition).

SEQ ID NO: 3

YFFGSSPNWYFDV amino acid sequence of the light chain CDR1 of eculizumab (as defined under Kabat definition)

SEQ ID NO: 4

GASENIYGALN amino acid sequence of light chain CDR2 of eculizumab (as defined under Kabat definition)

SEQ ID NO: 5

GATNLAD amino acid sequence of light chain CDR3 of eculizumab (as defined under Kabat definition)

SEQ ID NO: 6

QNVLNTPLT amino acid sequence of heavy chain variable region of eculizumab

SEQ ID NO: 7

QVQLVQSGAEVKKPGASVKVSCKASGYIFSNYWIQWVRQAPGQGLEWMGE

ILPGSGSTEYTENFKDRVTMTRDTSTSTVYMELSSLRSEDTAVYYCARYF

FGSSPNWYFDVWGQGTLVTVSS amino acid sequence of light chain variable region of eculizumab, ravulizumab, and BNJ421 antibody

SEQ ID NO: 8

DIQMTQSPSSLSASVGDRVTITCGASENIYGALNWYQQKPGKAPKLLIYG

ATNLADGVPSRFSGSGSGTDFTLTISSLQPEDFATYYCQNVLNTPLTFGQ

GTKVEIK

-continued amino acid sequence of heavy chain constant region of eculizumab and BNJ421 antibody

SEQ ID NO: 9

ASTKGPSVFPLAPCSRSTSESTAALGCLVKDYFPEPVTVSWNSGALTSGV
HTFPAVLQSSGLYSLSSVVTVPSSNFGTQTYTCNVDHKPSNTKVDKTVER
KCCVECPPCPAPPVAGPSVFLFPPKPKDTLMISRTPEVTCVVVDVSQEDP
EVQFNWYVDGVEVHNAKTKPREEQFNSTYRVVSVLTVLHQDWLNGKEYKC
KVSNKGLPSSIEKTISKAKGQPREPQVYTLPPSQEEMTKNQVSLTCLVKG
FYPSDIAVEWESNGQPENNYKTTPPVLDSDGSFFLYSRLTVDKSRWQEGN
VFSCSVMHEALHNHYTQKSLSLSLGK amino acid sequence of entire heavy chain of eculizumab

SEQ ID NO: 10

QVQLVQSGAEVKKPGASVKVSCKASGYIFSNYWIQWVRQAPGQGLEWMGE
ILPGSGSTEYTENFKDRVTMTRDTSTSTVYMELSSLRSEDTAVYYCARYF
FGSSPNWYFDVWGQGTLVTVSS*ASTKGPSVFPLAPCSRSTSESTAALGCL*
*VKDYFPEPVTVSWNSGALTSGVHTFPAVLQSSGLYSLSSVVTVPSSNFGT*
*QTYTCNVDHKPSNTKVDKTVERKCCVECPPCPAPPVAGPSVFLFPPKPKD*
*TLMISRTPEVTCVVVDVSQEDPEVQFNWYVDGVEVHNAKTKPREEQFNST*
*YRVVSVLTVLHQDWLNGKEYKCKVSNKGLPSSIEKTISKAKGQPREPQVY*
*TLPPSQEEMTKNQVSLTCLVKGFYPSDIAVEWESNGQPENNYKTTPPVLD*
*SDGSFFLYSRLTVDKSRWQEGNVFSCSVMHEALHNHYTQKSLSLSLGK* amino acid sequence of entire light chain of eculizumab, ravulizumab, and BNJ421 antibody

SEQ ID NO: 11

DIQMTQSPSSLSASVGDRVTITCGASENIYGALNWYQQKPGKAPKLLIYG
ATNLADGVPSRFSGSGSGTDFTLTISSLQPEDFATYYCQNVLNTPLTFGQ
GTKVEIK*RTVAAPSVFIFPPSDEQLKSGTASVVCLLNNFYPREAKVQWKV*
*DNALQSGNSQESVTEQDSKDSTYSLSSTLTLSKADYEKHKVYACEVTHQG*
*LSSPVTKSFNRGEC* amino acid sequence of heavy chain variable region of ravulizumab and BNJ421 antibody

SEQ ID NO: 12

QVQLVQSGAEVKKPGASVKVSCKASGHIFSNYWIQWVRQAPGQGLEWMGE
ILPGSGHTEYTENFKDRVTMTRDTSTSTVYMELSSLRSEDTAVYYCARYF
FGSSPNWYFDVWGQGTLVTVSS amino acid sequence of heavy chain constant region of ravulizumab

SEQ ID NO: 13

ASTKGPSVFPLAPCSRSTSESTAALGCLVKDYFPEPVTVSWNSGALTSGV
HTFPAVLQSSGLYSLSSVVTVPSSNFGTQTYTCNVDHKPSNTKVDKTVER
KCCVECPPCPAPPVAGPSVFLFPPKPKDTLMISRTPEVTCVVVDVSQEDP
EVQFNWYVDGVEVHNAKTKPREEQFNSTYRVVSVLTVLHQDWLNGKEYKC
KVSNKGLPSSIEKTISKAKGQPREPQVYTLPPSQEEMTKNQVSLTCLVKG
FYPSDIAVEWESNGQPENNYKTTPPVLDSDGSFFLYSRLTVDKSRWQEGN
VFSCSVLHEALHSHYTQKSLSLSLGK amino acid sequence of entire heavy chain of ravulizumab

SEQ ID NO: 14

QVQLVQSGAEVKKPGASVKVSCKASGHIFSNYWIQWVRQAPGQGLEWMGE
ILPGSGHTEYTENFKDRVTMTRDTSTSTVYMELSSLRSEDTAVYYCARYF
FGSSPNWYFDVWGQGTLVTVSS*ASTKGPSVFPLAPCSRSTSESTAALGCL*
*VKDYFPEPVTVSWNSGALTSGVHTFPAVLQSSGLYSLSSVVTVPSSNFGT*
*QTYTCNVDHKPSNTKVDKTVERKCCVECPPCPAPPVAGPSVFLFPPKPKD*
*TLMISRTPEVTCVVVDVSQEDPEVQFNWYVDGVEVHNAKTKPREEQFNST*
*YRVVSVLTVLHQDWLNGKEYKCKVSNKGLPSSIEKTISKAKGQPREPQVY*
*TLPPSQEEMTKNQVSLTCLVKGFYPSDIAVEWESNGQPENNYKTTPPVLD*
*SDGSFFLYSRLTVDKSRWQEGNVFSCSV*L*HEALH*S*HYTQKSLSLSLGK* amino acid sequence of IgG2 heavy chain constant region variant comprising YTE substitutions

SEQ ID NO: 15

ASTKGPSVFPLAPCSRSTSESTAALGCLVKDYFPEPVTVSWNSGALTSGV
HTFPAVLQSSGLYSLSSVVTVTSSNFGTQTYTCNVDHKPSNTKVDKTVER
KCCVECPPCPAPPVAGPSVFLFPPKPKDTLYITREPEVTCVVVDVSHEDP
EVQFNWYVDGMEVHNAKTKPREEQFNSTFRVVSVLTVVHQDWLNGKEYKC
KVSNKGLPAPIEKTISKTKGQPREPQVYTLPPSREEMTKNQVSLTCLVKG
FYPSDIAVEWESNGQPENNYKTTPPMLDSDGSFFLYSKLTVDKSRWQQGN
VFSCSVMHEALHNHYTQKSLSLSPGK amino acid sequence of entire heavy chain of eculizumab variant comprising heavy chain constant region depicted in SEQ ID NO: 15 (above)

SEQ ID NO: 16

QVQLVQSGAEVKKPGASVKVSCKASGYIFSNYWIQWVRQAPGQGLEWMGE
ILPGSGSTEYTENFKDRVTMTRDTSTSTVYMELSSLRSEDTAVYYCARYF
FGSSPNWYFDVWGQGTLVTVSSASTKGPSVFPLAPCSRSTSESTAALGCL
VKDYFPEPVTVSWNSGALTSGVHTFPAVLQSSGLYSLSSVVTVTSSNFGT
QTYTCNVDHKPSNTKVDKTVERKCCVECPPCPAPPVAGPSVFLFPPKPKD
TLYITREPEVTCVVVDVSHEDPEVQFNWYVDGMEVHNAKTKPREEQFNST
FRVVSVLTVVHQDWLNGKEYKCKVSNKGLPAPIEKTISKTKGQPREPQVY
TLPPSREEMTKNQVSLTCLVKGFYPSDIAVEWESNGQPENNYKTTPPMLD
SDGSFFLYSKLTVDKSRWQQGNVFSCSVMHEALHNHYTQKSLSLSPGK amino acid sequence of light chain CDR1 of eculizumab (as defined under Kabat definition) with glycine to histidine substitution at position 8 relative to SEQ ID NO: 4

SEQ ID NO: 17

GASENIYHALN depicts amino acid sequence of heavy chain CDR2 of eculizumab in which serine at position 8 relative to SEQ ID NO: 2 is substituted with histidine

SEQ ID NO: 18

EILPGSGHTEYTENFKD amino acid sequence of heavy chain CDR1 of eculizumab in which tyrosine at position 2 (relative to SEQ ID NO: 1) is substituted with histidine

SEQ ID NO: 19

GHIFSNYWIQ

-continued amino acid sequence of entire heavy chain of BNJ421 antibody

SEQ ID NO: 20

QVQLVQSGAEVKKPGASVKVSCKASGHIFSNYWIQWVRQAPGQGLEWMGE

ILPGSGHTEYTENFKDRVTMTRDTSTSTVYMELSSLRSEDTAVYYCARYF

FGSSPNWYFDVWGQGTLVTVSS*ASTKGPSVFPLAPCSRSTSESTAALGCL*

*VKDYFPEPVTVSWNSGALTSGVHTFPAVLQSSGLYSLSSVVTVPSSNFGT*

-continued

*QTYTCNVDHKPSNTKVDKTVERKCCVECPPCPAPPVAGPSVFLFPPKPKD*

*TLMISRTPEVTCVVVDVSQEDPEVQFNWYVDGVEVHNAKTKPREEQFNST*

*YRVVSVLTVLHQDWLNGKEYKCKVSNKGLPSSIEKTISKAKGQPREPQVY*

*TLPPSQEEMTKNQVSLTCLVKGFYPSDIAVEWESNGQPENNYKTTPPVLD*

*SDGSFFLYSRLTVDKSRWQEGNVFSCSV* *M* *HEALH* *N* *HYTQKSLSLSLGK*

The invention claimed is:

1. A stable aqueous solution comprising:

(a) an anti-C5 antibody at a concentration of about 100 mg/mL, wherein the anti-C5 antibody comprises a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6;

(b) about 50 mM Phosphate Buffer;

(c) about 5% sucrose; and (d) about 25 mM Arginine.

2. A stable aqueous solution comprising:

(a) an anti-C5 antibody, wherein the anti-C5 antibody comprises a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6;

(b) about 50 mM Phosphate Buffer;

(c) about 5% sucrose;

(d) about 0.05% Polysorbate 80; and (e) about 25 mM Arginine.

3. The stable aqueous solution of claim 1, further comprising a surfactant.

4. The stable aqueous solution of claim 3, wherein the surfactant is about 0.05% Polysorbate 80.

5. The stable aqueous solution of claim 2, wherein the an anti-C5 antibody is at a concentration of about 100 mg/mL.

6. The stable aqueous solution of claim 1 or 2, wherein the anti-C5 antibody further comprises a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering.

7. The stable aqueous solution of claim 1 or 2, wherein the anti-C5 antibody comprises a heavy chain variable region depicted in SEQ ID NO:12 and a light chain variable region depicted in SEQ ID NO:8.

8. The stable aqueous solution of claim 1 or 2, wherein the anti-C5 antibody comprises a heavy chain constant region depicted in SEQ ID NO:13.

9. The stable aqueous solution of claim 1 or 2, wherein the anti-C5 antibody comprises a heavy chain polypeptide comprising the amino acid sequence depicted in SEQ ID NO: 14 and a light chain polypeptide comprising the amino acid sequence depicted in SEQ ID NO: 11.

10. The stable aqueous solution of claim 1 or 2, wherein the anti-C5 antibody is ALXN1210 (ravulizumab).

11. The stable aqueous solution of claim 1 or 2, wherein the pH of the solution is between 7.2 and 7.6.

12. The stable aqueous solution of claim 11, wherein the pH of the solution is 7.4.

13. The stable aqueous solution of claim 1 or 2, wherein the solution is sterile.

14. The stable aqueous solution of claim 1 or 2, wherein:

(a) the anti-C5 antibody remains at least 97% monomeric during storage at 2° C. to 8° C. for at least six months as determined by SEC-HPLC;

(b) less than 3% of the anti-C5 antibody in the solution is aggregated as determined by SEC-HPLC; and/or (c) during storage at 2° C. to 8° C. for at least six months, the anti-C5 antibody retains at least 90% of its C5-binding activity, as compared to the anti-C5 antibody prior to storage.

15. The stable aqueous solution of claim 1 or 2, wherein the solution is suitable for subcutaneous or intravenous administration.

16. A method for producing a stable concentrated antibody solution comprising an anti-C5 antibody comprising a heavy chain CDR1 comprising the amino acid sequence depicted in SEQ ID NO:19, a heavy chain CDR2 comprising the amino acid sequence depicted in SEQ ID NO:18, a heavy chain CDR3 comprising the amino acid sequence depicted in SEQ ID NO:3, a light chain CDR1 comprising the amino acid sequence depicted in SEQ ID NO:4, a light chain CDR2 comprising the amino acid sequence depicted in SEQ ID NO:5, and a light chain CDR3 comprising the amino acid sequence depicted in SEQ ID NO:6, at a concentration of 100 mg/mL, 50 mM Phosphate Buffer, 5% sucrose; and 25 mM Arginine, the method comprising:

i) providing a first aqueous solution comprising the anti-C5 antibody, the first aqueous solution having a first formulation and comprising no more than 10 mg/mil, of the anti-C5 antibody;

ii) subjecting the first aqueous solution to diafiltration into a formulation comprising 50 mM Phosphate Buffer, 5% sucrose, and 25 mM Arginine, at pH 7.4 to thereby produce a second aqueous solution, wherein the second aqueous solution has a second formulation as a result of the diafiltration; and iii) concentrating the second aqueous solution to produce a stable concentrated antibody solution comprising 100 mg/mL of the anti-C5 antibody, 50 mM Phosphate Buffer, 5% sucrose; and 25 mM Arginine.

17. A therapeutic kit comprising the stable aqueous solution according to claim 1.

* * * * *

UNITED STATES PATENT AND TRADEMARK OFFICE

CERTIFICATE OF CORRECTION

PATENT NO. : 11,365,241 B2
APPLICATION NO. : 16/633930
DATED : June 21, 2022
INVENTOR(S) : Stephan Ortiz et al.

It is certified that error appears in the above-identified patent and that said Letters Patent is hereby corrected as shown below:

On the Title Page

In item (56), in Column 2, under “Other Publications”, Line 8, delete “al.l,” and insert -- al., --.

On the Page 2, in Column 2, under “Other Publications”, Line 26, delete “thera-peutics,”” and insert -- therapeutics,” --.

On the Page 2, in Column 2, under “Other Publications”, Line 45, delete “Opthalmol” and insert -- Ophthalmol --.

On the Page 3, in Column 1, under “Other Publications”, Line 9, delete “124” and insert -- 424 --.

On the Page 3, in Column 1, under “Other Publications”, Line 20, delete “Moris,” and insert -- Noris, --.

On the Page 3, in Column 1, under “Other Publications”, Line 23, delete “Gurr” and insert -- Curr --.

On the Page 3, in Column 2, under “Other Publications”, Line 17, delete “De-velopment” and insert -- Development --.

On the Page 3, in Column 2, under “Other Publications”, Line 25, delete “Fabrizi,” and insert -- Tabrizi, --.

On the Page 3, in Column 2, under “Other Publications”, Line 42, delete “Pharmaceu-tical” and insert -- Pharmaceutical --.

On the Page 4, in Column 1, under “Other Publications”, Line 11, delete “PCT/U52018/” and insert -- PCT/US2018/ --.

Signed and Sealed this
Sixteenth Day of August, 2022

Katherine Kelly Vidal

Katherine Kelly Vidal
*Director of the United States Patent and Trademark Office*

On the Page 4, in Column 1, under “Other Publications”, Line 25, delete “(1992). cited by applicant.” and insert -- (1992). --.

On the Page 4, in Column 2, under “Other Publications”, Line 26, delete “d331” and insert -- e331 --.

In the Specification

In Column 7, Line 55, delete “a)” and insert -- (a) --.

In Column 7, Line 58, delete “a)” and insert -- (a) --.

In Column 8, Line 4, delete “a)” and insert -- (a) --.

In Column 8, Line 14 (approx.), delete “a)” and insert -- (a) --.

In Column 12, Line 49, delete “embolus,” and insert -- embolism, --.

In Column 15, Line 27, delete “scale” and insert -- scale. --.

In Column 15, Line 29, delete “scale” and insert -- scale. --.

In Column 16, Line 35, delete “asceptic” and insert -- aseptic --.

In Column 17, Line 2, delete “high-perfornance” and insert -- high-performance --.

In Column 17, Line 3, delete “(GP-IPLC),” and insert -- (GP-HPLC), --.

In Column 18, Line 60, delete “condition” and insert -- condition. --.

In Column 29, Line 56, delete “more” and insert -- more) --.

In Column 35, Line 13, delete “5(2:” and insert -- 5(2): --.

In Column 35, Line 63-64, delete “3pentanol,” and insert -- 3-pentanol, --.

In Column 37, Line 38, delete “a)” and insert -- (a) --.

In Column 37, Line 46, delete “a)” and insert -- (a) --.

In Column 39, Line 36, delete “Arginine” and insert -- Arginine, --.

In Column 40, Line 35, delete “sialastic” and insert -- silastic --.

In Column 40, Line 40, delete “EP 430539,” and insert -- EP430539, --.

In Column 40, Line 57, delete “temperomandibular,” and insert -- temporomandibular, --.

In Column 41, Line 67, delete “embolus” and insert -- embolism --.

In Column 42, Line 30 (approx.), delete “the a” and insert -- the --.

In Column 42, Line 58, delete “embolus” and insert -- embolism --.

In Column 43, Line 38, delete “(Alleve®)” and insert -- (Aleve®) --.

In Column 43, Line 40, delete “tolementin” and insert -- tolmetin --.

In Column 43, Line 41, delete “(Trilasate®),” and insert -- (Trilisate®), --.

In Column 43, Line 42, delete “Diflusinal” and insert -- Diflunisal --.

In Column 43, Line 43, delete “indomethicin” and insert -- indomethacin --.

In Column 44, Line 42, delete “(AXLN1210)” and insert -- (ALXN1210) --.

In Column 46, Line 58 (approx.), delete “(MGI)” and insert -- (MFI) --.

In Column 46, Line 67, delete “mixing” and insert -- mixing. --.

In Column 49, Line 53, delete “pH7.2” and insert -- pH 7.2 --.

In Column 49, Line 55, delete “ALXN121” and insert -- ALXN1210 --.

In Column 49, Line 56, delete “pH7” and insert -- pH 7 --.

In Column 49, Line 62 (approx.), delete “Butter” and insert -- Buffer --.

In Column 50, Line 4, delete “Butter” and insert -- Buffer --.

In Column 50, Line 12 (approx.), delete “Formulalion” and insert -- Formulation --.

In Column 51, Line 28 (approx.), delete “Soribitol,” and insert -- Sorbitol, --.

In Column 52, Line 30 (approx.), delete “4117PS80” and insert -- 4117 PS80 --.

In Column 53, Line 52, delete “as light” and insert -- a slight --.

In Column 54, Line 24, delete “P80” and insert -- PS80 --.

In Column 54, Line 25, delete “P80” and insert -- PS80 --.

In Column 54, Line 28, delete “80” and insert -- PS80 --.

In Column 54, Line 33, delete “10.0%” and insert -- 0.05% --.

In Column 54, Line 33, delete “PS8” and insert -- PS80 --.

In Column 54, Line 36, delete “study” and insert -- study. --.

In Column 56, Line 27, delete “PS8” and insert -- PS80 --.

In Column 57, Line 62, delete “(>50 g/mL)” and insert -- (>50 μg/mL) --.

In Column 58, Line 48 (approx.), delete “or and” and insert -- and/or --.

In Column 71, Line 25, delete “SOL:” and insert -- SOI: --.

In Column 74, Line 26, delete “exposure” and insert -- exposure. --.

In Column 75, Line 5, delete “to be be” and insert -- to be --.

In the Claims

In Column 118, Line 20, in Claim 16, delete “10 mg/mil,” and insert -- 10 mg/mL --.

SEQUENCE LISTING

```
<160> NUMBER OF SEQ ID NOS: 20

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Tyr Ile Phe Ser Asn Tyr Trp Ile Gln
1               5                   10


<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Glu Ile Leu Pro Gly Ser Gly Ser Thr Glu Tyr Thr Glu Asn Phe Lys
1               5                   10                  15

Asp


<210> SEQ ID NO 3
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Tyr Phe Phe Gly Ser Ser Pro Asn Trp Tyr Phe Asp Val
1               5                   10


<210> SEQ ID NO 4
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Ala Ser Glu Asn Ile Tyr Gly Ala Leu Asn
1               5                   10
```

-continued

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 5

```
Gly Ala Thr Asn Leu Ala Asp
1               5
```

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 6

```
Gln Asn Val Leu Asn Thr Pro Leu Thr
1               5
```

<210> SEQ ID NO 7
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
        115                 120
```

<210> SEQ ID NO 8
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Asp Ile Gln Met Thr Gln Ser Pro Ser Ser Leu Ser Ala Ser Val Gly
1               5                   10                  15
```

```
Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys
            100                 105


<210> SEQ ID NO 9
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255
```

```
Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325
```

<210> SEQ ID NO 10
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
```

```
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 11
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210


<210> SEQ ID NO 12
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
        115                 120


<210> SEQ ID NO 13
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125
```

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Leu His Glu Ala Leu His Ser His Tyr Thr Gln Lys Ser Leu
305                 310                 315                 320

Ser Leu Ser Leu Gly Lys
                325

<210> SEQ ID NO 14
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr

```
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Leu His Glu Ala
            420                 425                 430

Leu His Ser His Tyr Thr Gln Lys Ser Leu Ser Leu Ser Leu Gly Lys
        435                 440                 445


<210> SEQ ID NO 15
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Tyr Ile Thr Arg Glu Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 16
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Thr Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Tyr Ile Thr Arg
                245                 250                 255

Glu Pro Glu Val Thr Cys Val Val Val Asp Val Ser His Glu Asp Pro
            260                 265                 270

Glu Val Gln Phe Asn Trp Tyr Val Asp Gly Met Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 17
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gly Ala Ser Glu Asn Ile Tyr His Ala Leu Asn
1 5 10

<210> SEQ ID NO 18
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 18

Glu Ile Leu Pro Gly Ser Gly His Thr Glu Tyr Thr Glu Asn Phe Lys
1 5 10 15

Asp

<210> SEQ ID NO 19
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 19

Gly His Ile Phe Ser Asn Tyr Trp Ile Gln
1 5 10

<210> SEQ ID NO 20
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

Gln Val Gln Leu Val Gln Ser Gly Ala Glu Val Lys Lys Pro Gly Ala
1 5 10 15

Ser Val Lys Val Ser Cys Lys Ala Ser Gly His Ile Phe Ser Asn Tyr
20 25 30

Trp Ile Gln Trp Val Arg Gln Ala Pro Gly Gln Gly Leu Glu Trp Met
35 40 45

Gly Glu Ile Leu Pro Gly Ser Gly His Thr Glu Tyr Thr Glu Asn Phe
50 55 60

Lys Asp Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Tyr Phe Phe Gly Ser Ser Pro Asn Trp Tyr Phe Asp Val Trp
100 105 110

Gly Gln Gly Thr Leu Val Thr Val Ser Ser Ala Ser Thr Lys Gly Pro
115 120 125

Ser Val Phe Pro Leu Ala Pro Cys Ser Arg Ser Thr Ser Glu Ser Thr
130 135 140

Ala Ala Leu Gly Cys Leu Val Lys Asp Tyr Phe Pro Glu Pro Val Thr
145 150 155 160

-continued

```
Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445
```